(12) United States Patent
Huang et al.

(10) Patent No.: US 11,447,498 B2
(45) Date of Patent: Sep. 20, 2022

(54) FUSED TETRACYCLIC COMPOUNDS AND USES THEREOF IN MEDICINE

(71) Applicant: SUNSHINE LAKE PHARMA CO., LTD., Guangdong (CN)

(72) Inventors: Jianzhou Huang, Dongguan (CN); Qingyun Ren, Dongguan (CN); Jinfeng Xiong, Dongguan (CN); Yang Liu, Dongguan (CN); Yingjun Zhang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

(21) Appl. No.: 17/276,735

(22) PCT Filed: Sep. 27, 2019

(86) PCT No.: PCT/CN2019/108562
§ 371 (c)(1),
(2) Date: Mar. 16, 2021

(87) PCT Pub. No.: WO2020/063870
PCT Pub. Date: Apr. 2, 2020

(65) Prior Publication Data
US 2022/0041614 A1    Feb. 10, 2022

(30) Foreign Application Priority Data

Sep. 30, 2018 (CN) .......................... 201811153527.2
Apr. 12, 2019 (CN) .......................... 201910292754.1
Jul. 8, 2019 (CN) .......................... 201910608198.4

(51) Int. Cl.
C07D 491/147    (2006.01)
A61K 45/06    (2006.01)
C07D 491/22    (2006.01)

(52) U.S. Cl.
CPC .......... *C07D 491/147* (2013.01); *A61K 45/06* (2013.01); *C07D 491/22* (2013.01)

(58) Field of Classification Search
None
See application file for complete search history.

(56) References Cited

U.S. PATENT DOCUMENTS

| | | |
|---|---|---|
| 9,458,153 B2 | 10/2016 | Han et al. |
| 9,637,485 B2 | 5/2017 | Han et al. |
| 9,845,325 B2 | 12/2017 | Fu et al. |
| 9,920,049 B2 | 3/2018 | Yang et al. |
| 10,053,461 B2 | 8/2018 | Han et al. |
| 10,093,671 B2 | 10/2018 | Han et al. |
| 10,093,673 B2 | 10/2018 | Fu et al. |
| 10,150,740 B2 | 12/2018 | Cheng et al. |
| 10,239,872 B2 | 3/2019 | Chen et al. |
| 10,301,312 B2 | 5/2019 | Fu et al. |
| 10,336,751 B2 | 7/2019 | Cheng et al. |
| 10,442,804 B2 | 10/2019 | Aktoudianakis et al. |
| 10,865,211 B2 | 12/2020 | Panarese et al. |
| 2019/0314347 A1 | 10/2019 | Bailey et al. |
| 2020/0113879 A1 | 4/2020 | Liu et al. |
| 2020/0255428 A1 | 8/2020 | Catalano et al. |

FOREIGN PATENT DOCUMENTS

| | | |
|---|---|---|
| CN | 106810548 A | 6/2017 |
| CN | 106928245 A | 7/2017 |
| CN | 108530449 A | 9/2018 |
| CN | 108727378 A | 11/2018 |
| CN | 106928215 B | 3/2019 |
| CN | 110903284 A | 3/2020 |
| CN | 110950860 A | 4/2020 |
| CN | 111116577 A | 5/2020 |
| CN | 111116588 A | 5/2020 |
| CN | 111217811 A | 6/2020 |
| CN | 110724140 B | 10/2020 |
| WO | 2015/113990 A1 | 8/2015 |
| WO | 2017/016960 A1 | 2/2017 |
| WO | 2017/216685 A1 | 12/2017 |
| WO | 2017/216686 A1 | 12/2017 |
| WO | 2018/019297 A1 | 2/2018 |
| WO | 2018/047109 A1 | 3/2018 |
| WO | 2018/073753 A1 | 4/2018 |
| WO | 2018/130152 A1 | 7/2018 |
| WO | 2018/154466 A1 | 8/2018 |
| WO | 2018/161960 A1 | 9/2018 |
| WO | 2018/214875 A1 | 11/2018 |

(Continued)

OTHER PUBLICATIONS

Dec. 30, 2019 Search Report issued in International Patent Application No. PCT/CN2019/108562.

(Continued)

*Primary Examiner* — Samantha L Shterengarts
(74) *Attorney, Agent, or Firm* — Oliff PLC

(57) ABSTRACT

A fused tetracyclic compound and application thereof in medicine, especially as a medicament for the treatment and/or prevention of hepatitis B. A compound having Formula (I) or a stereoisomer, a tautomer, an N-oxide, a solvate, a metabolite, a pharmaceutically acceptable salt or a prodrug thereof, in medicine, especially as a medicament for the treatment and/or prevention of hepatitis B, wherein each variable is as defined in the specification.

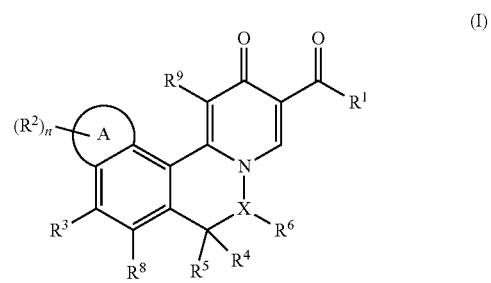

19 Claims, No Drawings
Specification includes a Sequence Listing.

(56) References Cited

FOREIGN PATENT DOCUMENTS

| | | |
|---|---|---|
| WO | 2019/100735 A1 | 5/2019 |
| WO | 2019/110352 A1 | 6/2019 |
| WO | 2019/123285 A1 | 6/2019 |
| WO | 2019/143902 A2 | 7/2019 |
| WO | 2019/169539 A1 | 9/2019 |
| WO | 2019/177937 A1 | 9/2019 |
| WO | 2019/200109 A1 | 10/2019 |
| WO | 2020/043080 A1 | 3/2020 |
| WO | 2020/143604 A1 | 7/2020 |
| WO | 2020/150366 A1 | 7/2020 |

OTHER PUBLICATIONS

Dec. 30, 2019 Written Opinion issued in International Patent Application No. PCT/CN2019/108562.

FUSED TETRACYCLIC COMPOUNDS AND USES THEREOF IN MEDICINE

CROSS-REFERENCE TO RELATED APPLICATIONS

This application claims priorities and benefits of Chinese Patent Application Serial No 201811153527.2, filed on Sep. 30, 2018; Chinese Patent Application Serial No 201910292754.1, filed on Apr. 12, 2019; and Chinese Patent Application Serial No 201910608198.4, filed on Jul. 8, 2019, all of which are hereby incorporated by reference in their entireties.

FIELD OF THE INVENTION

The present invention belongs to the field of medicines and relates to a fused tetracyclic compound and application thereof in medicine, especially as a medicament for the treatment and/or prevention of hepatitis B. The invention also relates to a composition of these fused tetracyclic compounds together with other antiviral agents, and their use for the treatment and/or prevention of hepatitis B (HBV) infection.

BACKGROUND OF THE INVENTION

The hepatitis B virus belongs to the family of hepadnaviridae. It can cause acute and/or persistent or progressive chronic diseases. Many other clinical manifestations in the pathological morphology can be also caused by HBV—in particular chronic hepatitis, cirrhosis and hepatocellular carcinoma. According to estimates by the World Health Organization, 2 billion people worldwide have been infected with HBV, and there are about 350 million chronically infected people. About 1 million people die each year from liver failure, liver cirrhosis and primary hepatocellular carcinoma (HCC) caused by HBV infection.

Currently, the treatment of chronic hepatitis B (CHB) is mainly antiviral therapy. Interferon α (IFN-α) and pegylated IFN-α and five nucleoside (acid) analogues (lamivudine, adefovir dipivoxil, entecavir, telbivudine and tenofovir) were approved by the US Food and Drug Administration (FDA) for clinical treatment. Interferon is the anti-HBV drug first approved by the FDA. It mainly achieves the effect of clearing the virus by direct antiviral action and inducing the body's immune response. However, due to its low response rate, various side effects, expensive price and the limited treatment target, etc., its application is subject to many restrictions. The anti-HBV of nucleoside (acid) drugs has a specific effect on viral DNA polymerase and has a strong inhibitory effect on viral replication. Patients are better tolerant to drugs than interferon. However, the widespread long-term use of nucleoside (acid) drugs can induce DNA polymerase mutations to form drug resistance, leading to the emergence of drug-resistant strains, making treatment far less than the desired effect.

Therefore, there is still a need in the clinic for new compounds which can be effectively used as antiviral drugs, especially as drugs for treating and/or preventing hepatitis B.

SUMMARY OF THE INVENTION

The present invention relates to a novel class of fused tetracyclic compounds and their use in the preparation of a medicament for the treatment and prevention of HBV infection. The inventors have found that the novel fused tetracyclic compounds of the present invention have good pharmacokinetic properties, good solubility, low toxicity, good liver microsome stability, and good inhibitory activity on the production or secretion of HBsAg and the replication of HBV DNA. It has a good application prospect in anti-HBV. In particular, the compounds of the present invention, and pharmaceutically acceptable compositions thereof, are also effective in inhibiting HBV infection.

In one aspect, the present invention provides a compound having Formula (I) or a stereoisomer, a tautomer, an N-oxide, a solvate, a metabolite, a pharmaceutically acceptable salt or a prodrug thereof,

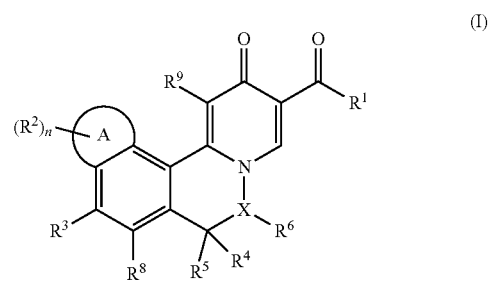

wherein $R^1$ is $R^{1a}O—$ or $R^aR^bN—$;

X is $CR^7$ or N;

ring A is a heterocyclyl consisting of 5 ring atoms, a heterocyclyl consisting of 6 ring atoms or a carbocyclyl consisting of 5 to 6 carbon atoms;

$R^3$ is hydrogen, deuterium, F, Cl, Br, hydroxy, cyano, $C_{1-6}$ alkyl, $C_{2-6}$ alkynyl, $C_{3-7}$ cycloalkyl, heterocyclyl consisting of 3 to 10 ring atoms, $C_{6-10}$ aryl, heteroaryl group of 5 to 10 ring atoms or $R^{10}—C_{0-4}$ alkylene-O—, wherein each of $C_{1-6}$ alkyl, $C_{2-6}$ alkynyl, $C_{3-7}$ cycloalkyl, heterocyclyl consisting of 3 to 10 ring atoms, $C_{6-10}$ aryl, heteroaryl group of 5 to 10 ring atoms and —$C_{0-4}$ alkylene of $R^{10}—C_{0-4}$ alkylene-O— is independently unsubstituted or substituted by 1, 2, 3 or 4 $R^g$;

$R^{10}$ is deuterium, $R^{11}O—$, $C_{1-6}$ alkyl, $C_{3-7}$ cycloalkyl, heterocyclyl consisting of 3 to 6 ring atoms, $C_{6-10}$ aryl or heteroaryl group consisting of 5 to 10 ring atoms, wherein each of $C_{1-6}$ alkyl, $C_{3-7}$ cycloalkyl, heterocyclyl consisting of 3 to 6 ring atoms, $C_{6-10}$ aryl and heteroaryl group consisting of 5 to 10 ring atoms is independently unsubstituted or substituted by 1, 2, 3, or 4 $R^j$;

each $R^j$ and $R^g$ is independently deuterium, F, Cl, Br, CN, =O, HO—, HOOC—, $R^{11}O—$, $R^{12}—S(=O)_2—$, $R^{13}—(C=O)—$, $R^{14}13\ S(=O)_2—O—$, $R^{15}13\ S(=O)_2—N(R^c)—$, $R^{16}—N(R^c)—S(=O)_2—$, $R^{17}—(C=O)—N(R^c)—S(=O)_2—$, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, $C_{3-7}$ cycloalkyl, heterocyclyl consisting of 3 to 10 ring atoms, $C_{6-10}$ aryl or heteroaryl group consisting of 5 to 10 ring atoms, wherein each of amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, $C_{3-7}$ cycloalkyl, heterocyclyl consisting of 3 to 10 ring atoms, $C_{6-10}$ aryl and heteroaryl group consisting of 5 to 10 ring atoms is independently unsubstituted or substituted by 1, 2, 3 or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN—$, $C_{1-6}$ alkyl, $C_{2-6}$ alkynyl, $C_{3-6}$ cycloalkyl, heterocyclyl consisting of 3 to 6 ring atoms, $C_{6-10}$ aryl, $C_{6-10}$ aryl $C_{1-3}$ alkylene or heteroaryl group consisting of 5 to 10 ring atoms, wherein each of $C_{1-6}$ alkyl, $C_{2-6}$ alkynyl, $C_{3-6}$ cycloalkyl, heterocyclyl consisting of 3 to 6 ring atoms, $C_{6-10}$ aryl, $C_{6-10}$ aryl $C_{1-3}$ alkylene and heteroaryl group consisting of 5 to 10 ring atoms is independently unsubstituted or substituted by 1, 2, 3 or 4 substituents selected from F, Cl, Br, CN, HO—, =O, HOOC—, $R^aR^bN$—S(=O)$_2$—, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-6}$ alkylamino, $C_{2-6}$ alkenyl, $C_{2-6}$ alkynyl, $C_{6-10}$ aryl, $C_{3-7}$ cycloalkyl, heteroaryl group consisting of 5 to 6 ring atoms, heterocyclyl of 3 to 6 ring atoms, $C_{1-6}$ alkoxy $C_{1-4}$ alkylene or $C_{1-4}$ alkylamino $C_{1-4}$ alkylene;

each $R^w$ is independently deuterium, F, Cl, Br, HO—, HOOC—, =O, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, tert-butoxycarbonyl (($CH_3)_3$C—O—C(=O)—), $C_{1-6}$ alkyl-S(=O)$_2$—, $C_{3-6}$ cycloalkyl-S(=O)$_2$— or $C_{3-7}$ cycloalkyl, wherein each of amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, tert-butoxycarbonyl (($CH_3)_3$C—O—C(=O)—), $C_{1-6}$ alkyl-S(=O)$_2$—, $C_{3-6}$ cycloalkyl-S(=O)$_2$— and $C_{3-7}$ cycloalkyl is independently unsubstituted or substituted by 1, 2, 3 or 4 substituents selected from F, Cl, Br, CN, OH, =O, amino, $C_{1-6}$ alkyl, $C_{1-6}$ haloalkyl, $C_{1-6}$ alkoxy, $C_{1-6}$ alkylthio, $C_{1-6}$ haloalkoxy or $C_{1-6}$ alkylamino;

each of $R^4$, $R^5$, $R^6$, $R^7$, $R^8$ and $R^9$ is independently hydrogen, deuterium, F, Cl, Br, $R^{12a}13$ S(=O)$_2$—, $R^{13a}$—(C=O)—, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl, heteroaryl group consisting of 5 to 6 ring atoms or heterocyclyl consisting of 3 to 10 ring atoms, wherein each of $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl, heteroaryl group consisting of 5 to 6 ring atoms and heterocyclyl consisting of 3 to 10 ring atoms is independently unsubstituted or substituted by 1, 2, 3, or 4 $R^w$;

or $R^6$ and $R^4$, together with the atom to which they are attached, form a carbocyclyl consisting of 5 to 6 ring atoms or a heterocyclyl consisting of 5 to 6 ring atoms, wherein each of carbocyclyl consisting of 5 to 6 ring atoms and heterocyclyl consisting of 5 to 6 ring atoms is independently unsubstituted or substituted by 1, 2, 3, or 4 $R^w$;

each $R^2$ is independently hydrogen, deuterium, F, Cl, Br, =O, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl or heterocyclyl consisting of 3 to 6 ring atoms, wherein each of $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl and heterocyclyl consisting of 3 to 6 ring atoms is independently unsubstituted or substituted by 1, 2, 3, or 4 $R^w$;

or two $R^2$ linked to the same carbon atom, together with the carbon atom to which they are attached, form a $C_{3-6}$ cycloalkyl or —(C=O)—, wherein $C_{3-6}$ cycloalkyl is unsubstituted or substituted by 1, 2, 3, or 4 $R^w$;

each $R^{1a}$, $R^a$, $R^b$ and $R^c$ is independently hydrogen, deuterium, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, heterocyclyl consisting of 3 to 6 ring atoms or heteroaryl consisting of 5 to 10 ring atoms, wherein each of $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, heterocyclyl consisting of 3 to 6 ring atoms and heteroaryl consisting of 5 to 10 ring atoms is independently unsubstituted or substituted by 1, 2, 3, or 4 substituents selected from F, Cl, Br, CN, HO—, amino, $C_{1-6}$ alkyl, $C_{1-6}$ haloalkyl, $C_{1-6}$ alkoxy or $C_{1-6}$ alkylamino;

n is 0, 1, 2, 3, 4, or 5.

In some embodiments, provided herein is a compound having Formula (II):

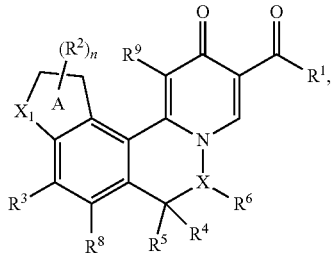

(II)

wherein $X_1$ is —O—, —NH—, —S—, —$CH_2$—O—, —$CH_2$—NH—, —$CH_2$—S—, —$CH_2$— or —$CH_2$—$CH_2$—;

wherein each of $R^1$, $R^2$, $R^3$, $R^4$, $R^5$, $R^6$, $R^8$, $R^9$, X and n is as defined herein.

In some embodiments, $R^3$ described herein is hydrogen, deuterium, F, Cl, Br, hydroxy, cyano, $C_{1-4}$ alkyl, $C_{2-4}$ alkynyl, $C_{3-6}$ cycloalkyl, heterocyclyl consisting of 3 to 6 ring atoms, phenyl, heteroaryl group consisting of 5 ring atoms, heteroaryl group consisting of 6 ring atoms or $R^{10}$—$C_{0-3}$alkylene-O—, wherein each of $C_{1-4}$ alkyl, $C_{2-4}$ alkynyl, $C_{3-6}$ cycloalkyl, heterocyclyl consisting of 3 to 6 ring atoms, phenyl, heteroaryl group consisting of 5 ring atoms, heteroaryl group consisting of 6 ring atoms and —$C_{0-3}$alkylene of $R^{10}$—$C_{0-3}$alkylene-O— is independently unsubstituted or substituted by 1, 2, 3 or 4 $R^g$;

$R^{10}$ is deuterium, $R^{11}$O—, $C_{1-4}$ alkyl, $C_{3-6}$ cycloalkyl, heterocyclyl consisting of 3 to 6 ring atoms, phenyl, heteroaryl group consisting of 5 ring atoms or heteroaryl group consisting of 6 ring atoms, wherein each of $C_{1-4}$ alkyl, $C_{3-6}$ cycloalkyl, heterocyclyl consisting of 3 to 6 ring atoms, phenyl, heteroaryl group consisting of 5 ring atoms and heteroaryl group consisting of 6 ring atoms is independently unsubstituted or substituted by 1, 2, 3, or 4 $R^j$;

wherein each $R^{11}$, $R^g$ and $R^j$ is as defined herein.

In some embodiments, $R^3$ described herein is hydrogen, deuterium, F, Cl, Br, hydroxy, cyano, methyl, ethyl, n-propyl isopropyl, n-butyl, isobutyl, sec-butyl, tert-butyl, ethynyl, propargyl, propynyl, but-1-yne-4-yl, but-2-yne-1-yl, but-1-yne-1-yl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $R^{10}$—O—, $R^{10}$—$CH_2$—O—, $R^{10}$—($CH_2)_2$—O— or $R^{10}$—($CH_2)_3$—O—, wherein each of methyl, ethyl, n-propyl, isopropyl, n-butyl, isobutyl, sec-butyl, tert-butyl, ethynyl, propargyl, propynyl, but-1-yne-4-yl, but-2-yne-1-yl, but-1-yne-1-yl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, —$CH_2$— of $R^{10}$—$CH_2$—O—, —($CH_2)_2$— of $R^{10}$—($CH_2)_2$—O— and —($CH_2)_3$— of $R^{10}$—($CH_2)_3$—O— is independently unsubstituted or substituted by 1, 2, 3 or 4 $R^g$;

$R^{10}$ is deuterium, $R^{11}$O—, methyl, ethyl, n-propyl, isopropyl, n-butyl, isobutyl, sec-butyl, tert-butyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, butyl, tert-butyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 $R^j$;

wherein each $R^{11}$, $R^g$ and $R^j$ is as defined herein.

In some embodiments, each $R^j$ and $R^g$ described herein is independently deuterium, F, Cl, Br, CN, =O, HO—, HOOC—, $R^{11}$O—, $R^{12}$—S(=O)$_2$—, $R^{13}$—(C=O)—, $R^{14}$13 S(=O)$_2$—O—, $R^{15}$13 S(=O)$_2$—N($R^c$)—, $R^{16}$—N($R^c$)—S(=O)$_2$—, $R^{17}$—(C=O)—N($R^c$)—S(=O)$_2$—, amino, $C_{1-4}$ alkyl, $C_{1-4}$ alkoxy, alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, heteroaryl group consisting of 5 ring atoms or heteroaryl group consisting of 6 ring atoms, wherein each of amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, heteroaryl group consisting of 5 ring atoms and heteroaryl group consisting of 6 ring atoms is independently unsubstituted or substituted by 1, 2, 3 or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, alkyl, $C_{2-4}$ alkynyl, $C_{3-6}$ cycloalkyl, heterocyclyl consisting of 3 to 6 ring atoms, phenyl, phenyl $C_{1-2}$ alkylene, heteroaryl group consisting of 5 ring atoms or heteroaryl group consisting of 6 ring atoms, wherein each of $C_{1-4}$ alkyl, $C_{2-4}$ alkynyl, $C_{3-6}$ cycloalkyl, heterocyclyl consisting of 3 to 6 ring atoms, phenyl, phenyl $C_{1-2}$ alkylene, heteroaryl group consisting of 5 ring atoms and heteroaryl group consisting of 6 ring atoms is independently unsubstituted or substituted by 1, 2, 3 or 4 substituents selected from F, Cl, Br, CN, HO—, =O, HOOC—, $R^aR^bN$—S(=O)$_2$—, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, phenyl, $C_{3-6}$ cycloalkyl, heteroaryl group consisting of 5 ring atoms, heteroaryl group consisting of 6 ring atoms, heterocyclyl of 3 to 6 ring atoms, $C_{1-4}$ alkoxy $C_{1-3}$ alkylene or $C_{1-4}$ alkylamino $C_{1-3}$ alkylene;

wherein, each $R^a$, $R^b$, $R^c$ and $R^w$ has the meaning described in the present invention.

In some embodiments, each $R^j$ and $R^g$ described herein is independently deuterium, F, Cl, Br, CN, =O, HO—, HOOC—, $R^{11}$O—, $R^{12}$—S(=O)$_2$—, $R^{13}$—(C=O)—, $R^{14}$13 S(=O)$_2$—O—, $R^{15}$13 S(=O)$_2$—N($R^c$)—, $R^{16}$—N($R^c$)—S(=O)$_2$—, $R^{17}$—(C=O)—N($R^c$)—S(=O)$_2$—, amino, methyl, ethyl, n-propyl, isopropyl, n-butyl, isobutyl, sec-butyl, tert-butyl, methoxy, ethoxy, 1-propoxy, 2-propoxy, 1-butoxy, 2-methyl-1-propoxy, 2-butoxy, $C_{1-3}$ alkylthio, $C_{1-3}$ alkylamino, $C_{2-4}$ alkenyl, $C_{2-4}$ alkynyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of amino, methyl, ethyl, n-propyl, isopropyl, n-butyl, isobutyl, sec-butyl, tert-butyl, methoxy, ethoxy, 1-propoxy, 2-propoxy, 1-butoxy, 2-methyl-1-propoxy, 2-butoxy, $C_{1-3}$ alkylthio, $C_{1-3}$ alkylamino, $C_{2-4}$ alkenyl, $C_{2-4}$ alkynyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, methyl, ethyl, n-propyl, isopropyl, n-butyl, isobutyl, sec-butyl, tert-butyl, $C_{2-4}$ alkynyl, cyclopropyl, cyclobutyl, cyclopentyl, cyclohexyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, phenyl $C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, sec-butyl, tert-butyl, $C_{2-4}$ alkynyl, cyclopropyl, cyclobutyl, cyclopentyl, cyclohexyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, phenyl $C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 substituents selected from F, Cl, Br, CN, HO—, =O, HOOC—, $R^aR^bN$—S(=O)$_2$—, amino, $C_{1-3}$ alkyl, $C_{1-3}$ haloalkyl, $C_{1-3}$ alkoxy, $C_{1-3}$ alkylthio, $C_{1-3}$ haloalkoxy, $C_{1-3}$ alkylamino, $C_{2-4}$ alkenyl, $C_{2-4}$ alkynyl, phenyl, $C_{3-6}$ cycloalkyl, heteroaryl group consisting of 5 ring atoms, heteroaryl group consisting of 6 ring atoms, heterocyclyl consisting of 3 to 6 ring atoms, $C_{1-3}$ alkoxy $C_{1-2}$ alkylene or $C_{1-3}$ alkylamino $C_{1-2}$ alkylene;

wherein, each $R^a$, $R^b$, $R^c$ and $R^w$ has the meaning described in the present invention.

In some embodiments, each $R^w$ described herein is independently deuterium, F, Cl, Br, HO—, HOOC—, =O, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, tert-butoxycarbonyl (($CH_3$)$_3$C—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$— or $C_{3-6}$ cycloalkyl, wherein each of amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, tert-butoxycarbonyl (($CH_3$)$_3$C—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$— and $C_{3-6}$ cycloalkyl is independently unsubstituted or substituted by 1, 2, 3 or 4 substituents selected from F, Cl, Br, CN, OH, =O, amino, $C_{1-4}$ alkyl, $C_{1-4}$ haloalkyl, $C_{1-4}$ alkoxy, $C_{1-4}$ haloalkoxy or $C_{1-4}$ alkylamino;

each of $R^4$, $R^5$, $R^6$, $R^7$, $R^8$ and $R^9$ is independently hydrogen, deuterium, F, Cl, Br, $R^{12a}$13 S(=O)$_2$—, $R^{13a}$—

(C=O)—, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{1-4}$ alkenyl, $C_{3-6}$ cycloalkyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl and heterocyclyl consisting of 3 to 6 ring atoms is independently unsubstituted or substituted by 1, 2, 3, or 4 $R^w$;

or $R^6$ and $R^4$, together with the atom to which they are attached, form cyclopentyl, cyclohexyl, pyrrolidinyl, pyrazolidinyl, imidazolidinyl, piperidinyl, morpholinyl, thiomorpholinyl or piperazinyl, wherein each of cyclopentyl, cyclohexyl, pyrrolidinyl, pyrazolidinyl, imidazolidinyl, piperidinyl, morpholinyl, thiomorpholinyl and piperazinyl is independently unsubstituted or substituted by 1, 2, 3, or 4 $R^w$;

wherein each $R^{12a}$, $R^{13a}$ and $R^w$ is as defined herein.

In some embodiments, each $R^w$ described herein is independently deuterium, F, Cl, Br, HO—, HOOC—, =O, amino, methyl, ethyl, n-propyl, isopropyl, n-butyl, isobutyl, sec-butyl, tert-butyl, $C_{1-4}$ alkoxy, $C_{1-4}$ alkylthio, $C_{1-4}$ alkylamino, $C_{2-4}$ alkenyl, ethynyl, propargyl, propynyl, but-1-yne-4-yl, but-2-yne-1-yl, but-1-yne-1-yl, tert-butoxycarbonyl (($CH_3)_3C$—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$—, cyclopropyl, cyclobutyl, cyclopentyl or cyclohexyl, wherein each of amino, methyl, ethyl, n-propyl, isopropyl, n-butyl, isobutyl, sec-butyl, tert-butyl, $C_{1-4}$ alkoxy, $C_{1-4}$ alkylthio, $C_{1-4}$ alkylamino, $C_{2-4}$ alkenyl, ethynyl, propargyl, propynyl, but-1-yne-4-yl, but-2-yne-1-yl, but-1-yne-1-yl, tert-butoxycarbonyl (($CH_3)_3C$—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$—, cyclopropyl, cyclobutyl, cyclopentyl and cyclohexyl is independently unsubstituted or substituted by 1, 2, 3 or 4 substituents selected from F, Cl, Br, CN, OH, =O, amino, $C_{1-4}$ alkyl, $C_{1-4}$ haloalkyl, $C_{1-4}$ alkoxy, $C_{1-4}$ alkylthio, $C_{1-4}$ haloalkoxy or $C_{1-4}$ alkylamino;

each of $R^4$, $R^5$, $R^6$, $R^7$, $R^8$ and $R^9$ is independently hydrogen, deuterium, F, Cl, Br, $R^{12a}$13 S(=O)$_2$—, $R^{13a}$—(C=O)—, methyl, ethyl, n-propyl, isopropyl, n-butyl, isobutyl, sec-butyl, tert-butyl, $C_{1-4}$ alkylamino, $C_{1-4}$ alkoxy, ethynyl, propargyl, propynyl, but-1-yne-4-yl, but-2-yne-1-yl, but-1-yne-1-yl, $C_{2-4}$ alkenyl, cyclopropyl, cyclobutyl, cyclopentyl, cyclohexyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl, wherein each of methyl, ethyl, n-propyl, isopropyl, n-butyl, isobutyl, sec-butyl, tert-butyl, $C_{1-4}$ alkylamino, $C_{1-4}$ alkoxy, ethynyl, propargyl, propynyl, but-1-yne-4-yl, but-2-yne-1-yl, but-1-yne-1-yl, $C_{1-4}$ alkenyl, cyclopropyl, cyclobutyl, cyclopentyl, cyclohexyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl and piperazinyl is independently unsubstituted or substituted by 1, 2, 3, or 4 $R^w$;

or $R^6$ and $R^4$, together with the atom to which they are attached, form cyclopentyl, cyclohexyl, pyrrolidinyl, pyrazolidinyl, imidazolidinyl, piperidinyl, morpholinyl, thiomorpholinyl or piperazinyl, wherein each of cyclopentyl, cyclohexyl, pyrrolidinyl, pyrazolidinyl, imidazolidinyl, piperidinyl, morpholinyl, thiomorpholinyl and piperazinyl is independently unsubstituted or substituted by 1, 2, 3, or 4 $R^w$;

wherein each $R^{12a}$, $R^{13a}$ and $R^w$ is as defined herein.

In some embodiments, each $R^2$ described herein is independently hydrogen, deuterium, F, Cl, Br, =O, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl or heterocyclyl consisting of 3 to 6 ring atoms, wherein each of methyl, ethyl, n-propyl, isopropyl, n-butyl, isobutyl, sec-butyl, tert-butyl, alkylamino, $C_{1-4}$ alkoxy, $C_{2-4}$ alkynyl, $C_{2-4}$ alkenyl, $C_{3-6}$ cycloalkyl, phenyl and heterocyclyl consisting of 3 to 6 ring atoms is independently unsubstituted or substituted by 1, 2, 3, or 4 $R^w$;

or two $R^2$ linked to the same carbon atom, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted by 1, 2, 3, or 4 $R^w$;

each $R^{1a}$, $R^a$, $R^b$ and $R^c$ is independently hydrogen, deuterium, methyl, ethyl, n-propyl, isopropyl, n-butyl, isobutyl, sec-butyl, tert-butyl, $C_{1-4}$ alkoxy, $C_{2-4}$ alkenyl, $C_{2-4}$ alkynyl, $C_{3-6}$ cycloalkyl, phenyl, heterocyclyl consisting of 3 to 6 ring atoms, heteroaryl group consisting of 5 ring atoms or heteroaryl group consisting of 6 ring atoms, wherein each of methyl, ethyl, n-propyl, isopropyl, n-butyl, isobutyl, sec-butyl, tert-butyl, $C_{1-4}$ alkoxy, $C_{2-4}$ alkenyl, $C_{2-4}$ alkynyl, $C_{3-6}$ cycloalkyl, phenyl, heterocyclyl consisting of 3 to 6 ring atoms, heteroaryl group consisting of 5 ring atoms and heteroaryl group consisting of 6 ring atoms is independently unsubstituted or substituted by 1, 2, 3, or 4 substituents selected from F, Cl, Br, CN, HO—, amino, $C_{1-4}$ alkyl, $C_{1-4}$ haloalkyl, $C_{1-4}$ alkoxy or $C_{1-4}$ alkylamino;

wherein each $R^w$ is as defined herein.

In some embodiments, provided herein is a compound having Formula (III):

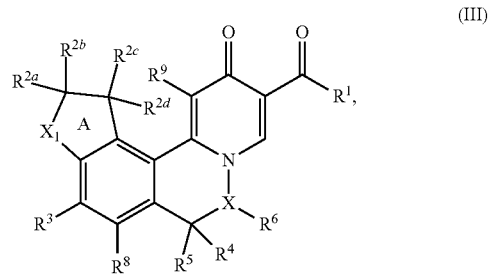

(III)

wherein $X_1$ is —O—, —NH—, —S—, —CH$_2$—O—, —O—CH$_2$—, —CH$_2$— or —CH$_2$—CH$_2$—;

each of $R^{2a}$, $R^{2b}$, $R^{2c}$ and $R^{2d}$ is independently hydrogen, deuterium, F, Cl, Br, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl and heterocyclyl consisting of 3 to 6 ring atoms is independently unsubstituted or substituted by 1, 2, 3 or 4 $R^w$;

or $R^{2a}$ and $R^{2b}$, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted with 1, 2, 3 or 4 $R^w$;

or $R^{2c}$ and $R^{2d}$, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted with 1, 2, 3 or 4 $R^w$;

wherein each of $R^1$, $R^3$, $R^4$, $R^5$, $R^6$, $R^8$, $R^9$ and X is as defined herein.

In other aspect, the invention also provides a pharmaceutical composition comprising a compound of the invention, optionally, wherein the pharmaceutical composition further comprises a pharmaceutically acceptable excipient or a combination of said excipients.

In some embodiments, the pharmaceutical compositions of the present invention further comprise other anti-HBV drugs.

In some embodiments, the pharmaceutical compositions of the present invention, wherein other anti-HBV drugs is HBV polymerase inhibitors, immunomodulators or interferons.

In some embodiments, the pharmaceutical compositions of the present invention, wherein other anti-HBV drugs are lamivudine, telbivudine, tenofovir, entecavir, adefovir dipivoxil, Alfaferone, Alloferon, celmoleukin, clafidine, emtricitabine, faciclovir, interferon, Baoganling CP, intepropen, interferon α-1b, interferon α, interferon α-2α, interferon β-1a, interferon α-2, interleukin-2, mivotate, nalozolidine, peginterferon α-2α, ribavirin, interferon-A, cilostaz, Euforavac, aplori, Phosphazid, Heplisav, interferon α-2b, levamisole or propafen.

In other aspect, provided herein is use of the compound or the pharmaceutical composition in the present invention in the manufacture of a medicament for preventing, treating or reducing viral disease in a subject.

In some embodiments, wherein the viral disease is hepatitis B virus infection or a disease caused by hepatitis B vims infection.

In other embodiments, wherein the disease caused by hepatitis B virus infection is cirrhosis or hepatocellular carcinoma.

In other aspect, provided herein is use of the compound or the pharmaceutical composition in the present invention in the manufacture of a medicament for inhibiting the formation or secretion of HBsAg, and/or inhibiting the formation of HBV DNA.

In other aspect, provided herein is the compound or the pharmaceutical composition in the present invention for use in preventing, treating or reducing viral disease in a subject.

In some embodiments, wherein the viral disease is hepatitis B virus infection or a disease caused by hepatitis B vims infection.

In other embodiments, wherein the disease caused by hepatitis B virus infection is cirrhosis or hepatocellular carcinoma.

In other aspect, provided herein is the compound or the pharmaceutical composition in the present invention for use in inhibiting the formation or secretion of HBs Ag, and/or inhibiting the formation of HBV DNA.

In other aspect, provided herein is a method for preventing, treating or reducing viral disease in a subject, comprising administering a therapeutically effective amount of the compound or the pharmaceutical composition in the present invention to the subject.

In some embodiments, wherein the viral disease is hepatitis B virus infection or a disease caused by hepatitis B vims infection.

In other embodiments, wherein the disease caused by hepatitis B virus infection is cirrhosis or hepatocellular carcinoma.

In other aspect, provided herein is a method for inhibiting the formation or secretion of HBsAg, and/or inhibiting the formation of HBV DNA, comprising administering a therapeutically effective amount of the compound or the pharmaceutical composition in the present invention to the subject.

In other aspect, provided herein is use of the compound or the pharmaceutical composition in the present invention in the manufacture of a medicament for preventing, treating or reducing hepatitis B disease inpatients.

Another aspect of the invention relates to a method of preventing, treating or ameliorating a patient's HBV illness, wherein the method comprises administering to a patient a pharmaceutically acceptable effective amount of the compound of the invention.

Another aspect of the invention relates to a method of preventing, treating or ameliorating a patient's HBV illness, wherein the method comprises administering to a patient a pharmaceutically acceptable effective amount of the pharmaceutical composition containing the compound of the present invention.

In other aspect, provided herein is use of the compound in the present invention in the manufacture of a medicament for preventing, managing or treating HBV illness in a patient, and lessening the severity thereof.

In other aspect, provided herein is use of the pharmaceutical composition containing the compound in the present invention in the manufacture of a medicament for preventing or treating HBV illness in a patient, and lessening the severity thereof.

Another aspect of the invention relates to a method of inhibiting HBV infection, wherein the method comprises contacting a cell with a compound or composition of the invention at a dose effective to inhibit HBV. In other embodiments, the method further comprises contacting the cells with other anti-HBV agents.

Another aspect of the invention relates to a method of treating a patient with HBV disease, wherein the method comprises administering to the patient a therapeutically effective amount of a compound of the invention or a composition thereof. In other embodiments, the method further comprises administering another HBV treatment.

Another aspect of the invention relates to a method of inhibiting HBV infection in a patient, wherein the method comprises administering to the patient a therapeutically effective amount of a compound of the invention or a composition thereof. In other embodiments, the method further comprises administering another HBV treatment.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

The present invention will list the documents corresponding to the specific content of the determination, and the examples are accompanied by the diagrams of the structural formula and the chemical formula. The present invention is intended to cover all alternatives, modifications, and equivalents, which may be included in the field of the invention as defined by the appended claims. Those skilled in the art will recognize many methods and materials that are similar or equivalent to those described herein, which can be used in the practice of the present invention. The invention is in no way limited to the description of methods and substances. There are many documents and similar substances that differ or contradict the application of the present invention, including but not limited to the definition of terms, the usage of terms, the techniques described, or the scope as controlled by the present application.

The invention will apply the following definitions unless otherwise indicated. For the purposes of the present invention, chemical elements are defined in accordance with the Periodic Table of the Elements, CAS version and Handbook of Chemicals, 75, $^{th}$Ed, 1994. Additionally, the general principles of organic chemistry are described in "Organic Chemistry," Thomas Sorrell, University Science Books, Sausalito: 1999, and "March's Advanced Organic Chemistry," by Michael B. Smith and Jerry March, John Wiley & Sons, New York: 2007, so all the content is a fusion of references.

As described herein, the compounds disclosed herein may optionally be substituted with one or more substituents, such as are illustrated generally below, or as exemplified by particular classes, subclasses, and species of the invention. In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

The term "alkyl" or "alkyl group" refers to a saturated linear or branched chain monovalent hydrocarbyl of 1 to 20 carbon atoms, wherein the alkyl may be optionally and independently substituted with one or more substituents described herein. In some embodiments, the alkyl group contains 1-12 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms. Further examples of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —CH($CH_3$)$_2$), n-butyl (n-Bu, —$CH_2CH_2CH_2CH_3$), 2-methylpropyl or isobutyl (i-Bu, —$CH_2CH(CH_3)_2$), 1-methylpropyl or sec-butyl (s-Bu, —CH($CH_3$)$CH_2CH_3$), tert-butyl (i-Bu, —C($CH_3$)$_3$), n-pentyl (—$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$), 3,3-dimethyl-butyl (—$CH_2CH_2C(CH_3)_3$), n-heptyl, n-octyl, etc.

The term "haloalkyl" refers to an alkyl group substituted with one or more halogen atoms, wherein the alkyl is as defined herein. In some embodiments, the haloalkyl group contains 1-12 carbon atoms. In other embodiments, the haloalkyl group contains 1-10 carbon atoms. In other embodiments, the haloalkyl group contains 1-8 carbon atoms. In still other embodiments, the haloalkyl group contains 1-6 carbon atoms. In yet other embodiments, the haloalkyl group contains 1-4 carbon atoms and in still yet other embodiments, the haloalkyl group contains 1-3 carbon atoms. Such examples include, but are not limited to, trifluoromethyl, trifluoroethyl, etc.

The term "carboxy" or "carboxyl", whether used alone or with other terms (e.g., "carboxyalkyl"), refers to —$CO_2H$ or —COOH.

The term "carbonyl", whether used alone or with other terms (e.g., "aminocarbonyl" or "acyloxy"), refers to —(C═O)—.

The terms "alkylamino" and "alkamino" are used interchangeably, including "N-alkylamino" and "N,N-dialkylamino", wherein the amino groups are independently substituted with one or two $C_{1-12}$ alkyl, respectively. In some embodiments, the alkylamino radical is "lower alkylamino" radical having one or two $C_{1-12}$ alkyl groups attached to a nitrogen atom. In other embodiments, the alkylamino radical refers to $C_{1-6}$ lower alkylamino group. In still other embodiments, the alkylamino radical refers to $C_{1-4}$ lower alkylamino group. Some non-limiting examples of the alkylamino group include monoalkylamino or dialkylamino such as N-methylamino, N-ethylamino, N,N-dimethylamino, N,N-diethylamino, N-propylamino, N, N-dipropylamino, and the like, wherein the alkylamino group may be independently unsubstituted or substituted by one or more substituents described herein.

The term "alkylene" refers to a saturated divalent hydrocarbyl group derived from a straight or branched chain saturated hydrocarbyl by the removal of two hydrogen atoms. Unless otherwise specified, the alkylene group contains 1-12 carbon atoms. In other embodiments, the alkylene group contains 1-6 carbon atoms. In other embodiments, the alkylene group contains 1-4 carbon atoms. In still other embodiments, the alkylene group contains 1-3 carbon atoms. In other embodiments, the alkylene group contains 1-2 carbon atoms. Such examples include methylene (—CH$_2$—), ethylene (—CH$_2$CH$_2$—), propylene (—CH$_2$CH$_2$CH$_2$—), isopropylidene (—CH(CH$_3$)CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), heptylene (—CH$_2$CH$_2$CH$_2$CH$_2$CH$_2$CH$_2$CH$_2$—), octylene (—CH$_2$CH$_2$CH$_2$CH$_2$CH$_2$CH$_2$CH$_2$CH$_2$—), etc, wherein the alkylene group may be independently unsubstituted or substituted by one or more substituents described herein.

The term "alkenyl" refers to a straight or branched chain monovalent hydrocarbyl containing 2-12 carbon atoms, or 2-8 carbon atoms, or 2-6 carbon atoms, or 2-4 carbon atoms, wherein at least one position of C—C is sp double bond, wherein the alkenyl group may be independently unsubstituted or substituted by one or more substituents described herein, including "Cis", "Trans" or "Z", isomers, wherein specific examples include, but are not limited to, vinyl (—CH=CH$_2$), propylene (—CH=CHCH$_3$), allyl (—CH$_2$CH=CH$_2$), etc, wherein the alkenyl group may be independently unsubstituted or substituted by one or more substituents described herein.

The term "alkynyl" refers to a straight or branched chain monovalent hydrocarbyl radical containing 2-12 carbon atoms, or 2-8 carbon atoms, or 2-6 carbon atoms, or 2-4 carbon atoms, wherein at least one position of C—C is sp triple bond, wherein the alkynyl group may be independently unsubstituted or substituted by one or more substituents described herein, specific examples include, but are not limited to, ethynyl (—C≡CH), propargyl (—CH$_2$C≡CH), propynyl (—C≡C—CH$_3$), but-1-yne-4-yl (—CH$_2$CH$_2$C≡CH), but-2-yne-1-yl (—CH$_2$C≡CCH$_3$), but-1-yne-1-yl (—C≡CCH$_2$CH$_3$), etc, wherein the alkynyl group may be independently unsubstituted or substituted by one or more substituents described herein.

The term "alkoxy" refers to an alkyl group, as previously defined, attached to the parent molecular moiety via an oxygen atom. Unless otherwise specified, the alkoxy group contains 1-20 carbon atoms. In some embodiments, the alkoxy group contains 1-12 carbon atoms. In other embodiments, the alkoxy group contains 1-8 carbon atoms. In still other embodiments, the alkoxy group contains 1-6 carbon atoms. In yet other embodiments, the alkoxy group contains 1-4 carbon atoms. In still yet other embodiments, the alkoxy group contains 1-3 carbon atoms.

Examples of the alkoxy group include, but are not limited to, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (z-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (z-BuO, z-butoxy, —OCH$_2$CH(CH$_3$)$_2$), 2-butoxy (s-BuO, s-butoxy, —OCH(CH$_3$)CH$_2$CH$_3$), 2-methyl-2-propoxy (Z-BuO, z-butoxy, —OC(CH$_3$)$_3$), 1-pentyloxy (n-pentyloxy, —OCH$_2$CH$_2$CH$_2$CH$_2$CH$_3$), 2-pentyloxy (—OCH(CH$_3$)CH$_2$CH$_2$CH$_3$), 3-pentyloxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), etc, wherein the alkoxy group may be independently unsubstituted or substituted by one or more substituents described herein.

The term "haloalkoxy" refers to an alkoxy group substituted with one or more halogen atoms, wherein the alkoxy is as defined herein. In some embodiments, the haloalkoxy group contains 1-12 carbon atoms. In other embodiments, the haloalkoxy group contains 1-10 carbon atoms. In other embodiments, the haloalkoxy group contains 1-8 carbon atoms. In still other embodiments, the haloalkoxy group contains 1-6 carbon atoms. In yet other embodiments, the haloalkoxy group contains 1-4 carbon atoms and in still yet other embodiments, the haloalkoxy group contains 1-3 carbon atoms. Such examples include, but are not limited to, trifluoromethyl, etc.

The terms "carbocycle" and "carbocyclyl" as used interchangeably herein refer to a non-aromatic carbon ring system which is saturated or contains one or more units of unsaturation and contains 3-14 carbon ring atoms. In some embodiments, the number of carbon atoms is 3-12; in other embodiments, the number of carbon atoms is 3-10; in other embodiments, the number of carbon atoms is 3-8; in other embodiments, the number of carbon atoms is 3-6; in other embodiments, the number of carbon atoms is 5-6; in other embodiments, the number of carbon atoms is 5-8. In other embodiments, the number of carbon atoms is 6-8; In other embodiments, the number of carbon atoms is 5; In other embodiments, the number of carbon atoms is 6. The "carbocyclyl" includes monocyclic, bicyclic or polycyclic fused, spiro or bridged carbocyclic ring systems, and also includes a polycyclic ring system in which a carbocyclic ring may be fused to one or more non-aromatic carbocyclic or heterocyclic rings or one or more aromatic rings or combinations thereof, wherein the attached atomic group or point is on the carbocyclic ring. The bicyclic carbocyclyl includes bridged bicyclic carbocyclyl, fused bicyclic carbocyclyl and spiro bicyclic carbocyclyl, and "fused" bicyclic ring system comprises two rings sharing two adjacent ring atoms. The bridged bicyclic group includes two rings sharing 3 or 4 adjacent ring atoms. The spiro ring system shares 1 ring atom. Some non-limiting examples of the carbocyclyl include cycloalkyl, cycloalkenyl and cycloalkynyl. Further non-limiting examples of the carbocyclyl include cyclopropyl, cyclobutyl, cyclopentyl, 1-cyclopentyl-1-enyl, l-cyclopentyl-2-enyl, 1-cyclopentyl-3-enyl, cyclohexyl, 1-cyclohexyl-1-enyl, 1-cyclohexyl-2-enyl, l-cyclohexyl-3-enyl, cyclohexadienyl, cycloheptyl, cyclooctyl, cyclononyl, cyclodecyl, cycloundecyl, cyclododecyl, and the like. Some non-limiting examples of the bridged carbocyclyl group include, but are not limited to, bicyclo[2,2,2]octyl, bicyclo[2,2,1]heptyl, bicyclo[3.3.1]nonyl, bicyclo[3,2,3]nonyl, etc.

The term "cycloalkyl" means a saturated mono-, bi- or tricyclic ring system consisting of 3-12 ring carbon atoms, in which one or more attachment points are attached to the remainder of the molecule. In some embodiments, cycloalkyl is a ring system containing 3-10 ring carbon atoms; in other embodiments, cycloalkyl is a ring system containing 3-8 ring carbon atoms; in other embodiments, cycloalkyl is a ring system containing 3-7 ring carbon atoms; in other embodiments, cycloalkyl is a ring system containing 5-8 ring carbon atoms; in other embodiments, cycloalkyl is a ring system containing 3-6 ring carbon atoms; in other embodiments, cycloalkyl is a ring system containing 5-6 ring carbon atoms; examples of the cycloalkyl group include, but are not limited to, cyclopropyl, cyclobutyl, cyclopentyl, cyclohexyl, etc, wherein the cycloalkyl group may be independently unsubstituted or substituted by one or more substituents described herein.

The terms "heterocyclyl" and "heterocycle" as used interchangeably herein refer to a saturated or partially saturated non-aromatic monocyclic, bicyclic or tricyclic ring system containing 3-12 ring atoms, wherein at least one ring atom is selected from nitrogen, sulfur and oxygen, and this ring system has one or more connection points connected to the rest of the molecule. The term "heterocyclyl" includes monocyclic, bicyclic or polycyclic fused, spiro or bridged heterocyclic ring systems, and also includes a polycyclic ring system in which a heterocyclic ring can be fused to one or more non-aromatic carbocyclic or heterocyclic rings or one or more aromatic rings or combinations thereof, wherein the attached atomic group or point is on the heterocyclic ring. The bicyclic heterocyclyl includes bridged bicyclic heterocyclyl, fused bicyclic heterocyclyl and spirobicyclic heterocyclyl. Unless otherwise specified, a —CH$_2$— group in the heterocyclyl can be optionally replaced by a —C(=O)— group. In which, the sulfur can be optionally oxygenized to S-oxide, and the nitrogen can be optionally oxygenized to N-oxide. In some embodiments, heterocyclyl is a ring system comprising 3-12 ring atoms; in other embodiments, heterocyclyl is a ring system comprising 3-8 ring atoms; in other embodiments, heterocyclyl is a ring system comprising 3-6 ring atoms; in other embodiments, heterocyclyl is a ring system comprising 5-7 ring atoms; in other embodiments, heterocyclyl is a ring system comprising 5-8 ring atoms; in other embodiments, heterocyclyl is a ring system comprising 6-8 ring atoms; in other embodiments, heterocyclyl is a ring system comprising 5-6 ring atoms; in other embodiments, heterocyclyl is a ring system comprising 3 ring atoms; in other embodiments, heterocyclyl is a ring system comprising 4 ring atoms; in other embodiments, heterocyclyl is a ring system comprising 5 ring atoms; in other embodiments, heterocyclyl is a ring system comprising 6 ring atoms; in other embodiments, heterocyclyl is a ring system comprising 7 ring atoms; in other embodiments, heterocyclyl is a ring system comprising 8 ring atoms.

Examples of the heterocycle include, but are not limited to, pyrrolidinyl, tetrahydrofuranyl, dihydrofuranyl, tetrahydrothiophenyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxiranyl, azepanyl, oxepanyl, thiepanyl, oxazepine, diazepine, thiazepine, 2-pyrrolinyl, 3-pyrrolinyl, dihydroindolyl, 2H-pyranyl, 4H-pyranyl, dioxanyl, 1,3-dioxopentyl, pyrazolinyl, dithiaalkyl, dithiolanyl, dihydrothienyl, pyrazolidinyl, imidazolinyl, imidazolidinyl, 1,2,3,4-tetrahydroisoquinolinyl, 3-azabicyclo[3.1.0] hexyl, 3-azabicyclo[4.1.0]heptyl, azabicyclo[2,2,2]hexyl, 3H-indolylquinazinyl and N-pyridyl urea. Examples of the heterocyclyl also include 1,1-dioxythiomorpholinyl; wherein non-limiting examples of the carbon atom on the ring replaced by the oxo (=O) group include pyrimidinedione, 1,2,4-thiadiazol-5(4H)-keto, 1,2,4-oxadiazol-5(4H)-keto, 1H-1,2,4-triazol-5(4H)-keto, etc; wherein examples of the ring carbon atom substituted with the =S group include, but are not limited to, 1,2,4-oxadiazol-5(4H)-thioketo, 1,3, 4-oxadiazol-2 (3H)-thioketo, etc. The heterocyclyl group may be optionally substituted with one or more substituents disclosed herein.

The term "consisting of M-M$_1$ ring atoms" means that the cyclic group consists of M-M1 ring atoms, wherein the ring atoms include carbon atoms and/or hetero atoms such as O, N, S, P, etc. For example, "heteroaryl consisting of 6-10 ring atoms" means a heteroaryl group is comprised of 6, 7, 8, 9 or 10 ring atoms.

The terms "heterocyclylalkylene" and "heterocyclylalkyl", as used interchangeably herein, means that the alkyl group is substituted with 1, 2, 3 or 4 heterocyclyls, wherein the heterocyclyl, alkyl and alkylene group have the meanings described herein. Some non-limiting examples of such group include pyrrole-2-methyl, morpholine-4-methyl, etc.

The term "heteroalkylene" means that the alkylene group is substituted with 1 or 2 heteroatoms, wherein the heteroatom is selected from O, S, N or P, wherein the heteroalkylene has the meanings described herein. Examples of the heteroalkylene group are —CH$_2$—O—CH$_2$—, —CH$_2$—NH—CH$_2$—, —CH$_2$—CH$_2$—NH—, etc.

The term "heterocyclylalkoxy" refers to that the alkoxy group is substituted with 1, 2, 3 or 4 heterocyclyls, wherein the heterocyclyl and alkoxy have the meanings described herein. Some non-limiting examples of such group include pyrrole-2-methoxy, piperidine-2-ethoxyl, etc.

The term "heterocyclylalkylamino" refers to heterocyclyl-substituted alkylamino, wherein the nitrogen atom is connected to the rest of the molecule; wherein the heterocyclyl and alkylamino are defined as the invention described herein. Examples of such group include, but are not limited to, piperazine-2-ethylamino, morpholine-4-ethylamino, and the like.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl, R represents a substituent described in the present invention).

The term "halogen" or "halogen atom" means F, Cl, Br or I.

The term "unsaturated" refers to a moiety having one or more units of unsaturation.

The term "aryl" used alone or as a substantial part of "aralkyl", "aralkyloxy" or "aryloxyalkyl", refers to monocyclic, bicyclic and tricyclic carbocyclic ring systems having a total of 6-14 carbon members, or 6-12 carbon members, or 6-10 carbon members, wherein at least one ring in the system is aromatic, wherein each ring in the system contains 3-7 carbon members and that has a single point or multipoint of attachment to the rest of the molecule. The term "aryl" may be used interchangeably with the term "aryl ring" or "aromatic ring". Some non-limiting examples of the aryl group include phenyl, naphthyl and anthracene. The aryl group may be independently unsubstituted or substituted with one or more substituents disclosed herein.

The term "heteroaryl" used alone or as a major part of "heteroarylalkyl" or "heteroarylalkoxy" refers to monocyclic, bicyclic and tricyclic carbocyclic ring systems having a total of 5-16 ring members, wherein at least one ring in the system is aromatic, and in which at least one ring member is selected from heteroatom, and wherein each ring in the system contains 5 to 7 ring members and that has a single point or multipoint of attachment to the rest of the molecule. The term "hetreroaryl" and "heteroaromatic ring" or "heteroaromatic compound" can be used interchangeably herein. In some embodiments, a 5-14 membered heteroaryl comprises 1, 2, 3 or 4 heteroatoms independently selected from O, S and N. In other embodiments, a 5-12 membered heteroaryl comprises 1, 2, 3 or 4 heteroatoms independently selected from O, S and N. In other embodiments, a 5-10 membered heteroaryl comprises 1, 2, 3 or 4 heteroatoms independently selected from O, S and N. In other embodiments, a 5-8 membered heteroaryl comprises 1, 2, 3 or 4 heteroatoms independently selected from O, S and N. In other embodiments, a 5-7 membered heteroaryl comprises 1, 2, 3 or 4 heteroatoms independently selected from O, S and N. In other embodiments, a 5-6 membered heteroaryl comprises 1, 2, 3 or 4 heteroatoms independently selected from O, S and N. In other embodiments, a 5 membered heteroaryl comprises 1, 2, 3 or 4 heteroatoms independently selected from O, S and N. In other embodiments, a 6 membered heteroaryl comprises 1, 2, 3 or 4 heteroatoms independently selected from O, S and N.

In other embodiments, heteroaryl groups include, but are not limited to the following monocyclic groups: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiodiazolyl, 1,3,4-thiadiazolyl, 1,2,5-thiadiazolyl, pyrazinyl, 1,3,5-triazinyl; heteroaryl groups also include, but are not limited to the following bis or tricyclic groups: benzimidazolyl, benzofuranyl, benzothienyl, indolyl (e.g., 2-indolyl), purinyl, quinolyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxathiinyl, dibenzimidazolyl, dibenzofuranyl or dibenzothiophene, etc. The heteroaryl group is optionally substituted with one or more substituents disclosed herein.

The terms "heteroarylalkyl" and "heteroarylalkylene" used interchangeably herein refer to the alkyl group substituted with one or more heteroaryl groups, wherein the alkylene group, alkyl group and heteroaryl group are as defined herein. Some non-limiting examples include pyridine-2-ethyl, thiazole-2-methyl, imidazole-2-ethyl, pyrimidine-2-propyl, and the like.

The term "sulfonyl", whether used alone or in conjunction with other term like "alkylsulfonyl", denotes a divalent group —SO$_2$—. The term "alkylsulfonyl" refers to an alkyl-substituted sulfonyl group which forms an alkylsulfonyl group (e.g., —SO$_2$CH$_3$).

The term "alkylthio" refers to a linear or branched C$_{1-12}$ alkyl chain binding to a bivalent sulphur atom, wherein the alkyl group is as defined herein. In some embodiments, alkylthio is a lower C$_{1-6}$ alkylthio group; in other embodiments, alkylthio is a lower C M alkylthio group; in other embodiments, alkylthio is a lower C$_{1-3}$ alkylthio group. Such examples include, but are not limited to methylthio (CH$_3$S—), ethylthio, etc.

The terms "aralkyl", "arylalkyl" and "arylalkylene" as used interchangeably herein denote the aryl-substituted alkyl group, wherein the alkylene group, aryl group and alkyl group have the meanings as described herein. In some embodiments, the arylalkyl group refers to a "lower aralkyl" radical having aryl radicals) attached to C$_{1-6}$ alkyl. In other embodiments, the arylalkyl radical refers to the aryl group attached to C$_{1-3}$ alkyl Some non-limiting examples of such radical include benzyl, diphenylmethyl, phenylethyl, and the like. The aralkyl group may be independently unsubstituted or substituted with one or more substituents disclosed herein.

The term "haloalkyl-substituted aryl" denotes an aryl group which may be substituted with one or more of the same or different haloalkyl groups; wherein haloalkyl and aryl groups have the meanings as described herein. Such examples include, but are not limited to, 2-trifluoromethylphenyl, 3,5-bis(trifluoromethyl)phenyl, 3-trifluoromethylphenyl, 4-trifluoromethylphenyl, 2,6-bis(trifluoromethyl) phenyl, etc.

The term "halogen-substituted aryl" denotes an aryl group which may be substituted with one or more of the same or different halogen atoms; wherein halogen atoms (halogen) and aryl group have the meanings as described herein. Such examples include, but are not limited to, fluorophenyl, difluorophenyl, trifluorophenyl, chlorophenyl, dichlorophenyl, trichlorophenyl, bromophenyl, tribromophenyl, dibromophenyl, fluorochlorophenyl, fluorobromophenyl, chlorobromophenyl, etc.

The terms "alkoxyalkylene" and "alkoxyalkyl" are used interchangeably herein to mean that the alkyl group is substituted with 1, 2, 3 or 4 alkoxy groups, wherein the alkoxy group, alkyl group and alkylene group have the meanings described herein. Such examples include, but are not limited to, methoxymethylene(CH$_3$OCH$_2$—), ethoxymethylene (CH$_3$CH$_2$OCH$_2$—), etc.

The terms "alkylaminoalkylene" and "alkylaminoalkyl" are used interchangeably herein to mean that the alkyl group is substituted with 1, or 2 alkylamino groups, wherein the alkylamino group, alkyl group and alkylene group have the meanings described herein. Such examples include, but are not limited to, N-methylaminomethylene(CH$_3$NHCH$_2$—), N-ethylaminomethylene(CH$_3$CH$_2$NHCH$_2$—), dimethylaminomethylene((CH$_3$)$_2$NCH$_2$—), etc.

As described herein, a bond drawn from a substituent (R$^2$)$_n$ to the center of one ring within a ring system represents substitution of n substituents R$^2$ at any substitutable position on the ring. For example, formula a represents that ring A can be optionally substituted with n R.

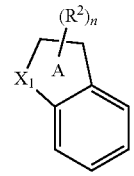

formula a

Unless otherwise stated, structures depicted herein are also meant to include all isomeric (e.g., enantiomeric, diastereomeric and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

An "N-oxide" means that when a compound contains several amine functions, one or more than one nitrogen atoms can be oxidized to form the N-oxide. Particular examples of the N-oxide are N-oxides of a tertiary amine or N-oxides of nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A. C. S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolites of a compound may be identified using routine techniques known in the art, and their activities can be determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore different stereoisomeric forms exist. It is intended that all stereo isomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (i.e., tautomers of proton transfer) include interconversions via migration of a proton, such as keto-enol and imine-enamine isomerizations. Valence tautomers include interconversions by reorganization of some of the bonding electrons.

The "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J.

Pharmaceutical Sciences, 66: 1-19, 1977, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid, perchloric acid, or with organic acids such as acetic acid, oxalic acid, maleic acid, tartaric acid, citric acid, succinic acid and malonic acid or by using other methods used in the art such as ion exchange. Other pharmaceutically acceptable salts include adipate, malate, 2-hydroxy propionate, alginate, ascorbate, aspartate, benzenesulfonate, benzoate, bisulfate, borate, butyrate, camphorate, camphorsulfonate, cyclopentyl propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethane-sulfonate, lactobionate, lactate, laurate, laurylsulfate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. If the compound disclosed herein is acidic, the desired salt may be prepared by a suitable method, for example, using an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$ aryl $C_{1-4}$alkyl, and the like; and cyclic amines, such as piperidine, morpholine and piperazine, and inorganic salts derived from sodium, calcium, potassium, magnesium, manganese, iron, copper, zinc, aluminum, lithium, and the like; and further include, when appropriate, nontoxic ammonium, quaternary ammonium and amine cations formed using counterions such as halide, hydroxide, carboxylate, sulfate, phosphate, nitrate, $C_{1-8}$ sulfonate and aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and aminoethanol. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC), benzyloxycarbonyl (CBZ) and 9-fluorenylmethoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl) ethoxy-methyl, 2-(p-toluenesulfonyl) ethyl, 2-(p-nitrophenylsulfonyl) ethyl, 2-(diphenylphosphino) ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

In particular, the compounds of the present invention and pharmaceutically acceptable compositions thereof are effective in inhibiting HBV infection.

In one aspect, the present invention provides a compound having Formula (I) or a stereoisomer, a tautomer, an N-oxide, a solvate, a metabolite, a pharmaceutically acceptable salt or a prodrug thereof, wherein:

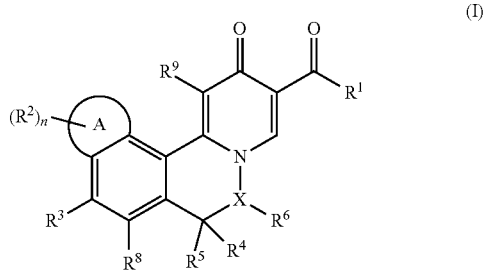

(I)

wherein $R^1$ is $R^{1a}O$— or $R^aR^bN$—;

X is $CR^7$ or N;

ring A is a heterocyclyl consisting of 5 ring atoms, a heterocyclyl consisting of 6 ring atoms or a carbocyclyl consisting of 5 to 6 carbon atoms;

$R^3$ is hydrogen, deuterium, F, Cl, Br, hydroxy, cyano, $C_{1-6}$ alkyl, $C_{2-6}$ alkynyl, $C_{3-7}$ cycloalkyl, heterocyclyl consisting of 3 to 10 ring atoms, $C_{6-10}$ aryl, heteroaryl group of 5 to 10 ring atoms or $R^{10}$—$C_{0-4}$ alkylene —O—, wherein each of $C_{1-6}$ alkyl, $C_{2-6}$ alkynyl, $C_{3-7}$ cycloalkyl, heterocyclyl consisting of 3 to 10 ring atoms, $C_{6-10}$ aryl, heteroaryl group of 5 to 10 ring atoms and —$C_{0-4}$ alkylene of $R^{10}$—$C_{0-4}$ alkylene —O— is independently unsubstituted or substituted by 1, 2, 3 or 4 $R^g$;

$R^{10}$ is deuterium, $R^{11}O$—, $C_{1-6}$ alkyl, $C_{3-7}$ cycloalkyl, heterocyclyl consisting of 3 to 6 ring atoms, $C_{6-10}$ aryl or heteroaryl group consisting of 5 to 10 ring atoms, wherein each of $C_{1-6}$ alkyl, $C_{3-7}$ cycloalkyl, heterocyclyl consisting of 3 to 6 ring atoms, $C_{6-10}$ aryl and heteroaryl group consisting of 5 to 10 ring atoms is independently unsubstituted or substituted by 1, 2, 3, or 4 $R^j$;

each $R^j$ and $R^g$ is independently deuterium, F, Cl, Br, CN, =O, HO—, HOOC—, $R^{11}O$—, $R^{12}$—$S(=O)_2$—, $R^{13}$—(C=O)—, $R^{14}$13 $S(=O)_2$—O—, $R^{15}$13 $S(=O)_2$—N (R$^c$)—, $R^{16}$—N(R$^c$)—$S(=O)_2$—, $R^{17}$—(C=O)—N(R$^c$)—$S(=O)_2$—, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, $C_{3-7}$ cycloalkyl, heterocyclyl consisting of 3 to 10 ring atoms, $C_{6-10}$ aryl or heteroaryl group consisting of 5 to 10 ring atoms, wherein each of amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, $C_{3-7}$ cycloalkyl, heterocyclyl consisting of 3 to 10 ring atoms, $C_{6-10}$ aryl and heteroaryl group consisting of 5 to 10 ring atoms is independently unsubstituted or substituted by 1, 2, 3 or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, $C_{1-6}$ alkyl, $C_{2-6}$ alkynyl, $C_{3-6}$ cycloalkyl, heterocyclyl consisting of 3 to 6 ring atoms, $C_{6-10}$ aryl, $C_{6-10}$ aryl $C_{1-3}$ alkylene or heteroaryl group consisting of 5 to 10 ring atoms, wherein each of $C_{1-6}$ alkyl, $C_{2-6}$ alkynyl, $C_{3-6}$ cycloalkyl, heterocyclyl consisting of 3 to 6 ring atoms, $C_{6-10}$ aryl, $C_{6-10}$ aryl $C_{1-3}$ alkylene and heteroaryl group consisting of 5 to 10 ring atoms is independently unsubstituted or substituted by 1, 2, 3 or 4 substituents selected from F, Cl, Br, CN, HO—, =O, HOOC—, $R^aR^bN$—$S(=O)_2$—, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-6}$ alkylamino, $C_{2-6}$ alkenyl, $C_{2-6}$ alkynyl, $C_{6-10}$ aryl, $C_{3-7}$ cycloalkyl, heteroaryl group consisting of 5 to 6 ring atoms, heterocyclyl of 3 to 6 ring atoms, $C_{1-6}$ alkoxy $C_{1-4}$ alkylene or $C_{1-4}$ alkylamino $C_{1-4}$ alkylene;

each $R^w$ is independently deuterium, F, Cl, Br, HO—, HOOC—, =O, amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, tert-butoxycarbonyl (($CH_3$)$_3$C—O—C(=O)—), $C_{1-6}$ alkyl-$S(=O)_2$—, $C_{3-6}$ cycloalkyl-$S(=O)_2$— or $C_{3-7}$ cycloalkyl, wherein each of amino, $C_{1-6}$ alkyl, $C_{1-6}$ alkoxy, $C_{1-6}$ alkylthio, $C_{1-6}$ alkylamino, $C_{2-6}$ alkenyl, $C_{2-6}$ alkynyl, tert-butoxycarbonyl (($CH_3$)$_3$C—O—C(=O)—), $C_{1-6}$ alkyl-$S(=O)_2$—, $C_{3-6}$ cycloalkyl-$S(=O)_2$— and $C_{3-7}$ cycloalkyl is independently unsubstituted or substituted by 1, 2, 3 or 4 substituents selected from F, Cl, Br, CN, OH, =O, amino, $C_{1-6}$ alkyl, $C_{1-6}$ haloalkyl, $C_{1-6}$ alkoxy, $C_{1-6}$ alkylthio, $C_{1-6}$ haloalkoxy or $C_{1-6}$ alkylamino;

each of $R^4$, $R^5$, $R^6$, $R^7$, $R^8$ and $R^9$ is independently hydrogen, deuterium, F, Cl, Br, $R^{12a}$—$S(=O)_2$—, $R^{13a}$—(C=O)—, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl, heteroaryl group consisting of 5 to 6 ring atoms or heterocyclyl consisting of 3 to 10 ring atoms, wherein each of $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl, heteroaryl group consisting of 5 to 6 ring atoms and heterocyclyl consisting of 3 to 10 ring atoms is independently unsubstituted or substituted by 1, 2, 3, or 4 $R^w$;

or $R^6$ and $R^4$, together with the atom to which they are attached, form a carbocyclyl consisting of 5 to 6 ring atoms or a heterocyclyl consisting of 5 to 6 ring atoms, wherein each of carbocyclyl consisting of 5 to 6 ring atoms and heterocyclyl consisting of 5 to 6 ring atoms is independently unsubstituted or substituted by 1, 2, 3, or 4 $R^w$;

each $R^2$ is independently hydrogen, deuterium, F, Cl, Br, =O, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl or heterocyclyl consisting of 3 to 6 ring atoms, wherein each of $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl, phenyl and heterocyclyl consisting of 3 to 6 ring atoms is independently unsubstituted or substituted by 1, 2, 3, or 4 $R^w$;

or two $R^2$ linked to the same carbon atom, together with the carbon atom to which they are attached, form a $C_{3-6}$ cycloalkyl or —(C=O)—, wherein $C_{3-6}$ cycloalkyl is unsubstituted or substituted by 1, 2, 3, or 4 $R^w$;

each $R^{1a}$, $R^a$, $R^b$ and $R^c$ is independently hydrogen, deuterium, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, heterocyclyl consisting of 3 to 6 ring atoms or heteroaryl consisting of 5 to 10 ring atoms, wherein each of $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, heterocyclyl consisting of 3 to 6 ring atoms and heteroaryl consisting of 5 to 10 ring atoms is independently unsubstituted or substituted by 1, 2, 3, or 4 substituents selected from F, Cl, Br, CN, HO—, amino, $C_{1-6}$ alkyl, $C_{1-6}$ haloalkyl, $C_{1-6}$ alkoxy or $C_{1-6}$ alkylamino;

n is 0, 1, 2, 3, 4, or 5.

In some embodiments, provided herein is a compound having Formula (II):

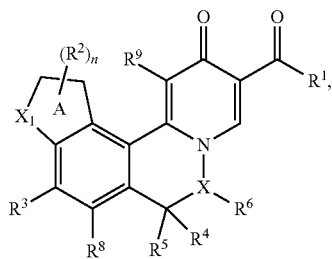

(II)

wherein $X_1$ is —O—, —NH—, —S—, —CH$_2$—O—, —CH$_2$—NH—, —CH$_2$—S—, —CH$_2$— or —CH$_2$—CH$_2$—;

wherein each of $R^1$, $R^2$, $R^3$, $R^4$, $R^5$, $R^6$, $R^8$, $R^9$, X and n is as defined herein.

In some embodiments, $R^3$ described herein is hydrogen, deuterium, F, Cl, Br, hydroxy, cyano, $C_{1-4}$ alkyl, $C_{2-4}$ alkynyl, $C_{3-6}$ cycloalkyl, heterocyclyl consisting of 3 to 6 ring atoms, phenyl, heteroaryl group consisting of 5 ring atoms, heteroaryl group consisting of 6 ring atoms or $R^{10}$—$C_{0-3}$ alkylene-O—, wherein each of $C_{1-4}$ alkyl, $C_{2-4}$ alkynyl, $C_{3-6}$ cycloalkyl, heterocyclyl consisting of 3 to 6 ring atoms, phenyl, heteroaryl group consisting of 5 ring atoms, heteroaryl group consisting of 6 ring atoms and —$C_{0-3}$ alkylene of $R^{10}$—$C_{0-3}$ alkylene-O— is independently unsubstituted or substituted by 1, 2, 3 or 4 $R^g$;

$R^{10}$ is deuterium, $R^{11}$O—, $C_{1-4}$ alkyl, $C_{3-6}$ cycloalkyl, heterocyclyl consisting of 3 to 6 ring atoms, phenyl, heteroaryl group consisting of 5 ring atoms or heteroaryl group consisting of 6 ring atoms, wherein each of $C_{1-4}$ alkyl, $C_{3-6}$ cycloalkyl, heterocyclyl consisting of 3 to 6 ring atoms, phenyl, heteroaryl group consisting of 5 ring atoms and heteroaryl group consisting of 6 ring atoms is independently unsubstituted or substituted by 1, 2, 3, or 4 $R^j$;

wherein each $R^{11}$, $R^g$ and $R^j$ is as defined herein.

In some embodiments, $R^3$ described herein is hydrogen, deuterium, F, Cl, Br, hydroxy, cyano, methyl, ethyl, n-propyl, isopropyl, n-butyl, isobutyl, sec-butyl, tert-butyl, ethynyl, propargyl, propynyl, but-1-yne-4-yl, but-2-yne-1-yl, but-1-yne-1-yl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $R^{10}$—O—, $R^{10}$—CH$_2$—O—, $R^{10}$—(CH$_2$)$_2$—O— or $R^{10}$—(CH$_2$)$_3$—O—, wherein each of methyl, ethyl, n-propyl, isopropyl, n-butyl, isobutyl, sec-butyl, tert-butyl, ethynyl, propargyl, propynyl, but-1-yne-4-yl, but-2-yne-1-yl, but-1-yne-1-yl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, —CH$_2$— of $R^{10}$—CH$_2$—O—, —(CH$_2$)$_2$— of $R^{10}$—(CH$_2$)$_2$—O— and —(CH$_2$)$_3$— of $R^{10}$—(CH$_2$)$_3$—O— is independently unsubstituted or substituted by 1, 2, 3, or 4 $R^g$;

$R^{10}$ is deuterium, $R^{11}$O—, methyl, ethyl, n-propyl, isopropyl, n-butyl, isobutyl, sec-butyl, tert-butyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, sec-butyl, tert-butyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 $R^j$;

wherein each $R^{11}$, $R^g$ and $R^j$ is as defined herein.

In some embodiments, each $R^j$ and $R^g$ described herein is independently deuterium, F, Cl, Br, CN, =O, HO—, HOOC—, $R^{11}$O—, $R^{12}$—S(=O)$_2$—, $R^{13}$—(C=O)—, $R^{14}$13 S(=O)$_2$—O—, $R^{15}$13 S(=O)$_2$—N($R^c$)—, $R^{16}$—N($R^c$)—S(=O)$_2$—, $R^{17}$—(C=O)—N($R^c$)—S(=O)$_2$—, amino, $C_{1-4}$ alkyl, $C_{1-4}$ alkoxy, alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, heteroaryl group consisting of 5 ring atoms or heteroaryl group consisting of 6 ring atoms, wherein each of amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, heteroaryl group consisting of 5 ring atoms and heteroaryl group consisting of 6 ring atoms is independently unsubstituted or substituted by 1, 2, 3 or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, alkyl, $C_{2-4}$ alkynyl, $C_{3-6}$ cycloalkyl, heterocyclyl consisting of 3 to 6 ring atoms, phenyl, phenyl $C_{1-2}$ alkylene, heteroaryl group consisting of 5 ring atoms or heteroaryl group consisting of 6 ring atoms, wherein each of $C_{1-4}$ alkyl, $C_{2-4}$ alkynyl, $C_{3-6}$ cycloalkyl, heterocyclyl consisting of 3 to 6 ring atoms, phenyl, phenyl $C_{1-2}$ alkylene, heteroaryl group consisting of 5 ring atoms and heteroaryl group consisting of 6 ring atoms is independently unsubstituted or substituted by 1, 2, 3 or 4 substituents selected from F, Cl, Br, CN, HO—, =O, HOOC—, $R^aR^bN$—S(=O)$_2$—, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, phenyl, $C_{3-6}$ cycloalkyl, heteroaryl group consisting of 5 ring atoms, heteroaryl group consisting of 6 ring atoms, heterocyclyl of 3 to 6 ring atoms, $C_{1-4}$ alkoxy $C_{1-3}$ alkylene or $C_{1-4}$ alkylamino $C_{1-3}$ alkylene;

wherein each $R^a$, $R^b$, $R^c$ and $R^w$ has the meaning described in the present invention.

In some embodiments, each $R^j$ and $R^g$ described herein is independently deuterium, F, Cl, Br, CN, =O, HO—, HOOC—, $R^{11}$O—, $R^{12}$—S(=O)$_2$—, $R^{13}$—(C=O)—, $R^{14}$13 S(=O)$_2$—O—, $R^{15}$13 S(=O)$_2$—N($R^c$)—, $R^{16}$—N($R^c$)—S(=O)$_2$—, $R^{17}$—(C=O)—N($R^c$)—S(=O)$_2$—, amino, methyl, ethyl, n-propyl, isopropyl, n-butyl, isobutyl, sec-butyl, tert-butyl, methoxy, ethoxy, 1-propoxy, 2-propoxy, 1-butoxy, 2-methyl-1-propoxy, 2-butoxy, $C_{1-3}$ alkylthio, $C_{1-3}$ alkylamino, $C_{2-4}$ alkenyl, $C_{2-4}$ alkynyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of amino, methyl, ethyl, n-propyl, isopropyl, n-butyl, isobutyl, sec-butyl, tert-butyl, methoxy, ethoxy, 1-propoxy, 2-propoxy, 1-butoxy, 2-methyl-1-propoxy, 2-butoxy, $C_{1-3}$ alkylthio, $C_{1-3}$ alkylamino, $C_{2-4}$ alkenyl, $C_{2-4}$ alkynyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, methyl, ethyl, n-propyl, isopropyl, n-butyl, isobutyl, sec-butyl, tert-butyl, $C_{2-4}$ alkynyl, cyclopropyl, cyclobutyl, cyclopentyl, cyclohexyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, phenyl $C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, sec-butyl, tert-butyl, $C_{2-4}$ alkynyl, cyclopropyl, cyclobutyl, cyclopentyl, cyclohexyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, phenyl $C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 substituents selected from F, Cl, Br, CN, HO—, =O, HOOC—, $R^aR^bN$—S(=O)$_2$—, amino, $C_{1-3}$ alkyl, $C_{1-3}$ haloalkyl, $C_{1-3}$ alkoxy, $C_{1-3}$ alkylthio, $C_{1-3}$ haloalkoxy, $C_{1-3}$ alkylamino, $C_{2-4}$ alkenyl, $C_{2-4}$ alkynyl, phenyl, $C_{3-6}$ cycloalkyl, heteroaryl group consisting of 5 ring atoms, heteroaryl group consisting of 6 ring atoms, heterocyclyl consisting of 3 to 6 ring atoms, $C_{1-3}$ alkoxy $C_{1-2}$ alkylene or $C_{1-3}$ alkylamino $C_{1-2}$ alkylene;

wherein, each $R^a$, $R^b$, $R^c$ and $R^w$ has the meaning described in the present invention.

In some embodiments, each $R^w$ described herein is independently deuterium, F, Cl, Br, HO—, HOOC—, =O, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, tert-butoxycarbonyl $((CH_3)_3C$—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$— or $C_{3-6}$ cycloalkyl, wherein each of amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, tert-butoxycarbonyl $((CH_3)_3C$—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$— and $C_{3-6}$ cycloalkyl is independently unsubstituted or substituted by 1, 2, 3 or 4 substituents selected from F, Cl, Br, CN, OH, =O, amino, $C_{1-4}$ alkyl, $C_{1-4}$ haloalkyl, $C_{1-4}$ alkoxy, $C_{1-4}$ alkylthio, $C_{1-4}$ haloalkoxy or $C_{1-4}$ alkylamino;

each of $R^4$, $R^5$, $R^6$, $R^7$, $R^8$ and $R^9$ is independently hydrogen, deuterium, F, Cl, Br, $R^{12a}$13 S(=O)$_2$—, $R^{13a}$—(C=O)—, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{1-4}$ alkenyl, $C_{3-6}$ cycloalkyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl and heterocyclyl consisting of 3 to 6 ring atoms is independently unsubstituted or substituted by 1, 2, 3, or 4 $R^w$;

or $R^6$ and $R^4$, together with the atom to which they are attached, form cyclopentyl, cyclohexyl, pyrrolidinyl, pyrazolidinyl, imidazolidinyl, piperidinyl, morpholinyl, thiomorpholinyl or piperazinyl, wherein cyclopentyl, cyclohexyl, pyrrolidinyl, pyrazolidinyl, imidazolidinyl, piperidinyl, morpholinyl, thiomorpholinyl and piperazinyl is independently unsubstituted or substituted by 1, 2, 3, or 4 $R^w$;

wherein each of $R^{12a}$, $R^{13a}$ and $R^w$ is as defined herein.

In some embodiments, each $R^w$ described herein is independently deuterium, F, Cl, Br, HO—, HOOC—, =O, amino, methyl, ethyl, n-propyl, isopropyl, n-butyl, isobutyl, sec-butyl, tert-butyl, $C_{1-4}$ alkoxy, $C_{1-4}$ alkylthio, $C_{1-4}$ alkylamino, $C_{2-4}$ alkenyl, ethynyl, propargyl, propynyl, but-1-yne-4-yl, but-2-yne-1-yl, but-1-yne-1-yl, tert-butoxycarbonyl $((CH_3)_3C$—O—C(=O)—), CM alkyl-S(=O)$_2$—, cyclopropyl-S(=O)$_2$—, cyclopentyl-S(=O)$_2$—, cyclohexyl-S(=O)$_2$—, cyclopropyl, cyclobutyl, cyclopentyl or cyclohexyl, wherein each of amino, methyl, ethyl, n-propyl, isopropyl, n-butyl, isobutyl, sec-butyl, tert-butyl, $C_{1-4}$ alkoxy, $C_{1-4}$ alkylthio, $C_{1-4}$ alkylamino, $C_{2-4}$ alkenyl, ethynyl, propargyl, propynyl, but-1-yne-4-yl, but-2-yne-1-yl, but-1-yne-1-yl, tert-butoxycarbonyl $((CH_3)_3C$—O—C(=O)—), $C_{1-4}$ alkyl-S(=O)$_2$—, cyclopropyl-S(=O)$_2$—, cyclopentyl-S(=O)$_2$—, cyclohexyl-S(=O)$_2$—, cyclopropyl, cyclobutyl, cyclopentyl and cyclohexyl is independently unsubstituted or substituted by 1, 2, 3 or 4 substituents selected from F, Cl, Br, CN, OH, =O, amino, $C_{1-4}$ alkyl, $C_{1-4}$ haloalkyl, $C_{1-4}$ alkoxy, $C_{1-4}$ alkylthio, $C_{1-4}$ haloalkoxy or $C_{1-4}$ alkylamino;

each of $R^4$, $R^5$, $R^6$, $R^7$, $R^8$ and $R^9$ is independently hydrogen, deuterium, F, Cl, Br, $R^{12a}$13 S(=O)$_2$—, $R^{13a}$—(C=O)—, methyl, ethyl, n-propyl, isopropyl, n-butyl, isobutyl, sec-butyl, tert-butyl, $C_{1-4}$ alkylamino, $C_{1-4}$ alkoxy, ethynyl, propargyl, propynyl, but-1-yne-4-yl, but-2-yne-1-yl, but-1-yne-1-yl, $C_{2-4}$ alkenyl, cyclopropyl, cyclobutyl, cyclopentyl, cyclohexyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl, wherein each of methyl, ethyl, n-propyl, isopropyl, n-butyl, isobutyl, sec-butyl, tert-butyl. $C_{1-4}$ alkylamino, $C_{1-4}$ alkoxy, ethynyl, propargyl, propynyl, but-1-yne-4-yl, but-2-yne-1-yl, but-1-yne-1-yl, $C_{2-4}$ alkenyl, cyclopropyl, cyclobutyl, cyclopentyl, cyclohexyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl and piperazinyl is independently unsubstituted or substituted by 1, 2, 3, or 4 $R^w$;

or $R^6$ and $R^4$, together with the atom to which they are attached, form cyclopentyl, cyclohexyl, pyrrolidinyl, pyrazolidinyl, imidazolidinyl, piperidinyl, morpholinyl, thiomorpholinyl or piperazinyl, wherein cyclopentyl, cyclohexyl, pyrrolidinyl, pyrazolidinyl, imidazolidinyl, piperidinyl, morpholinyl, thiomorpholinyl and piperazinyl is independently unsubstituted or substituted by 1, 2, 3, or 4 $R^w$;

wherein each $R^{12a}$, $R^{13a}$ and $R^w$ is as defined herein.

In some embodiments, each R described herein is independently hydrogen, deuterium, F, Cl, Br, =O, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl or heterocyclyl consisting of 3 to 6 ring atoms, wherein each of methyl, ethyl, n-propyl, isopropyl, n-butyl, isobutyl, sec-butyl, tert-butyl, alkylamino, $C_{1-4}$ alkoxy, $C_{2-4}$ alkynyl, $C_{2-4}$ alkenyl, $C_{3-6}$ cycloalkyl, phenyl and heterocyclyl consisting of 3 to 6 ring atoms is independently unsubstituted or substituted by 1, 2, 3, or 4 $R^w$;

or two R linked to the same carbon atom, together with the carbon atom to which they are attached, form cyclopropyl, cyclobutyl, cyclopentyl, cyclohexyl or =O, wherein each of cyclopropyl, cyclobutyl, cyclopentyl and cyclohexyl is independently unsubstituted or substituted by 1, 2, 3, or 4 $R^w$;

each $R^{1a}$, $R^a$, $R^b$ and $R^c$ is independently hydrogen, deuterium, methyl, ethyl, n-propyl, isopropyl, n-butyl, isobutyl, sec-butyl, tert-butyl, alkoxy, $C_{2-4}$ alkenyl, $C_{2-4}$ alkynyl, $C_{3-6}$ cycloalkyl, phenyl, heterocyclyl consisting of 3 to 6 ring atoms, heteroaryl group consisting of 5 ring atoms or heteroaryl group consisting of 6 ring atoms, wherein each of methyl, ethyl, n-propyl, isopropyl, n-butyl, isobutyl, sec-butyl, tert-butyl, $C_{1-4}$ alkoxy, $C_{2-4}$ alkenyl, $C_{2-4}$ alkynyl, $C_{3-6}$ cycloalkyl, phenyl, heterocyclyl consisting of 3 to 6 ring atoms, heteroaryl group consisting of 5 ring atoms and heteroaryl group consisting of 6 ring atoms is independently unsubstituted or substituted by 1, 2, 3, or 4 substituents selected from F, Cl, Br, CN, HO—, amino, $C_{1-4}$ alkyl, $C_{1-4}$ haloalkyl, $C_{1-4}$ alkoxy or $C_{1-4}$ alkylamino;

wherein each $R^w$ is as defined herein.

In some embodiments, provided herein is a compound having Formula (III):

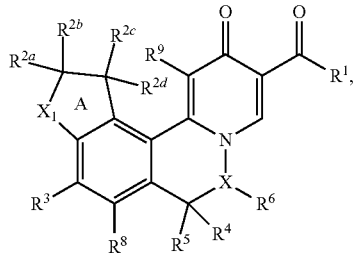

(III)

wherein $X_1$ is —O—, —NH—, —S—, —CH$_2$—O—, —O—CH$_2$—, —CH$_2$— or —CH$_2$—CH$_2$—;

each of $R^{2a}$, $R^{2b}$, $R^{2c}$ and $R^{2d}$ is independently hydrogen, deuterium, F, Cl, Br, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl and heterocyclyl consisting of 3 to 6 ring atoms is independently unsubstituted or substituted by 1, 2, 3 or 4 $R^w$;

or $R^{2a}$ and $R^{2b}$, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted with 1, 2, 3 or 4 $R^w$;

or $R^{2C}$ and $R^{2d}$, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted with 1, 2, 3 or 4 $R^w$;

wherein each of $R^1$, $R^3$, $R^4$, $R^5$, $R^6$, $R^8$, $R^9$ and X is as defined herein.

In some embodiments, provided herein is a compound having one of the following structures, or a stereoisomer, a tautomer, an N-oxide, a solvate, a metabolite, a pharmaceutically acceptable salt or a prodrug thereof, but is in no way limited to these compounds:

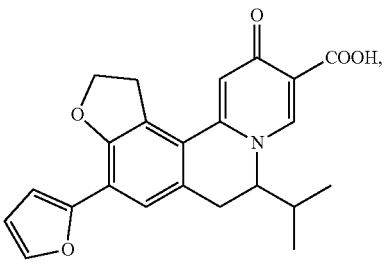

(1)

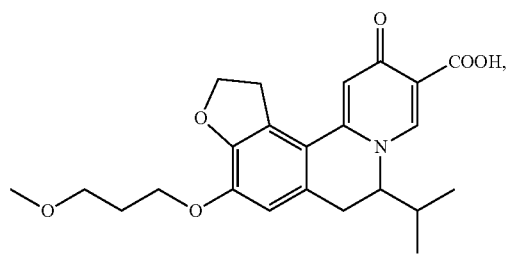

(2)

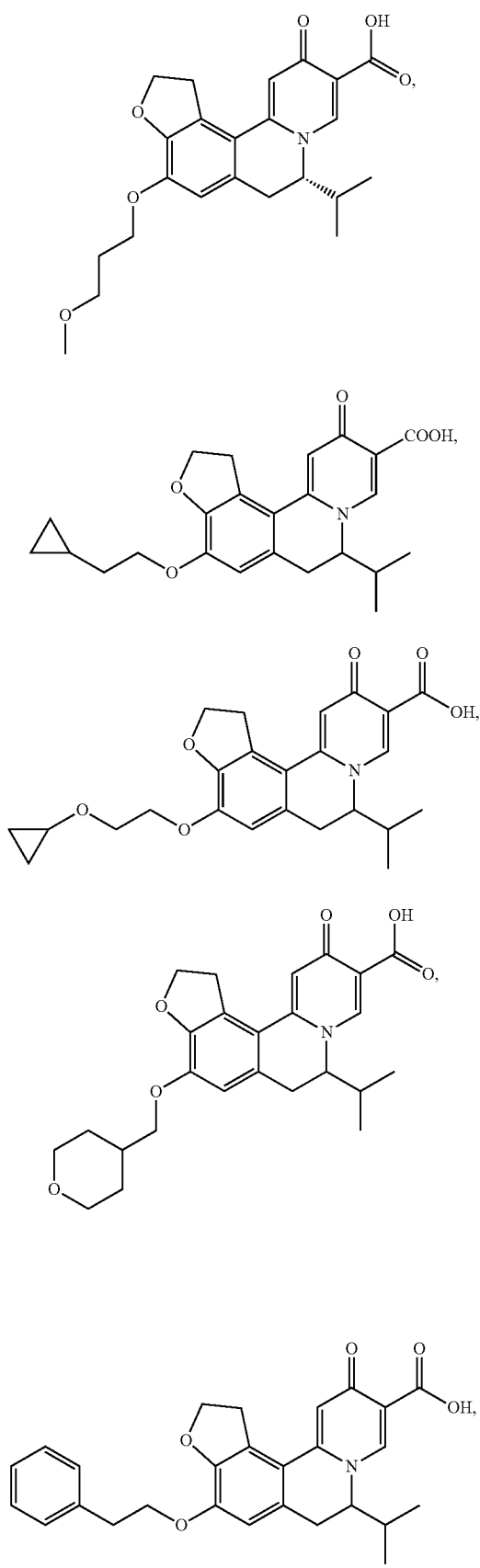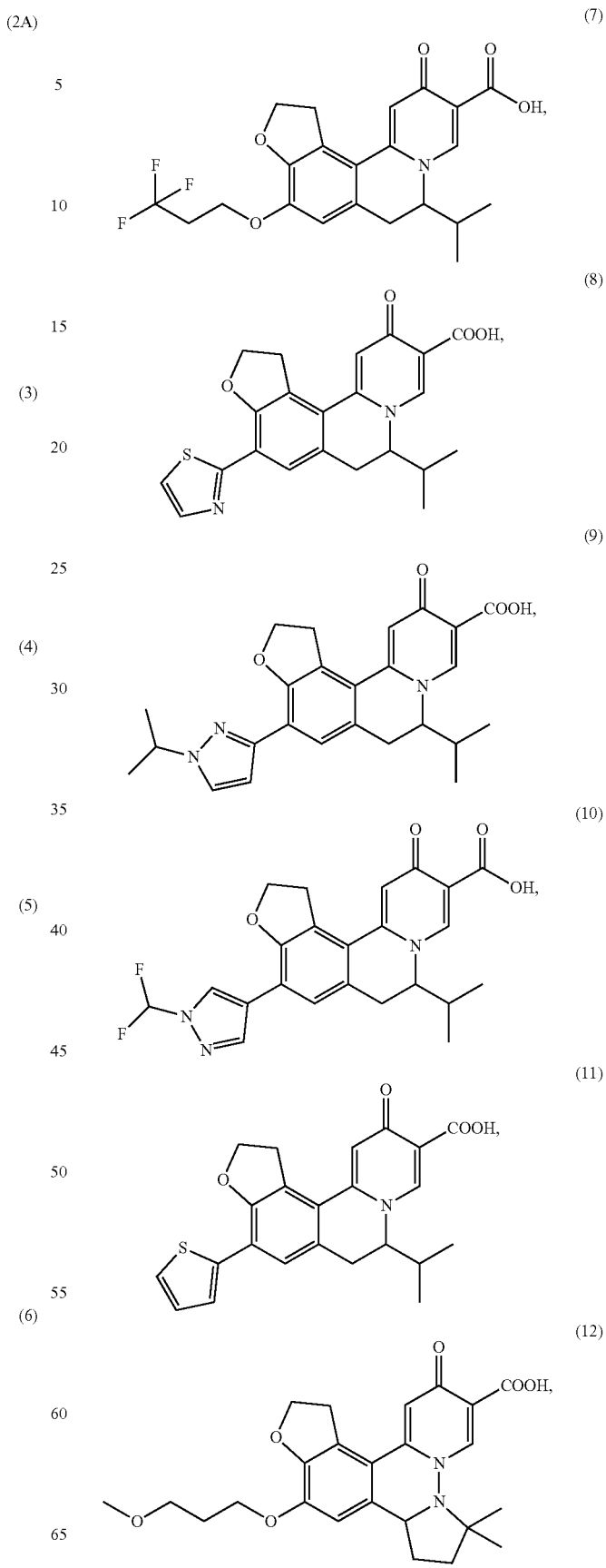

(13)
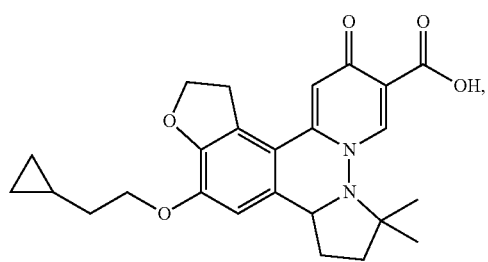
(14)
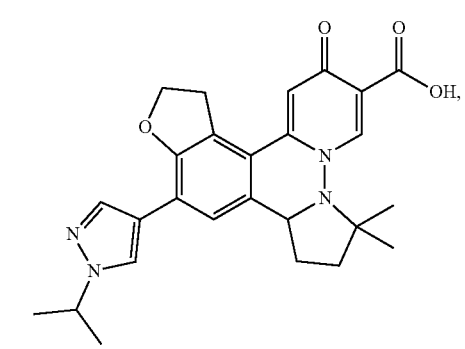
(15)
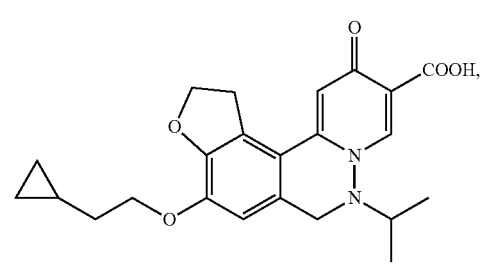
(16)
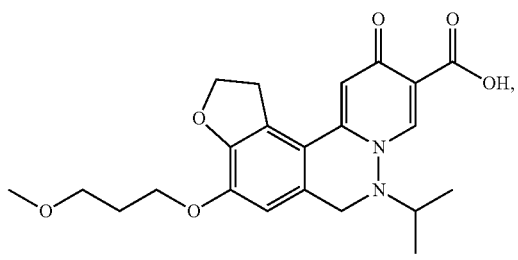
(17)
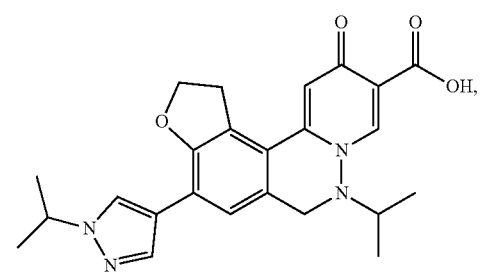
(3A)
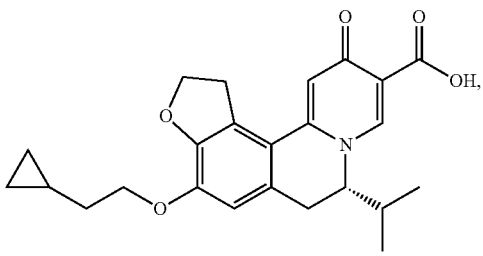
(10A)
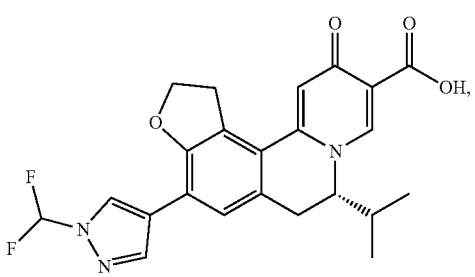
(18)
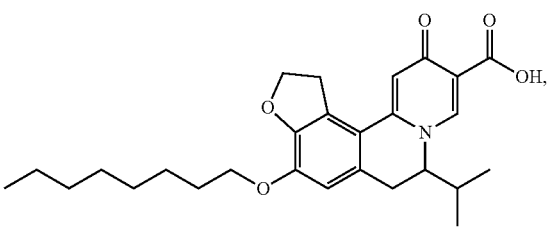
(19)
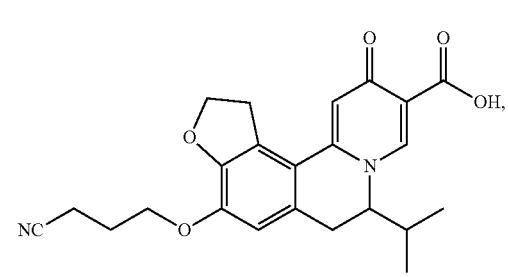
(20)
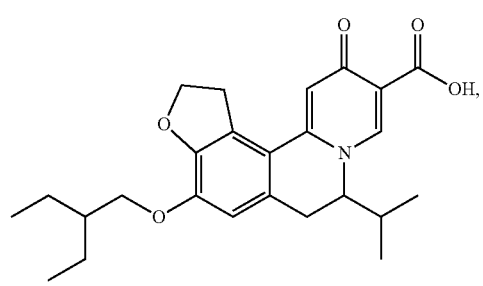
(21)
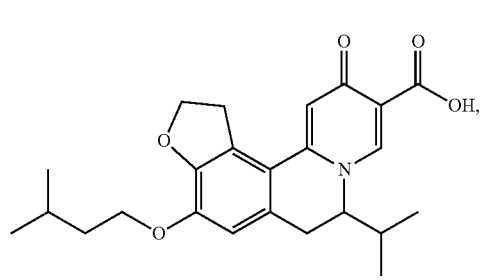

(21A) 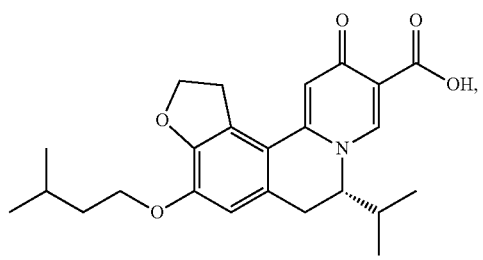
(22) 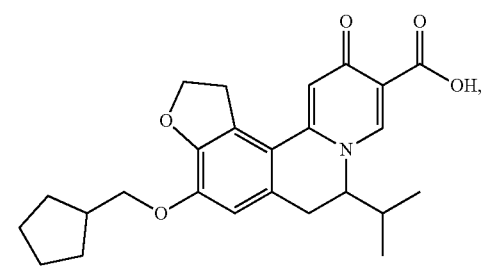
(22A) 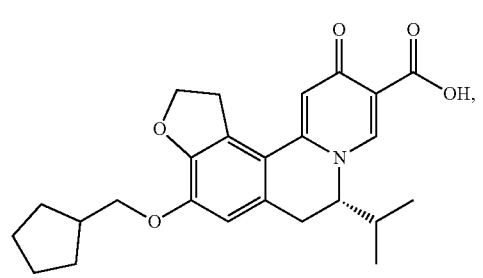
(23) 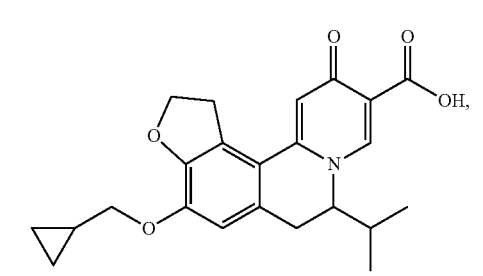
(23A) 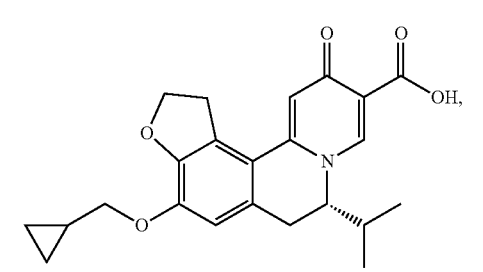
(24) 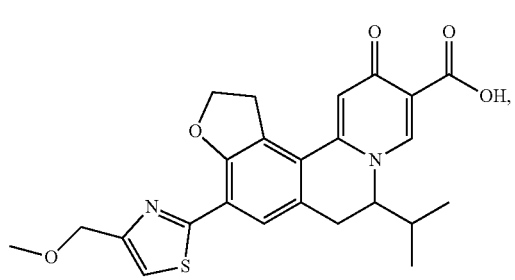
(25) 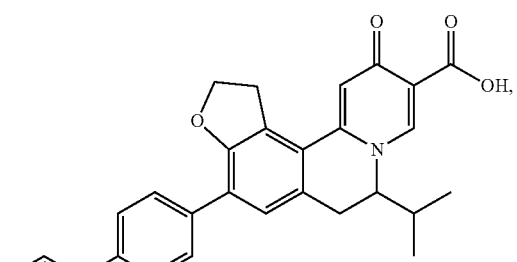
(26) 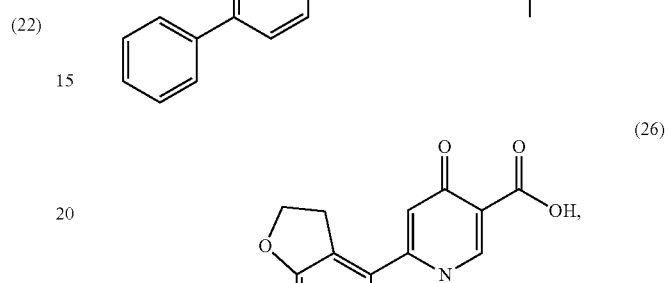
(27) 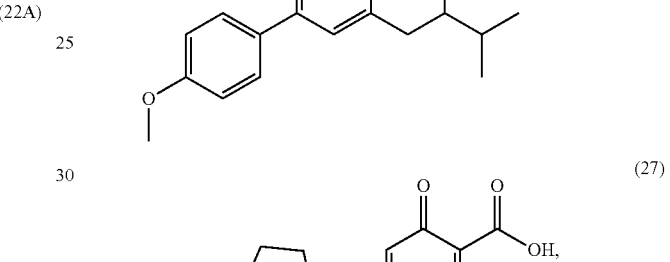
(28) 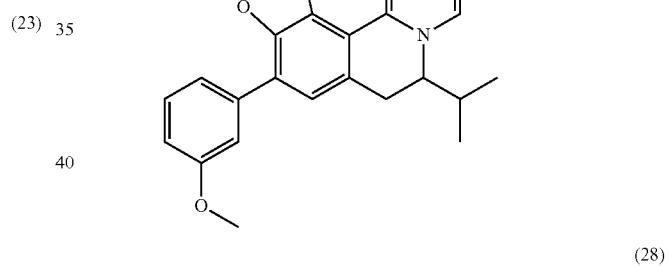
(29) 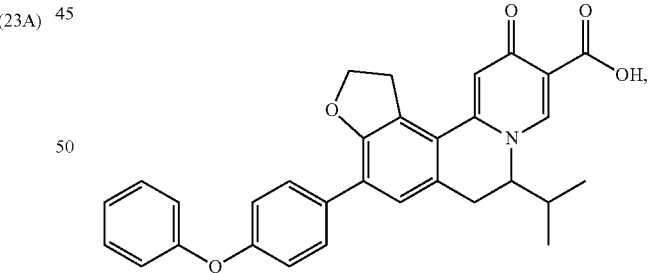

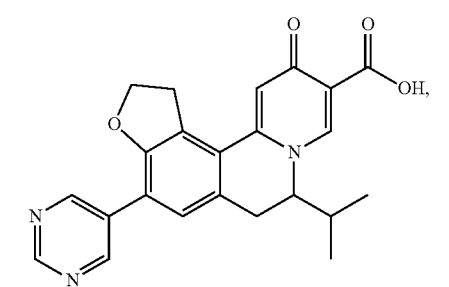 (30)
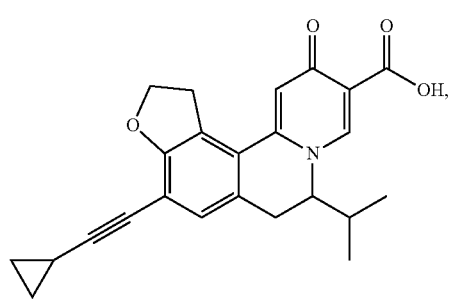 (31)
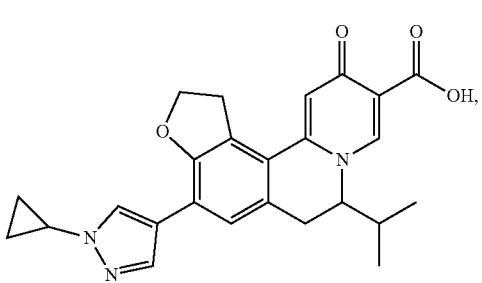 (32)
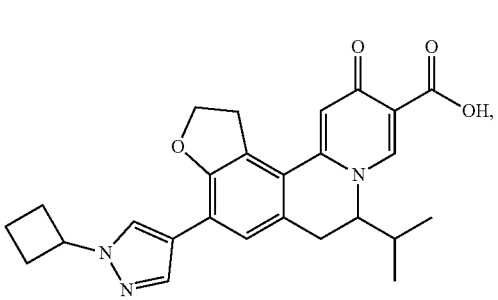 (33)
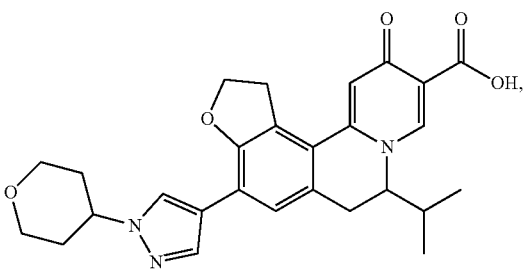 (34)
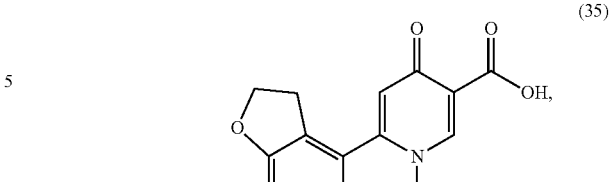 (35)
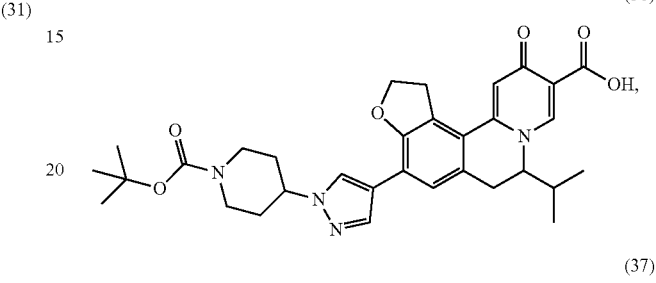 (36)
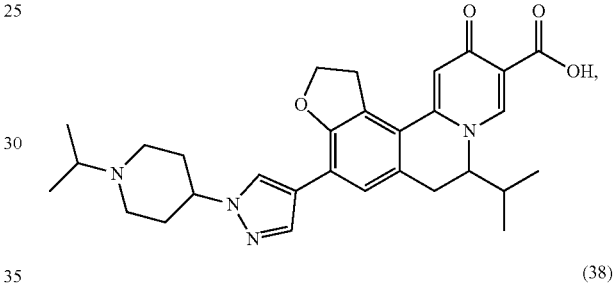 (37)
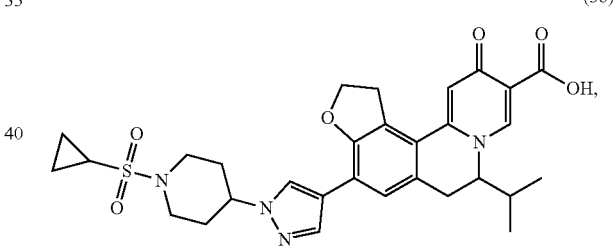 (38)
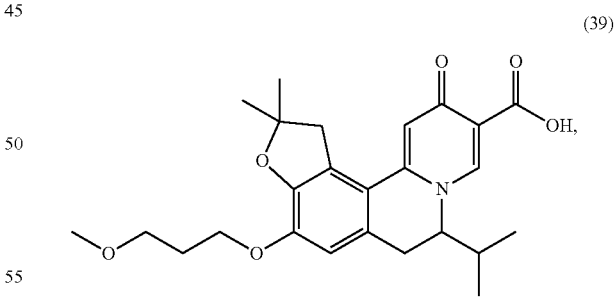 (39)
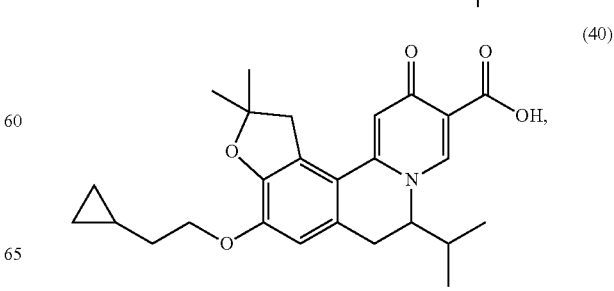 (40)

(41) 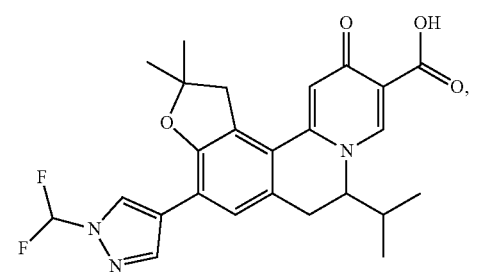
(42) 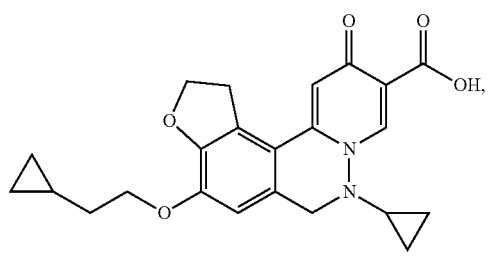
(43) 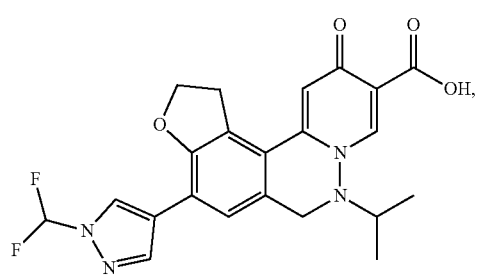
(44) 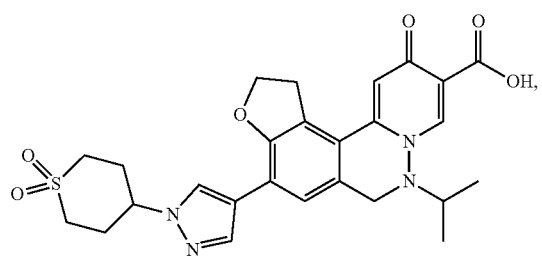
(45) 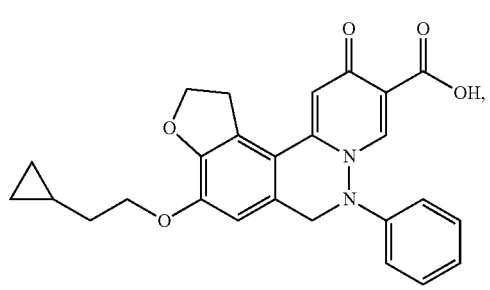
(46) 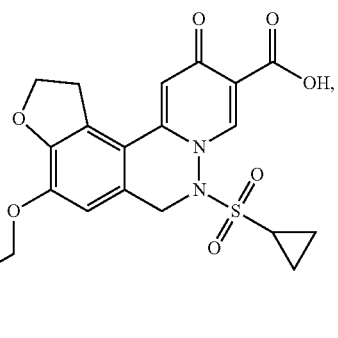
(47) 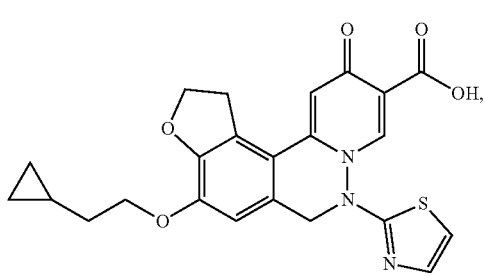
(48) 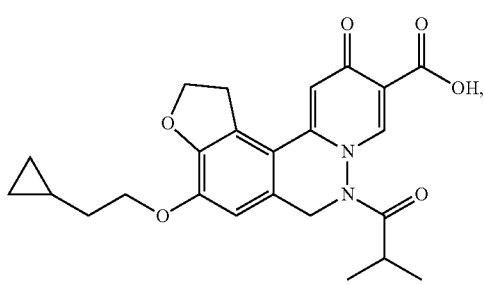
(49) 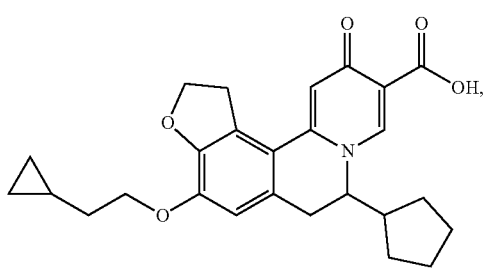
(50) 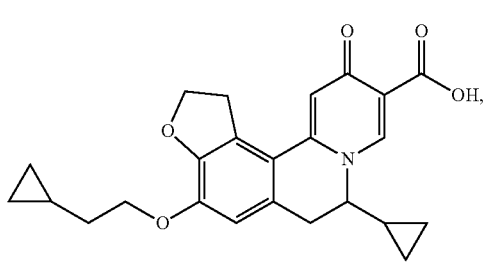

(51)
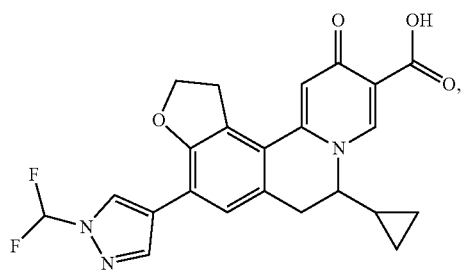
(52)
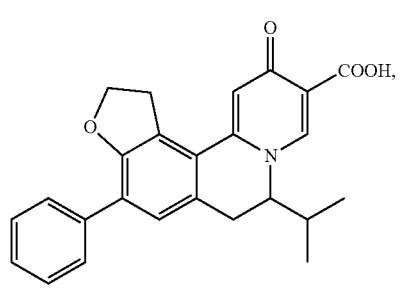
(53)
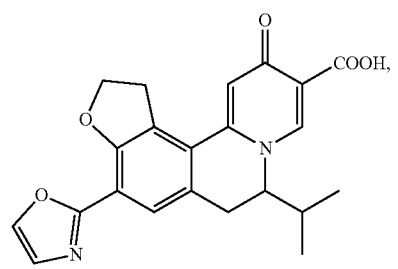
(54)
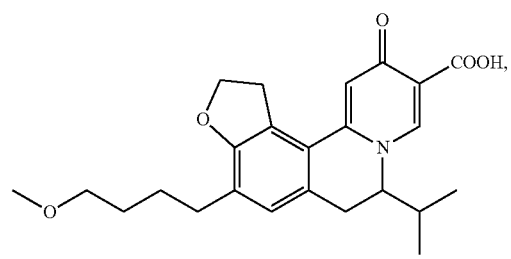
(55)
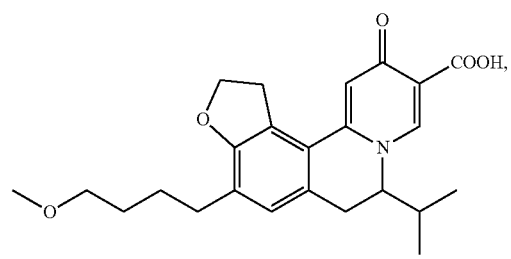
(56)
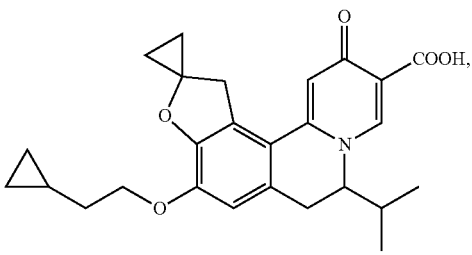
(57)
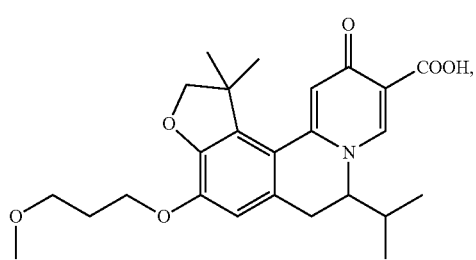
(58)
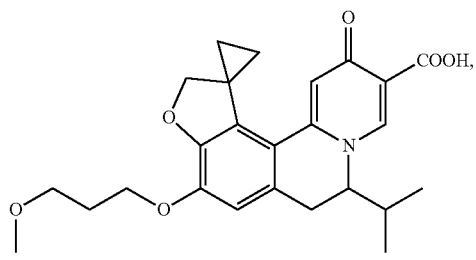
(59)
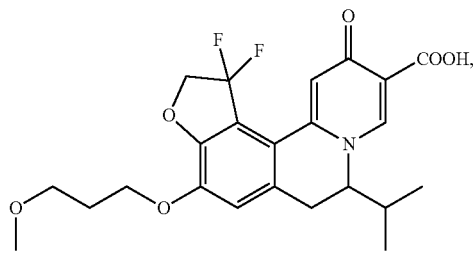
(60)
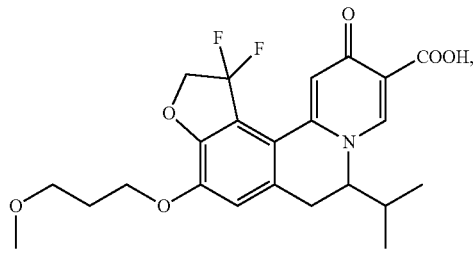
(61)
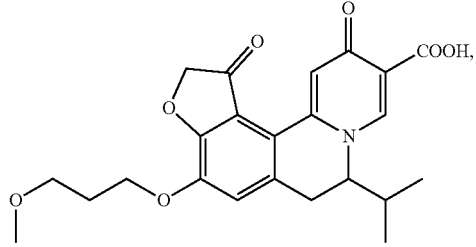

(62)
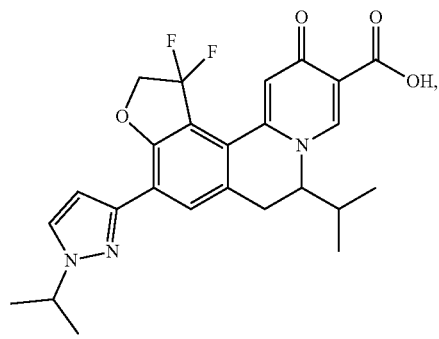
(63)
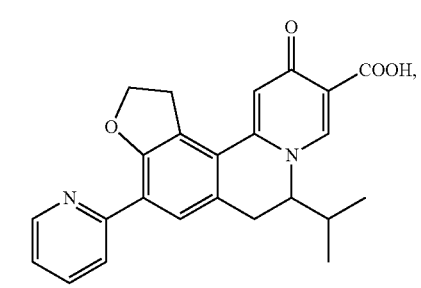
(64)
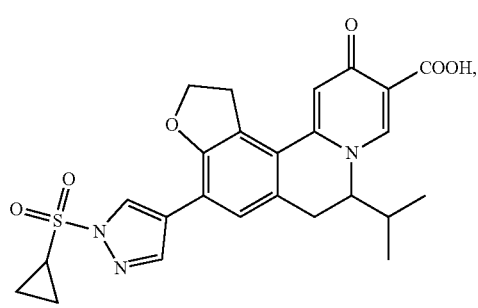
(65)
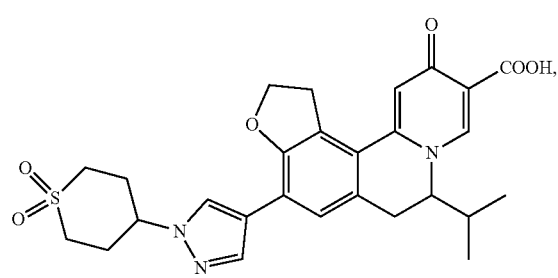
(66)
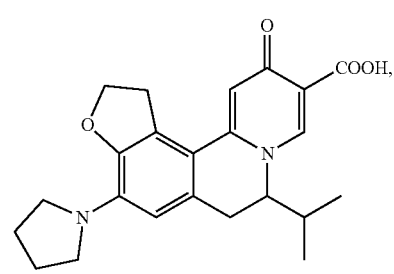
(67)
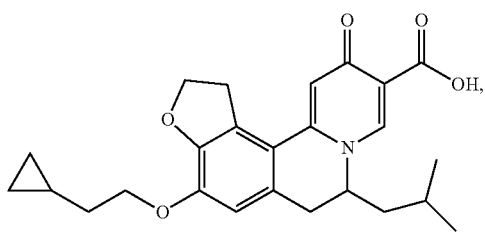
(68)
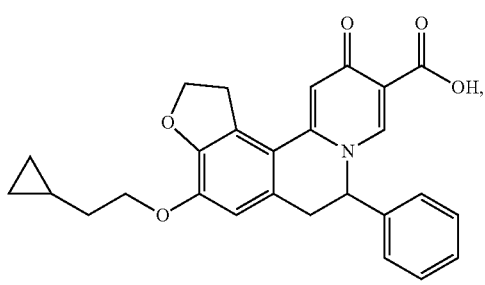
(69)
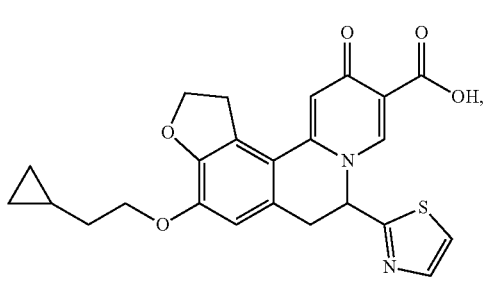
(70)
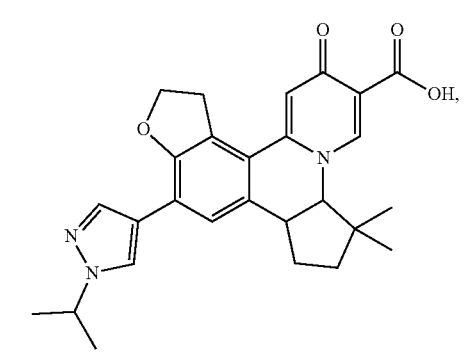
(71)
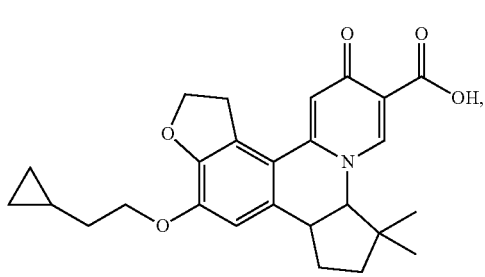

(72)
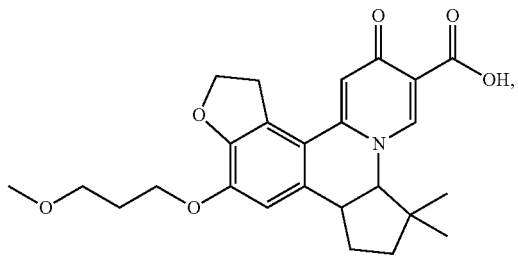
(73)
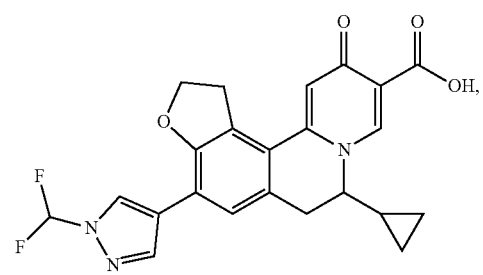
(74)
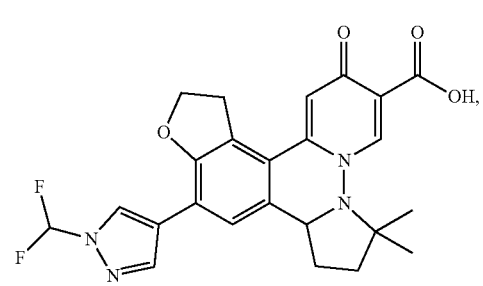
(75)
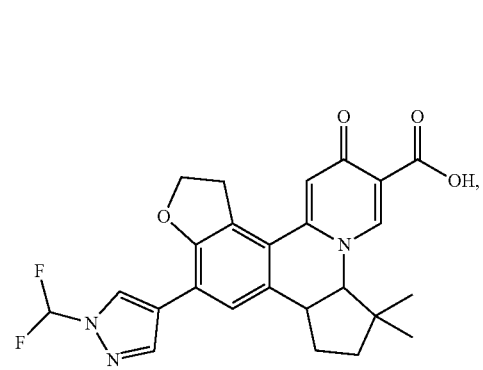
(76)
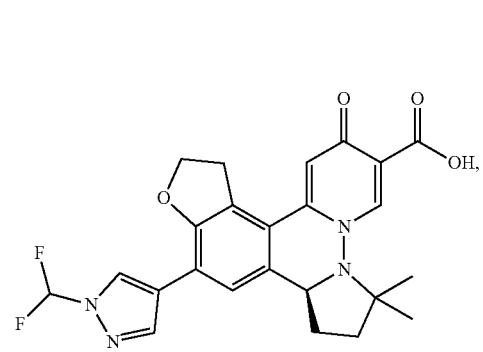
(77)
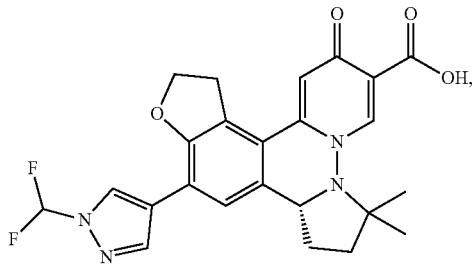
(78)
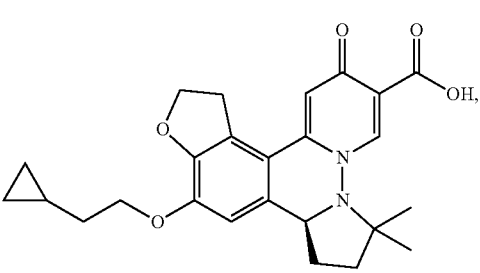
(79)
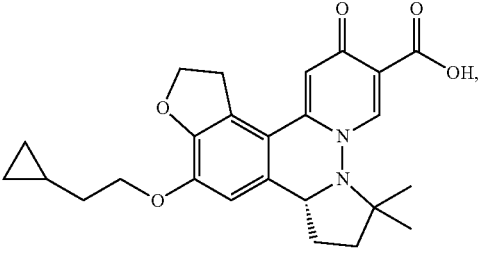
(80)
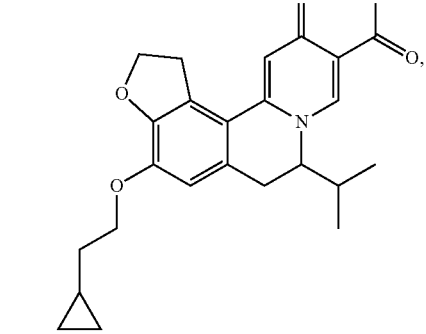
(81)
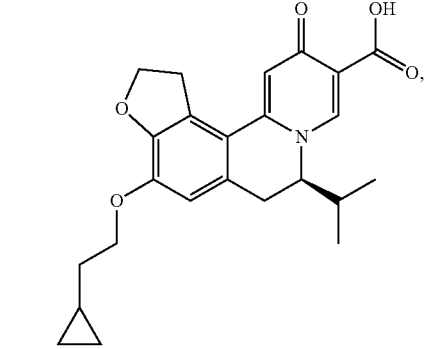

(82)

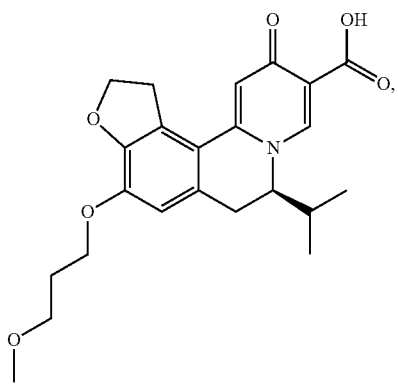

(83)

(84)

(85)

(86)

(87)

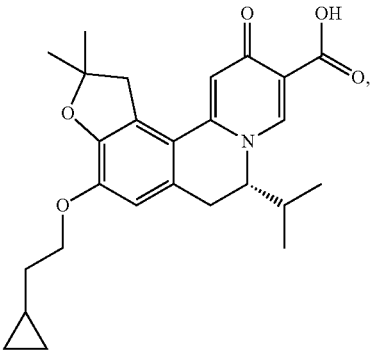

Unless otherwise specified, a compound having Formula (I) or a stereoisomer, a tautomer, an N-oxide, a solvate, a metabolite, a pharmaceutically acceptable salt or a prodrug thereof, are all embraced within the scope of the invention.

In other aspect, the invention also provides a pharmaceutical composition comprising a compound of the invention, optionally further comprising a pharmaceutically acceptable excipient or a combination of said excipients.

In some embodiments, the pharmaceutical compositions of the present invention further comprise other anti-HBV drugs.

In some embodiments, the pharmaceutical compositions of the present invention, wherein the anti-HBV drug is a HBV polymerase inhibitor, an immunomodulator or an interferon.

In some embodiments, the pharmaceutical compositions of the present invention, wherein the anti-HBV drug is lamivudine, telbivudine, tenofovir, entecavir, adefovir dipivoxil, Alfaferone, Alloferon, celmoleukin, clafidine, emtricitabine, faciclovir, interferon, Baoganling CP, intepropen, interferon α-1b, interferon α, interferon α-2α, interferon β-1α, interferon α-2, interleukin-2, mivotate, nalozolidine, peginterferon α-2α, ribavirin, interferon-A, cilostaz, Euforavac, aplori, Phosphazid, Heplisav, interferon α-2b, levamisole or propafen.

In other aspect, provided herein is use of the compound or the pharmaceutical composition in the present invention in the manufacture of a medicament for preventing, treating or reducing viral disease.

In some embodiments, the viral disease is hepatitis B viral infection or a disease caused by hepatitis B viral infection.

In other embodiments, the disease caused by hepatitis B viral infection is cirrhosis or hepatocellular carcinoma.

In other aspect, provided herein is use of the compound or the pharmaceutical composition in the present invention in the manufacture of a medicament for inhibiting the formation or secretion of HBsAg, and/or inhibiting the formation or replication of HBV DNA.

In other aspect, provided herein is use of the compound or the pharmaceutical composition in the present invention in the manufacture of a medicament for preventing, treating or reducing Hepatitis B disease.

Another aspect of the invention relates to a method of preventing, treating or ameliorating a patient's HBV illness, wherein the method comprises administering to a patient a pharmaceutically acceptable effective amount of a compound of the invention.

Another aspect of the invention relates to a method of preventing, treating or ameliorating a patient's HBV illness, wherein the method comprises administering to a patient a pharmaceutically acceptable effective amount of the pharmaceutical composition comprising a compound of the invention.

In other aspect, provided herein is use of the compound disclosed herein in the manufacture of a medicament for preventing, managing or treating HBV illness in a patient, and lessening the severity thereof.

In other aspect, provided herein is use of the pharmaceutical composition containing the compound disclosed herein in the manufacture of a medicament for preventing or treating HBV illness in a patient, and lessening the severity thereof.

Another aspect of the invention relates to a method of inhibiting HBV infection, wherein the method comprises contacting a cell with a compound or composition of the invention which can effectively inhibit the dose contact of HBV. In other embodiments, the method further comprises contacting the cells with other anti-HBV agents.

Another aspect of the invention relates to a method of treating a patient with HBV disease, the method comprising administering to the patient a therapeutically effective amount of a compound of the invention or a composition thereof. In other embodiments, the method further comprises administering another HBV treatment.

Another aspect of the invention relates to a method of inhibiting HBV infection in a patient, wherein the method comprises administering to the patient a therapeutically effective amount of a compound of the invention or a composition thereof. In other embodiments, the method further comprises administering another HBV treatment.

In other aspect, provided herein is a method of preparing, separating or purifying the compound of Formula (I).

The present invention also comprises uses of the compound and pharmaceutically acceptable salts thereof in the manufacture of a medicine for effectively inhibiting HBV infection, including those described in the invention: the use of the compounds of the invention in the manufacture of a medicament for the effective inhibition of HBV infection. The compound disclosed herein also can be used in the manufacture of a medicine for lessening, preventing, managing or treating hepatitis B in a patient. The present invention provides a pharmaceutical composition comprising the compound of Formula (I) at the therapeutically effective amount required for the combination of at least one pharmaceutically acceptable excipient.

The present invention also provides a method of effectively inhibiting HBV infection, or sensitive to these diseases in a patient, wherein the method comprises administering to the patient a therapeutically effective amount of the compound of Formula (I).

Unless otherwise stated, all stereoisomers, tautomers, N-oxides, solvates, metabolites, salts and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The salt of the compound of the present invention further includes an intermediate for preparing or purifying the compound of the formula (I) or a salt of the formula (I) or an isomer thereof, but not necessarily a pharmaceutically acceptable salt.

The term "pharmaceutically acceptable" refers to a material that is acceptable for pharmaceutical use and does not adversely interact with the active ingredient from a toxicological point of view.

If the compound of the invention is basic, the desired salt can be prepared by any suitable method provided in the literature, for example, using inorganic acids such as hydrochloric acid, hydrobromic acid, sulfuric acid, nitric acid, and phosphoric acid, etc; or using organic acids such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluene sulfonic acid, benzenesulfonic acid, methanesulfonic acid, ethane sulfonic acid, trifluoromethanesulfonic acid, and the like; or the combination thereof.

If the compound of the present invention is acidic, the desired salt can be obtained by a suitable method, with an inorganic base, such as a lithium, sodium, potassium, calcium, magnesium, aluminum, iron, ferrous, manganese, manganese, copper, zinc and ammonium salts of a compound of the formula (I), etc; with an organic base, such as a salt of a compound of the formula (I) with methylamine, dimethylamine, trimethylamine, ethylamine, diethylamine, triethylamine, tromethamine, diethylaminoethanol, isopropylamine, 2-ethylaminoethanol, pyridine, picoline, ethanolamine, diethanolamine, ammonium, dimethylethanolamine, tetramethylammonium, tetraethylammonium, triethanolamine, piperidine, piperazine, morpholine, imidazolium salt, lysine, arginine, L-arginine, histidine, N-methylglucamine, dimethyl glucosamine, ethyl glucosamine, dicyclohexylamine, 1,6-hexanediamine, ethylenediamine, glucosamine, sarcosine, serinol, aminopropanediol, 1-amino-2,3,4-butanetriol, L-lysine, ornithine, etc.

Pharmaceutical Compositions, Formulations, Administrations and Uses of the Compounds and Compositions Thereof The invention features pharmaceutical compositions that include a compound of Formula (I) or a compound named in Examples, or a stereoisomer, a tautomer, an N-oxide, a solvate, a metabolite, a pharmaceutically acceptable salt or a prodrug thereof, and a pharmaceutically acceptable excipient. Chronic viral diseases caused by HBV maylead to serious disease. Chronic hepatitis B virus infection can lead to cirrhosis and/or hepatocellular carcinogenesis in many cases. The compound in the composition of the present invention can effectively inhibit hepatitis B virus and is suitable for the treatment of diseases caused by viruses, especially acute and chronic persistent HBV infection.

The compounds of the invention are especially suitable for the treatment of chronic hepatitis B virus infection and acute hepatitis B vims infection.

The invention includes pharmaceutical preparations which, in addition to the non-toxic, inert, pharmaceutically suitable excipients, also comprise one or more compounds (I) or compositions of the invention.

The above pharmaceutical preparation may also contain other active pharmaceutical ingredients other than the compound (I).

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutical compositions comprising any one of the compounds of formula (I) of the present invention further comprise pharmaceutically acceptable excipients, such as solvents, solid excipients, diluents, binders, disintegrating agents, or other liquid excipients, dispersing agents, flavoring or suspending agents, surfactants, isotonic agents, thickening agents, emulsifiers, preservative, solid binder or lubricant, as suited to the particular dosage form desired. As described in the following: In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, both of which are herein incorporated by reference in their entireties, discloses various excipients used in formulating pharmaceutically acceptable compositions and known techniques for the preparation thereof. Except insofar as any conventional excipients incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable excipients include ion exchanger; aluminum; aluminum stearate; lecithin; serum protein such as human serum albumin; buffer substance such as phosphate; glycine; sorbic acid; potassium sorbate; partial glyceride mixture of saturated vegetable fatty acid; water; salt or electrolyte such as protamine sulfate, disodium hydrogen phosphate, potassium hydrogen phosphate, sodium chloride and zinc salt; colloidal silica; magnesium trisilicate; polyvinyl pyrrolidone; polyacrylate; wax; polyethylene-polyoxypropylene-block polymer; wool fat; sugar such as lactose, glucose and sucrose; starch such as corn starch and potato starch; cellulose and its derivative such as sodium carboxymethyl cellulose, ethyl cellulose and cellulose acetate; powdered tragacanth; malt; gelatin; talc; excipients such as cocoa butter and suppository waxes; oil such as peanut oil, cottonseed oil, safflower oil, sesame oil, olive oil, corn oil and soybean oil; glycol such as propylene glycol and polyethylene glycol; ester such as ethyl oleate and ethyl laurate; agar; buffering agent such as magnesium hydroxide and aluminum hydroxide; alginic acid; pyrogen-free water; isotonic saline; Ringer's solution; ethyl alcohol and phosphate buffer solution, as well as other non-toxic compatible lubricant such as sodium lauryl sulfate and magnesium stearate, coloring agent, releasing agent, coating agent, sweetening, flavoring and perfuming agent, preservative and antioxidant.

The pharmaceutical composition of the compound of the present invention can be administered in any of the following aspects: oral administration, spray inhalation, topical administration, rectal administration, nasal administration, vaginal administration, parenteral administration such as subcutaneous, intravenous, intramuscular, intraperitoneal, intrapulmonary, intrathecal, intraventricular, intrasternal, or intracranial injection or infusion, or by means of an explanted reservoir. The preferred modes of administration are administered orally, intramuscularly, intraperitoneally or intravenously.

The compound of the invention or a pharmaceutically acceptable composition may be administered in unit dosage form. The dosage form can be a liquid dosage form or a solid dosage form Liquid dosage forms can be true solutions, colloids, microparticulates, suspensions. Other dosage forms such as tablets, capsules, dropping pills, aerosols, pills, powders, solutions, suspensions, emulsions, granules, suppositories, lyophilized powders, inclusions, implants, patches, wipes agents, etc.

Oral tablets and capsules may contain excipients such as binders such as syrup, acacia, sorbitol, tragacanth, or polyvinylpyrrolidone; fillers such as lactose, sucrose, cornstarch, calcium phosphate, sorbitol, glycine; lubricants such as magnesium stearate, talc, polyethylene glycol, silica; disintegrants such as potato starch; or acceptable humectants such as sodium lauryl sulfate. Tablets can be coated by methods known in the art of pharmacy.

The oral solution can be made into a suspension of water and oil, a solution, an emulsion, a syrup or a tincture, or it can be made into a dry product, supplemented with water or other suitable medium before use. This liquid preparation may contain conventional additives, such as suspending agents, sorbitol, cellulose methyl ether, glucose syrup, gel, hydroxyethyl cellulose, carboxymethyl cellulose, aluminum stearate gel, hydrogenated edible oils; emulsifiers, such as lecithin, sorbitol monooleate, gum arabic; or non-aqueous excipients (may contain edible oils) such as almond oil; greases such as glycerin, ethylene glycol or ethanol; preservatives such as methyl or propyl paraben, sorbic acid. Flavors or colorants are added if needed.

Suppositories may contain conventional suppository bases such as cocoa butter or other glycerides.

For parenteral administration, liquid dosage forms are usually made of a compound and a sterile excipient. Water is preferred for excipients. Depending on the concentration of the selected excipient and the drug, the compound can be dissolved in the excipient and can also be made into the suspension. In the preparation of the injectable solution, the compound is dissolved in water, filtered and sterilized, and then placed in a sealed bottle or ampoule.

When applied topically to the skin, the compounds of the invention may be formulated in the form of a suitable ointment, lotion, or cream, wherein the active ingredient is suspended or dissolved in one or more excipients, wherein excipients that can be used in ointment preparations include, but are not limited to, mineral oil, liquid petroleum jelly, white petrolatum, propylene glycol, polyethylene oxide, polypropylene oxide, emulsifying wax and water; adjuvants for lotions and creams include, but are not limited to, mineral oil, sorbitan monostearate, Tween 60, cetyl esters wax, hexadecene aryl alcohol, 2-octyldodecanol, benzyl alcohol and water.

In general, it has proven to be advantageous if the total amount of active compound administered according to the invention is from about 0.01 to 500 mg/kg body weight per 24 hours, preferably from 0.01 to 100 mg/kg body weight, whether in human or veterinary medicine. If appropriate, a single dose is administered repeatedly to achieve the desired effect. The amount of the active compound contained in a single dose is preferably from about 1 to 80 mg/kg body weight, more preferably from 1 to 50 mg/kg body weight, but it may not be in accordance with the above-mentioned dosage, namely, it depends on the type and weight of the subject, the nature and severity of the disease, type of formulation and mode of administration of the drug, as well as dosing cycle or time interval.

The pharmaceutical composition provided by the invention further comprises anti-HBV drugs. Wherein anti-HBV drugs are HBV polymerase inhibitors, immunomodulators, interferons or other novel anti-HBV agents such as HBV RNA replication inhibitors, HBsAg secretion inhibitors, HBV capsid inhibitors, antisense oligomers, siRNA, HBV therapeutic vaccine, HBV prophylactic vaccine, HBV antibody therapy (monoclonal or polyclonal), and agonists for the treatment or prevention of HBV.

Anti-HBV drugs include lamivudine, telbivudine, tenofovir, entecavir, adefovir dipivoxil, Alfaferone, Alloferon, celmoleukin, clafidine, emtricitabine, faciclovir, interferon, Baoganling CP, intepropen, interferon α-1b, interferon α, interferon α-2α, interferon β-1a, interferon α-2, interleukin-2, mivotate, nalozolidine, peginterferon α-2α, ribavirin, interferon-A, cilostaz, Euforavac, aplori, Phosphazid, Heplisav, interferon α-2b, levamisole or propafen, etc.

In one aspect, a compound or pharmaceutical composition of the invention is used in the manufacture of a medicament for preventing, managing, treating or reducing hepatitis B disease. Hepatitis B disease refers to hepatitis B virus infection or liver diseases caused by hepatitis B virus infection, including acute hepatitis, chronic hepatitis, cirrhosis and liver cancer. Acute hepatitis B virus infection can be asymptomatic or manifest as acute hepatitis symptoms. Patients with chronic viral infections have active diseases that can progress to cirrhosis and liver cancer.

The use of a compound or pharmaceutical composition of the invention comprises inhibiting the production or secretion of HBsAg, and further comprising administering to a patient a pharmaceutically acceptable effective amount of a compound or pharmaceutical composition of the invention.

The use of a compound or pharmaceutical composition of the invention comprises inhibiting the production of HBV DNA, and further comprising administering to a patient a pharmaceutically acceptable effective amount of a compound or pharmaceutical composition of the invention.

In one aspect, the use of a compound or pharmaceutical composition of the invention for inhibiting the expression of a HBV gene comprises administering to a patient a pharmaceutically acceptable effective amount of a compound or pharmaceutical composition of the invention.

Other anti-HBV drugs can be administered separately from the pharmaceutical composition comprising the compound of the present invention, as a part of the multi-administration regimen. Alternatively, those drugs may be part of a single dosage form, mixed with the compound of the present invention to form a single composition. If the administration is part of a multi-dosing regimen, the two active agents can be delivered to each other either continuously or over a period of time to obtain the target reagent activity.

The amount change of compound and composition that can be combined with the excipient material to produce a single dosage form (the one comprising a composition as described herein) depends on the attending and the particular mode of administration.

The compounds of the invention show a strong antiviral effect. These compounds have unexpected antiviral activity against HBV and are therefore suitable for the treatment of various diseases caused by the virus, especially those caused by acute and chronic persistent HBV infection. Chronic viral diseases caused by HBV can lead to a variety of syndromes of varying severity. It is well known that chronic hepatitis B virus infection can lead to cirrhosis and/or liver cancer.

Examples of indications that can be treated with the compounds of the invention are the treatment of acute and chronic viral infections that can cause infectious hepatitis, such as Hepatitis B virus infection, particularly preferably the treatment of chronic hepatitis B virus infection and acute hepatitis B vims infection.

The invention further relates to the use of the compounds and compositions of the invention for the manufacture of a medicament for the treatment and prevention of viral diseases, in particular hepatitis B.

General Synthetic Procedures

To describe the invention, the examples are listed below. However, it should be understood that the invention is not limited to the embodiments, but merely provides a method of practicing the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin Yu Yu Fine Chemical Ltd., Qingdao Tenglong Reagent Chemical Ltd., and Qingdao Ocean Chemical Factory.

$^1$H NMR spectra were recorded by a Bruker Avance 400 MHz spectrometer or Bruker Avance III HD 600 spectrometer, using $CDCl_3$, -DMSO-$d_6$, $CD_3OD$ or acetone-$d_6$ (reported in ppm) as solvent, and using TMS (0 ppm) or chloroform (7.26 ppm) as the reference standard. When peak multiplicities are reported, the following abbreviations are used: s (singlet), s, s (singlet, singlet), d (doublet), t (triplet), m (multiplet), br (broadened), dd (doublet of doublets), ddd (doublet of doublet of doublets), dt (doublet of triplets), ddt (doublet of doublet of triplets), td (triplet of doublets), br.s (broadened singlet). Coupling constants J, when given, were reported in Hertz (Hz).

Low-resolution mass spectral (MS) data were also determined on an Agilent 6320 series LC-MS spectrometer equipped with G1312A binary pumps and a G1316A TCC (Temperature Control of Column, maintained at 30° C.). A G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A quaternary pumps and a G1316A TCC (Temperature Control of Column, maintained at 30° C.). A G1329A autosampler and a G1315D DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1:

TABLE 1

The gradient elution conditions

| Time (min) | A (CH$_3$CN, 0.1% HCOOH) | B (H$_2$O, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purification of compounds was assessed by Agilent 1100 Series high performance liquid chromatography (HPLC) with UV detection at 210 nm and 254 nm (Zorbax SB-C18, 2.1×30 mm, 4 μm). The run time was 10 min, and the flow rate was 0.6 mL/min. The elution was performed with a gradient of 5 to 95% phase A (0.1% formic acid in CH$_3$CN) in phase B (0.1% formic acid in H$_2$O). Column was operated at 40° C.

The following abbreviations are used throughout the specification:

AcOK potassium acetate
MeCN, CH$_3$CN acetonitrile
MeOH methanol
DCM, CH$_2$Cl$_2$ dichloromethane
DBU 1,8-diazabicycloundec-7-ene
D$_2$O heavy water
DME dimethoxyethane
DMSO dimethylsulfoxide
DMF N,N-dimethylformamide
DMAP 4-dimethylaminopyridine
DIBAH diisobutylaluminum hydride
DMF-DMA N,N-dimethylformamide dimethylacetal
CHCl$_3$ chloroform, trichloromethane
dppf 1,1'-bis(diphenylphosphino)ferrocene
CDCl$_3$ chloroform-d
CCl$_4$ tetrachloro methane
Boc tert-butoxycarbonyl
BOC$_2$O di-tert-butyl dicarbonate
Bn benzyl
PE petroleum ether
Pd(dba)$_2$ bis(dibenzylideneacetone)palladium
Pd$_2$(dba)$_3$ tris(dibenzylideneacetone)dipalladium
Ph phenyl
DPEPhos bis(2-diphenylphosphino)phenyl ether
PhN(OTf)$_2$ N-phenylbis(trifluoromethanesulfonyl)imide
PTSA p-toluenesulfonic acid
EtOAc, EA ethyl acetate
EtOH ethyl alcohol
HCl hydrochloric acid
K$_2$CO$_3$ potassium carbonate
NaHCO$_3$ sodium bicarbonate
NH$_4$OAc ammonium acetate
NaOH sodium hydroxide
NaBH$_3$CN sodium cyanoborohydride
NaCl sodium chloride
Na$_2$SO$_4$ sodium sulfate
n-Bu n-butyl
n-BuLi n-butyllithium
Et$_3$N, TEA triethylamine
NBS N-bromosuccinimide
H$_2$O water
mL milliliter
min minute, minutes
m-CPBA m-chloroperoxybenzoic acid
M mol/L
h hour, hours
RT, rt room temperature
Rt retention time
H$_2$ hydrogen
HATU 2-(7-azobenzotriazole)-N, N, N',N'-tetramethyluron hexafluorophosphate
HCl/EtOAc ethyl chloride solution of hydrogen chloride
HOAT 1-hydroxy-7-azabenzotriazole
DIPEA N,N-diisopropylethylamine
DCC N,N'-dicyclohexylcarbodiimide
DMA N,N-dimethylacetamide
THF tetrahydrofuran
TFA trifluoroacetic acid
Tf trifluoromethanesulfonyl
LiOH·H$_2$O lithium hydroxide monohydrate
IPA isopropanol
CuCN cuprous cyanide
CH$_3$OH methanol
N$_2$ nitrogen
NH$_4$Cl ammonium chloride
NH$_4$OAc ammonium acetate
Ac$_2$O acetic anhydride
Xantphos 4,5-bisdiphenylphosphino-9,9-dimethyloxazepine
t$_{1/2}$ half life
t-BuOH tert-butanol
AUC the calculated Area Under the Curve
Vss the apparent volume of distribution at steady-state
CL, clearance
F, absolute bioavailability
Dose
T$_{max}$ maximum time
C$_{max}$ maximum concentration
hr*ng/mL blood concentration*time
Synthesis Method The following synthetic schemes set forth the synthetic steps for the preparation of the compounds disclosed in the present invention. Wherein each of R$^3$, R$^4$, R$^5$, R$^6$ and X$_1$ has the meaning as described in the present invention, and X is halogen. R$^{1a}$ is C$_{1-6}$ alkyl group or C$_{3-6}$ cycloalkyl group.

Scheme 1
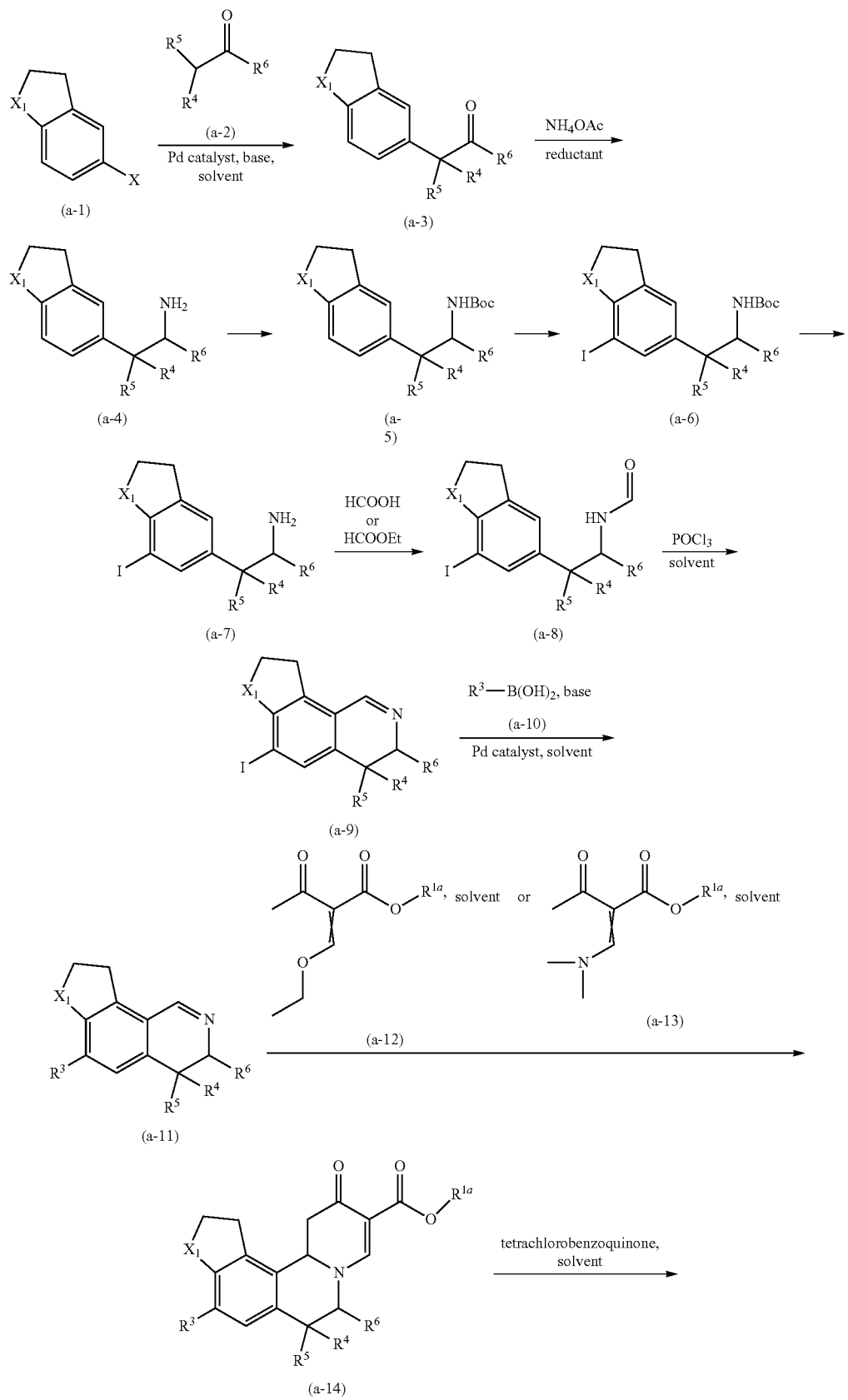

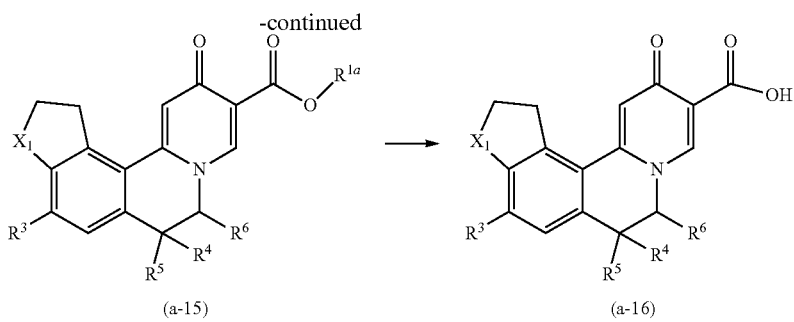

(a-15)　　　　(a-16)

Compound (a-16) disclosed herein can be prepared by the process illustrated in scheme 1. First, compound (α-1) is subjected to couple reaction with compound (a-2) in a palladium catalyst (e.g., Pd(dba)$_2$, Pd$_2$(dba)$_3$), a ligand (such as Xantphos), a suitable base (e.g., sodium tert-butoxide) and a suitable solvent (e.g., THF, toluene) to give compound (a-3). A reductive amination reaction of compound (a-3) and NH$_4$OAc occurs in a reducing agent (e.g., NaBH$_3$CN) and a suitable solvent (e.g., methanol) to give compound (a-4). Compound (a-4) is reacted with (BOC)$_2$O under basic conditions to give compound (a-5). Compound (a-5) is substituted with iodine to give compound (a-6). Then compound (a-6) is detached from amino protecting group Boc to give compound (a-7). Compound (a-7) is reacted with formic acid or ethyl formate to give compound (a-8). Then the ring formation reaction of compound (a-8) and phosphorus oxychloride occurs in a suitable solvent (e.g., DCM) to form compound (a-9). Next, the coupling reaction of compound (a-9) and compound (a-10) occurs in a palladium catalyst (e.g., tetratriphenylphosphine palladium), a suitable solvent (e.g., 1,4-dioxane, water) and a suitable base (e.g., sodium carbonate, potassium phosphate, potassium carbonate) to give compound (a-11). Compound (a-11) is cyclized with compound (a-12) or compound (a-13) in a suitable solvent (e.g., isopropanol, ethanol, DMSO) to give the compound (a-14). Compound (a-14) is dehydrogenated with tetrachlorophenyl hydrazine in a suitable solvent (e.g., DME) to give the compound (a-15). Last, compound (a-15) undergoes a hydrolysis reaction to give compound (a-16).

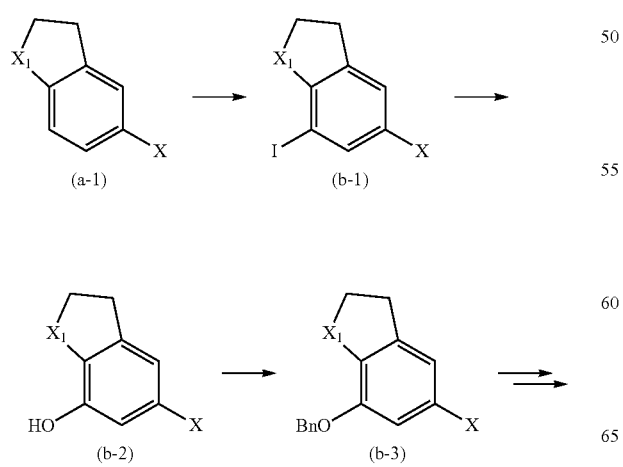

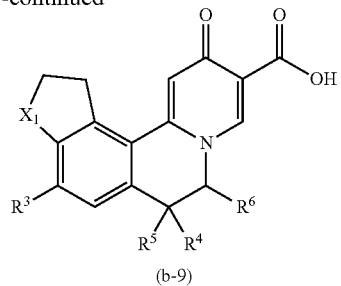

(b-9)

Compound (b-9) disclosed herein can be prepared by the process illustrated in scheme 2, wherein the double arrow in the synthesis scheme indicates a multi-step reaction. First, compound (a-1) is substituted with iodine in the existence of silver sulfate to form compound (b-1). A substitution reaction of compound (b-1) occurs under basic conditions (e.g., potassium hydroxide) to give compound (b-2). Compound (b-2) is protected with a benzyl group under basic conditions (e.g., $K_2CO_3$) to give the compound (b-3). Starting from compound (b-3), the synthesis procedure of compound (a-4) to compound (a-9) in the synthesis scheme 1 is carried out to give compound (b-4). Then starting from compound (a-4), referring to the synthetic procedure of compound (a-11) to compound (a-15) in the synthesis scheme 1, compound (b-5) can be obtained. Compound (b-5) is detached from benzyl protecting group in a palladium/carbon catalyst to give compound (b-6). Compound (b-6) is reacted with compound (b-7) or compound (B-7) under basic conditions (e.g., potassium carbonate) and in a suitable solvent (e.g., DMF) to give compound (b-8). Last, compound (b-8) is reacted in a base (e.g., lithium hydroxide) and a suitable solvent (e.g., methanol) to give compound (b-9).

Scheme 3

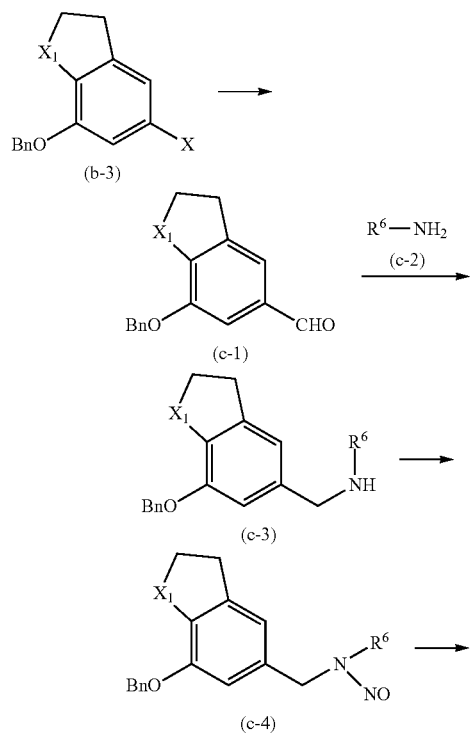

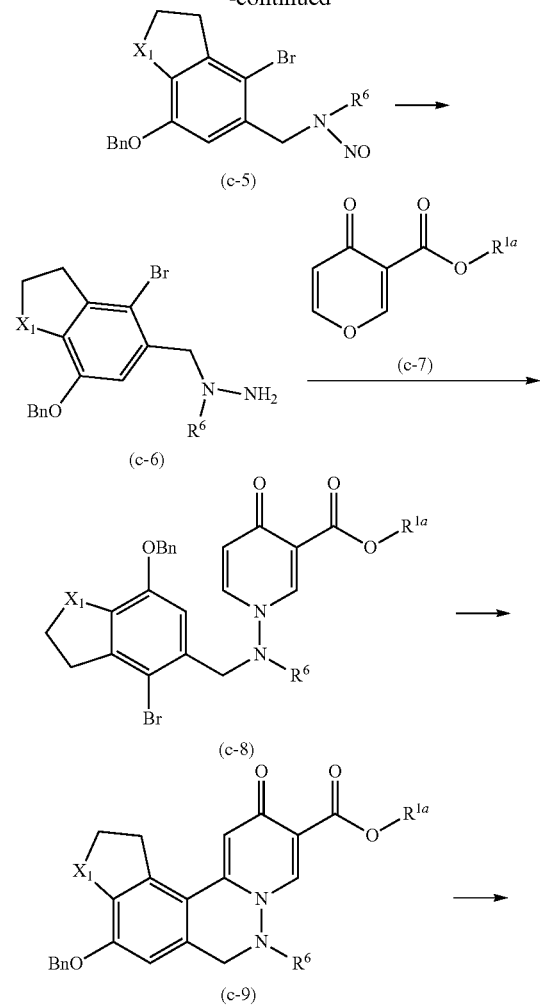

Compound (c-10) disclosed herein can be prepared by the process illustrated in scheme 3. First, compound (b-3) is reacted with DMF under low temperature conditions and in a suitable solvent (e.g., THF) to give the compound (c-1). A reductive animation reaction of compound (c-1) and compound (c-2) occurs in a suitable solvent (e.g., methanol) to give compound (c-3). Compound (c-3) is reacted with sodium nitrite under acidic conditions to give compound (c-4). Compound (c-4) is substituted with bromine to give compound (c-5). A reduction reaction of compound (c-5) occurs under acidic conditions (e.g., trifluoroacetic acid) to give compound (c-6). Compound (c-6) is reacted with compound (c-7) in a suitable solvent (e.g., methanol) to give compound (c-8). Then, a ring closure reaction of compound (c-8) occurs to give compound (c-9). Last, compound (c-9) is detached from benzyl protecting group to give compound (c-10).

Scheme 4

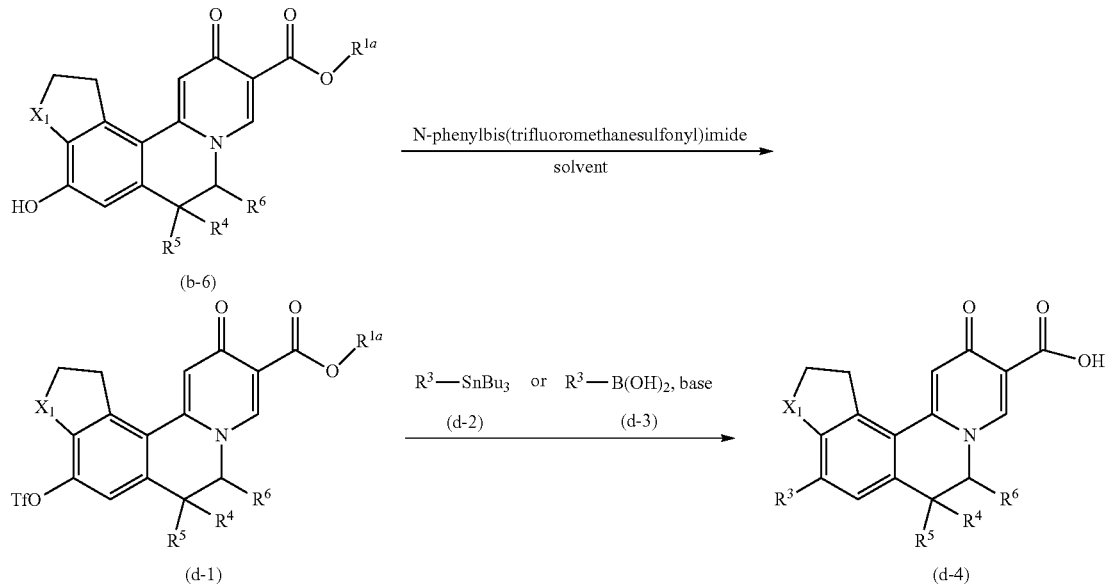

Compound (d-4) disclosed herein can be prepared by the process illustrated in scheme 4. First, compound (b-6) is reacted with N-phenylbis(trifluoromethanesulfonyl)imide under basic conditions (such as triethylamine) and in a suitable solvent (such as dichloromethane) to give compound (d-1). Then compound (d-1) is subjected to couple reaction with compound (d-2) in a palladium catalyst (such as [1,1'-bis(diphenylphosphino)ferrocene]palladium dichloride, bistriphenylphosphine dichloride palladium) and a suitable solvent (such as DMF) to give compound (d-4), or compound (d-1) is subjected to couple reaction with compound (d-3) in a suitable base (such as sodium carbonate, potassium phosphate, potassium carbonate) to give compound (d-4).

Scheme 5

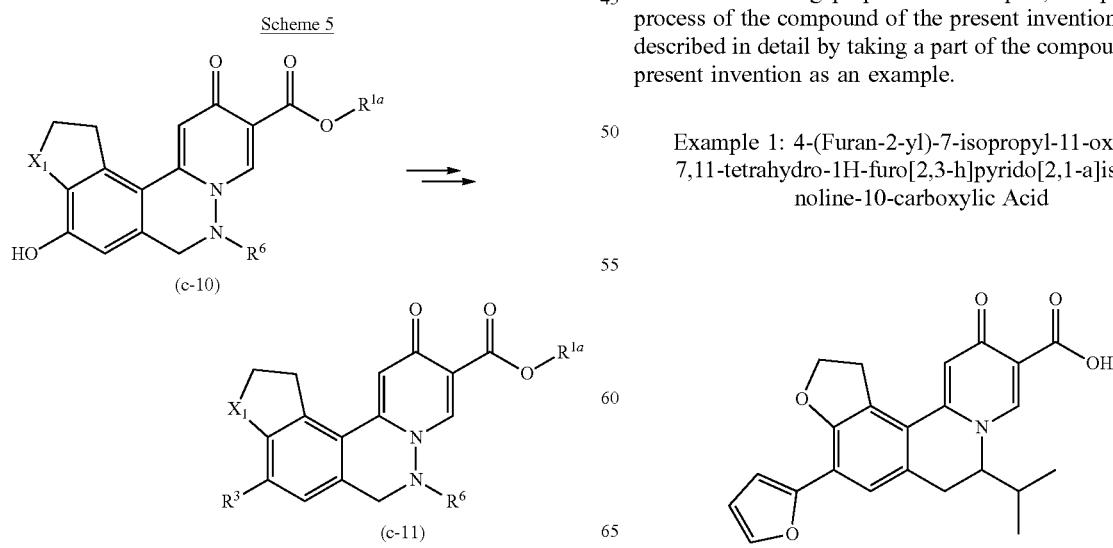

Starting from compound (c-10), referring to the synthetic procedure of compound (b-6) to compound (b-9) in the synthesis scheme 2 or the synthetic procedure in the synthesis scheme 4, compound (c-11) can be obtained.

EXAMPLES

The following examples are intended to illustrate the invention but are not intended to limit the scope of the invention.

Preparation Examples

In the following preparation examples, the preparation process of the compound of the present invention has been described in detail by taking a part of the compounds of the present invention as an example.

Example 1: 4-(Furan-2-yl)-7-isopropyl-11-oxo-2,6,7,11-tetrahydro-1H-furo[2,3-h]pyrido[2,1-a]isoquinoline-10-carboxylic Acid

63

Step 1: 5-iodo-2,3-dihydrobenzofuran

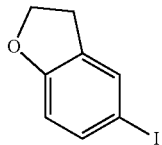

2,3-Dihydrobenzofuran (10.0 g, 83.2 mmol) and DCM (200 mL) were added into a 25 mL single-necked bottle, then N-iodosuccinimide (19.7 g, 87.6) was added in portions. The mixture was stirred at room temperature for 2 h. After the reaction was completed, the mixture was washed with saturated saline (200 mL) and extracted to get separated layers. The aqueous layer was extracted with DCM (100 mL×3), and the organic layers were combined and concentrated. The residue was purified by silica gel column chromatography (PE/EA (V/V)=10/1) to give the title compound as a brown solid (18 g, 73.159 mmol, 88%).

Step 2: 1-(2,3-Dihydrobenzofuran-5-yl)-3-methylbutan-2-one

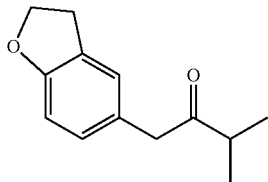

5-Iodo-2,3-dihydrobenzofuran (11.00 g, 44.71 mmol), Pd(dba)$_2$ (0.642 g, 1.12 mmol), Xantphos (1.035 g, 1.789 mmol), sodium tert-butoxide (12.89 g, 134.1 mmol), dioxane (110 mL) and 3-methyl-butan-2-one (11.55 g, 134.1 mmol) were added into a 500 mL two-necked flask, then the mixture was heated to 90° C. and stirred overnight. After the reaction was completed, the mixture was diluted with water (200 mL) and EA (300 mL), and was extracted to get separated layers. The aqueous layer was washed with EA (100 mL×2), then the organic layers were combined and concentrated. The residue was purified by silica gel column chromatography (PE/EA (V/V)=1/1) to give the title compound as brown oil (9.134 g, 44.71 mmol, 100.0%).

MS (ESI, pos.ion) m/z: 205.2 [M+H]$^+$.

Step 3: 1-(2,3-Dihydrobenzofuran-5-yl)-3-methylbutan-2-amine

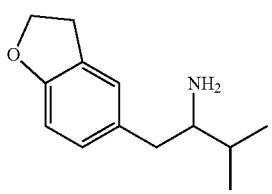

1-(2,3-Dihydrobenzofuran-5-yl)-3-methylbutan-2-one (9.134 g, 44.71 mmol), MeOH (100 mL) and NH$_4$OAc (17.23 g, 223.5 mmol) were added into a 50 mL single-necked bottle. The mixture was stirred at room temperature

64 for 1 h, cooled to 0° C. and added with NaBH$_3$CN (8.428 g, 134.1 mmol). Then the resulting mixture was heated to room temperature and stirred overnight. After the reaction was completed, the residue was concentrated. Then the mixture was diluted with water (150 mL), EA (200 mL) and aqueous ammonia (10 mL), and was extracted to get separated layers. The aqueous layer was extracted with EA (100 mL×3). The combined organic layers were concentrated in vacuo to give the title compound as brown oil (9.179 g, 44.71 mmol, 100.0%).

MS (ESI, pos.ion) m/z: 206.2 [M+H]$^+$.

Step 4: tert-Butyl (1-(2,3-dihydrobenzofuran-5-yl)-3-methylbutan-2-yl)carbamate

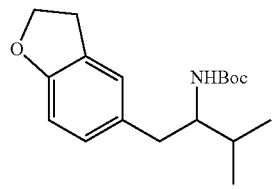 [SMILES: CC(C)C(Cc1ccc2c(c1)CCO2)NC(=O)OC(C)(C)C]

BOC$_2$O (13 g, 59.565 mmol), 1-(2,3-dihydrobenzofuran-5-yl)-3-methylbutan-2-amine (8.0 g, 39 mmol), THF (100 mL) and K$_2$CO$_3$ (16 g, 115.94 mmol) were added into a 100 mL single-necked bottle, then the mixture was warmed to 60° C. and stirred overnight. After the reaction was completed, the mixture was filtered, and the filtrate was concentrated in vacuo. The residue was purified by silica gel column chromatography (PE) twice to give the title compound as canary yellow oil (8.5 g, 28 mmol, 71%).

MS (ESI, pos.ion) m/z: 250.2 [M+H−56]$^+$.

Step 5: tert-Butyl (1-(7-iodo-2,3-dihydrobenzofuran-5-yl)-3-methylbutan-2-yl) carbamate

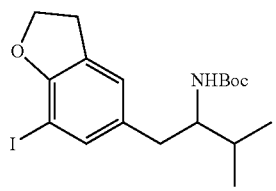 [SMILES: CC(C)C(Cc1cc(I)c2c(c1)CCO2)NC(=O)OC(C)(C)C]

tert-Butyl (1-(2,3-dihydrobenzofuran-5-yl)-3-methylbutan-2-yl)carbamate (8.5 g, 28 mmol), MeOH (200 mL) and Ag$_2$SO$_4$ (9.5 g, 31 mmol) were added into a 100 mL single-necked flask, then a solution of I$_2$ (0.740 g, 2.92 mmol) in MeOH (200 mL) was added dropwise. The mixture was stirred at room temperature for 1 h. Sodium sulfite (10 g) was added. The mixture was stirred for 10 min and filtered. The filter cake was washed with methanol (100 mL), and the filtrate was concentrated. The residue was purified by silica gel column chromatography (PE/EA (V/V)=10/1) to give the title compound as a white solid (10 g, 23.19 mmol, 83%).

MS (ESI, pos.ion) m/z: 332.1 [M+H−Boc]$^+$.

Step 6: 1-(7-Iodo-2,3-dihydrobenzofuran-5-yl)-3-methylbutan-2-amine

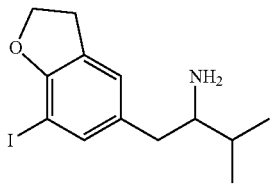 [SMILES: CC(C)C(N)Cc1cc(I)c2c(c1)CCO2]

tert-Butyl 1-(7-iodo-2,3-dihydrobenzofuran-5-yl)-3-methylbutan-2-yl) carbamate (1.0 g, 2.3 mmol) and DCM (9 mL) were added into a 100 mL single-necked flask, then TFA (3 mL) was added. The mixture was stirred at room temperature for 5 h and concentrated in vacuo, then 1M NaOH was added to the residue to adjust pH to 10-11. The resulting mixture was extracted with DCM (30 mL×3). The combined organic layers were concentrated in vacuo to give the title compound as brown oil (0.77 g, 2.3 mmol, 100%).
MS (ESI, pos.ion) m/z: 332.1 [M+H]$^+$.

Step 7: N-(1-(7-Iodo-2,3-dihydrobenzofuran-5-yl)-3-methylbutan-2-yl) carboxamide

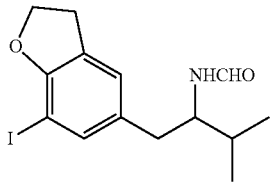

1-(7-Iodo-2,3-dihydrobenzofuran-5-yl)-3-methylbutan-2-amine (0.77 g, 2.3 mmol) and ethyl formate (15 mL) were added into a 50 mL single-necked flask, then the mixture was warmed to 75° C. and stirred overnight. The mixture was cooled to room temperature, then concentrated in vacuo. The residue was purified by silica gel column chromatography (PE/EA (V/V)=10/1) to give the title compound as a white solid (0.84 g, 2.3 mmol, 100%).
MS (ESI, pos.ion) m/z: 360.0 [M+H]$^+$.

Step 8: 6-Iodo-3-isopropyl-3,4,8,9-tetrahydrofuro[2,3-h]isoquinoline

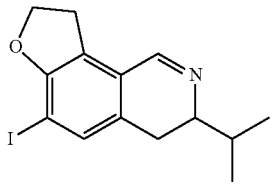 [SMILES: CC(C)C1Cc2cc(I)c3c(c2C=N1)CCO3]

N-(1-(7-Iodo-2,3-dihydrobenzofuran-5-yl)-3-methylbutan-2-yl) carboxamide (2.0 g, 5.6 mmol), acetonitrile (40 mL) and POCl$_3$ (1.3 mL, 14 mmol) were added into a 25 mL single-necked flask, then the mixture was warmed to 80° C. and stirred for 5 h. The mixture was cooled to room temperature and concentrated in vacuo. Then to the residue was added aqueous ammonia to adjust pH to 9-10. The resulting mixture was extracted with EA (30 mL×3). The combined organic layers were concentrated in vacuo. The residue was purified by silica gel column chromatography (EA) to give the title compound as brown oil (400 mg, 1.172 mmol, 21%).
MS (ESI, pos.ion) m/z: 342.1 [M+H]$^+$.

Step 9: 6-(Furan-2-yl)-3-isopropyl-3,4,8,9-tetrahydrofuro[2,3-h]isoquinoline

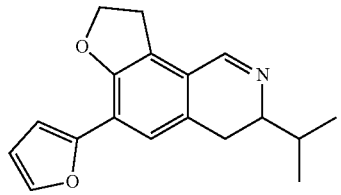 [SMILES: CC(C)C1Cc2cc(-c3ccco3)c3c(c2C=N1)CCO3]

6-Iodo-3-isopropyl-3,4,8,9-tetrahydrofuro[2,3-h]isoquinoline (300 mg, 0.8792 mmol), tetratriphenylphosphine palladium (101 mg, 0.087 mmol), H$_2$O (2 mL), K$_2$CO$_3$ (364 mg, 2.63 mmol), 1,4-dioxane (8 mL) and 2-furanboronic acid (147 mg, 1.31 mmol) were added into a 25 mL single-necked flask. The mixture was heated to 100° C. under nitrogen protection and stirred for 3 h. The mixture was cooled to room temperature and to the mixture was added saturated saline (20 mL). Then the resulting mixture was extracted with EA (30 mL×3). The combined organic layers were dried over anhydrous sodium sulfate and filtered, and the residue was purified by thin layer chromatography (PE/EA (V/V)=1/1) to give the title compound as brown oil (100 mg, 0.35 mmol, 40%).
MS (ESI, pos.ion) m/z: 282.1 [M+H]$^+$.

Step 10: Ethyl 4-(furan-2-yl)-7-isopropyl-11-oxo-2,6,7,11,12,12a-hexahydro-1H-furo[2,3-h]pyrido[2,1-a]isoquinoline-10-carboxylate

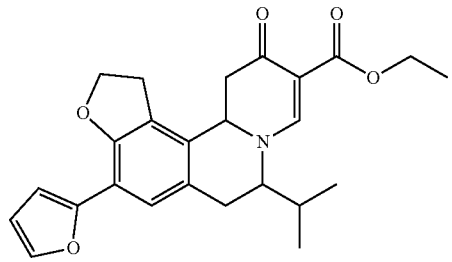 [SMILES: CCOC(=O)C1=CN2C(CC1=O)c1c(cc(-c3ccco3)c3c1CCO3)CC2C(C)C]

6-Iodo-3-isopropyl-3,4,8,9-tetrahydrofuro[2,3-h]isoquinoline (100 mg, 0.35 mmol), EtOH (10 mL) and ethyl 2-(ethoxymethylene)-3-oxo-butyrate (132 mg, 0.71 mmol) were added into a 50 mL single-necked flask. The mixture was heated to 90° C. under nitrogen protection and stirred overnight. After the reaction was completed, the mixture was concentrated in vacuo. The residue was purified by silica gel column chromatography (PE/EA (V/V)=1/1) to give the title compound as brown oil (46 mg, 0.11 mmol, 31%).
MS (ESI, pos.ion) m/z: 422.3 [M+H]$^+$.

Step 11: Ethyl 4-(furan-2-yl)-7-isopropyl-11-oxo-2,6,7,11 tetrahydro-1H-furo[2,3-h]pyrido[2,1-a]isoquinoline-10-carboxylate

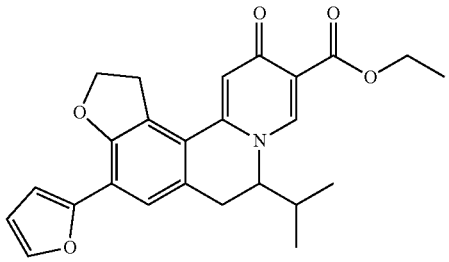 [SMILES: CCOC(=O)c1cn2c(cc1=O)-c1c(cc(-c3ccco3)c3c1CCO3)CC2C(C)C]

Ethyl 4-(furan-2-yl)-7-isopropyl-11-oxo-2,6,7,11,12,12a-hexahydro-1H-furo[2,3-h]pyrido[2,1-a]isoquinoline-10-carboxylate (46 mg, 0.1091 mmol) and ethylene glycol dimethyl ether (5 mL) were added to a 100 mL single-necked flask, then to the mixture was added tetrachlorophenylhydrazine (53 mg, 0.21557 mmol). The mixture was stirred overnight at room temperature, then warmed to 90° C. and stirred for 3 h. The mixture was concentrated and the residue was purified by thin layer chromatography (DCM/MeOH (V/V)=10/1) to give the title compound as brown oil (46 mg, 0.11 mmol).

Step 12: 4-(Furan-2-yl)-7-isopropyl-11-oxo-2,6,7,11 tetrahydro-1H-furo[2,3-h]pyrido[2,1-a]isoquinoline-10-carboxylic Acid

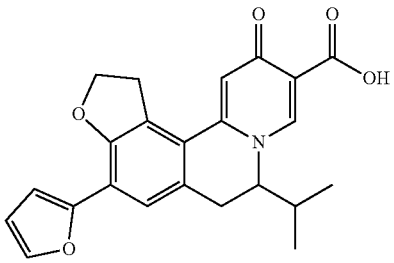

A mixture of ethyl 4-(furan-2-yl)-7-isopropyl-11-oxo-2,6,7,11 tetrahydro-1H-furo[2,3-h]pyrido[2,1-a]isoquinoline-10-carboxylate (40 mg, 0.09535 mmol), LiOH (16 mg, 0.381 mmol), EtOH (2 mL), H$_2$O (1 mL) and THF (2 mL) was stirred overnight at room temperature, then concentrated in vacuo. The residue was diluted with water (5 mL), and then added with 1M HCl to adjust pH to 3-4. The resulting mixture was extracted with DCM (10 mL×3). The combined organic layers were concentrated in vacuo. The residue was purified by thin layer chromatography (DCM/MeOH (V/V)=10/1) to give the title compound as a yellow solid (30 mg, 0.077 mmol, 80%).

MS (ESI, pos.ion) m/z: 392.1 [M+H]$^+$;

$^1$H NMR (400 MHz, CDCl$_3$) δ (ppm) 15.882 (b, 1H), 8.518 (s, 1H), 7.562 (d, J=10.8, 2H), 7.100 (d, J=10.8, 1H), 7.042 (s, 1H), 6.579 (s, 1H), 5.014-4.958 (m, 1H), 4.698-4.627 (m, 1H), 3.951-3.843 (m, 1H), 3.789-3.677 (m, 1H), 3.460-3.328 (m, 2H), 3.259-3.167 (m, 1H), 1.8275-1.743 (m, 1H), 0.971 (d, J=6.4 Hz, 3H), 0.881 (d, J=6.8 Hz, 3H).

Example 2: 7-Isopropyl-4-(3-methoxypropoxy)-11-oxo-2,6,7,11-tetrahydro-1H-furo[2,3-h]pyrido[2,1-a]isoquinoline-10-carboxylic Acid

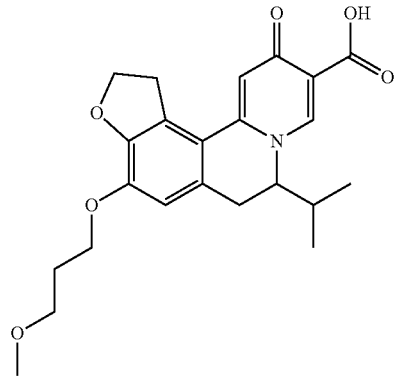 [SMILES: COCCCOc1cc2c(c3c1OCC3)-c1cc(=O)c(C(=O)O)cn1C(C(C)C)C2]

Step 1: 5-Bromo-2,3-dihydrobenzofuran

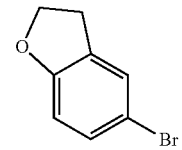

2,3-Dihydrobenzofuran (15.26 g, 127.00 mmol) was dissolved in DCM (300 mL). To the resulting solution was added pyridine tribromide (45.13 g, 127.00 mmol) at 0° C. The mixture was stirred for 10 min, then warmed to room temperature and stirred for 60 min. The reaction was quenched with saturated sodium hydrogen sulfite solution (the solution was changed from brownish red to pale yellow). The mixture was partitioned. The organic layers were collected and the aqueous phase was extracted with dichloromethane (100 mL×1). The organic layers were combined, and the combined organic layers were washed with saturated sodium chloride solution, dried over anhydrous sodium sulfate and filtered. The solvent was evaporated in vacuo to give the title compound as a pale yellow solid (22.8 g, 90%).

1H NMR (400 MHz, CDCl$_3$) δ 7.28 (s, 1H), 7.20 (d, J=8.4 Hz, 1H), 6.66 (d, J=8.4 Hz, 1H), 4.57 (t, J=8.7 Hz, 2H), 3.20 (t, J=8.7 Hz, 2H).

Step 2: 5-Bromo-7-iodo-2,3-dihydrobenzofuran

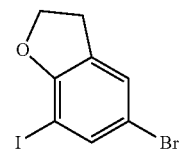

5-Bromo-2,3-dihydrobenzofuran (20.9 g, 105 mmol) was dissolved in methanol (300 mL), then to the mixture were added silver sulfate (16.5 g, 52.7 mmol, 0.5 eq) and iodine (29.3 g, 115 mmol, 1.1 eq). The mixture was stirred for 3 h at room temperature, then quenched with sodium bisulfite solid (the solution was changed from brownish red to pale yellow). The solid was removed by suction filtration through a celite pad, then the filter cake was washed with ethyl acetate (100 mL×2). The filtrate was collected, and the solvent was evaporated in vacuo. The residue was diluted with ethyl acetate (200 mL) and saturated aqueous sodium bisulfite solution (200 mL). The mixture was partitioned. The upper organic layer was collected. The organic layer was washed with saturated sodium chloride solution, dried over anhydrous sodium sulfate and filtered. The solvent was evaporated in vacuo to give the title compound as a yellow solid (30.23 g, 93.03 mmol, 88.6%).

$^1$H NMR (400 MHz, CDCl$_3$) δ 7.55 (s, 1H), 7.23 (s, 1H), 4.65 (t, J=8.8 Hz, 2H), 3.33 (t, J=8.8 Hz, 2H).

Step 3: 5-Bromo-2,3-dihydrobenzofuran-7-ol

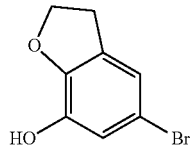

5-Bromo-7-iodo-2,3-dihydrobenzofuran (9.65 g, 29.7 mmol), N,N'-bis(4-hydroxy-2,6-dimethylphenyl)oxamide (585 mg, 1.78 mmol), copper acetylacetonate (467 mg, 1.78 mmol), dimethyl sulfoxide (24 mL) and a solution of potassium hydroxide (5 g, 89.11 mmol) in water (6 mL) were added into the dried reaction flask. The reaction mixture was degassed and refilled with nitrogen for three times, then heated to 60° C. and stirred for 5 h under nitrogen protection. After completion of the reaction, the reaction mixture was filtered through a celite pad to remove solids, and the filter cake was washed with aqueous sodium hydroxide (100 mL, pH=10) and methyl tert-butyl ether (100 mL). The filtrate was collected and partitioned, and the lower aqueous layer was collected and washed with methyl tert-butyl ether (50 mL×2). 1M Hydrochloric acid was added into the aqueous layer to adjust pH to about 4, then ethyl acetate (100 mL) was added. The resulting mixture was partitioned. The upper organic layer was collected. The aqueous phase was extracted with ethyl acetate (50 mL×2). The combined organic layers were washed with saturated sodium chloride solution three times, dried over anhydrous sodium sulfate and filtered. The solvent was evaporated in vacuo to give the title compound as a brownish black solid (6.12 g, 28.5 mmol, 95.8%).

$^1$H NMR (400 MHz, CDCl$_3$) δ 6.97-6.62 (m, 2H), 5.07 (s, 1H), 4.62 (t, J=8.7 Hz, 2H), 3.23 (t, J=8.7 Hz, 2H).

Step 4: 7-(Benzyloxy)-5-bromo-2,3-dihydrobenzofuran

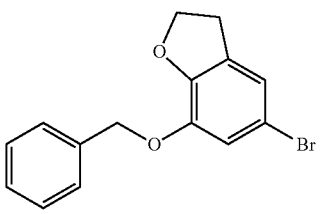 [SMILES: Brc1cc2c(c(OCc3ccccc3)c1)OCC2]

5-Bromo-2,3-dihydrobenzofuran-7-ol (4.562 g, 21.21 mmol) was dissolved in acetonitrile (100 mL), then to the solution were added K$_2$CO$_3$ (8.8 g, 63.65 mmol) and benzyl bromide (2.77 mL, 23.3 mmol). The reaction mixture was heated to 80° C. and stirred for 5 h. The mixture was filtered to remove insoluble solids, then the filtrate was concentrated in vacuo. The residue was purified by silica gel column chromatography (PE/EA (V/V)=5/1) to give the title compound as awhile solid (6.3 g, 21 mmol, 97%).

$^1$H NMR (400 MHz, CDCl$_3$) δ 7.36 (ddd, J=22.6, 16.0, 7.1 Hz, 5H), 6.96 (s, 1H), 6.90 (s, 1H), 5.11 (s, 2H), 4.63 (t, J=8.8 Hz, 2H), 3.21 (t, J=8.8 Hz, 2H).

Step 5: 1-(7-(Benzyloxy)-2,3-dihydrobenzofuran-5-yl)-3-methylbutan-2-one

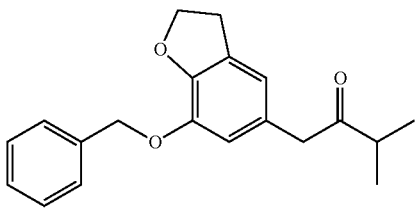 [SMILES: CC(C)C(=O)Cc1cc2c(c(OCc3ccccc3)c1)OCC2]

To the reaction flask were sequentially added 7-(benzyloxy)-5-bromo-2,3-dihydrobenzofuran (1 g, 3.277 mmol), xantphos (0.189 g, 0.327 mmol), sodium tert-butoxide (0.629 g, 6.54 mmol), Pd$_2$(dba)$_3$ (0.15 g, 0.16 mmol), sodium tert-butoxide (0.629 g, 6.54 mmol) and THF (15 mL), then 3-methyl-butan-2-one (1.05 mL, 9.79 mmol) was added in an ice-bath. After addition, the air in the flask was replaced with nitrogen, and then the mixture was heated to 60° C. and stirred for 7 h. The reaction was stopped. The reaction mixture was cooled to room temperature, then concentrated in vacuo. The resulting residue was diluted with ethyl acetate (50 mL) and water (50 mL). The organic layer was separated and concentrated in vacuo. The residue was purified by silica gel column chromatography (PE/EA (V/V)=20/1) to give the title compound as a white solid (0.68 g, 2.2 mmol, 67%).

MS (ESI, pos.ion) m/z: 311.1[M+H]$^+$.

Step 6: 1-(7-(Benzyloxy)-2,3-dihydrobenzofuran-5-yl)-3-methylbutan-2-amine

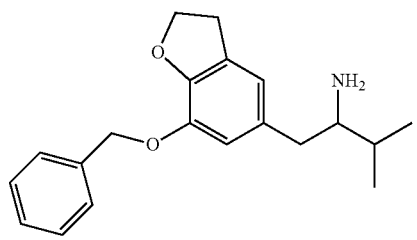 [SMILES: CC(C)C(N)Cc1cc2c(c(OCc3ccccc3)c1)OCC2]

1-(7-(Benzyloxy)-2,3-dihydrobenzofuran-5-yl)-3-methylbutan-2-one (0.68 g, 2.2 mmol) was dissolved in MeOH (6.8 mL, 170 mmol), then to the solution was added ammonium acetate (1.2 g, 16 mmol). The mixture was stirred at room temperature for 30 min, then cooled to 0° C. Then sodium cyanoborohydride (0.28 g, 4.4 mmol) was added. After addition, the reaction mixture was warmed to room temperature and stirred for 12 h. After completion of the reaction, the reaction mixture was evaporated in vacuo to remove methanol. Then the reaction was quenched with saturated aqueous sodium bicarbonate solution (20 mL) and the resulting mixture was extracted with ethyl acetate (20 mL×2). The combined organic phases were washed with saturated sodium chloride solution (20 mL×1), dried over anhydrous sodium sulfate, and concentrated in vacuo to give the title compound as yellow oily liquid which was used directly in the next step.

MS (ESI, pos.ion) m/z: 312.5[M+H]+.

Step 7: N-(1-(7-(benzyloxy)-2,3-dihydrobenzofuran-5-yl)-3-methylbutan-2-yl) carboxamide

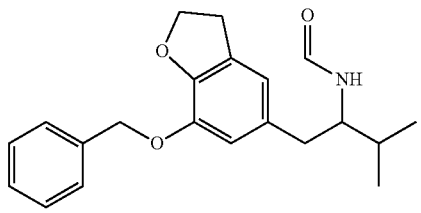 [SMILES: CC(C)C(Cc1cc2c(c(OCc3ccccc3)c1)OCC2)NC=O]

1-(7-(Benzyloxy)-2,3-dihydrobenzofuran-5-yl)-3-methylbutan-2-amine (0.68 g, 2.2 mmol), dichloromethane (6.8 mL), EDCI (0.63 g, 3.3 mmol) and DIPEA (0.42 g, 3.2 mmol) were added into a reaction flask and cooled to 0° C. Then formic acid (0.17 mL, 4.4 mmol) was added dropwise and the mixture was heated to room temperature and stirred for 3 h. After completion of the reaction, hydrochloric acid (5 mL, 1 M) was added and the mixture was partitioned. The organic layer was dried over anhydrous sodium sulfate and filtered. The filtrate was concentrated in vacuo. The residue was purified by silica gel column chromatography (DCM/MeOH(V/V)=20/1) to give the title compound as a white solid (0.503 g, 1.48 mmol, 68%).

MS (ESI, pos.ion) m/z: 340.5 [M+H]+.

Step 8: 6-(Benzyloxy)-3-isopropyl-3,4,8,9-tetrahydrofuro[2,3-h]isoquinoline

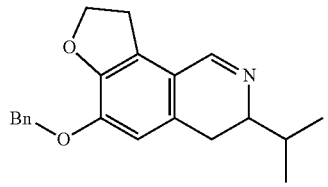 [SMILES: CC(C)C1Cc2cc(OCc3ccccc3)c3c(c2C=N1)CCO3]

N-(1-(7-(Benzyloxy)-2,3-dihydrobenzofuran-5-yl)-3-methylbutan-2-yl) carboxamide (0.503 g, 1.48 mmol) and DCM (5 mL) were added into a reaction flask and cooled to 0° C. Then phosphorus oxychloride (0.419 mL, 4.45 mmol) was added dropwise into the mixture. The resulting mixture was then stirred at room temperature for 1 h, then concentrated in vacuo. Water (50 mL) and ethyl acetate (50 mL) were added to the residue, then potassium carbonate solid was slowly added portionwise in an ice bath to adjust pH to basicity. The resulting mixture was partitioned and the aqueous phase was extracted with ethyl acetate (100 mL×1). The organic layers were combined and the combined organic layers were washed with saturated sodium chloride solution (100 mL×1), dried over anhydrous sodium sulfate, filtered, and concentrated in vacuo. The residue was purified by silica gel column chromatography (PE/EA(V/V)=1/1) to give the title compound as a pale yellow solid (0.23 g, 0.72 mmol, 48%).

MS (ESI, pos.ion) m/z: 322.3[M+H]+.

Step 9: Ethyl 4-(benzyloxy)-7-isopropyl-11-oxo-2,6,7,11,12,12a-hexahydro-1H-furo[2,3-h]pyrido[2,1-a]isoquinoline-10-carboxylate

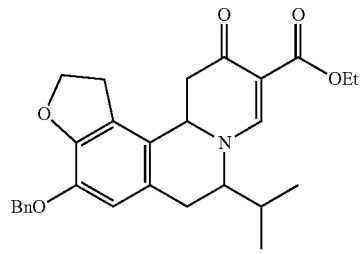 [SMILES: CCOC(=O)C1=CN2C(CC1=O)c1c(cc(OCc3ccccc3)c3c1CCO3)CC2C(C)C]

To the reaction flask were added 6-(benzyloxy)-3-isopropyl-3,4,8,9-tetrahydrofuro [2,3-h]isoquinoline (0.205 g, 0.64 mmol), ethyl 2-(ethoxymethylene)-3-oxobutanoate (0.24 g, 1.28 mmol) and ethanol (8 mL). The mixture was warmed to 90° C. and stirred for 2 h. After the reaction was completed, the mixture was concentrated in vacuo. The residue was purified by silica gel column chromatography (DCM/MeOH(V/V)=10/1) to give the title compound as brown oil (0.229 g, 0.496 mmol, 77.8%).

MS (ESI, pos.ion) m/z: 462.2[M+H]+.

Step 10: Ethyl 4-(benzyloxy)-7-isopropyl-11-oxo-2,6,7,11-tetrahydro-1H-furo[2,3-h]pyrido [2,1-a]isoquinoline-10-carboxylate

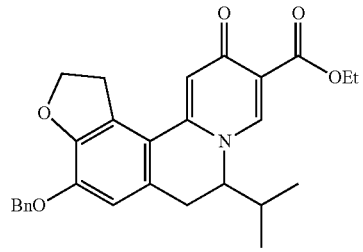 [SMILES: CCOC(=O)c1cn2c(cc1=O)-c1c(cc(OCc3ccccc3)c3c1CCO3)CC2C(C)C]

4-(Benzyloxy)-7-isopropyl-11-oxo-2,6,7,11,12,12a-hexahydro-1H-furo[2,3-h]pyrido[2,1-a]isoquinoline-10-carboxylic acid (0.229 g, 0.496 mmol) was dissolved in ethylene glycol dimethyl ether (5 mL, 47.6 mmol), then to the mixture was added tetrachlorobenzene (0.134 g, 0.545 mmol). The mixture was warmed to 90° C. and stirred for 5 h. The filtrate was concentrated in vacuo and the residue was purified by silica gel column chromatography (DCM/MeOH (V/V)=10/1) to give the title compound as a brown solid (0.147 g, 0.320 mmol, 65%).

MS (ESI, pos.ion) m/z: 460.8[M+H]+.

Step 11: Ethyl 4-hydroxy-7-isopropyl-11-oxo-2,6,7,11-tetrahydro-1H-furo[2,3-h]pyrido[2,1-a]isoquinoline-10-carboxylate

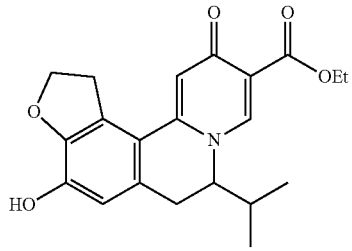 [SMILES: CCOC(=O)c1cn2c(cc1=O)-c1c(cc(O)c3c1CCO3)CC2C(C)C]

Ethyl 4-(benzyloxy)-7-isopropyl-11-oxo-2,6,7,11-tetrahydro-1H-furo[2,3-h]pyrido[2,1-a]isoquinoline-10-carboxylate (0.147 g, 0.320 mmol) was added into the reaction flask, then methanol (5 mL) was added to dissolved it. To the solution was added 10% palladium carbon (0.147 g, 0.691 mmol). The air in the flask was replaced with hydrogen, then the mixture was stirred at room temperature for 3 h. After the reaction was completed, the mixture was filtered through a celite pad and the filtrate was concentrated in vacuo to give the title compound as a yellow solid (95 mg, 0.26 mmol, 80%).

MS (ESI, pos.ion) m/z: 370.1[M+H]$^+$.

Step 12: Ethyl 7-isopropyl-4-(3-methoxypropoxy)-11-oxo-2,6,7,11-tetrahydro-1H-furo[2,3h]pyrido[2,1-a]isoquinoline-10-carboxylate

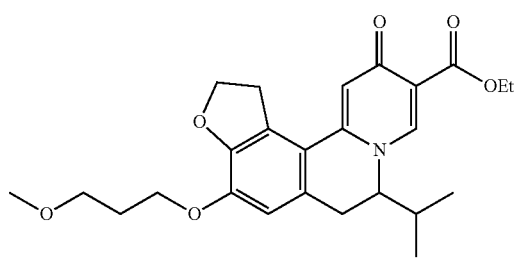 [SMILES: CCOC(=O)c1cn2c(cc1=O)-c1c(cc(OCCCOC)c3c1CCO3)CC2C(C)C]

To the reaction flask were added ethyl 4-hydroxy-7-isopropyl-11-oxo-2,6,7,11-tetrahydro-1H-furo[2,3-h]pyrido[2,1-a]isoquinoline-10-carboxylate (0.095 g, 0.26 mmol), DMF (5 mL), potassium carbonate (0.071 g, 0.51 mmol) and 1-bromo-3-methoxypropane (0.079 g, 0.52), then the mixture was heated to 70° C. and stirred for 2 h. After completion of the reaction, water (10 mL) was added. The mixture was extracted with dichloromethane (10 mL×2). The organic layers were combined, dried over anhydrous sodium sulfate and filtered. The filtrate was concentrated in vacuo to give brown oily liquid which was used directly in the next step.

MS (ESI, pos.ion) m/z: 442.3[M+H]$^+$.

Step 13: 7-Isopropyl-4-(3-methoxypropoxy)-11-oxo-2,6,7,11-tetrahydro-1H-furo[2,3-h]pyrido[2,1-a]isoquinoline-10-carboxylic Acid

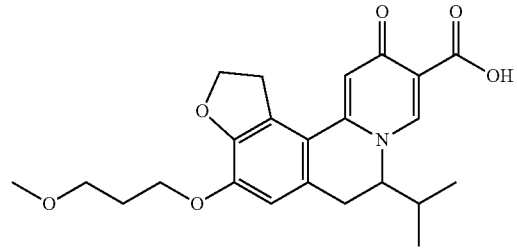 [SMILES: COCCCOc1cc2c(c3c1OCC3)-c1cc(=O)c(C(=O)O)cn1C(C(C)C)C2]

To the reaction flask were added ethyl 7-isopropyl-4-(3-methoxypropoxy)-11-oxo-2,6,7,11-tetrahydro-1H-furo[2,3-h]pyrido [2,1-a]isoquinoline-10-carboxylate (110 mg, 0.25 mmol), methanol (5 mL) and lithium hydroxide mono hydrate (11 mg, 2.6 mmol), then the mixture was stirred at room temperature for 4 h. After the reaction was completed, the reaction mixture was concentrated in vacuo. Water (5 mL) was added to dissolve the residue and 1M hydrochloric acid was added to adjust pH to 5. Then the resulting mixture was extracted with dichloromethane (10 mL×2). The organic layers were combined, dried over anhydrous sodium sulfate and filtered. The filtrate was concentrated in vacuo and to the residue was added methanol (1 mL). The resulting mixture was stirred at room temperature for 4 h and filtered to give the title compound as a white solid (13 mg, 0.031 mmol, 13%).

MS (ESI, pos.ion) m/z: 414.2[M+H]$^+$;

$^1$H NMR (400 MHz, CDCl$_3$) δ 16.01 (s, 1H), 8.50 (s, 1H), 6.92 (s, 1H), 6.72 (s, 1H), 4.88 (td, J=9.8, 4.0 Hz, 1H), 4.57 (q, J=9.5 Hz, 1H), 4.27-4.14 (m, 2H), 3.89 (dd, J=9.5, 3.8 Hz, 1H), 3.69 (dt, J=15.3, 10.5 Hz, 1H), 3.63-3.52 (m, 2H), 3.43-3.28 (m, 5H), 3.08 (d, J=15.9 Hz, 1H), 2.13 (p, J=6.1 Hz, 2H), 1.77 (qd, J=13.3, 6.6 Hz, 1H), 0.95 (d, J=6.6 Hz, 3H), 0.85 (d, 7=6.7 Hz, 3H).

Example 2A: (S)-7-Isopropyl-4-(3-methoxypropoxy)-11-oxo-2,6,7,11-tetrahydro-1H-furo [2,3-h]pyrido[2,1-a]isoquinoline-10-carboxylic Acid

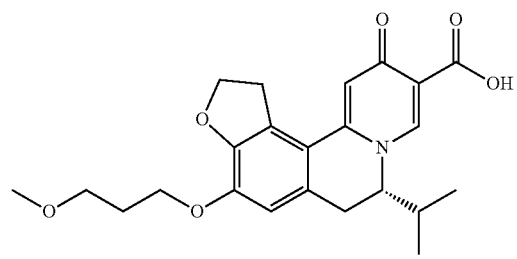

Step 1: (S)-1-(7-(Benzyloxy)-2,3-dihydrobenzo-furan-5-yl)-3-methylbutan-2-amine

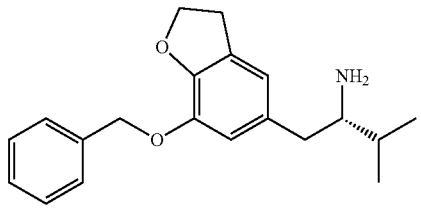 [SMILES: CC(C)[C@@H](N)Cc1cc2c(c(OCc3ccccc3)c1)OCC2]

1-(7-(benzyloxy)-2,3-dihydrobenzofuran-5-yl)-3-methylbutan-2-amine (10.0 g, 32.15 mmol) was added into EA (1000 mL). The mixture was stirred for 30 min, and then a solution of (2S) 2-acetylamino-3-methyl-butyric acid (2.59 g, 16.26 mmol) in EA (1000 mL) was added. The resulting mixture was stirred for 1 h at room temperature. Then the mixture was filtered and the filter cake was washed with EA (100 mL). The resulting solid was added into a solution of Na$_2$CO$_3$ (10.3 g, 97.2 mmol) in H$_2$O (100 mL) and DCM (100 mL) and the mixture was stirred for 2 h at room temperature. The organic layer was separated, dried over anhydrous sodium sulfate, filtered and concentrated in vacuo to give the title compound as a white solid (3.3 g, 10.6 mmol, 30%, ee=98.98%).

Step 2: Ethyl (S)-4-hydroxy-7-isopropyl-11-oxo-2,6,7,11-tetrahydro-1H-furo[2,3-h]pyrido[2,1-a]isoquinoline-10-carboxylate

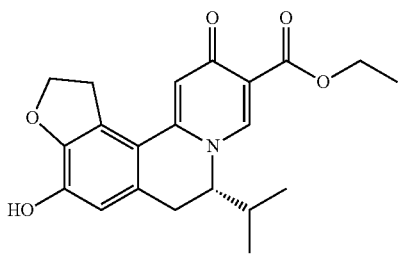 [SMILES: CCOC(=O)c1cn2c(cc1=O)-c1c(cc(O)c3c1CCO3)C[C@H]2C(C)C]

Starting from (S)-1-(7-(benzyloxy)-2,3-dihydrobenzofuran-5-yl)-3-methylbutan-2-amine, referring to the synthesis steps 7 to 11 in Example 2, the title compound was obtained as a white solid.
MS (ESI, pos.ion) m/z: 370.2[M+H]$^+$.

Step 3: (S)-7-Isopropyl-4-(3-Methoxypropoxy)-11—Oxo-2,6,7,11-Tetrahydro-1H-Furo[2,3-h]Pyrido[2,1-a]isoquinoline-10-Carboxylic Acid

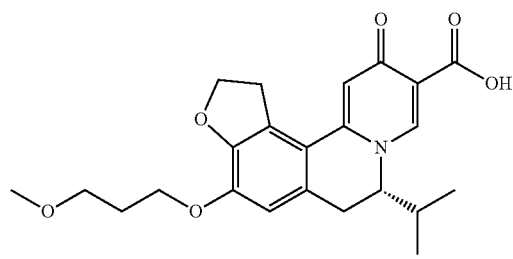

Starting from ethyl (S)-4-hydroxy-7-isopropyl-11-oxo-2,6,7,11-tetrahydro-1H-furo[2,3-h]pyrido[2,1-a]isoquinoline-10-carboxylate, referring to the synthesis steps 12 to 13 in Example 2, the title compound was obtained as a white solid.
MS (ESI, pos.ion) m/z: 414.2[M+H]$^+$;
$^1$H NMR (400 MHz, CDCl$_3$) δ 8.56 (s, 1H), 7.02 (s, 1H), 6.72 (s, 1H), 4.88 (td, J=10.0, 3.9 Hz, 1H), 4.58 (q, J=9.5 Hz, 1H), 4.29-4.16 (m, 2H), 3.99-3.88 (m, 1H), 3.70 (m, 1H), 3.64-3.54 (m, 2H), 3.42-3.29 (m, 5H), 3.09 (d, J=15.9 Hz, 1H), 2.13 (p, J=6.2 Hz, 2H), 1.79 (m, 1H), 0.96 (d, J=6.6 Hz, 3H), 0.86 (d, J=6.7 Hz, 3H).

Example 3: 4-(2-Cyclopropylethoxy)-7-isopropyl-11-oxo-2,6,7,11-tetrahydro-1H-furo[2,3-h]pyrido[2,1-a]isoquinoline-10-carboxylic Acid

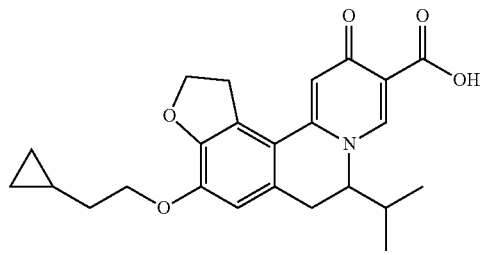 [SMILES: CC(C)C1Cc2cc(OCCC3CC3)c3c(c2-c2cc(=O)c(C(=O)O)cn21)CCO3]

Starting from ethyl 4-hydroxy-7-isopropyl-11-oxo-2,6,7,11-tetrahydro-1H-furo[2,3-h]pyrido[2,1-a]isoquinoline-10-carboxylate and 2-cyclopropylethyl methanesulfonate, referring to the experimental method of the synthesis steps 12 to 13 in Example 2, the title compound was obtained as a white solid.
MS (ESI, pos.ion) m/z: 410.4[M+H]$^+$;
$^1$H NMR (400 MHz, CDCl$_3$) δ 15.99 (s, 1H), 8.48 (s, 1H), 6.93 (s, 1H), 6.71 (s, 1H), 4.88 (td, J=10.1, 4.1 Hz, 1H), 4.58 (dd, J=19.5, 9.4 Hz, 1H), 4.25-4.14 (m, 2H), 3.86 (dd, J=9.9, 3.6 Hz, 1H), 3.70 (dt, J=15.5, 10.5 Hz, 1H), 3.36 (ddd, J=15.6, 9.2, 4.3 Hz, 2H), 3.09 (d, J=15.8 Hz, 1H), 1.79 (dq, J=13.7, 6.8 Hz, 3H), 0.96 (d, J=6.6 Hz, 3H), 0.88 (t, J=6.5 Hz, 4H), 0.53 (q, J=5.0 Hz, 2H), 0.15 (q, J=4.9 Hz, 2H).

Example 4: 4-(2-Cyclopropoxyethoxy)-7-isopropyl-11-oxo-2,6,7,11-tetrahydro-1H-furo [2,3-h]pyrido[2,1-a]isoquinoline-10-carboxylic Acid

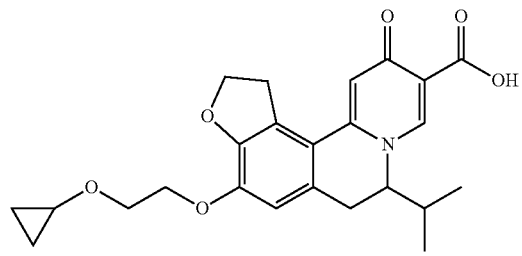 [SMILES: CC(C)C1Cc2cc(OCCOC3CC3)c3c(c2-c2cc(=O)c(C(=O)O)cn21)CCO3]

Starting from ethyl 4-hydroxy-7-isopropyl-11-oxo-2,6,7,11-tetrahydro-1H-furo[2,3-h]pyrido[2,1-a]isoquinoline-10-carboxylate and 2-(cyclopropoxy) ethyl-4-methylbenzenesulfonate, referring to the experimental method of the synthesis steps 12 to 13 in Example 2, the title compound was obtained as a white solid.

MS (ESI, pos.ion) m/z: 426.0[M+H]+;

¹H NMR (400 MHz, CDCl₃) δ 16.01 (s, 1H), 8.49 (s, 1H), 6.91 (s, 1H), 6.70 (d, J=12.3 Hz, 1H), 4.85 (td, J=9.4, 3.8 Hz, 1H), 4.55 (q, J=9.5 Hz, 1H), 4.26 (d, J=4.6 Hz, 2H), 3.93-3.84 (m, 3H), 3.67 (dt, J=15.4, 10.6 Hz, 1H), 3.46-3.26 (m, 3H), 3.06 (d, J=15.8 Hz, 1H), 1.74 (qd, J=13.2, 6.5 Hz, 1H), 0.95 (t, J=14.2 Hz, 3H), 0.81 (dd, J=30.0, 6.2 Hz, 3H), 0.61 (s, 2H), 0.54-0.43 (m, 2H).

Example 5: 7-Isopropyl-11-oxo-4-((tetrahydro-2H-pyran-4-yl)methoxy)-2,6,7,11-tetrahydro-1H-furo[2,3-h]pyrido[2,1-a]isoquinoline-10-carboxylic Acid

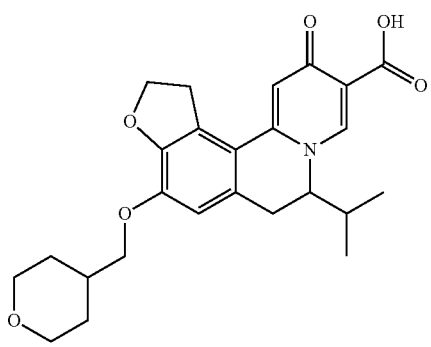 [SMILES: CC(C)C1Cc2cc(OCC3CCOCC3)c3c(c2-c2cc(=O)c(C(=O)O)cn21)CCO3]

Starting from ethyl 4-hydroxy-7-isopropyl-11-oxo-2,6,7,11-tetrahydro-1H-furo[2,3-h]pyrido[2,1-a]isoquinoline-10-carboxylate and 4-(bromomethyl)tetrahydropyran, referring to the experimental method of the synthesis steps 12 to 13 in Example 2, the title compound was obtained as a white solid.

¹H NMR (400 MHz, CDCl₃) δ 15.99 (s, 1H), 8.49 (s, 1H), 6.92 (s, 1H), 6.68 (s, 1H), 4.87 (td, J=9.8, 3.9 Hz, 1H), 4.57 (q, J=9.5 Hz, 1H), 4.03 (dd, J=113, 3.3 Hz, 2H), 3.95 (d, J=6.6 Hz, 2H), 3.89 (d, J=6.0 Hz, 1H), 3.69 (dt, J=15.4, 10.6 Hz, 1H), 3.46 (t, J=11.6 Hz, 2H), 3.41-3.27 (m, 2H), 3.08 (d, J=15.9 Hz, 1H), 2.16 (dd, J=9.3, 5.5 Hz, 1H), 1.79 (t, J=12.6 Hz, 3H), 1.46 (td, J=12.0, 3.3 Hz, 2H), 0.95 (d, J=6.6 Hz, 3H), 0.84 (t, J=12.5 Hz, 3H).

Example 6: 7-Isopropyl-11-oxo-4-phenylethoxy-2,6,7,11-tetrahydro-1H-furo[2,3-h]pyrido [2,1-a]isoquinoline-10-carboxylic Acid

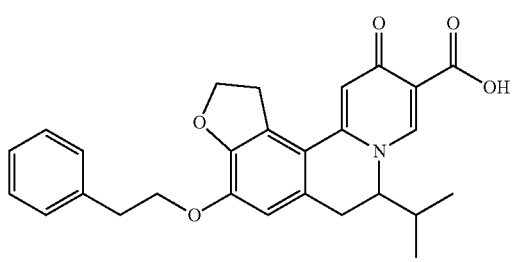 [SMILES: CC(C)C1Cc2cc(OCCc3ccccc3)c3c(c2-c2cc(=O)c(C(=O)O)cn21)CCO3]

Starting from ethyl 4-hydroxy-7-isopropyl-11-oxo-2,6,7,11-tetrahydro-1H-furo[2,3-h]pyrido[2,1-a]isoquinoline-10-carboxylate and (2-bromomethyl) benzene, referring to the synthesis steps 12 to 13 in Example 2, the title compound was obtained as awhile solid.

MS (ESI, pos.ion) m/z: 446.1[M+H]+;

¹H NMR (400 MHz, CDCl₃) δ 15.99 (s, 1H), 8.48 (s, 1H), 7.38-7.26 (m, 5H), 6.91 (d, J=10.6 Hz, 1H), 6.64 (s, 1H), 4.89 (td, J=9.7, 4.0 Hz, 1H), 4.58 (dd, J=19.5, 9.4 Hz, 1H), 4.32 (t, J=7.4 Hz, 2H), 3.85 (dd, J=9.6, 3.9 Hz, 1H), 3.69 (dt, J=15.5, 10.5 Hz, 1H), 3.43-3.26 (m, 2H), 3.19 (t, J=7.4 Hz, 2H), 3.04 (d, J=15.9 Hz, 1H), 1.73 (d, J=6.7 Hz, 1H), 0.92 (t, J=8.8 Hz, 3H), 0.85 (d, J=6.7 Hz, 3H).

Example 7: 7-Isopropyl-11-oxo-4-(3,3,3-trifluoropropoxy)-2,6,7,11-tetrahydro-1H-furo [2,3-h]pyrido [2,1-a]isoquinoline-10-carboxylic Acid

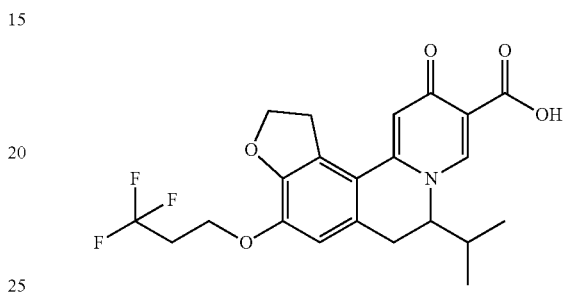

Starting from ethyl 4-hydroxy-7-isopropyl-11-oxo-2,6,7,11-tetrahydro-1H-furo[2,3-h]pyrido[2,1-a]isoquinoline-10-carboxylate and 3-bromo-1,1,1-trifluoropropane, referring to the experimental method of the synthesis steps 12 to 13 in Example 2, the title compound was obtained as a white solid.

MS (ESI, pos.ion) m/z: 438.1[M+H]+;

¹H NMR (400 MHz, CDCl₃) δ 15.91 (s, 1H), 8.49 (s, 1H), 6.94 (s, 1H), 6.71 (s, 1H), 4.90 (td, J=10.0, 4.0 Hz, 1H), 4.58 (dd, J=19.5, 9.4 Hz, 1H), 4.38 (t, J=6.7 Hz, 2H), 3.87 (dd, J=9.8, 3.7 Hz, 1H), 3.71 (dt, J=15.7, 10.5 Hz, 1H), 3.43-3.28 (m, 2H), 3.10 (d, J=15.9 Hz, 1H), 2.80-2.63 (m, 2H), 1.82-1.72 (m, 1H), 0.96 (d, J=6.6 Hz, 3H), 0.87 (d, J=6.7 Hz, 3H).

Example 8: 7-isopropyl-11-oxo-4-(thiazol-2-yl)-2,6,7,11-tetrahydro-1H-furo[2,3-h]pyrido [2,1-a]isoquinoline-10-carboxylic Acid

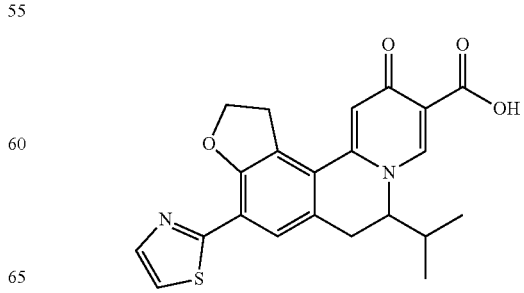

Step 1: Ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate

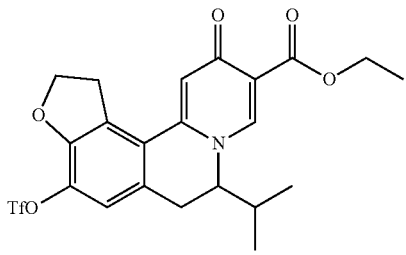 [SMILES: CCOC(=O)c1cn2c(cc1=O)-c1c(cc(OS(=O)(=O)C(F)(F)F)c3c1CCO3)CC2C(C)C]

Ethyl 4-hydroxy-7-isopropyl-11-oxo-2,6,7,11-tetrahydro-1H-furo[2,3-h]pyrido[2,1-a]isoquinoline-10-carboxylate (320 mg, 0.8663 mmol) was dissolved in DCM (10 mL), then the mixture was cooled to 0° C. Triethylamine (208 mg, 2.63 mmol) was added and the mixture was stirred for 30 min, then PhN(OTf)$_2$ (618 mg, 1.73 mmol) was added in portions and the mixture was slowly warmed to room temperature and stirred overnight. The mixture was concentrated and the residue was purified by silica gel column chromatography (DCM/MeOH(V/V)=15/1) to give the title compound as a yellow solid (301 mg, 0.60 mmol, 69%).

MS (ESI, pos.ion) m/z: 502.1[M+H]$^+$.

Step 2: 7-Isopropyl-11-oxo-4-(thiazol-2-yl)-2,6,7,11-tetrahydro-1H-furo[2,3-h]pyrido [2,1-a]isoquinoline-10-carboxylic Acid

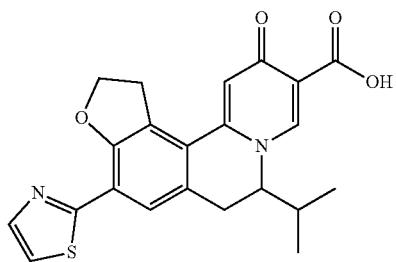 [SMILES: CC(C)C1Cc2cc(-c3nccs3)c3c(c2-c2cc(=O)c(C(=O)O)cn21)CCO3]

Ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate (260 mg, 0.52 mmol), tributyl(thiazol-2-yl)tin (485 mg, 1.296 mmol), anhydrous DMF (9 mL) and [1,1'-bis(diphenylphosphino)ferrocene]palladium dichloride (75 mg, 0.1025 mmol) were added to a 50 mL single-necked flask, then the mixture was heated to 100° C. under nitrogen protection and stirred for 12 h. Postprocessing: the mixture was cooled to room temperature, then water (20 mL) was added. The resulting mixture was extracted with DCM (20 mL×4) and the organic layers were combined. The combined organic layers were washed with water (20 mL×3) and concentrated. The residue was purified by silica gel column chromatography (DCM/MeOH(V/V)=15/1) to give the title compound as yellow oil (80 mg, 0.20 mmol, 38%).

MS (ESI, pos.ion) m/z: 409.2[M+H]$^+$;
$^1$H NMR (400 MHz, CDCl$_3$) δ 15.75 (s, 1H), 8.54 (s, 1H), 8.11 (s, 1H), 7.99 (s, 1H), 7.54 (s, 1H), 7.08 (s, 1H), 5.13-5.07 (m, 1H), 4.76 (q, J=9.4 Hz, 1H), 3.97-3.70 (m, 2H), 3.50 (dd, J=13.4, 8.6 Hz, 1H), 3.33 (dd, J=35.5, 15.2 Hz, 2H), 1.85-1.70 (m, 1H), 0.97 (d, J=6.5 Hz, 3H), 0.88 (d, J=6.6 Hz, 3H).

Example 9: 7-Isopropyl-4-(1-isopropyl-1H-pyrazol-4-yl)-11-oxo-2,6,7,11-tetrahydro-1H-furo[2,3-h]pyrido[2,1-a]isoquinoline-10-carboxylic Acid

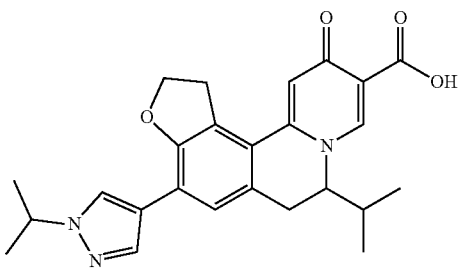 [SMILES: CC(C)C1Cc2cc(-c3cnn(C(C)C)c3)c3c(c2-c2cc(=O)c(C(=O)O)cn21)CCO3]

Ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate (1.60 g, 3.19 mmol), 1-isopropyl-4-(4,4,5,5-tetramethyl-1,3,2-dioxaborolan-2-yl)-1H-pyrazole (2.64 g, 11.2 mmol), dppfPdCl$_2$ (467 mg, 0.638 mmol), DMF (24 mL), K$_2$CO$_3$ (1.76 g, 12.8 mmol) and H$_2$O (6 mL) were added to a 50 mL single-necked flask, then the mixture was heated to 100° C. under nitrogen protection and stirred for 12 h. The mixture was cooled to room temperature and lithium hydroxide monohydrate (402 mg, 9.6 mmol) was added. Then the resulting mixture was stirred at room temperature for 12 h. The mixture was diluted with water (240 mL) and 1M HCl aqueous solution was added to adjust PH to 2~3. The resulting mixture was filtered and the filter cake was washed with water (50 mL). The filter cake and ethanol (20 mL) were added to a flask. The mixture was stirred for 4 h and filtered. Then the filter cake was washed with ethanol (10 mL) and dried to give the title compound as an off-white solid (1.25 g, 2.9 mmol, 90%).

MS (ESI, pos.ion) m/z: 434.3[M+H]$^+$;
$^1$H NMR (400 MHz, CDCl$_3$) δ 15.92 (s, 1H), 8.50 (s, 1H), 8.06 (s, 1H), 7.99 (s, 1H), 7.31 (s, 1H), 7.02 (s, 1H), 4.95 (td, J=10.2, 3.9 Hz, 1H), 4.68-4.53 (m, 2H), 3.93-3.84 (m, 1H), 3.73 (dt, J=15.7, 10.2 Hz, 1H), 3.46-3.30 (m, 2H), 3.18 (d, J=15.6 Hz, 1H), 1.85-1.73 (m, 1H), 1.59 (d, J=6.7 Hz, 6H), 0.97 (d, J=6.6 Hz, 3H), 0.88 (d, J=6.7 Hz, 3H).

Example 10: 4-(l (Difluoromethyl)-1H-pyrazol-4-yl)-7-isopropyl-11-oxo-2,6,7,11-tetrahydro-1H-furo[2,3-h]pyrido[2,1-a]isoquinoline-10-carboxylic Acid

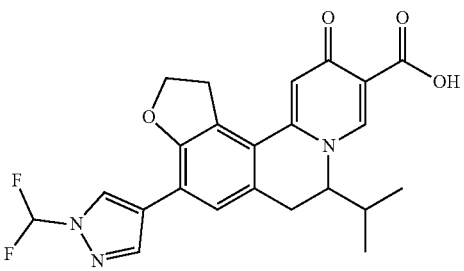

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 1-(difluoromethyl)-4-(4,4,5,5-tetramethyl-1,3,2-dioxaborolan-2-yl)-1H-pyrazole, referring to the synthesis method in Example 9, the title compound was obtained as an off-white solid.

MS (ESI, pos.ion) m/z: 441.9[M+H]$^+$;

$^1$H NMR (400 MHz, CDCl$_3$) δ 15.82 (s, 1H), 8.53 (s, 1H), 8.45 (s, 1H), 8.15 (s, 1H), 7.26 (d, J=60.5 Hz, 1H), 7.34 (s, 1H), 7.04 (s, 1H), 4.99 (td, J=10.0, 3.8 Hz, 1H), 4.66 (dd, J=19.2, 9.5 Hz, 1H), 3.92 (d, J=7.4 Hz, 1H), 3.76 (dt, J=15.8, 10.5 Hz, 1H), 3.48-3.32 (m, 2H), 3.20 (d, J=15.7 Hz, 1H), 1.84-1.73 (m, 1H), 0.98 (d, J=6.5 Hz, 3H), 0.89 (d, J=6.6 Hz, 3H).

Example 11: 7-Isopropyl-11-oxo-4-(thiophen-2-yl)-2,6,7,11-tetrahydro-1H-furo[2,3-h]pyrido[2,1-a]isoquinoline-10-carboxylic Acid

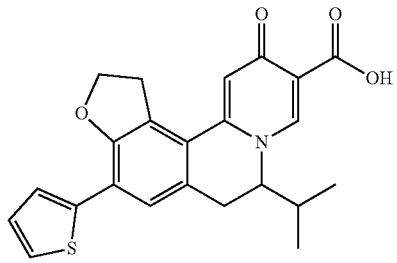 [SMILES: CC(C)C1Cc2cc(-c3cccs3)c3c(c2-c2cc(=O)c(C(=O)O)cn21)CCO3]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and tributyl (thiophen-2-yl) tin, referring to the synthesis method in Example 8, the title compound was obtained as a gray solid.

MS (ESI, pos.ion) m/z: 408.2[M+H]$^+$;

$^1$H NMR (400 MHz, CDCl$_3$) δ 15.87 (s, 1H), 8.53 (s, 1H), 7.75 (d, J=3.2 Hz, 1H), 7.46-7.36 (m, 2H), 7.22-7.13 (m, 1H), 7.03 (s, 1H), 4.98 (td, J=10.0, 3.7 Hz, 1H), 4.66 (q, J=9.4 Hz, 1H), 3.92 (d, J=8.6 Hz, 1H), 3.74 (dt, J=15.2, 10.5 Hz, 1H), 3.47-3.29 (m, 2H), 3.19 (d, J=15.4 Hz, 1H), 1.84-1.75 (m, 1H), 0.97 (d, J=6.6 Hz, 3H), 0.88 (d, J=6.6 Hz, 3H).

Example 12: 5-(3-Methoxypropoxy)-1,1-dimethyl-10-oxo-2,3,3a,7,8,10-hexahydro-1H-furo[3,2-f]pyrido[1,2-c]pyrrolo[2,1-a]phthalazine-11-carboxylic Acid

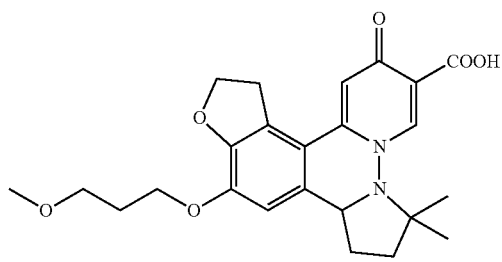 [SMILES: COCCCOc1cc2c(c3c1OCC3)-c1cc(=O)c(C(=O)O)cn1N1C2CCC1(C)C]

Step 1: (5-7-(Benzyloxy)-2,3-dihydrobenzofuran-5-yl)-dimethylpyrrolidin-1-ol

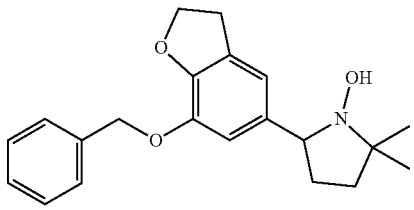 [SMILES: CC1(C)CCC(c2cc3c(c(OCc4ccccc4)c2)OCC3)N1O]

To the reaction flask were added magnesium (0.88 g, 36 mmol), THF (2 mL) and a solution of diisobutylaluminum hydride in toluene (1.1 mL, 1.7 mmol, 1.5 mol/L). The air in the flask was replaced with nitrogen. 7-(Benzyloxy)-5-bromo-2,3-dihydrobenzofuran (10 g, 32.77 mmol) was dissolved in THF (50 mL). A small amount of the solution was added dropwise to the above reaction mixture. The resulting mixture was slightly heated with the hair dryer. The reaction was triggered when a small amount of bubbles generated were observed. Then the remaining solution of 7-(benzyloxy)-5-bromo-2,3-dihydrobenzofuran in THF was added continuously. After the addition was completed, the reaction mixture was reacted at 60° C. for 8 h. The reaction mixture was filtered to remove excess magnesium dust and the filtrate was cooled to −10° C. Then 5,5-dimethyl-1-pyrroline-N-oxide (4.1 g, 36 mmol) was added. After the addition, the reaction was continued for 15 min. To the mixture was added saturated aqueous ammonium chloride solution (50 mL) to quench the reaction. The resulting mixture was extracted with ethyl acetate (100 mL×2). The organic layers were combined and the combined organic layers were washed with saturated aqueous sodium chloride solution (100 mL) and concentrated. The residue was purified by silica gel column chromatography (PE/EA(V/V)=10/1) to give the title compound as a pale yellow solid (5.0 g, 15 mmol, 45%).

MS (ESI, pos.ion) m/z: 340.2[M+1]$^+$.

Step 3: (5-7-(Benzyloxy)-2,3-dihydrobenzofuran-5-yl)-dimethylpyrrolidine

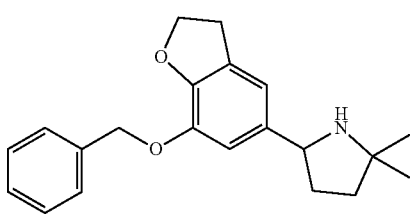 [SMILES: CC1(C)CCC(c2cc3c(c(OCc4ccccc4)c2)OCC3)N1]

(5-7-(Benzyloxy)-2,3-dihydrobenzofuran-5-yl)-dimethylpyrrolidin-1-ol (5.0 g, 15 mmol), methanol (25 mL) and glacial acetic acid (25 mL) were added to the reaction flask. Zinc powder (19 g, 290 mmol) was added under the ice-bath. After the addition, the mixture was heated to 60° C. and stirred for 6 h. LC-MS detected the complete reaction of raw materials. The reaction mixture was filtered and the filtrate was concentrated. The residue was diluted with water (20 mL), then potassium carbonate was added to adjust pH to 8~9. The resulting mixture was extracted with ethyl acetate (20 mL×2) and the organic layers were combined. The combined organic layers were washed with saturated aqueous sodium chloride solution (30 mL) and dried over anhydrous sodium sulfate. The solvent was evaporated under reduced pressure to give the title compound as a yellow solid (4.5 g, 14 mmol, 94%).

MS (ESI, pos.ion) m/z: 323.9[M+1]$^+$.

Step 4: (5-7-(Benzyloxy)-2,3-dihydrobenzofuran-5-yl)-dimethyl-1-nitrosopyrrolidine

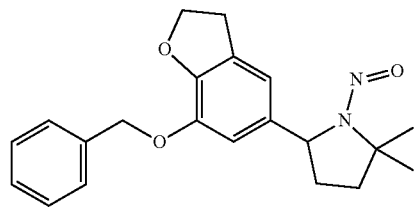 [SMILES: CC1(C)CCC(c2cc3c(c(OCc4ccccc4)c2)OCC3)N1N=O]

5-7-(Benzyloxy)-2,3-dihydrobenzofuran-5-yl)-dimethylpyrrolidine (1.6 g, 4.9 mmol) was dissolved in tetrahydrofuran (10 mL), then a solution of sodium nitrite (0.85 g, 12 mmol) in water (5 mL) and glacial acetic acid (0.74 g, 12 mmol) were added sequentially. After the addition, the mixture was warmed to 50° C. and stirred for 1 h. LC-MS detected the completion of the reaction. The reaction mixture was concentrated in vacuo. Ethyl acetate (20 mL) was added to dissolve the residue. Then the mixture was washed with saturated aqueous sodium chloride solution (20 mL) and the organic layer was concentrated in vacuo. The residue was purified by silica gel column chromatography (PE/EA (V/V)=2/1) to give the title compound as a pale yellow solid (1.1 g, 3.1 mmol, 63%).

MS (ESI, pos.ion) m/z: 353.3[M+1]$^+$.

Step 5: 5-(7-(Benzyloxy)-4-bromo-2,3-dihydrobenzofuran-5-yl)-2,2-dimethyl-1-nitrosopyrrolidine

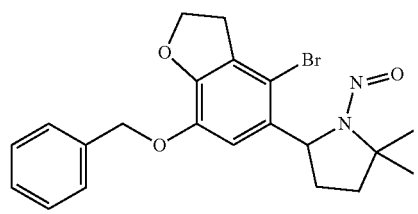 [SMILES: CC1(C)CCC(c2cc(OCc3ccccc3)c3c(c2Br)CCO3)N1N=O]

(5-7-(Benzyloxy)-2,3-dihydrobenzofuran-5-yl)-dimethyl-1-nitrosopyrrolidine (2.20 g, 6.24 mmol), DMF (20 mL) and NBS (1.2 g, 6.6 mmol) were added into the reaction flask. The mixture was stirred at room temperature for 2 h. LC-MS detected the completion of the reaction. To the mixture was added water (50 mL) to quench the reaction. The resulting mixture was extracted with EA (30 mL×2). The organic layers were combined and the combined organic layers were washed with saturated aqueous sodium chloride solution (50 mL×3) and concentrated. The residue was purified by silica gel column chromatography (PE/EA(V/V)=2/1) to give the title compound as a pale yellow solid (2.3 g, 5.3 mmol, 85%).

MS (ESI, pos.ion) m/z: 431.1[M+1]$^+$.

Step 6: Ethyl 2-((dimethylamino)methylene)-3-oxobutanoate

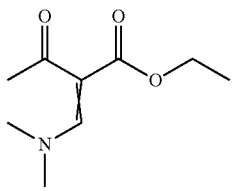

Ethyl acetoacetate (20 g, 153.68 mmol), 1,4-dioxane (200 mL) and N, N-dimethylformamide dimethyl acetal (36.62 g, 307.3 mmol) were sequentially added to the reaction flask. The mixture was stirred at room temperature for 12 h. After the completion of the reaction was monitored by TLC, the mixture was stopped stirring and concentrated in vacuo. Water (200 mL) and dichloromethane (200 mL) were added and the mixture was partitioned. The lower organic layer was collected, and the aqueous layer was extracted with dichloromethane (200 mL×3). The organic layers were combined, washed with saturated sodium chloride solution (300 mL), dried over anhydrous sodium sulfate, filtered and the filtrate was concentrated in vacuo to give a brownish red oily product (29.14 g, 157.3 mmol, 102.4%).

MS (ESI, pos.ion)m/z: 186.1[M+H]$^+$.

Step 7: Ethyl 4-oxo-4H-pyran-3-carboxylate

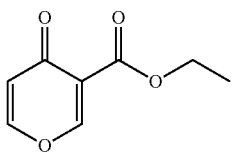

Ethyl 2-((dimethylamino)methylene)-3-oxobutanoate (28.46 g, 153.7 mmol), tetrahydrofuran (280 mL) and ethyl carboxylate (28.46 g, 384.2 mmol) were sequentially added to the reaction flask. The mixture was cooled to 0° C. and sodium tert-butoxide (38.06 g, 384.1 mmol) was added. The resulting mixture was stirred for 10 min, then transferred to room temperature and stirred for 14 h. Post processing: After the completion of the reaction was monitored by LC-MS, the stirring was stopped. The reaction mixture was added into 1 M hydrochloric acid (500 mL) and stirred at room temperature for 1 h. Dichloromethane (200 mL) was added and the mixture was partitioned. The lower organic layer was collected, and the aqueous layer was extracted with dichloromethane (250 mL×2). The organic layers were combined, washed with saturated aqueous sodium chloride solution (350 mL) and distilled in vacuo. The residue was purified by silica gel column chromatography (PE/EA(v/v)=1/1) to give a brownish black oily product (15.15 g, 90.1 mmol, 58.64%).

MS (ESI, pos.ion)m/z: 169.2[M+H]$^+$.

Step 8: Ethyl 1-(5-(7-(benzyloxy)-4-bromo-2,3-dihydrobenzofuran-5-yl)-dimethylpyrrolidin-1-yl)-4-oxo-1,4-dihydropyridine-3-carboxylate

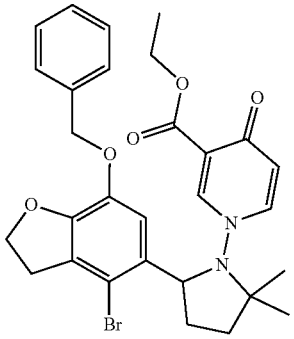 [SMILES: CCOC(=O)c1cn(N2C(c3cc(OCc4ccccc4)c4c(c3Br)CCO4)CCC2(C)C)ccc1=O]

5-(7-(Benzyloxy)-4-bromo-2,3-dihydrobenzofuran-5-yl)-2,2-dimethyl-1-nitrosopyrrolidine (2.3 g, 5.3 mmol), trifluoroacetic acid (15 mL, 261 mmol) and ethanol (5 mL) were added sequentially into the reaction flask. Zinc powder (1.7 g, 26 mmol) was added under the ice-bath. After the addition, the mixture was heated to 50° C. and stirred for 1 h. The reaction mixture was filtered and the solvent was evaporated in vacuo. To the residue was added ethanol (25 mL) and ethyl 4-oxo-4H-pyran-3-carboxylate (0.9 g, 5 mmol). The mixture was heated to reflux and reacted for 4 h. The reaction mixture was concentrated in vacuo. Ethyl acetate (50 mL) was added to dissolve the residue. Then the mixture was sequentially washed with 1 M hydrochloric acid (50 mL), saturated sodium bicarbonate (50 mL) and saturated aqueous sodium chloride (50 mL). The organic layer was concentrated in vacuo and the residue was purified by silica gel column chromatography (DCM/MeOH(V/V)=10/1) to give the title compound as a brown solid (2.4 g, 4.2 mmol, 80%).

MS (ESI, pos.ion) m/z: 567.3[M+1]$^+$.

Step 9: Ethyl 5-(benzyloxy)-1,1-dimethyl-10-oxo-2,3,3a,7,8,10-hexahydro-1H-furo[3,2-f]pyrido [1,2-c]pyrrolo[2,1-a]phthalazine-11-carboxylate

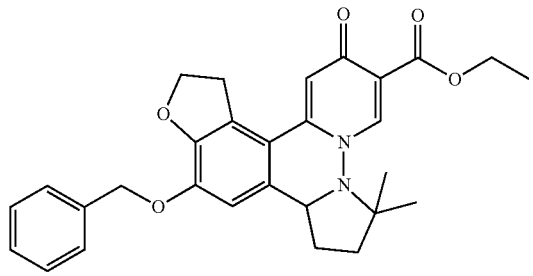 [SMILES: CCOC(=O)c1cn2c(cc1=O)-c1c(cc(OCc3ccccc3)c3c1CCO3)C1CCC(C)(C)N12]

Ethyl 1-(5-(7-(benzyl)-4-bromo-2,3-dihydrobenzofuran-5-yl)-dimethylpyrrolidin-1-yl)-4-oxo-1,4-dihydropyridine-3-carboxylate (1.0 g, 1.76 mmol), DMF (20 mL), DPEPhos (bis(2-diphenylphosphinophenyl)ether) (95 mg, 0.17 mmol), potassium carbonate (0.72 g, 5.2 mmol) and palladium acetate (40 mg, 0.17 mmol) were added into the reaction flask. The mixture was reacted at 110° C. for 12 h under nitrogen protection. LC-MS detected the completion of the reaction. To the mixture was added water (50 mL). The resulting mixture was extracted with EA (50 mL×2). The organic layers were combined and the combined organic layers were washed with saturated aqueous sodium chloride solution (50 mL×3) and concentrated. The residue was purified by preparative chromatography to give the title compound as a yellow solid (0.65 g, 1.3 mmol, 76%).

MS (ESI, pos.ion) m/z: 486.9[M+1]$^+$.

Step 10: Ethyl 5-hydroxy-1,1-dimethyl-10-oxo-2,3,3a,7,8,10-hexahydro-1H-furo[3,2-f]pyrido [1,2-c]pyrrolo[2,1-a]phthalazine-11-carboxylate

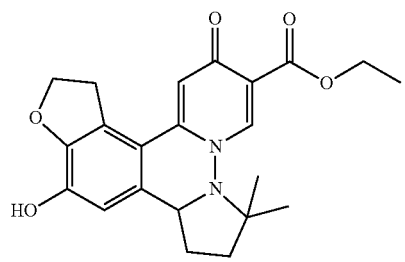 [SMILES: CCOC(=O)c1cn2c(cc1=O)-c1c(cc(O)c3c1CCO3)C1CCC(C)(C)N12]

Ethyl 5-(benzyloxy)-1,1-dimethyl-10-oxo-2,3,3a,7,8,10-hexahydro-1H-furo[3,2-f]pyrido[1,2-c]pyrrolo[2,1-a]phthalazine-11-carboxylate (0.6 g, 1 mmol), methanol (5 mL) and Pd/C (0.07 g, 0.07 mmol, 10 mass %) were added into the reaction flask. The reaction mixture was degassed and refilled with hydrogen and then reacted for 8 h at room temperature in hydrogen atmosphere. LC-MS detected the completion of the reaction. The reaction was filtered and the filtrate was concentrated. The residue was purified by silica gel column chromatography (DCM/MeOH(V/V)=15/1) to give the title compound as a light yellow solid (0.36 g, 0.91 mmol, 70%).

MS (ESI, pos.ion) m/z: 396.9[M+1]$^+$.

Step 11: Ethyl 5-(3-methoxypropoxy)-1,1-dimethyl-10-oxo-2,3,3a,7,8,10-hexahydro-1H-furo [3,2-f]pyrido[1,2-c]pyrrolo[2,1-a]phthalazine-11-carboxylate

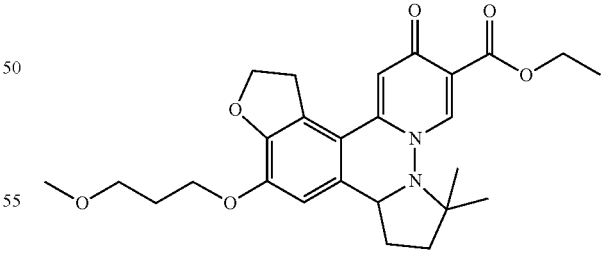

Ethyl 5-hydroxy-1,1-dimethyl-10-oxo-2,3,3a,7,8,10-hexahydro-1H-furo[3,2-f]pyrido [1,2-c]pyrrolo[2,1-a]phthalazine-11-carboxylate (0.18 g, 0.45 mmol), 1-bromo-3-methoxypropane (0.21 g, 1.4 mmol), DMF (5 mL) and potassium carbonate (0.2 g, 1 mmol) were added into the reaction flask. The reaction mixture was warmed to 90° C. and reacted for 4 h. LC-MS detected the completion of the reaction. To the mixture was added water (50 mL). The resulting mixture was extracted with DCM (50 mL×2). The organic layers were combined and the combined organic layers were washed with saturated aqueous sodium chloride solution (50 mL×3) and dried over anhydrous sodium sulfate. The solvent was evaporated under reduced pressure to carry out the next step directly.

MS (ESI, pos.ion) m/z: 469.4[M+1]⁺.

Step 12: 5-(3-Methoxypropoxy)-1,1-dimethyl-10-oxo-2,3,3a,7,8,10-hexahydro-1H-furo[3,2-f]Pyrido[1,2-c]pyrrolo[2,1-a]phthalazine-11-carboxylic Acid

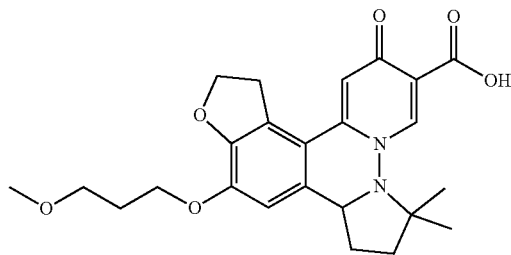 [SMILES: COCCCOc1cc2c(c3c1OCC3)-c1cc(=O)c(C(=O)O)cn1N1C2CCC1(C)C]

Ethyl 5-(3-methoxypropoxy)-1,1-dimethyl-10-oxo-2,3,3a,7,8,10-hexahydro-1H-furo [3,2-f]pyrido[1,2-c]pyrrolo[2,1-a]phthalazine-11-carboxylate (0.21 g, 0.45 mmol), methanol (5 mL) and lithium hydroxide (55 mg, 2.2 mmol) were added into the reaction flask. The reaction mixture was reacted for 4 h at room temperature. LC-MS detected the completion of the reaction. To the reaction mixture was added 1 M hydrochloric acid to adjust pH to 5~6. The resulting mixture was extracted with dichloromethane (20 mL×2). The organic layers were combined and concentrated. The residue was purified by silica gel column chromatography (DCM/MeOH(V/V)=15/1) to give the title compound as a white solid (75 mg, 0.17 mmol, 38%).

MS (ESI, pos.ion) m/z: 440.9[M+1]⁺;
$^1$H NMR (400 MHz, CDCl$_3$) δ 15.98 (s, 1H), 8.57 (s, 1H), 6.95 (s, 1H), 6.78 (s, 1H), 4.95-4.85 (m, 1H), 4.80-4.72 (m, 1H), 4.64-4.53 (m, 1H), 4.29-4.16 (m, 2H), 3.75-3.52 (m, 3H), 3.47-3.38 (m, 1H), 3.37 (s, 3H), 2.52-2.32 (m, 2H), 2.19-2.06 (m, 2H), 1.93-1.84 (m, 1H), 1.69-1.56 (m, 1H), 1.38 (s, 3H), 0.67 (s, 3H).

Example 13: 5-(2-Cyclopropylethoxy)-1,1-dimethyl-10-oxo-2,3,3a,7,8,10-hexahydro-1H-furo[3,2-f]pyrido[1,2-c]pyrrolo[2,1-a]phthalazine-11-carboxylic Acid

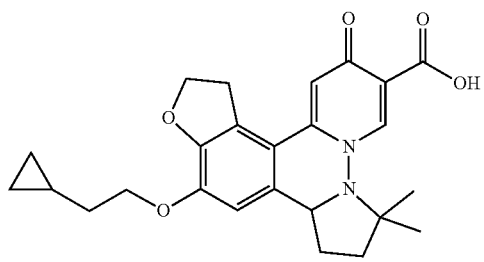 [SMILES: CC1(C)CCC2c3cc(OCCC4CC4)c4c(c3-c3cc(=O)c(C(=O)O)cn3N21)CCO4]

Starting from ethyl 5-hydroxy-1,1-dimethyl-10-oxo-2,3,3a,7,8,10-hexahydro-1H-furo [3,2-f]pyrido[1,2-c]pyrrolo[2,1-a]phthalazine-11-carboxylate and (2-bromoethyl)cyclopropane, referring to the synthesis method of the steps 11 to 12 in Example 12, the title compound was obtained as a white solid.

MS (ESI, pos.ion) m/z: 436.9[M+1]⁺;
$^1$H NMR (400 MHz, CDCl$_3$) δ 16.00 (s, 1H), 8.58 (s, 1H), 6.95 (s, 1H), 6.77 (s, 1H), 4.95-4.85 (m, 1H), 4.83-4.74 (m, 1H), 4.64-4.51 (m, 1H), 4.25-4.13 (m, 2H), 3.77-3.63 (m, 1H), 3.47-3.35 (m, 1H), 2.52-2.33 (m, 2H), 1.93-1.83 (m, 1H), 1.79-1.75 (m, 2H), 1.69-1.57 (m, 1H), 1.39 (s, 3H), 0.93-0.79 (m, 1H), 0.68 (s, 3H), 0.56-0.47 (m, 2H), 0.19-0.11 (m, 2H).

Example 14: 5-(1-Isopropyl-1H-pyrazol-4-yl)-1,1-dimethyl-10-oxo-2,3,3a,7,8,10-hexahydro-1H-furo [3,2-f]pyrido[1,2-c]pyrrolo[2,1-a]phthalazine-11-carboxylic Acid

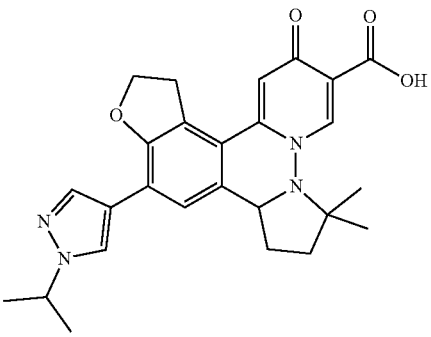 [SMILES: CC(C)n1cc(-c2cc3c(c4c2OCC4)-c2cc(=O)c(C(=O)O)cn2N2C3CCC2(C)C)cn1]

Starting from ethyl 5-hydroxy-1,1-dimethyl-10-oxo-2,3,3a,7,8,10-hexahydro-1H-furo [3,2-f]pyrido[1,2-c]pyrrolo[2,1-a]phthalazine-11-carboxylate and PhN(OTf)$_2$, referring to the synthesis method of step 1 in Example 8. ethyl 1,1-dimethyl-10-oxo-5-(((trifluoromethyl) sulfonyl)oxy)-2,3,3a,7,8,10-hexahydro-1H-furo[3,2-/]pyrido[1,2-c]pyrrolo[2,1-a]phthalazine-11-carboxylate was obtained. Then starting from ethyl 1,1-dimethyl-10-oxo-5-(((trifluoromethyl) sulfonyl)oxy)-2,3,3a,7,8,10-hexahydro-1H-furo[3,2-f]pyrido[1,2-c]pyrrolo[2,1-a]phthalazine-11-carboxylate and isopropyl-4-(4,4,5,5-tetramethyl-1,3,2-dioxaborolan-2-yl)-1H-pyrazole, referring to the synthesis method in Example 9, the desired product was obtained as a white solid.

MS (ESI, pos.ion) m/z: 461.4[M+1]⁺;
$^1$H NMR (400 MHz, CDCl$_3$) δ 15.93 (s, 1H), 8.60 (s, 1H), 8.07 (s, 1H), 7.98 (s, 1H), 7.37 (s, 1H), 7.03 (s, 1H), 4.96 (td, J=10.2, 3.8 Hz, 1H), 4.79 (s, 1H), 4.70-4.51 (m, 2H), 3.73 (dt, J=15.6, 10.6 Hz, 1H), 3.53-3.38 (m, 1H), 2.61-2.37 (m, 2H), 1.98-1.80 (m, 2H), 1.58 (d, J=6.7 Hz, 6H), 1.39 (s, 3H), 0.68 (s, 3H).

Example 15: 4-(2-Cyclopropylethoxy)-7-isopropyl-11-oxo-2,6,7,11-tetrahydro-1H-furo [2,3-h]pyrido[2,1-a]phthalazine-10-carboxylic Acid

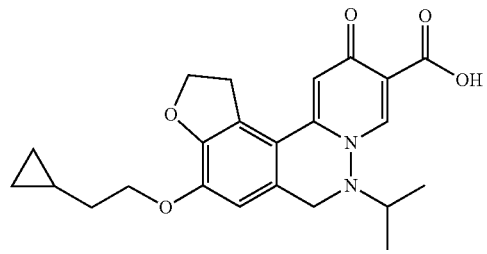 [SMILES: CC(C)N1Cc2cc(OCCC3CC3)c3c(c2-c2cc(=O)c(C(=O)O)cn21)CCO3]

Step 1: 7-(Benzyloxy)-2,3-dihydrobenzofuran-5-formaldehyde

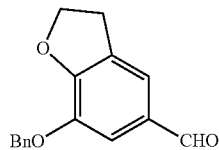 [SMILES: O=Cc1cc2c(c(OCc3ccccc3)c1)OCC2]

7-(Benzyloxy)-5-bromo-2,3-dihydrobenzofuran (21.0 g, 68.8 mmol) and anhydrous THF (650 mL) were sequentially added to a two-necked flask. The reaction mixture was degassed and refilled with nitrogen for three times and stirred for 30 min at −78° C. Then a solution of n-BuLi in n-hexane (2.50 M, 36.5 mL) was slowly added into the mixture. After the addition, the mixture was stirred for 1 h. DMF (11.7 mL) was quickly added in one portion. After the addition, the reaction was continued for 7 h. The reaction mixture was then slowly poured into a saturated ammonium chloride solution (1000 mL) cooled in an ice bath. After the addition, the mixture was stirred for 5 min and stand overnight. To the mixture was added 200 mL EA and the organic layers were collected. The collected organic layers were washed with saturated brine, dried over anhydrous sodium sulfate and concentrated in vacuo. The residue was purified by silica gel column chromatography (PE/EA (V/V)=5/1) to give the title compound as a yellow solid (8.00 g, 31.5 mmol, 45.70%).

Step 2: N—((7-(Benzyloxy)-2,3-dihydrobenzofuran-5-yl)methyl)propan-2-amine

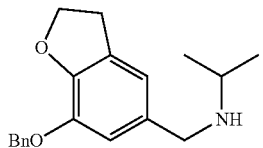 [SMILES: CC(C)NCc1cc2c(c(OCc3ccccc3)c1)OCC2]

7-(Benzyloxy)-2,3-dihydrobenzofuran-5-carbaldehyde (7.50 g, 29.5 mmol), MeOH (177 mL), 2-isopropylamine (6.10 g, 103 mmol) and AcOH (354 mg, 5.90 mmol) were sequentially added into a two-necked flask. After the addition, the mixture was heated to 60° C. under nitrogen protection and stirred until the system is clarified. The mixture was stirred for 2 h continuously and then moved to 0° C. NaBH$_4$ (3.35 g, 88.6 mmol) was added in portions into the mixture. The resulting mixture was warmed to room temperature and reacted at room temperature for 3 h, then concentrated in vacuo. The mixture was diluted with ethyl acetate (120 mL) and water (100 mL) and then partitioned. The upper organic layer was collected. The aqueous phase was extracted with ethyl acetate (120 mL×1). The organic layers were combined.

The combined organic layers were washed with saturated sodium chloride solution, dried over anhydrous sodium sulfate and filtered. The filtrate was concentrated in vacuo to give the title compound as a colorless oily product (8.77 g, 29.5 mmol, 100%).

MS (ESI, pos.ion) m/z: 298.0 [M+H]$^+$.

Step 3: N-((7-(Benzyloxy)-2,3-dihydrobenzofuran-5-yl)methyl)-N-isopropylnitrosamine

N-((7-(Benzyloxy)-2,3-dihydrobenzofuran-5-yl)methyl) propan-2-amine (8.77 g, 29.5 mmol) and THF (118 mL) were sequentially added into a two-necked flask. Then a solution of sodium nitrite (5.09 g, 73.8 mmol) in H$_2$O (22.4 g) and acetic acid (4.42 mL, 77.1 mmol) were added. The resulting mixture was warmed to 50° C. and stirred for 1 h. The reaction mixture was concentrated in vacuo. Ethyl acetate (60 mL) was added to dissolve the residue. Then the mixture was washed with saturated sodium chloride solution, dried over anhydrous sodium sulfate and filtered. The filtrate was concentrated in vacuo. The residue was purified by silica gel column chromatography (PE/EA(V/V)=10/1) to give the title compound as a pale yellow oily product (8.96 g, 27.5 mmol, 93.10%).

Step 4: N-((7-(Benzyloxy)-4-bromo-2,3-dihydrobenzofuran-5-yl)methyl)-N-isopropylnitrosamine

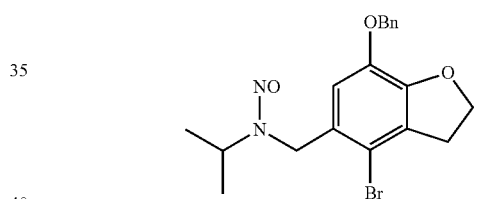

N—((7-(Benzyloxy)-2,3-dihydrobenzofuran-5-yl) methyl)-AA isopropylnitrosamine (8.96 g, 27.5 mmol), DMF (90.0 mL) and NBS (5.13 g, 28.8 mmol) were sequentially added to a two-necked flask. After the addition, the mixture was stirred at room temperature for 2 h. To the mixture were added EA (200 mL) and saturated saline (200 mL). The organic layers were collected. The collected organic layers were dried over anhydrous sodium sulfate and concentrated in vacuo to give the title compound as a black solid (11.1 g, 27.4 mmol, 99.80%).

Step 5: 1-((7-(Benzyloxy)-4-bromo-2,3-dihydrobenzofuran-5-yl)methyl)-1-isopropylhydrazine

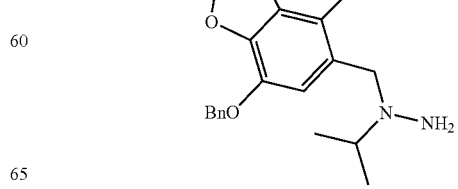

N-((7-(Benzyloxy)-4-bromo-2,3-dihydrobenzofuran-5-yl)methyl)-N-isopropylnitrosamine (11.1 g, 27.4 mmol), TFA (78.0 mL) and ethanol (26.0 mL) were sequentially added into a two-necked flask. Then the mixture was heated to 50° C. and Zn (10.4 g, 159 mmol) was added in three portions. The resulting mixture was stirred for 1 h. The mixture was filtered through a celite pad and the filter cake was washed with EA (80 mL). The filtrate was collected and the solvent was evaporated under reduced pressure to give the title compound as a grayish black solid which was used directly in the next step.

Step 6: Ethyl 1-(((7-(benzyloxy)-4-bromo-2,3-dihydrobenzofuran-5-yl)methyl)(isopropyl)amino)-4-oxo-1,4-dihydropyridine-3-carboxylate

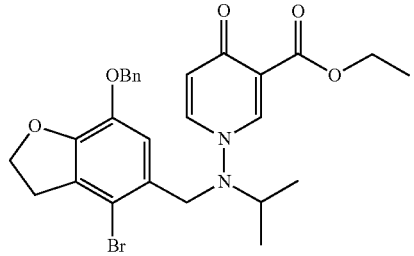 [SMILES: CCOC(=O)c1cn(N(Cc2cc(OCc3ccccc3)c3c(c2Br)CCO3)C(C)C)ccc1=O]

1-((7-(Benzyloxy)-4-bromo-2,3-dihydrobenzofuran-5-yl)methyl)-1-isopropylhydrazine (10.7 g, 27.3 mmol), ethyl 4-oxo-4H-pyran-3-carboxylate (7.0 g, 41.6 mmol) and ethanol (160 mL) were sequentially added into a two-necked flask. The reaction mixture was degassed and refilled with nitrogen for three times and then heated to 60° C. and stirred for 12 h under nitrogen protection. The mixture was diluted with saturated sodium bicarbonate solution (200 mL). The organic layers were collected, dried over anhydrous sodium sulfate and concentrated in vacuo. The residue was purified by silica gel column chromatography (DCM/MeOH(V/V)=20/1) to give the title compound as a reddish brown solid (8.00 g, 14.8 mmol, 54.00%).

MS (ESI, pos.ion) m/z: 541.2 [M+H]$^+$.

Step 7: Ethyl 4-(benzyloxy)-7-isopropyl-11-oxo-2,6,7,11-tetrahydro-1H-furo[2,3-h]pyrido[2,1-a]phthalazine-10-carboxylate

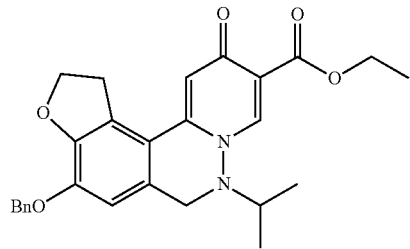

Ethyl 1-(((7-(benzyloxy)-4-bromo-2,3-dihydrobenzofuran-5-yl)methyl)(isopropyl)amino)-4-oxo-1,4-dihydropyridine-3-carboxylate (4.82 g, 8.90 mmol), PdBr$_2$ (237 mg, 0.89021 mmol), potassium acetate (1.75 g, 17.8 mmol) and DMF (53.0 mL) were sequentially added into a two-necked flask. After the addition, the reaction mixture was degassed and refilled with nitrogen and then heated to 130° C. and stirred for 12 h under nitrogen protection. The mixture was filtered through a celite pad and the filter cake was washed with EA (100 mL). The filtrate was collected and EA (75 mL) and water (100 mL) were added. The organic layer was collected and washed with saturated brine (100 mL). The collected organic layer was dried over anhydrous sodium sulfate and concentrated in vacuo to give the title compound as a brown solid (2.0 g, 4.34 mmol, 48.80%).

MS (ESI, pos.ion) m/z: 461.4 [M+H]$^+$.

Step 8: Ethyl 4-hydroxy-7-isopropyl-11-oxo-2,6,7,11-tetrahydro-1H-furo[2,3-h]pyrido[2,1-a]phthalazine-10-carboxylate

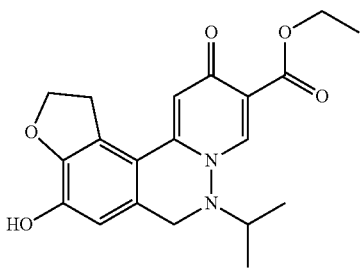 [SMILES: CCOC(=O)c1cn2c(cc1=O)-c1c(cc(O)c3c1CCO3)CN2C(C)C]

Ethyl 4-(benzyloxy)-7-isopropyl-11-oxo-2,6,7,11-tetrahydro-1H-furo[2,3-h]pyrido[2,1-a]phthalazine-10-carboxylate (2.00 g, 4.34 mmol), MeOH (20.0 mL) and Pd/C (400 mg, mass ratio: 10%) were sequentially added into a two-necked flask. The reaction mixture was degassed and refilled with hydrogen for three times and then reacted for 12 h at room temperature in hydrogen atmosphere. The mixture was filtered and the filter cake was washed with methanol (30 mL) and DCM (60 mL). The filtrate was collected and concentrated in vacuo to give the title compound as a brownish yellow solid (1.40 g, 3.78 mmol, 87%).

Step 9: Ethyl 4-(2-cyclopropylethoxy)-7-isopropyl-11-oxo-2,6,7,11-tetrahydro-1H-furo[2,3-h]pyrido[2,1-a]phthalazine-10-carboxylate

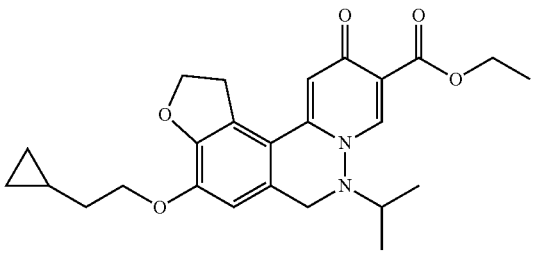 [SMILES: CCOC(=O)c1cn2c(cc1=O)-c1c(cc(OCCC3CC3)c3c1CCO3)CN2C(C)C]

Ethyl 4-hydroxy-7-isopropyl-11-oxo-2,6,7,11-tetrahydro-1H-furo[2,3-h]pyrido[2,1-a]phthalazine-10-carboxylate (300 mg, 0.81 mmol), DMF (10.0 mL), 2-cyclopropylethyl methanesulfonate (332 mg, 2.02 mmol) and K$_2$CO$_3$ (279 mg, 2.02 mmol) were sequentially added into a two-necked flask. After the addition, the mixture was reacted at 70° C. for 8 h. The reaction mixture was diluted with EA (30 mL) and saturated brine (30 mL). The organic layers were collected, dried over anhydrous sodium sulfate and concentrated in vacuo. The residue was purified by silica gel column chromatography (DCM/MeOH(V/V)=20/1) to give the title compound as a brownish yellow solid (355 mg, 0.81 mmol, 99.96%).

MS (ESI, pos.ion) m/z: 438.8 [M+H]⁺.

Step 10: 4-(2-Cyclopropylethoxy)-7-isopropyl-11-oxo-2,6,7,11-tetrahydro-1H-furo[2,3-h]pyrido [2,1-a]phthalazine-10-carboxylic Acid

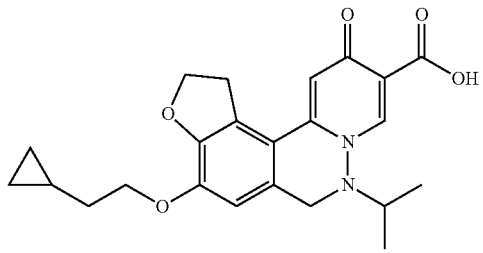 [SMILES: CC(C)N1Cc2cc(OCCC3CC3)c3c(c2-c2cc(=O)c(C(=O)O)cn21)CCO3]

Ethyl 4-(2-cyclopropylethoxy)-7-isopropyl-11-oxo-2,6,7,11-tetrahydro-177-furo[2,3-h]pyrido[2,1-a]phthalazine-10-carboxylate (355 mg, 0.81 mmol), MeOH (5.00 mL), THF (5.00 mL) and lithium hydroxide monohydrate (170 mg, 4.05 mmol) were sequentially added into a two-necked flask. After the addition, the mixture was reacted for 5 h at room temperature. The mixture was concentrated in vacuo. The reaction mixture was diluted with methanol (3 mL) and 3 M dilute hydrochloric acid was added dropwise slowly to adjust pH to 3-4. Then the resulting mixture was stood for 10 min under an ice-bath and filtered. The filter cake was washed with methanol (5 mL) and dried in vacuo to give the title compound as a pale yellow solid (148 mg, 0.36 mmol, 44%).

MS (ESI, pos.ion) m/z: 411.8 [M+H]⁺.
¹H NMR (600 MHz, CDCl₃) δ 15.78 (s, 1H), 8.61 (s, 1H), 6.90 (s, 1H), 6.68 (s, 1H), 4.33 (s, 2H), 4.18 (t, J=6.8 Hz, 2H), 3.50-3.48 (m, 3H), 3.03-2.94 (m, 2H), 1.76 (dd, J=13.8, 6.9 Hz, 2H), 1.02 (s, 6H), 0.84-0.78 (m, 1H), 0.51 (dd, J=8.0, 4.5 Hz, 2H), 0.14 (q, J=5.4 Hz, 2H).

Example 16: 7-Isopropyl-4-(3-methoxypropoxy)-11-oxo-2,6,7,11-tetrahydro-1H-furo[2,3-h]pyrido[2,1-a] phthalazine-10-carboxylic Acid

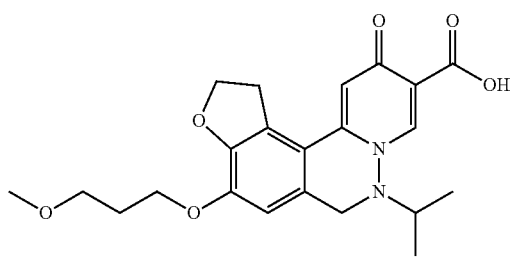 [SMILES: COCCCOc1cc2c(c3c1OCC3)-c1cc(=O)c(C(=O)O)cn1N(C(C)C)C2]

Starting from ethyl 4-hydroxy-7-isopropyl-11-oxo-2,6,7,11-tetrahydro-1H-furo[2,3-h]pyrido[2,1-a]phthalazine-10-carboxylate and 1-bromo-3-methoxypropane, referring to the experimental method of the synthesis steps 12-13 in Example 2, the title compound was obtained as a pale yellow solid.

MS (ESI, pos.ion) m/z: 414.8 [M+H]⁺;
¹H NMR (400 MHz, CDCl₃) δ 15.78 (s, 1H), 8.61 (s, 1H), 6.90 (s, 1H), 6.69 (s, 1H), 4.85-4.65 m, 2H), 4.33 (s, 2H), 4.21 (t, J=6.4 Hz, 2H), 3.57 (t, J=5.9 Hz, 3H), 3.49 (s, 1H), 3.36 (s, 3H), 3.01-2.92 (m, 1H), 2.17-2.06 (m, 2H), 1.01 (s, 6H).

Example 17: 7-Isopropyl-4-(1-isopropyl-11-pyrazol-4-yl)-11-oxo-2,6,7,11-tetrahydro-1H-furo[2,3-h] pyrido[2,1-a]phthalazine-10-carboxylic Acid

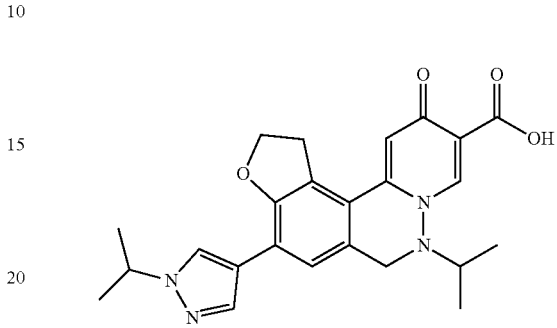

Starting from ethyl 4-hydroxy-7-isopropyl-11-oxo-2,6,7,11-tetrahydro-1H-furo[2,3-h]pyrido[2,1-a]phthalazine-10-carboxylate, PhN(OTf)₂ and isopropyl-4-(4,4,5,5-tetramethyl-1,3,2-dioxaborolan-2-yl)-1H-pyrazole, referring to the synthesis method in Example 9, the desired product was obtained as a white solid.

MS (ESI, pos.ion) m/z: 435.3 [M+H]⁺;
¹H NMR (400 MHz, CDCl₃) δ 15.75 (s, 1H), 8.66 (s, 1H), 8.07 (s, 1H), 7.99 (s, 1H), 7.31 (s, 1H), 7.01 (s, 1H), 4.84 (s, 2H), 4.63-4.54 (m, 1H), 4.41 (s, 2H), 3.59 (s, 2H), 3.05-2.94 (m, 1H), 1.68-1.54 (m, 12H).

Example 3A: (S)-4-(2-Cyclopropylethoxy)-7-isopropyl-11-oxo-2,6,7,11-tetrahydro-1H-furo [2,3-h] pyrido[2,1-a]isoquinoline-10-carboxylic Acid

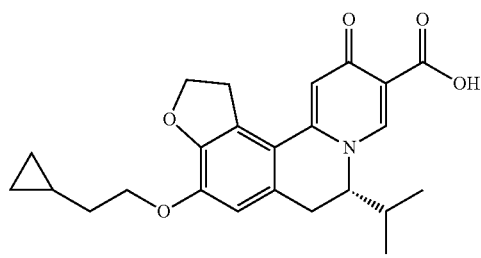 [SMILES: CC(C)[C@@H]1Cc2cc(OCCC3CC3)c3c(c2-c2cc(=O)c(C(=O)O)cn21)CCO3]

Step 1: (S)-1-(7-(Benzyloxy)-2,3-dihydrobenzofuran-5-yl)-3-methylbutan-2-amine

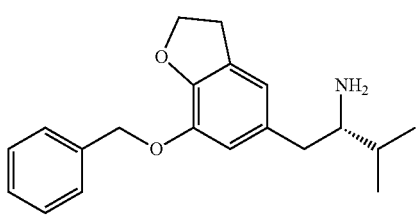 [SMILES: CC(C)[C@@H](N)Cc1cc2c(c(OCc3ccccc3)c1)OCC2]

1-(7-(Benzyloxy)-2,3-dihydrobenzofuran-5-yl)-3-methylbutan-2-amine (10.0 g, 32.15 mmol) was added into EA (1000 mL). The mixture was stirred for 30 min, then to the mixture was added a solution of (2S)-2-acetylamino-3-methyl-butyric acid (2.59 g, 16.26 mmol) in EA (1000 mL). The resulting mixture was stirred for 1 h at room temperature. Then the mixture was filtered and the filter cake was washed with EA (100 mL). A solution of $Na_2CO_3$ (10.3 g, 97.2 mmol) in $H_2O$ (100 mL) and DCM (100 mL) was added into the resulting solid. The mixture was stirred for 2 h. The organic phase was collected, dried over anhydrous sodium sulfate, filtered and concentrated in vacuo to give the title compound as a white solid (3.3 g, 10.6 mmol, 30%, ee=98.98%).

Step 2: (S)-4-(2-cyclopropylethoxy)-7-isopropyl-11-oxo-2,6,7,11-tetrahydro-1H-furo[2,3-h]pyrido[2,1-a]isoquinoline-10-carboxylic Acid

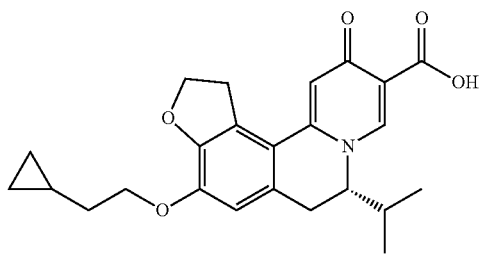 [SMILES: CC(C)[C@@H]1Cc2cc(OCCC3CC3)c3c(c2-c2cc(=O)c(C(=O)O)cn21)CCO3]

First, starting from (S)-1-(7-(benzyloxy)-2,3-dihydrobenzofuran-5-yl)-3-methylbutan-2-amine, referring to the synthesis steps 7 to 11 in the Example 2, ethyl (S)-4-hydroxy-7-isopropyl-11-oxo-2,6,7,11-tetrahydro-1H-furo[2,3-]pyrido-[2,1-a]isoquinoline-10-carboxylate can be obtained. Then, starting from ethyl (S)-4-hydroxy-7-isopropyl-11-oxo-2,6,7,11-tetrahydro-1H-furo[2,3-h]pyrido [2,1-a]isoquinoline-10-carboxylate and 2-cyclopropylethyl methanesulfonate, referring to the synthesis method in Example 3, the title compound was obtained as a white solid.

MS (ESI, pos.ion) m/z: 410.1[M+H]$^+$;
$^1$H NMR (400 MHz, $CDCl_3$) 516.016 (b, 1H), 8.494 (s, 1H), 6.927 (s, 1H), 6.709 (s, 1H), 4.906-4.849 (m, 1H), 4.609-4.537 (m, 1H), 4.212-4.172 (m, 2H), 3.894-3.861 (m, 1H), 3.739-3.648 (m, 1H), 3.407-3.320 (m, 2H), 3.104-3.065 (m, 1H), 1.829-1.668 (m, 4H), 0.958 (d, J=6.4 Hz, 3H), 0.862 (d, J=6.8 Hz, 3H), 0544-0.500 (m, 2H), 0.156-0.132 (m, 2H).

Example 10A: 4-(1-(Difluoromethyl)-1H-pyrazol-4-yl)-7-isopropyl-11-oxo-2,6,7,11-tetrahydro-1H-furo [2,3-h]pyrido[2,1-a]isoquinoline-10-carboxylic Acid

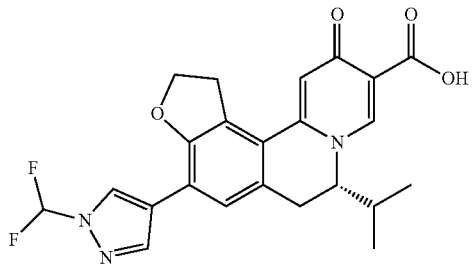 [SMILES: CC(C)[C@@H]1Cc2cc(-c3cnn(C(F)F)c3)c3c(c2-c2cc(=O)c(C(=O)O)cn21)CCO3]

First, starting from ethyl (S)-4-hydroxy-7-isopropyl-11-oxo-2,6,7,11-tetrahydro-1H-furo [2,3-h]pyrido[2,1-a]isoquinoline-10-carboxylate, referring to the synthetic step 1 in the Example 8, ethyl (S)-7-isopropyl-11-oxo-4-(((trifluoromethyl)sulfonyl)oxy)-2,6,7,11-tetrahydro-1H-furo [2,3-h]pyrido[2,1-a]isoquinoline-10-carboxylate can be obtained. Then, starting from ethyl (S)-7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 1-(difluoromethyl)-4-(4,4,5,5-tetramethyl-1,3,2-dioxaborolan-2-yl)-1H-pyrazole, referring to the synthetic method in Example 9, the title compound was obtained as a white solid.

MS (ESI, pos.ion) m/z: 442.0 [M+H]$^+$;
$^1$H NMR (400 MHz, DMSO-$d_6$/$D_2O$) δ16.044 (b, 1H), 8.596 (s, 1H), 8.413 (s, 1H), 8.114 (s, 1H), 7.602-7.495 (m, 1H), 7.352 (s, 1H), 6.953 (s, 1H), 4.960-4.862 (m, 1H), 4.678-4.526 (m, 1H), 4.174-3.988 (m, 1H), 3.790-3.632 (m, 1H), 3.443-3.237 (m, 2H), 3.191-3.098 (m, 1H), 1.723-1.613 (m, 1H), 0.889-0.750 (m, 6H).

Example 18: 7-Isopropyl-4-(n-octyloxy)-11-oxo-2,6,7,11-tetrahydro-1H-furo[2,3-h]pyrido [2,1-a]isoquinoline-10-carboxylic Acid

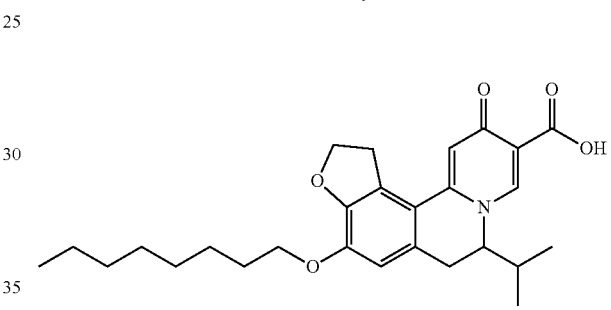

Starting from ethyl 4-hydroxy-7-isopropyl-11-oxo-2,6,7,11-tetrahydro-1H-furo[2,3-h]pyrido[2,1-a]isoquinoline-10-carboxylate and n-octyl bromide, referring to the synthesis steps 12 to 13 in Example 2, the title compound was obtained as a white solid.

MS (ESI, pos.ion) m/z: 454.30[M+H]$^+$;
$^1$H NMR (400 MHz, $CDCl_3$) δ 16.01 (s, 1H), 8.49 (s, 1H), 6.93 (s, 1H), 6.68 (s, 1H), 4.88 (td, J=10.2, 4.1 Hz, 1H), 4.57 (dd, J=19.5, 9.4 Hz, 1H), 4.11 (td, J=6.7, 3.4 Hz, 2H), 3.87 (dd, J=9.9, 3.5 Hz, 1H), 3.69 (dt, J=15.4, 10.5 Hz, 1H), 3.36 (ddd, J=17.0, 10.8, 4.4 Hz, 2H), 3.12-3.02 (m, 1H), 1.95-1.71 (m, 4H), 1.54-1.21 (m, 9H), 1.01-0.83 (m, 9H).

Example 19: 4-(3-Cyanopropoxy)-7-Isopropyl-11—Oxo-2,6,7,11-Tetrahydro-1H-Furo[2,3-h]Pyrido[2,1-a]Isoquinoline-10-Carboxylic Acid

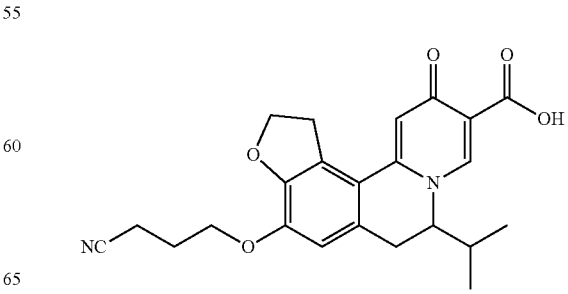

Starting from ethyl 4-hydroxy-7-isopropyl-11-oxo-2,6,7,11-tetrahydro-1H-furo[2,3-h]pyrido[2,1-a]isoquinoline-10-carboxylate and 4-bromobutyronitrile, referring to the synthesis steps 12 to 13 in Example 2, the title compound was obtained as a white solid.

MS (ESI, pos.ion) m/z: 409.2 [M+H]$^+$;

$^1$H NMR (400 MHz, CDCl$_3$) δ 8.47 (s, 1H), 6.92 (s, 1H), 6.69 (s, 1H), 4.91-4.81 (m, 1H), 4.56 (dd, J=19.6, 9.3 Hz, 1H), 4.30-4.19 (m, 2H), 3.85 (dd, J=9.8, 3.7 Hz, 1H), 3.68 (dt, J=15.6, 10.5 Hz, 1H), 3.43-3.27 (m, 2H), 3.07 (dd, J=16.0, 1.1 Hz, 1H), 2.71-2.56 (m, 2H), 2.26-2.12 (m, 2H), 1.83-1.69 (m, 1H), 0.94 (d, J=6.7 Hz, 3H), 0.85 (d, J=6.7 Hz, 3H).

Example 20: 4-(2-Ethylbutoxy)-7-isopropyl-11-oxo-2,6,7,11-tetrahydro-1H-furo[2,3-h]pyrido[2,1-a]isoquinoline-10-carboxylic Acid

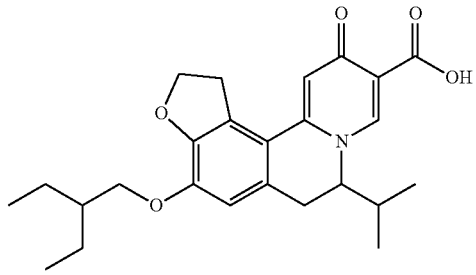 [SMILES: CCC(CC)COc1cc2c(c3c1OCC3)-c1cc(=O)c(C(=O)O)cn1C(C(C)C)C2]

Starting from ethyl 4-hydroxy-7-isopropyl-11-oxo-2,6,7,11-tetrahydro-1H-furo[2,3-h]pyrido[2,1-a]isoquinoline-10-carboxylate and 3-(bromomethyl)pentane, referring to the synthesis steps 12 to 13 in Example 2, the title compound was obtained as awhile solid.

MS (ESI, pos.ion) m/z: 426.3 [M+H]$^+$;

$^1$H NMR (400 MHz, CDCl$_3$) δ 8.47 (s, 1H), 6.90 (s, 1H), 6.66 (s, 1H), 4.91-4.80 (m, 1H), 4.54 (dd, J=19.5, 9.4 Hz, 1H), 3.97 (d, J=6.0 Hz, 2H), 3.86 (dd, J=9.8, 3.7 Hz, 1H), 3.66 (dt, J=15.4, 10.5 Hz, 1H), 3.42-3.27 (m, 2H), 3.06 (d, J=15.9 Hz, 1H), 1.82-1.69 (m, 2H), 1.58-1.40 (m, 4H), 1.00-0.89 (m, 9H), 0.84 (d, J=6.7 Hz, 3H).

Example 21: 4-(Isopentyloxy)-7-isopropyl-11-oxo-2,6,7,11-tetrahydro-1H-furo[2,3-h]pyrido [2,1-a]isoquinoline-10-carboxylic Acid

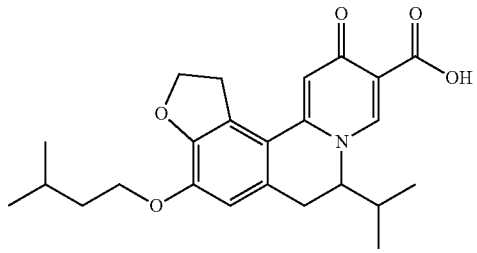 [SMILES: CC(C)CCOc1cc2c(c3c1OCC3)-c1cc(=O)c(C(=O)O)cn1C(C(C)C)C2]

Starting from ethyl 4-hydroxy-7-isopropyl-11-oxo-2,6,7,11-tetrahydro-1H-furo[2,3-h]pyrido[2,1-a]isoquinoline-10-carboxylate and 1-bromo-3-methylbutane, referring to the synthesis steps 12 to 13 in Example 2, the title compound was obtained as awhile solid.

MS (ESI, pos.ion) m/z: 412.2 [M+H]$^+$;

$^1$H NMR (400 MHz, CDCl$_3$) δ 8.52-8.40 (m, 1H), 6.90 (s, 1H), 6.66 (s, 1H), 4.94-4.77 (m, 1H), 4.55 (dd, J=19.5, 9.4 Hz, 1H), 4.18-4.06 (m, 2H), 3.86 (dd, J=9.8, 3.6 Hz, 1H), 3.67 (dt, J=15.4, 10.5 Hz, 1H), 3.41-3.26 (m, 2H), 3.06 (dd, J=16.0, 1.0 Hz, 1H), 1.91-1.80 (m, 1H), 1.80-1.67 (m, 3H), 0.97 (d, J=2.1 Hz, 3H), 0.96 (d, J=2.2 Hz, 3H), 0.93 (d, J=6.7 Hz, 3H), 0.84 (d, J=6.7 Hz, 3H).

Example 21A: (S)-4-(Isopentyloxy)-7-isopropyl-11-oxo-2,6,7,11-tetrahydro-1H-furo[2,3-h]pyrido[2,1-a]isoquinoline-10-carboxylic Acid

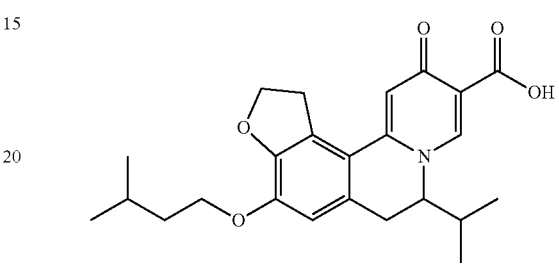

Starting from ethyl (S)-4-hydroxy-7-isopropyl-11-oxo-2,6,7,11-tetrahydro-1H-furo [2,3-h]pyrido[2,1-a]isoquinoline-10-carboxylate and 1-bromo-3-methylbutane, referring to the synthesis method in Example 21, the title compound was obtained as a white solid.

MS (ESI, pos.ion) m/z: 412.2[M+H]$^+$;

$^1$H NMR (600 MHz, CDCl$_3$) δ 16.03 (s, 1H), 8.50 (s, 1H), 6.93 (s, 1H), 6.69 (s, 1H), 4.88 (td, J=10.0, 4.0 Hz, 1H), 4.57 (dd, J=19.4, 9.4 Hz, 1H), 4.14 (h, J=9.2 Hz, 2H), 3.89 (d, J=5.9 Hz, 1H), 3.69 (dt, J=15.5, 10.5 Hz, 1H), 3.41-3.29 (m, 2H), 3.08 (d, J=15.8 Hz, 1H), 1.86 (tt, J=13.3, 6.7 Hz, 1H), 1.76 (dt, J=6.6, 4.6 Hz, 3H), 0.99 (dd, J=6.6, 3.4 Hz, 6H), 0.96 (d, J=6.6 Hz, 3H), 0.86 (d, J=6.7 Hz, 3H).

Example 22: 4-(Cyclopentylmethoxy)-7-isopropyl-11-oxo-2,6,7,11-tetrahydro-1H-furo[2,3-h]pyrido[2,1-a]isoquinoline-10-carboxylic Acid

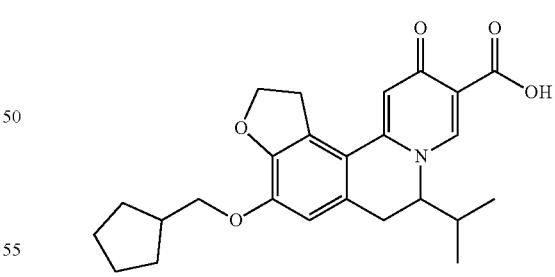

Starting from ethyl 4-hydroxy-7-isopropyl-11-oxo-2,6,7,11-tetrahydro-1H-furo[2,3-h]pyrido[2,1-a]isoquinoline-10-carboxylate and (bromomethyl)cyclopentane, referring to the synthesis steps 12 to 13 in Example 2, the title compound was obtained as awhile solid.

MS (ESI, pos.ion) m/z: 424.3 [M+H]$^+$;

$^1$H NMR (400 MHz, CDCl$_3$) δ 8.47 (s, 1H), 6.90 (s, 1H), 6.66 (s, 1H), 4.89-4.80 (m, 1H), 4.54 (dd, J=19.5, 9.4 Hz, 1H), 4.01-3.91 (m, 2H), 3.86 (dd, J=9.6, 3.5 Hz, 1H), 3.66 (dt, J=15.4, 10.5 Hz, 1H), 3.39-3.24 (m, 2H), 3.05 (d, J=15.7

Hz, 1H), 2.49-2.35 (m, 1H), 1.93-1.82 (m, 2H), 1.82-1.70 (m, 2H), 1.69-1.53 (m, 3H), 1.44-1.29 (m, 2H), 0.93 (d, J=6.6 Hz, 3H), 0.83 (d, J=6.7 Hz, 3H).

Example 22A: (S)-4-(Cyclopentylmethoxy)-7-isopropyl-11-oxo-2,6,7,11-tetrahydro-1H-furo [2,3-h]pyrido[2,1-a]isoquinoline-10-carboxylic Acid

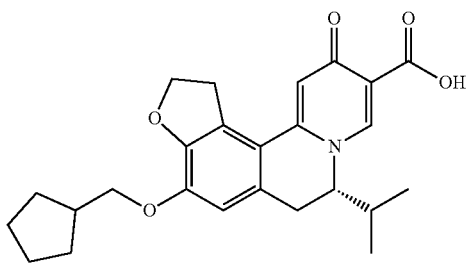 [SMILES: CC(C)[C@@H]1Cc2cc(OCC3CCCC3)c3c(c2-c2cc(=O)c(C(=O)O)cn21)CCO3]

Starting from ethyl (S)-4-hydroxy-7-isopropyl-11-oxo-2,6,7,11-tetrahydro-1H-furo [2,3-h]pyrido[2,1-a]isoquinoline-10-carboxylate and (bromomethyl)cyclopentane, referring to the synthesis method in Example 22, the title compound was obtained as a white solid.

MS (ESI, pos.ion) m/z: 424.2[M+H]$^+$;
$^1$H NMR (600 MHz, CDCl$_3$) δ 16.03 (s, 1H), 8.50 (s, 1H), 6.93 (s, 1H), 6.68 (s, 1H), 4.88 (td, J=10.1, 4.0 Hz, 1H), 4.57 (dd, J=19.5, 9.4 Hz, 1H), 3.98 (p, J=9.0 Hz, 2H), 3.88 (dd, J=9.8, 3.9 Hz, 1H), 3.69 (dt, J=15.4, 10.5 Hz, 1H), 3.36 (ddd, J=21.3, 13.0, 4.4 Hz, 2H), 3.08 (d, J=15.1 Hz, 1H), 2.49-2.38 (m, 1H), 1.96-1.85 (m, 2H), 1.81-1.77 (m, 1H), 1.67 (dd, J=15.8, 9.1 Hz, 2H), 1.61 (ddd, J=11.8, 7.6, 3.5 Hz, 2H), 1.43-1.33 (m, 2H), 0.94 (t, J=12.3 Hz, 3H), 0.87 (t, J=11.1 Hz, 3H).

Example 23: 4-(Cyclopropylmethoxy)-7-isopropyl-11-oxo-2,6,7,11-tetrahydro-11-furo [2,3-h]pyrido[2,1-a]isoquinoline-10-carboxylic Acid

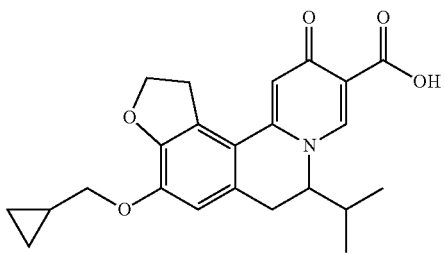 [SMILES: CC(C)C1Cc2cc(OCC3CC3)c3c(c2-c2cc(=O)c(C(=O)O)cn21)CCO3]

Starting from ethyl 4-hydroxy-7-isopropyl-11-oxo-2,6,7,11-tetrahydro-1H-furo[2,3-h]pyrido[2,1-a]isoquinoline-10-carboxylate and (bromomethyl)cyclopropane, referring to the synthesis steps 12 to 13 in Example 2, the title compound was obtained as awhile solid.

MS (ESI, pos.ion) m/z: 396.2 [M+H]$^+$; $^1$H NMR (400 MHz, CDCl$_3$) δ 8.46 (s, 1H), 6.91 (s, 1H), 6.64 (s, 1H), 4.97-4.77 (m, 1H), 4.56 (dd, J=19.5, 9.4 Hz, 1H), 3.94 (d, J=7.1 Hz, 2H), 3.84 (dd, J=9.8, 3.5 Hz, 1H), 3.67 (dt, J=15.5, 10.5 Hz, 1H), 3.41-3.24 (m, 2H), 3.04 (dd, J=15.9, 1.2 Hz, 1H), 1.82-1.72 (m, 1H), 1.39-1.28 (m, 1H), 0.92 (d, J=6.7 Hz, 3H), 0.84 (d, J=6.7 Hz, 3H), 0.71-0.59 (m, 2H), 0.44-0.22 (m, 2H).

Example 23A: (S)-4-(Cyclopropylmethoxy)-7-isopropyl-11-oxo-2,6,7,11-tetrahydro-11-furo [2,3-h]pyrido[2,1-a]isoquinoline-10-carboxylic Acid

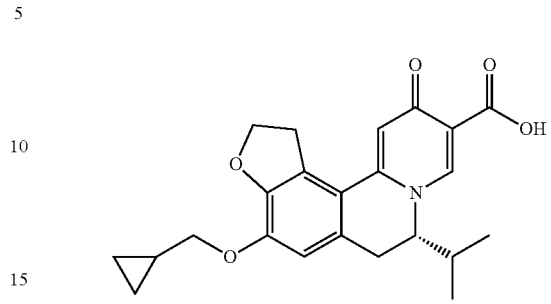

Starting from ethyl (S)-4-hydroxy-7-isopropyl-11-oxo-2,6,7,11-tetrahydro-1H-furo [2,3-h]pyrido[2,1-a]isoquinoline-10-carboxylate and (bromomethyl)cyclopropane, referring to the synthesis method in Example 23, the title compound was obtained as a white solid.

MS (ESI, pos.ion) m/z: 396.1[M+H]$^+$;
$^1$H NMR (400 MHz, CDCl$_3$) δ 16.02 (s, 1H), 8.50 (s, 1H), 6.92 (s, 1H), 6.66 (s, 1H), 4.88 (td, J=10.1, 4.1 Hz, 1H), 4.58 (dd, J=19.4, 9.4 Hz, 1H), 3.94 (t, J=9.6 Hz, 2H), 3.93-3.85 (m, 1H), 3.69 (dt, J=15.5, 10.5 Hz, 1H), 3.36 (ddd, J=13.9, 9.0, 4.1 Hz, 2H), 3.06 (d, J=15.8 Hz, 1H), 1.94-1.66 (m, 1H), 1.43-1.21 (m, 1H), 0.94 (d, J=6.6 Hz, 3H), 0.85 (d, J=6.7 Hz, 3H), 0.73-0.62 (m, 2H), 0.44-0.34 (m, 2H).

Example 24: 7-Isopropyl-4-(4-(methoxymethyl)thiazol-2-yl)-M-oxo-2,6,7,11-tetrahydro-1H-furo[2,3-h]pyrido[2,1-a]isoquinoline-10-carboxylic Acid

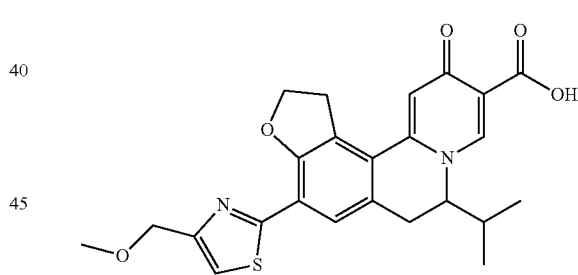

Step 1: (2-Bromothiazol-5-yl)methanol

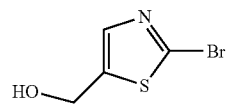

Methyl 2-bromothiazole-5-carboxylate (4.0 g, 18 mmol) was dissolved in THF (80 mL), then NaBH$_4$ (2.0 g, 53 mmol), LiCl (2.3 g, 54 mmol) and H$_2$O (16 mL) were added into the solution. The resulting mixture was stirred at room temperature for 6 h. Post processing: a saturated aqueous solution of ammonium chloride (30 mL) was added into the mixture, then the mixture was extracted with ethyl acetate (50 mL×3). The organic layers were combined and concentrated. The residue was purified by silica gel column chromatography (EA) to give the title compound as awhile solid (3.2 g, 16 mmol, 92%).

MS (ESI, pos.ion) m/z: 194.0 [M+H]⁺.

Step 2: 2-Bromo-5-(methoxymethyl)thiazole

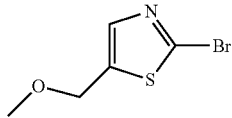

NaH (1.1 g, 28 mmol, 60 mass %) was added into a 100 mL two-necked flask, then THF (30 mL) was added. The mixture was cooled to −10° C. A solution of (2-bromothiazole-5-yl) methanol (2.66 g, 13.7 mmol) in THF (30 mL) was added dropwise into the mixture. The resulting mixture was stirred for 1 h. Then CH₃I (1.71 mL, 27.5 mmol) was added slowly and the reaction was stirred at −10° C. overnight. Postprocessing: To the mixture was slowly added water (15 mL) to quench the reaction, then the resulting mixture was extracted with EA (35 mL×3). The organic layers were combined and concentrated. The residue was purified by silica gel column chromatography (PE/EA(V/V) =5/1) to give the title compound as brown oil (1.0 g, 4.8 mmol, 35%).

MS (ESI, pos.ion) m/z: 208.0 [M+H]⁺.

Step 3: 4-(Methoxymethyl)-2-(tributylstannyl)thiazole

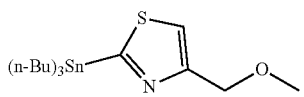

2-Bromo-4-(methoxymethyl)thiazole (200 mg, 0.96 mmol) was dissolved in THF (10 mL). The solution was cooled to −78° C. and stirred for 30 min, then n-butyl lithium (1.2 mL, 3.0 mmol) was added dropwise. The mixture was stirred for 1 h. Tri-n-butyltin chloride (0.32 mL, 1.15 mmol) was added and the resulting mixture was continuously stirred for 1 h. Then the mixture was slowly warmed to room temperature and stirred overnight. The resulting mixture was filtered, and the filter cake was washed with PE. The filtrate was concentrated in vacuo to give the title compound as colorless liquid (0.40 g, 0.96 mmol, 100.0%) which was used directly in the next reaction.

MS (ESI, pos.ion) m/z: 419.8 [M+H]⁺.

Step 4: 7-Isopropyl-4-(4-(methoxymethyl)thiazol-2-yl)-11-oxo-2,6,7,11-tetrahydro-1H-furo [2,3-h]pyrido[-a]isoquinoline-10-carboxylic Acid

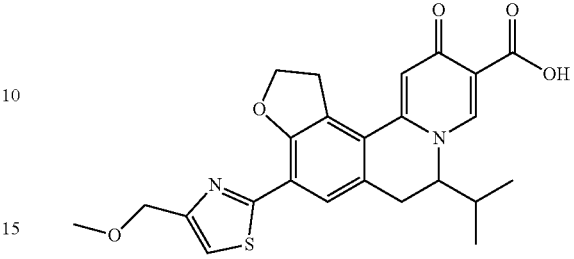

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 4-(methoxymethyl)-2-tributylstannyl)thiazole, referring to the synthesis step 2 in Example 8, the title compound was obtained as a white solid.

MS (ESI, pos.ion) m/z: 452.7 [M+H]⁺;

¹H NMR (400 MHz, CDCl₃) 515.72 (b, 1H), 8.89 (s, 1H), 8.55 (s, 1H), 7.41 (s, 1H), 7.06 (s, 1H), 4.97-4.88 (m, 1H), 4.67-4.54 (m, 3H), 3.97-3.89 (m, 1H), 3.85-3.72 (m, 1H), 3.55-3.43 (m, 4H), 3.40-3.33 (m, 1H), 3.26-3.18 (m, 1H), 2.08-2.00 (m, 1H), 0.99 (d, J=3.2 Hz, 3H), 0.92 (d, J=2.4 Hz, 3H).

Example 25: 4-([1,1'-Biphenyl]-4-yl)-7-isopropyl-11-oxo-2,6,7,11-tetrahydro-1H-furo[2,3-h]pyrido[2,1-a]isoquinoline-10-carboxylic Acid

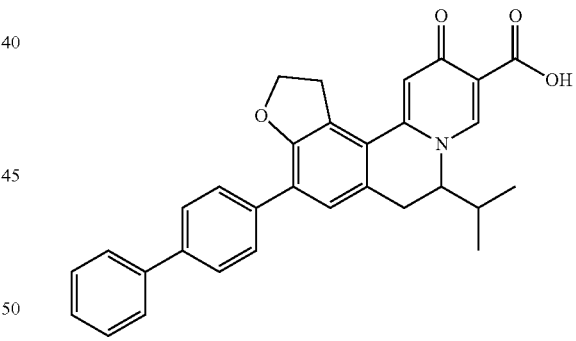

Starting from [1,1'-biphenyl]-4-ylboronic acid and ethyl 7-isopropyl-11-oxo-4-(((trifluoromethyl)sulfonyl)oxy)-2,6,7,11-tetrahydro-177-furo[2,3-h]pyrido[2,1-a]isoquinoline-10-carboxylate, referring to the synthesis method in Example 9, the title compound was obtained as a white solid.

MS (ESI, pos.ion) m/z: 478.0 [M+H]⁺;

¹H NMR (400 MHz, CDCl₃) δ 15.82 (s, 1H), 8.51 (s, 1H), 7.81 (d, J=8.3 Hz, 2H), 7.70 (d, J=8.3 Hz, 2H), 7.64 (d, J=7.3 Hz, 2H), 7.47 (t, J=7.6 Hz, 2H), 7.38 (t, J=7.2 Hz, 1H), 7.29 (s, 1H), 7.07 (s, 1H), 4.91 (td, J=10.0, 3.9 Hz, 1H), 4.60 (q, J=19.5, 9.3 Hz, 1H), 3.89 (dd, J=9.6, 3.9 Hz, 1H), 3.80-3.69 (m, 1H), 3.47-3.39 (m, 1H), 3.36 (dd, J=16.2, 4.4 Hz, 1H), 3.20 (d, J=16.0 Hz, 1H), 1.85-1.76 (m, 1H), 0.97 (d, J=6.6 Hz, 3H), 0.89 (d, J=6.7 Hz, 3H).

Example 26: 7-Isopropyl-4-(4-methoxyphenyl)-11-oxo-2,6,7,11-tetrahydro-1H-furo[2,3-h]pyrido[2,1-a]isoquinoline-10-carboxylic Acid

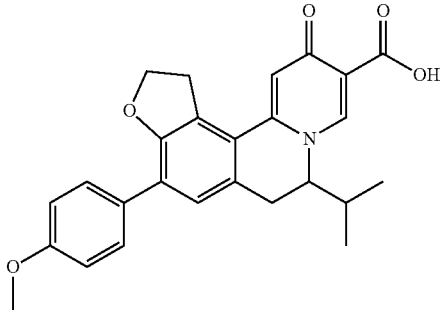 [SMILES: COc1ccc(-c2cc3c(c4c2OCC4)-c2cc(=O)c(C(=O)O)cn2C(C(C)C)C3)cc1]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 2-(4-methoxyphenyl)-4,4,5,5-tetramethyl-1,3,2-dioxaborane, referring to the synthesis method in Example 9, the title compound was obtained as a white solid.

MS (ESI, pos.ion) m/z: 432.2[M+H]$^+$;

$^1$H NMR (400 MHz, CDCl$_3$) δ 15.95 (s, 1H), 8.55 (s, 1H), 7.70 (d, J=8.0 Hz, 2H), 7.22 (s, 1H), 7.12-6.89 (m, 3H), 4.87 (s, 1H), 4.57 (dd, J=18.3, 9.0 Hz, 1H), 4.05-3.80 (m, 4H), 3.72 (dd, J=24.9, 10.4 Hz, 1H), 3.51-3.26 (m, 2H), 3.20 (s, 1H), 1.82 (s, 1H), 0.93 (dd, J=35.4, 5.9 Hz, 6H).

Example 27: 7-Isopropyl-4-(3-methoxyphenyl)-11-oxo-2,6,7,11-tetrahydro-1H-furo[2,3-h]pyrido[2,1-a]isoquinoline-10-carboxylic Acid

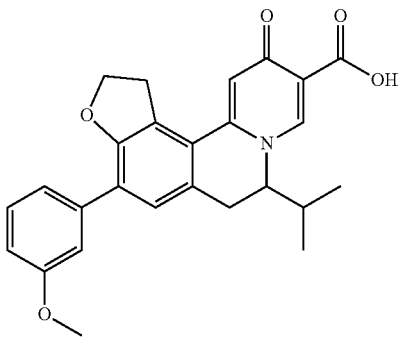 [SMILES: COc1cccc(-c2cc3c(c4c2OCC4)-c2cc(=O)c(C(=O)O)cn2C(C(C)C)C3)c1]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 2-(3-methoxyphenyl)-4,4,5,5-tetramethyl-1,3,2-dioxaborolane, referring to the synthesis method in Example 9, the title compound was obtained as a white solid.

MS (ESI, pos.ion) m/z: 432.3M+H]$^+$;

$^1$H NMR (400 MHz, CDCl$_3$) δ 15.90 (s, 1H), 8.56 (s, 1H), 7.39 (t, J=7.9 Hz, 1H), 7.31 (d, J=7.5 Hz, 2H), 7.25 (s, 1H), 7.06 (s, 1H), 6.97-6.91 (m, 1H), 4.88 (td, J=10.0, 3.7 Hz, 1H), 4.58 (q, J=9.3 Hz, 1H), 4.02-3.91 (m, 1H), 3.88 (s, 3H), 3.80-3.65 (m, 1H), 3.48-3.28 (m, 2H), 3.19 (d, J=15.4 Hz, 1H), 1.84-1.71 (m, 1H), 0.91 (dt, J=29.6, 14.7 Hz, 6H).

Example 28: 7-Isopropyl-11-oxo-4-(4-phenoxyphenyl)-2,6,7,11-tetrahydro-1H-furo[2,3-h]pyrido[2,1-a]isoquinoline-10-carboxylic Acid

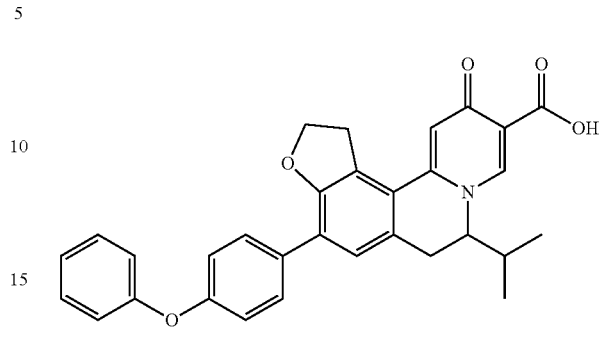

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 4-phenoxyphenylboronic acid, referring to the synthesis method in Example 9, the title compound was obtained as a white solid.

MS (ESI, pos.ion) m/z: 494.4 [M+H]$^+$;

$^1$H NMR (600 MHz, CDCl$_3$) δ 15.81 (s, 1H), 8.50 (s, 1H), 7.70 (d, J=8.8 Hz, 2H), 7.40-7.35 (m, 2H), 7.22 (s, 1H), 7.17-7.13 (m, 1H), 7.11-7.05 (m, 4H), 7.04 (s, 1H), 4.90-4.85 (m, 1H), 4.58 (q, J=19.6, 9.2 Hz, 1H), 3.86 (d, J=11.2 Hz, 1H), 3.74-3.70 (m, 1H), 3.44-3.40 (m, 1H), 3.34 (dd, J=15.6, 3.7 Hz, 1H), 3.18 (d, J=16.1 Hz, 1H), 1.82-1.77 (m, 1H), 0.96 (d, J=6.7 Hz, 3H), 0.88 (d, J=6.7 Hz, 3H).

Example 29: 7-Isopropyl-11-oxo-4-(pyridine-4-yl)-2,6,7,11-tetrahydro-1H-furo[2,3-h]pyrido [2,1-a]isoquinoline-10-carboxylic Acid

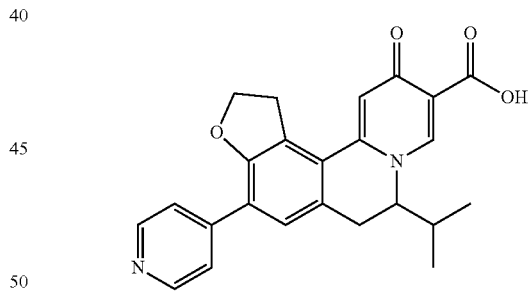

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and pyridine-4-boronic acid, referring to the synthesis method in Example 9, the title compound was obtained as a white solid.

MS (ESI, pos.ion) m/z: 403.0 [M+H]$^+$;

$^1$H NMR (400 MHz, CD$_3$OD) δ 8.68 (d, J=6.2 Hz, 2H), 8.48 (s, 1H), 8.29 (d, J=5.2 Hz, 2H), 7.48 (s, 1H), 7.00 (s, 1H), 4.93-4.86 (m, 1H), 4.58 (dd, J=19.2, 9.0 Hz, 2H), 3.73-3.64 (m, 2H), 3.40-3.30 (m, 2H), 1.58 (dd, J=8.1, 5.0 Hz, 1H), 0.85 (d, J=6.5 Hz, 3H), 0.75 (d, J=6.7 Hz, 3H).

Example 30: 7-Isopropyl-11-oxo-4-(pyrimidin-5-yl)-2,6,7,11-tetrahydro-1H-furo[2,3-h]pyrido[2,1-a]isoquinoline-10-carboxylic Acid

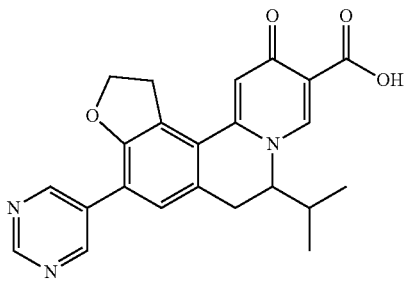 [SMILES: CC(C)C1Cc2cc(-c3cncnc3)c3c(c2-c2cc(=O)c(C(=O)O)cn21)CCO3]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and pyrimidine-5-boronic acid, referring to the synthesis method in Example 9, the title compound was obtained as a white solid.

MS (ESI, pos.ion) m/z: 404.2[M+H]$^+$;

$^1$H NMR (400 MHz, DMSO-d$_6$) δ 16.34 (s, 1H), 9.21 (s, 2H), 9.17 (s, 1H), 8.86 (s, 1H), 7.68 (s, 1H), 7.11 (s, 1H), 4.88 (s, 1H), 4.57 (dd, J=18.5, 9.1 Hz, 1H), 4.49 (d, J=6.5 Hz, 1H), 3.98-3.83 (m, 1H), 3.27 (s, 1H), 1.57 (s, 1H), 1.24 (s, 2H), 0.88 (t, J=8.8 Hz, 3H), 0.78 (d, J=6.5 Hz, 3H).

Example 31: 4-(Cyclopropylethynyl)-7-isopropyl-11-oxo-2,6,7,11-tetrahydro-1H-furo[2,3-h]pyrido[2,1-a]isoquinoline-10-carboxylic Acid

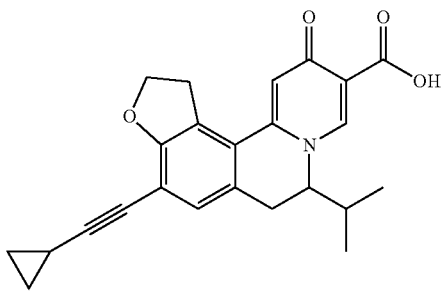 [SMILES: CC(C)C1Cc2cc(C#CC3CC3)c3c(c2-c2cc(=O)c(C(=O)O)cn21)CCO3]

Step 1: Ethyl 4-(cyclopropylethynyl)-7-isopropyl-11-oxo-2,6,7,11-tetrahydro-1H-furo[2,3-h]pyrido[2,1-a]isoquinoline-10-carboxylate

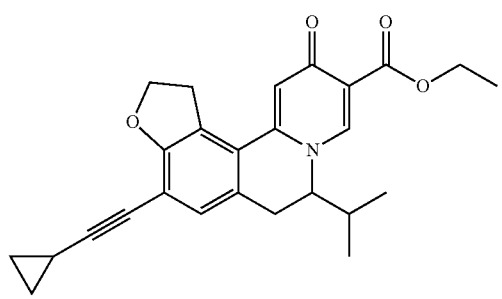 [SMILES: CCOC(=O)c1cn2c(cc1=O)-c1c(cc(C#CC3CC3)c3c1CCO3)CC2C(C)C]

Cyclopropane acetylene (0.05 mL, 0.60 mmol), 7-isopropyl-11-oxo-4-(((trifluoromethyl) sulfonyl)oxy)-2,6,7,11-tetrahydro-11-furo[2,3-h]pyrido[2,1-a]isoquinoline-10-carboxylic acid (150 mg, 0.30 mmol), triethylamine (0.17 mL), DMF (6.00 mL), CuI (11.0 mg, 0.06 mmol) and (PPh$_3$)$_2$PdCl$_2$ (42.0 mg, 0.06 mmol) were sequentially added into a two-necked flask. After the addition, the air in the flask was replaced with nitrogen three times. The mixture was heated to 90° C. under nitrogen protection and reacted for 2.5 h. To the reaction mixture were added DCM (20 mL) and saturated brine (20 mL). The organic layers were collected, dried over anhydrous sodium sulfate and distilled in vacuo to remove the solvent. The residue was purified by thin layer chromatography (DCM/MeOH(V/V)=20/1) to give the title compound as a yellow solid (124 mg, 0.30 mmol, 99.30%).

MS (ESI, pos.ion) m/z: 418.0[M+H]$^+$.

Step 2: 4-(Cyclopropylethynyl)-7-isopropyl-11-oxo-2,6,7,11-tetrahydro-1H-furo[2,3-h]pyrido [2,1-a]isoquinoline-10-carboxylic Acid

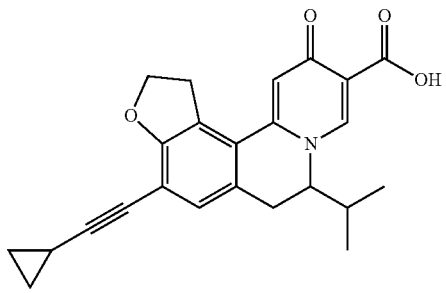 [SMILES: CC(C)C1Cc2cc(C#CC3CC3)c3c(c2-c2cc(=O)c(C(=O)O)cn21)CCO3]

Ethyl 4-(cyclopropylethynyl)-7-isopropyl-11-oxo-2,6,7,11-tetrahydro-177-furo[2,3-h]pyrido[2,1-a]isoquinoline-10-carboxylate (124 mg, 0.30 mmol), MeOH (8.00 mL), THF (2.00 mL) and lithium hydroxide monohydrate (100 mg, 2.38 mmol) were sequentially added into a single-necked flask. After the addition, the mixture was reacted for 12 h at room temperature. The solvent was distilled off under reduced pressure and the residue was purified by thin layer chromatography (DCM/MeOH(V/V)=20/1) to give the title compound as a pale yellow solid (100 mg, 0.26 mmol, 86.46%).

MS (ESI, pos.ion) m/z: 390.1 [M+H]$^+$.

$^1$H NMR (600 MHz, CDCl$_3$) δ 15.73 (s, 1H), 8.46 (s, 1H), 7.08 (s, 1H), 6.98 (s, 1H), 4.91-4.84 (m, 1H), 4.58 (q, J=19.3, 9.4 Hz, 1H), 3.81 (dd, J=10.0, 3.1 Hz, 1H), 3.74-3.62 (m, 2H), 3.39-3.32 (m, 1H), 3.23 (dd, J=15.5, 4.6 Hz, 1H), 3.07 (dd, J=15.9, 1.6 Hz, 1H), 1.72-1.66 (m, 1H), 0.96-0.80 (m, 10H).

Example 32: 4-(1-Cyclopropyl-1H-pyrazol-4-yl)-7-isopropyl-11-oxo-2,6,7,11-tetrahydro-1H-furo[2,3-h]pyrido[2,1-a]isoquinoline-10-carboxylic Acid

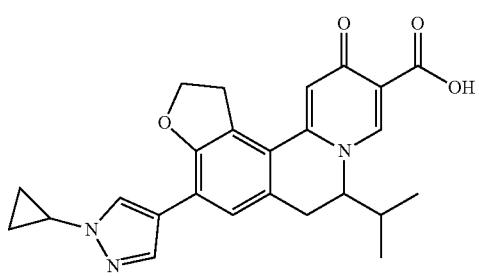 [SMILES: CC(C)C1Cc2cc(-c3cnn(C4CC4)c3)c3c(c2-c2cc(=O)c(C(=O)O)cn21)CCO3]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 1-cyclopropyl-4-(4,4,5,5-tetramethyl-1,3,2-dioxaborolan-2-yl)-1H-pyrazole, referring to the synthesis method in Example 9, the title compound was obtained as a white solid.

MS (ESI, pos.ion) m/z: 432.4[M+H]+;

1H NMR (400 MHz, CDCl3) δ 15.91 (s, 1H), 8.51 (s, 1H), 8.09 (s, 1H), 7.95 (s, 1H), 7.29 (s, 1H), 7.01 (s, 1H), 5.32 (s, 2H), 4.94 (s, 1H), 4.62 (d, J=9.2 Hz, 1H), 3.88 (s, 1H), 3.69 (d, J=9.3 Hz, 1H), 3.34 (d, J=16.5 Hz, 1H), 3.17 (d, J=15.6 Hz, 1H), 1.77 (s, 1H), 1.13 (dd, J=33.8, 12.1 Hz, 4H), 0.92 (dd, J=36.3, 5.6 Hz, 6H).

Example 33: 4-(1-Cyclobutyl-1H-pyrazol-4-yl)-7-isopropyl-11-oxo-2,6,7,11-tetrahydro-1H-furo[2,3-h]pyrido[2,1-a]isoquinoline-10-carboxylic Acid

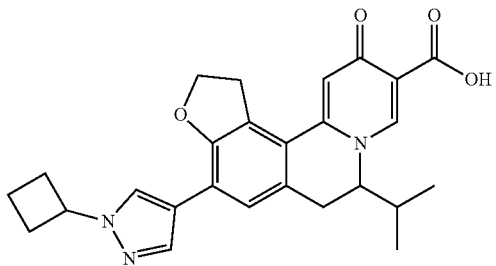 [SMILES: CC(C)C1Cc2cc(-c3cnn(C4CCC4)c3)c3c(c2-c2cc(=O)c(C(=O)O)cn21)CCO3]

Starting from ethyl 7-isopropyl-11-oxo-4-(((trifluoromethyl)sulfonyl)oxy)-2,6,7,11-tetrahydro-11-furo[2,3-h]pyrido[2,1-a]isoquinoline-10-carboxylate and 11-cyclobutyl-4-(4,4,5,5-tetramethyl-1,3,2-dioxaborolan-2-yl)-1H-pyrazole, referring to the synthesis method in Example 9, the title compound was obtained as a white solid.

MS (ESI, pos.ion) m/z: 446.4 [M+H]+;

1H NMR (400 MHz, CDCl3) δ 8.48 (s, 1H), 8.06 (s, 1H), 7.98 (s, 1H), 7.29 (s, 1H), 7.00 (s, 1H), 4.97-4.89 (m, 1H), 4.82 (t, 1H), 4.61 (q, J=19.7, 9.1 Hz, 1H), 3.89-3.82 (m, 1H), 3.78-3.62 (m, 2H), 3.44-3.35 (m, 1H), 3.34-3.27 (m, 1H), 3.18-3.11 (m, 1H), 2.66-2.44 (m, 4H), 1.95-1.82 (m, 2H), 0.95 (d, J=6.7 Hz, 3H), 0.86 (d, J=6.7 Hz, 3H).

Example 34: 7-Isopropyl-11-oxo-4-(1-(tetrahydro-2H-pyran-4-yl)-1H-pyrazol-4-yl)-2,6,7,11-tetrahydro-1H-furo[2,3-h]pyrido[2,1-a]isoquinoline-10-carboxylic Acid

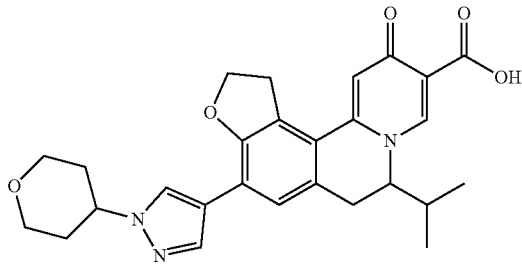 [SMILES: CC(C)C1Cc2cc(-c3cnn(C4CCOCC4)c3)c3c(c2-c2cc(=O)c(C(=O)O)cn21)CCO3]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 1-(tetrahydro-2H-pyran-4-yl)-4-(4,4,5,5-tetramethyl-1,3,2-dioxaborolan-2-yl)-1H-pyrazole, referring to the synthesis method in Example 9, the title compound was obtained as a white solid.

MS (ESI, pos.ion) m/z: 476.2 [M+H]+;

1H NMR (400 MHz, CDCl3) δ 8.48 (s, 1H), 8.08 (s, 1H), 7.98 (s, 1H), 7.29 (s, 1H), 7.00 (s, 1H), 4.97-4.89 (m, 1H), 4.61 (q, J=19.6, 9.4 Hz, 1H), 4.46-4.37 (m, 1H), 4.19-4.09 (m, 2H), 3.89-3.81 (m, 1H), 3.76-3.67 (m, 1H), 3.62-3.53 (m, 2H), 3.45-3.27 (m, 3H), 3.20-3.12 (m, 1H), 2.22-2.07 (m, 4H), 0.95 (d, J=6.6 Hz, 3H), 0.86 (d, J=6.7 Hz, 3H).

Example 35: 7-Isopropyl-4-(1-(oxetan-3-yl)-1H-pyrazol-4-yl)-11-oxo-2,6,7,11-tetra hydro-1H-furo[2,3-h]pyrido[2,1-a]isoquinoline-10-carboxylic Acid

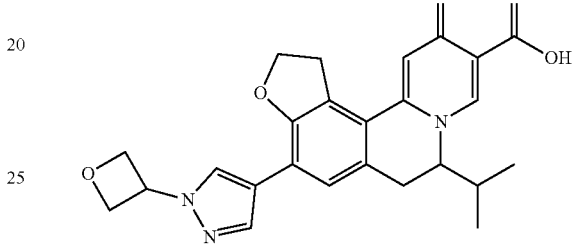

Starting from ethyl 7-isopropyl-11-oxo-4-(((trifluoromethyl)sulfonyl)oxy)-2,6,7,11-tetrahydro-11-furo[2,3-h]pyrido[2,1-a]isoquinoline-10-carboxylate and 1-(oxetan-3-yl)-4-(4,4,5,5-tetramethyl-1,3,2-dioxaborolan-2-yl)-1H-pyrazole, referring to the synthesis method in Example 9, the title compound was obtained as a white solid.

MS (ESI, pos.ion) m/z: 448.4 [M+H]+;

1H NMR (400 MHz, CDCl3) δ 15.83 (s, 1H), 8.48 (s, 1H), 8.24 (s, 1H), 8.05 (s, 1H), 7.31 (s, 1H), 7.01 (s, 1H), 5.56-5.48 (m, 1H), 5.10 (d, J=6.9 Hz, 3H), 4.98-4.90 (m, 1H), 4.62 (q, J=19.2, 9.4 Hz, 1H), 3.86 (d, J=5.6 Hz, 1H), 3.77-3.67 (m, 1H), 3.49 (s, 1H), 3.45-3.37 (m, 1H), 3.33 (dd, J=15.4, 4.3 Hz, 1H), 3.17 (d, J=15.7 Hz, 1H), 1.80-1.73 (m, 1H), 0.95 (d, J=6.6 Hz, 3H), 0.86 (d, J=6.7 Hz, 3H).

Example 36: 4-(1-(1-(tert-Butoxycarbonyl)piperidin-4-yl)-1H-pyrazol-4-yl)-7-isopropyl-11-oxo-2,6,7,11-tetrahydro-1H-furo[2,3-h]pyrido[2,1-a]isoquinoline-10-carboxylic Acid

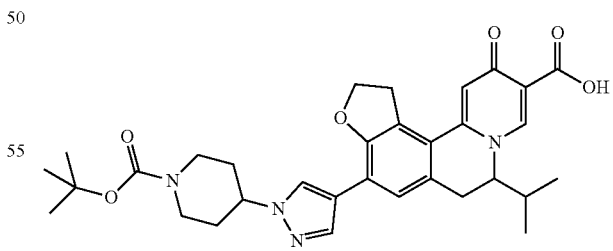

Starting from ethyl 7-isopropyl-11-oxo-4-(((trifluoromethyl)sulfonyl)oxy)-2,6,7,11-tetrahydro-11-furo[2,3-h]pyrido[2,1-a]isoquinoline-10-carboxylate and tert-butyl 4-(4-(4,4,5,5-tetramethyl-1,3,2-dioxaborolan-2-yl)-1H-pyrazol-1-yl)piperidine-1-carboxylate, referring to the synthesis method in Example 9, the title compound was obtained as a pale yellow solid.

MS (ESI, pos.ion) m/z: 575.5[M+H]+;

¹H NMR (400 MHz, CDCl₃) δ 15.92 (s, 1H), 8.51 (s, 1H), 8.08 (s, 1H), 7.99 (s, 1H), 7.30 (s, 1H), 7.00 (s, 1H), 5.31 (s, 2H), 4.93 (td, J=10.1, 3.8 Hz, 1H), 4.61 (q, J=9.3 Hz, 1H), 4.38-4.29 (m, 2H), 3.90 (dd, J=9.8, 3.4 Hz, 1H), 3.72 (dt, J=15.7, 10.5 Hz, 1H), 3.47-3.28 (m, 2H), 3.17 (d, J=15.6 Hz, 1H), 2.92 (s, 1H), 2.18 (d, J=11.0 Hz, 2H), 2.06-1.91 (m, 2H), 1.78-1.71 (m, 1H), 1.49 (s, 9H), 0.96 (d, J=6.6 Hz, 3H), 0.86 (d, J=6.7 Hz, 3H).

Example 37: 7-Isopropyl-4-(1-(1-isopropylpiperidin-4-yl)-1H-pyrazol-4-yl)-11-oxo-2,6,7,11-tetrahydro-1H-furo[2,3-h]pyrido[2,1-a]isoquinoline-10-carboxylic Acid

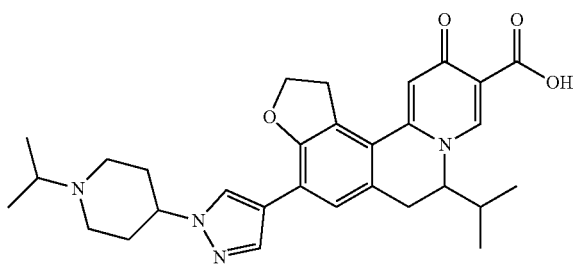 [SMILES: CC(C)C1Cc2cc(-c3cnn(C4CCN(C(C)C)CC4)c3)c3c(c2-c2cc(=O)c(C(=O)O)cn21)CCO3]

Step 1: 4-(4-(4,4,5,5-tetramethyl-1,3,2-dioxaborolan-2-yl)-1H-pyrazol-1-yl)piperidine

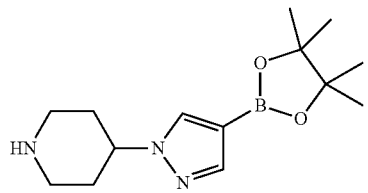 [SMILES: CC1(C)OB(c2cnn(C3CCNCC3)c2)OC1(C)C]

tert-Butyl 4-(4-(4,4,5,5-tetramethyl-1,3,2-dioxaborolan-2-yl)-1H-pyrazol-1-yl) piperidine-1-carboxylate (1.5 g, 4.0 mmol) and DCM (5 mL) were added into the reaction flask. The mixture was cooled to 0° C., then trifluoroacetic acid (5 mL) was added dropwise. The resulting mixture was warmed to room temperature and stirred for 4 h. After the reaction was completed, the solvent was distilled off in vacuo. Methanol (50 mL) was added. The pH was adjusted to 6 with potassium carbonate solid. The solid was removed by filtration, and the filtrate was concentrated in vacuo to give the title compound as pale yellow oily liquid (1.1 g, 4.0 mmol, 100%) Which was directly used in the next step.

Step 2: 1-Isopropyl-4-(4-(4,4,5,5-tetramethyl-1,3,2-dioxaborolan-2-yl)-1H-pyrazol-1-yl) piperidine

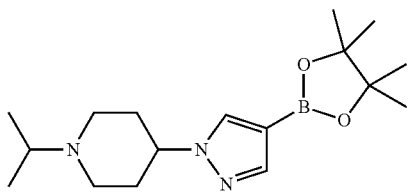 [SMILES: CC(C)N1CCC(n2cc(B3OC(C)(C)C(C)(C)O3)cn2)CC1]

4-(4-(4,4,5,5-Tetramethyl-1,3,2-dioxaborolan-2-yl)-1H-pyrazol-1-yl)piperidine (1.10 g, 4.0 mmol) was added to the reaction flask, then acetonitrile (20 mL) was added to dissolve it. To the solution were added K₂CO₃ (1.1 g, 8.0 mmol) and 2-iodopropane (1 g, 5.88 mmol). The resulting mixture was heated to 70° C. and reacted for 5 h. After the reaction was completed, the solvent was distilled off under reduced pressure. The mixture was diluted with water (10 mL) and then extracted with dichloromethane (10 mL×3). The organic layers were combined, dried over anhydrous sodium sulfate and filtered. The filtrate was distilled in vacuo to remove the solvent to give the title compound as pale yellow oily liquid (1.17 g, 3.67 mmol, 92.4%) which was directly used in the next step.

MS (ESI, pos.ion) m/z: 320.1[M+H]⁺.

Step 3: 7-Isopropyl-4-(1-(1-isopropylpiperidin-4-yl)-1H-pyrazol-4-yl)-11-oxo-2,6,7,11-tetrahydro-1H-furo[2,3-h]pyrido[2,1-a]isoquinoline-10-carboxylic Acid

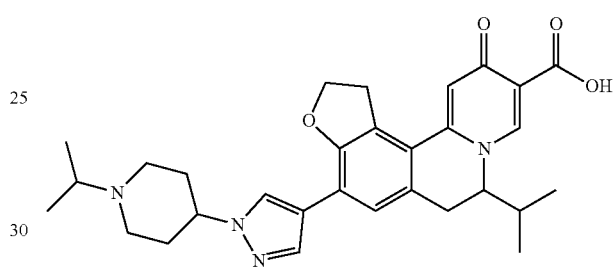

Starting from ethyl 7-isopropyl-11-oxo-4-((((trifluoromethyl)sulfonyl)oxy)-2,6,7,11-tetrahydro-1H-furo[2,3-h]pyrido[2,1-a]isoquinoline-10-carboxylate and 1-isopropyl-4-(4-(4,4,5,5-tetramethyl-1,3,2-dioxaborolan-2-yl)-1H-pyrazole-1-yl)piperidine, referring to the synthesis method in Example 9, the title compound was obtained as a white solid.

MS (ESI, pos.ion) m/z: 517.2[M+H]⁺;
¹H NMR (400 MHz, CDCl₃) δ 15.94 (s, 1H), 8.51 (s, 1H), 8.13 (s, 1H), 7.96 (s, 1H), 7.30 (s, 1H), 7.01 (s, 1H), 4.93 (td, J=9.9, 3.7 Hz, 1H), 4.61 (q, J=9.4 Hz, 1H), 4.26-4.13 (m, 1H), 3.89 (d, J=6.4 Hz, 1H), 3.72 (dt, J=15.5, 10.4 Hz, 1H), 3.46-3.27 (m, 2H), 3.17 (d, J=15.7 Hz, 1H), 3.05 (d, J=11.4 Hz, 2H), 2.82 (dt, J=13.0, 6.5 Hz, 1H), 2.35 (t, J=11.2 Hz, 2H), 2.24 (d, J=11.8 Hz, 2H), 2.13-2.00 (m, 2H), 1.79-1.72 (m, 1H), 1.08 (t, J=11.3 Hz, 6H), 0.96 (d, J=6.6 Hz, 3H), 0.87 (d, J=6.7 Hz, 3H).

Example 38: 4-(1-(1-(Cyclopropylsulfonyl)piperidin-4-yl)-1H-pyrazol-4-yl)-7-isopropyl-11-oxo-2,6,7,11-tetrahydro-1H-furo[2,3-h]pyrido[2,1-a]isoquinoline-10-carboxylic Acid

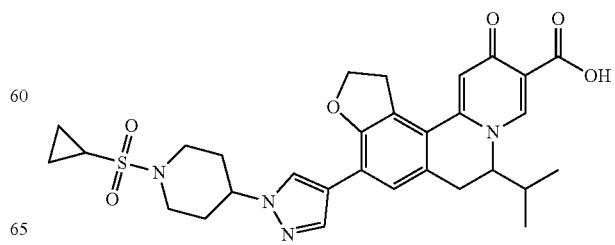

Step 1: 1-(Cyclopropylsulfonyl)-4-(4-(4,4,5,5-tetramethyl-1,3,2-dioxaborolan-2-yl)-1H-pyrazol-1-yl)piperidine

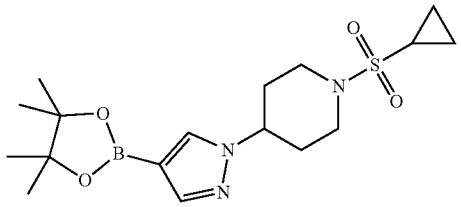 [SMILES: CC1(C)OB(c2cnn(C3CCN(S(=O)(=O)C4CC4)CC3)c2)OC1(C)C]

4-(4-(4,4,5,5-tetra methyl-1,3,2-dioxaborolan-2-yl)-1H-pyrazole-1-yl) piperidine (700 mg, 2.5 mmol) was dissolved in DCM (12 mL) and methanol (3 mL) at −10° C. Triethylamine (3.54 mL, 25.3 mmol) was added into the solution, then cyclopropylsulfonyl chloride (0.643 mL, 6.31 mmol) was slowly added dropwise. The mixture was stirred at room temperature for 3 h.

Post processing: To the resulting mixture was added saturated ammonium chloride (20 mL) to quench the reaction. The mixture was extracted with DCM (10 mL×2). The organic layers were combined and washed with saturated saline (20 mL). Then the organic layers were collected, dried over anhydrous sodium sulfate, filtered and concentrated to give the title compound as a pale yellow solid (0.89 g, 2.3 mmol, 92%).

MS (ESI, pos.ion) m/z: 382.1[M+H]$^+$.

Step 2: 4-(1-(1-(Cyclopropylsulfonyl)piperidin-4-yl)-1H-pyrazol-4-yl)-7-isopropyl-11-oxo-2,6,7,11-tetrahydro-1H-furo[2,3-h]pyrido[2,1-a]isoquinoline-10-carboxylic Acid

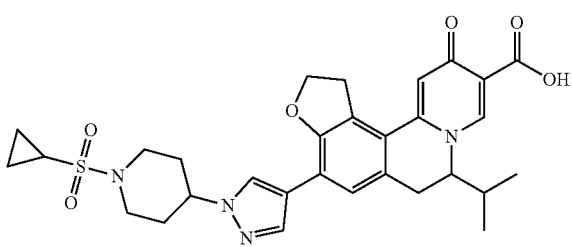 [SMILES: CC(C)C1Cc2cc(-c3cnn(C4CCN(S(=O)(=O)C5CC5)CC4)c3)c3c(c2-c2cc(=O)c(C(=O)O)cn21)CCO3]

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 1-(cyclopropylsulfonyl)-4-(4-(4,4,5,5-tetramethyl-1,3,2-dioxaborolan-2-yl)-1H-pyrazol-1-yl]piperidine, referring to the synthesis method in Example 9, the title compound was obtained as a pale yellow solid. MS (ESI, pos.ion) m/z: 579.7[M+H]$^+$;

$^1$H NMR (400 MHz, CD$_3$OD) δ 8.57 (s, 1H), 8.14 (s, 1H), 8.01 (s, 1H), 7.35 (s, 1H), 7.05 (s, 1H), 5.01-4.87 (m, 1H), 4.62 (dd, J=19.1, 9.5 Hz, 1H), 4.04 (d, J=7.8 Hz, 1H), 3.95 (d, J=12.7 Hz, 2H), 3.81-3.68 (m, 1H), 3.41 (dd, J=10.0, 5.7 Hz, 1H), 3.33 (s, 2H), 3.20 (d, J=15.9 Hz, 1H), 3.08 (t, J=11.2 Hz, 2H), 2.39 (td, J=8.0, 4.0 Hz, 1H), 2.28 (d, J=10.9 Hz, 2H), 2.23-2.08 (m, 2H), 1.77 (s, 1H), 1.16 (d, J=4.5 Hz, 2H), 1.05 (dd, J=10.1, 4.8 Hz, 2H), 0.96 (d, 7=6.6 Hz, 3H), 0.85 (d, J=6.7 Hz, 3H).

Example 39: 7-Isopropyl-4-(3-methoxypropoxy)-2,2-dimethyl-11-oxo-2,6,7,11-tetrahydro-1H-furo[2,3h]pyrido[2,1-a]isoquinoline-10-carboxylic Acid

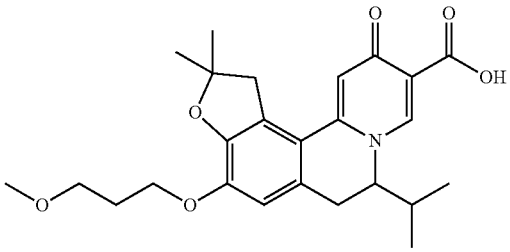 [SMILES: COCCCOc1cc2c(c3c1OC(C)(C)C3)-c1cc(=O)c(C(=O)O)cn1C(C(C)C)C2]

Step 1: 2,2-Dimethyl-2,3-dihydrobenzofuran-7-yl acetate

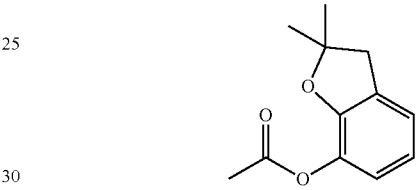

2,2-Dimethyl-2,3-dihydrobenzofuran-7-ol (5 g, 30.45 mmol), DCM (100 mL), triethylamine (6.35 mL, 45.6 mmol) and DMAP (0.379 g, 3.04 mmol) were added into a reaction flask and the mixture was cooled to 0° C. Acetic anhydride (3.17 mL, 33.5 mmol) was added dropwise and the mixture was heated to room temperature and stirred for 12 h. After the reaction was completed, the mixture was sequentially wash with saturated sodium bicarbonate (100 mL), water (100 mL), hydrochloric acid (100 mL, 1M) and saturated sodium chloride (100 mL). Then the resulting mixture was dried over anhydrous sodium sulfate, filtered and distilled in vacuo to remove the solvent. The residue was purified by silica gel column chromatography (PE/EA(V/V) =10/1) to give the title compound as colorless oily liquid (6.28 g, 30.45 mmol, 100%).

$^1$H NMR (400 MHz, CDCl$_3$) δ 7.02 (d, J=7.2 Hz, 1H), 6.89 (d, J=7.9 Hz, 1H), 6.81 (t, J=7.7 Hz, 1H), 3.06 (s, 2H), 2.31 (d, J=15.6 Hz, 3H), 1.48 (d, J=20.2 Hz, 6H).

Step 2: 5-Bromo-2,2-dimethyl-2,3-dihydrobenzofuran-7-yl acetate

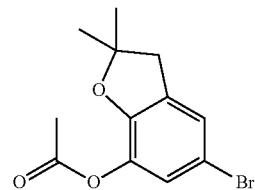 [SMILES: CC(=O)Oc1cc(Br)cc2c1OC(C)(C)C2]

To the reaction flask were added 2,2-dimethyl-2,3-dihydrobenzofuran-7-yl acetate (6.28 g, 30.45 mmol), acetonitrile (100 mL) and NBS (8.30 g, 45.67 mmol). After the addition, the mixture was heated to 60° C. and stirred for 12 h. After the reaction was completed, the solvent was distilled off in vacuo. To the residue was added saturated sodium thiosulfate solution (100 mL) to quench the reaction. The resulting mixture was extracted with ethyl acetate (40 mL×3). The organic layers were combined and the combined organic layers were dried over anhydrous sodium sulfate and filtered. The filtrate was distilled in vacuo. The residue was purified by silica gel column chromatography (PE/EA(V/V)=20/1) to give the title compound as a pale yellow solid (6.56 g, 23.0 mmol, 75.6%).

$^1$H NMR (400 MHz, CDCl$_3$) δ 7.13 (s, 1H), 7.04 (s, 1H), 3.03 (s, 2H), 2.30 (s, 3H), 1.48 (s, 6H).

Step 3:
5-Bromo-2,2-dimethyl-2,3-dihydrobenzofuran-7-ol

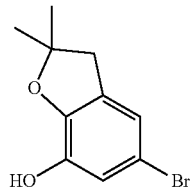

To the reaction flask was added 5-bromo-2,2-dimethyl-2,3-dihydrobenzofuran-7-yl acetate (6.56 g, 23.0 mmol), and methanol (100 mL) was added to dissolved it. Then potassium carbonate (3.04 g, 46.1 mmol) was added. The mixture was heated to 70° C. and stirred overnight. The solvent was distilled off in vacuo. To the mixture was added water (20 mL), then the mixture was added 1 M hydrochloric acid to adjust pH to acidity. The resulting mixture was extracted with ethyl acetate (20 mL×2). The organic layers were combined and the combined organic layers were dried over anhydrous sodium sulfate and filtered. The solvent was distilled off in vacuo. The residue was purified by silica gel column chromatography (PE/EA(V/V)=10/1) to give the title compound as colorless oily liquid (3.96 g, 16.31 mmol, 70.9%). $^1$H NMR (400 MHz, CDCl$_3$) δ 6.91 (s, 1H), 6.86 (s, 1H), 5.25 (s, 1H), 3.04 (s, 2H), 1.50 (s, 6H).

Step 4: 7-Isopropyl-4-(3-methoxypropoxy)-2,2-dimethyl-11-oxo-2,6,7,11-tetrahydro-1H-furo [2,3-h]pyrido[2,1-a]isoquinoline-10-carboxylic Acid

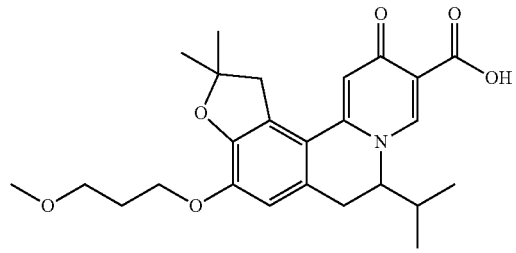 [SMILES: COCCCOc1cc2c(c3c1OC(C)(C)C3)-c1cc(=O)c(C(=O)O)cn1C(C(C)C)C2]

Starting from 5-bromo-2,2-dimethyl-2,3-dihydrobenzofuran-7-ol, referring to the synthesis steps 4-13 in Example 2, the title compound was obtained as awhile solid.
MS (ESI, pos.ion) m/z: 442.3[M+H]$^+$;

$^1$H NMR (400 MHz, CDCl$_3$) δ 16.04 (s, 1H), 8.49 (d, J=9.0 Hz, 1H), 6.88 (d, J=10.5 Hz, 1H), 6.71 (s, 1H), 4.28-4.19 (m, 2H), 3.86 (dd, J=9.5, 3.9 Hz, 1H), 3.62-3.53 (m, 2H), 3.48 (d, J=15.6 Hz, 1H), 3.39 (d, J=9.1 Hz, 3H), 3.32 (dd, J=15.6, 4.4 Hz, 1H), 3.23-3.15 (m, 1H), 3.06 (d, J=15.8 Hz, 1H), 2.13 (p, J=6.1 Hz, 2H), 1.11-1.74 (m, 1H), 1.66 (d, J=10.3 Hz, 3H), 1.43 (d, J=10.4 Hz, 3H), 0.95 (d, J=6.6 Hz, 3H), 0.87 (d, J=6.7 Hz, 3H).

Example 40: 4-(2-Cyclopropylethoxy)-7-isopropyl-2,2-dimethyl-11-oxo-2,6,7,11-tetrahydro-1H-furo[2,3-h]pyrido[2,1-a]isoquinoline-10-carboxylic Acid

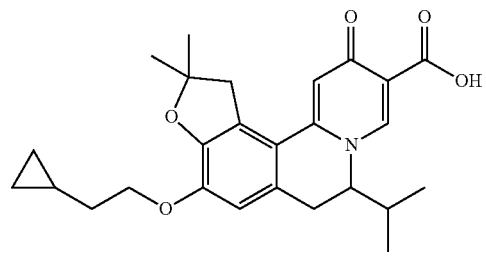 [SMILES: CC(C)C1Cc2cc(OCCC3CC3)c3c(c2-c2cc(=O)c(C(=O)O)cn21)CC(C)(C)O3]

First, starting from 5-bromo-2,2-dimethyl-2,3-dihydrobenzofuran-7-ol, referring to the synthesis steps 4-11 in Example 2, ethyl 4-hydroxy-7-isopropyl-2,2-dimethyl-11-oxo-2,6,7,11-tetrahydro-1H-furo[2,3-h]pyrido[2,1-a]isoquinoline-10-carboxylate can be obtained. Then, starting from ethyl 4-hydroxy-7-isopropyl-2,2-dimethyl-11-oxo-2,6,7,11-tetrahydro-1H-furo[2,3-h]pyrido[2,1-a]isoquinoline-10-carboxylate and (2-bromoethyl)cyclopropane, referring to the synthesis steps 12-13 in Example 2, the title compound was obtained as a white solid.
MS (ESI, pos.ion) m/z: 438.3[M+H]$^+$;

$^1$H NMR (400 MHz, CDCl$_3$) δ 16.05 (s, 1H), 8.48 (s, 1H), 6.86 (d, J=25.5 Hz, 1H), 6.66 (d, J=25.9 Hz, 1H), 4.27-4.15 (m, 2H), 3.86 (dd, J=9.7, 3.7 Hz, 1H), 3.48 (d, J=15.7 Hz, 1H), 3.33 (dd, J=15.8, 4.8 Hz, 1H), 3.19 (d, J=15.7 Hz, 1H), 3.12-3.01 (m, 1H), 1.76 (dd, J=14.1, 7.1 Hz, 3H), 1.64 (d, J=25.7 Hz, 3H), 1.45 (s, 3H), 0.96 (d, J=6.7 Hz, 3H), 0.87 (d, J=6.7 Hz, 3H), 0.85-0.80 (m, 1H), 0.56-0.46 (m, 2H), 0.14 (q, J=4.9 Hz, 2H).

Example 41: 4-(1-(Difluoromethyl)-1H-pyrazol-4-yl)-7-isopropyl-2,2-dimethyl-11-oxo-2,6,7,11-tetrahydro-1H-furo[2,3-h]pyrido[2,1-a]isoquinoline-10-carboxylic Acid

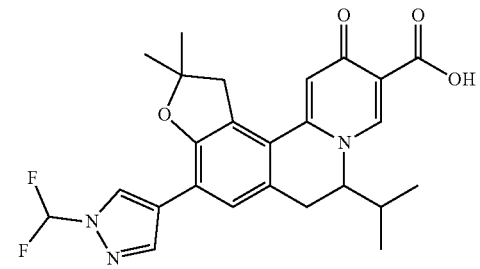 [SMILES: CC(C)C1Cc2cc(-c3cnn(C(F)F)c3)c3c(c2-c2cc(=O)c(C(=O)O)cn21)CC(C)(C)O3]

Starting from e thy 14-hydroxy-7-isopropyl-2,2-dimethyl-11-oxo-2,6,7,11-tetrahydro-1H-furo[2,3-h]pyrido[2,1-a]isoquinoline-10-carboxylate and 1-(difluoromethyl)-4-

(tributyltin) 1H-pyrazole, referring to the synthesis method in Example 10, the title compound was obtained as a white solid.

MS (ESI, pos.ion) m/z: 470.2[M+H]$^+$;

$^1$H NMR (400 MHz, CDCl$_3$) δ 15.83 (s, 1H), 8.51 (s, 1H), 8.41 (s, 1H), 8.16 (s, 1H), 7.37 (d, J=36.9 Hz, 1H), 7.19 (d, J=60.5 Hz, 1H), 7.01 (s, 1H), 3.90 (d, J=8.1 Hz, 1H), 3.54 (d, J=16.1 Hz, 1H), 3.35 (d, J=14.0 Hz, 1H), 3.27 (d, J=16.0 Hz, 1H), 3.19 (d, J=15.7 Hz, 1H), 1.74 (s, 3H), 1.50 (s, 3H), 1.28 (s, 1H), 0.98 (d, J=6.6 Hz, 3H), 0.90 (d, J=6.7 Hz, 3H).

Example 42: 7-Cyclopropyl-4-(2-cyclopropylethoxy)-11-oxo-2,6,7,11-tetrahydro-1H-furo[2,3-h]pyrido[2,1-a]phthalazine-10-carboxylic Acid

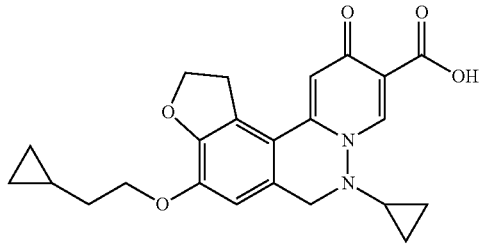 [SMILES: O=C(O)c1cn2c(cc1=O)-c1c(cc(OCCC3CC3)c3c1CCO3)CN2C1CC1]

Starting from 7-(benzyloxy)-2,3-dihydrobenzofuran-5-carbaldehyde and cyclopropylamine, referring to the synthesis steps 2 to 10 in Example 15, the title compound was obtained as a white solid.

MS (ESI, pos.ion) m/z: 409.2[M+H]$^+$;

$^1$H NMR (400 MHz, CDCl$_3$) δ 15.84 (s, 1H), 8.52 (s, 1H), 6.93 (s, 1H), 6.74 (s, 1H), 4.76 (s, 2H), 4.32 (s, 2H), 4.20 (t, J=6.8 Hz, 2H), 3.57 (s, 1H), 3.49 (s, 1H), 2.43 (dq, J=10.0, 3.5 Hz, 1H), 1.77 (q, J=6.9 Hz, 2H), 0.86 (s, 3H), 0.59 (d, J=5.9 Hz, 2H), 0.51 (dt, J=5.5, 5.1 Hz, 2H), 0.14 (q, J=4.9 Hz, 2H).

Example 43: 4-(1-(Difluoromethyl)-1H-pyrazol-4-yl)-7-isopropyl-11-oxo-2,6,7,11-tetrahydro-1H-furo[2,3-h]pyrido[2,1-a]phthalazine-10-carboxylic Acid

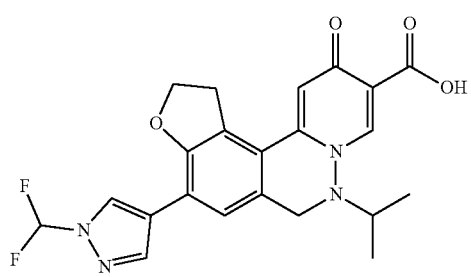

Starting from ethyl 4-hydroxy-7-isopropyl-11-oxo-2,6,7,11-tetrahydro-1H-furo[2,3-h]pyrido[2,1-a]phthalazine-10-carboxylate, PhN(OTf)$_2$ and 1-difluoromethyl-4-(4,4,5,5-tetramethyl-1,3,2-dioxaborolan-2-yl)-1H-pyrazole, referring to the synthesis method in Example 17, the title compound was obtained as a white solid.

MS (ESI, pos.ion) m/z: 443.1[M+H]$^+$;

$^1$H NMR (400 MHz, DMSO-d$_6$) δ 16.22 (s, 1H), 8.68 (s, 1H), 8.51 (s, 1H), 8.37 (s, 1H), 8.05-7.73 (m, 2H), 7.08 (s, 1H), 4.50 (s, 2H), 3.34 (s, 4H), 2.90-2.81 (m, 1H), 0.96 (s, 6H).

Example 44: 4-(1-(1,1-Dioxotetrahydro-2H-thiopyran-4-yl)-1H-pyrazol-4-yl)-7-isopropyl-11-oxo-2,6,7,11-tetrahydro-1H-furo[2,3-h]pyrido[2,1-a]phthalazine-10-carboxylic Acid

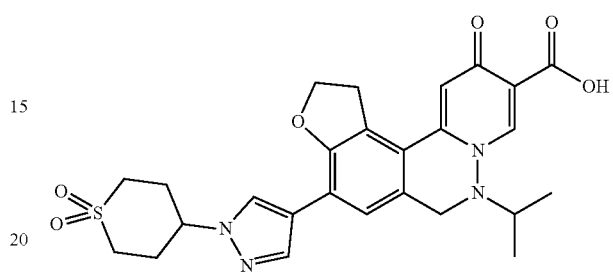

Starting from ethyl 7-isopropyl-11-oxo-4-(((trifluoromethyl)sulfonyl)oxy)-2,6,7,11-tetrahydro-1H-furo[2,3-h]pyrido[2,1-a]isoquinoline-10-carboxylate and 4-[4-(4,4,5,5-tetramethyl-1,3,2-dioxaborolan-2-yl)pyrazol-1-yl]tetrahydrothiopyran 1,1-dioxide, referring to the synthesis method in Example 9, the title compound was obtained as an off-white solid.

MS (ESI, pos.ion) m/z: 524.4[M+H]$^+$;

$^1$H NMR (400 MHz, CD$_3$OD) δ 8.58 (s, 1H), 8.17 (s, 1H), 8.03 (s, 1H), 7.36 (s, 1H), 7.07 (s, 1H), 5.03-4.92 (m, 1H), 4.71-4.54 (m, 2H), 4.05 (d, J=6.6 Hz, 1H), 3.77 (dd, J=10.5, 5.2 Hz, 1H), 3.42 (d, J=4.1 Hz, 2H), 3.36 (s, 2H), 3.24 (t, J=15.3 Hz, 3H), 2.81-2.65 (m, 2H), 2.60 (s, 2H), 0.98 (d, J=6.6 Hz, 3H), 0.88 (d, J=6.7 Hz, 4H).

Example 45: 4-(2-Cyclopropylethoxy)-11-oxo-7-phenyl-2,6,7,11-tetrahydro-1H-furo[2,3-h]pyrido[2,1-a]phthalazine-10-carboxylic Acid

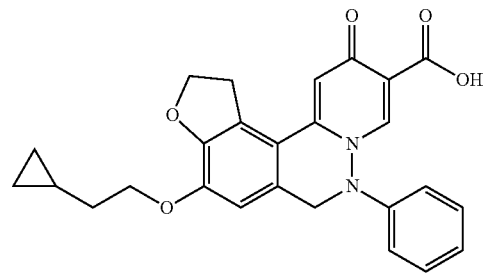 [SMILES: O=C(O)c1cn2c(cc1=O)-c1c(cc(OCCC3CC3)c3c1CCO3)CN2c1ccccc1]

Step 1: Ethyl 1-((tert-butoxycarbonyl)amino)-4-oxo-1,4-dihydropyridine-3-carboxylate

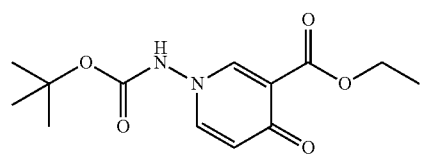 [SMILES: CCOC(=O)c1cn(NC(=O)OC(C)(C)C)ccc1=O]

To a dry reaction flask was added ethyl 4-oxo-4H-pyran-3-carboxylate (8.5 g, 51 mmol), and ethanol (85 mL) was added to dissolve it. Then tert-butyl carbazate (13 g, 98.37 mmol) was added. The mixture was warmed to reflux and stirred overnight. The stirring was stopped, and the solvent was distilled off under reduced pressure. The residue was purified by silica gel column chromatography (DCM/MeOH (V/V)=10/1) to give the title compound as a yellow solid (9.24 g, 32.7 mmol, 65%).

MS(ESI,pos.ion)m/z: 283.1[M+H]+.

Step 2: 7-(Benzyloxy)-4-iodo-2,3-dihydrobenzofuran-5-formaldehyde

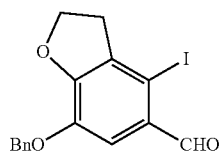 [SMILES: O=Cc1cc(OCc2ccccc2)c2c(c1I)CCO2]

7-Benzyloxy-2,3-dihydrobenzofuran-5-formaldehyde (3.2 g, 13 mmol), methanol (32 mL, 791 mmol), iodine (3.4 g, 13 mmol) and silver sulfate (4.1 g, 12 mmol) were added into a single-necked flask. The mixture was stirred at room temperature for 1.5 h. Postprocessing: To the reaction mixture was added sodium thiosulfate solid to quench the reaction. The resulting mixture was filtered and the filtrate was concentrated in vacuo to give the title compound as a yellow solid (4.2 g, 11 mmol, 88%) which was used directly in the next step.

MS (ESI, pos.ion) m/z: 380.9[M+H]+.

Step 3: (7-(Benzyloxy)-4-iodo-2,3-dihydrobenzofuran-5-yl)methanol

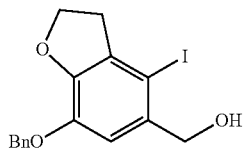 [SMILES: OCc1cc(OCc2ccccc2)c2c(c1I)CCO2]

7-(Benzyloxy)-4-iodo-2,3-dihydrobenzofuran-5-formaldehyde (4.0 g, 11 mmol) was dissolved in THF (40 mL). The mixture was stirred at room temperature. Then NaBH4 (0.88 g, 21 mmol) was added slowly at 0° C. The resulting mixture was then stirred at room temperature for 1 h and concentrated in vacuo. Then the aqueous layer was extracted with water (20 mL) and EA (20 mL×3). The organic layers were combined and concentrated in vacuo. The residue was purified by silica gel column chromatography (PE/EA (V/V)=1/1) to give the title compound as awhile solid (3.3 g, 8.6 mmol, 82%).

Step 4: 7-(Benzyloxy)-5-chloromethyl-4-iodo-2,3-dihydrobenzofuran

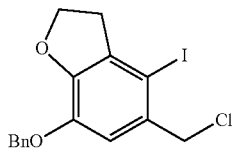 [SMILES: ClCc1cc(OCc2ccccc2)c2c(c1I)CCO2]

(7-(Benzyloxy)-4-iodo-2,3-dihydrobenzofuran-5-yl)methanol (3 g, 7.85 mmol), DCM (15 mL) and dichlorosulfoxide (1.1 mL) were added into a 100 mL single-necked flask. The mixture was stirred at room temperature for 2 h. Post processing: The resulting mixture was concentrated in vacuo to give the tide compound as a white solid (3.0 g, 7.5 mmol, 95%).

Step 5: Methyl 1-(((7-(benzyloxy)-4-iodo-2,3-dihydrobenzofuran-5-yl)methyl)(tert-butoxycarbonyl)amino)-4-oxo-1,4-dihydropyridine-3-carboxylate

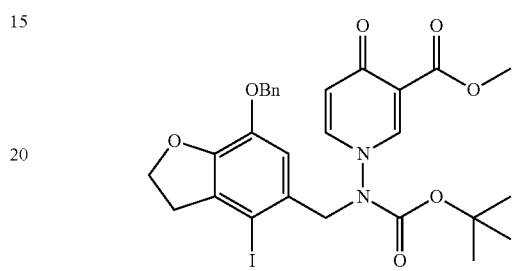

7-(Benzyloxy)-5-chloromethyl-4-iodo-2,3-dihydrobenzofuran (3.0 g, 7.5 mmol) and ethyl 1-((tert-butoxycarbonyl)amino)-4-oxo-1,4-dihydropyridine-3-carboxylate (1.6 g, 5.7 mmol) were dissolved in MeCN (30 mL), then potassium carbonate (3.2 g, 23 mmol) and potassium iodide (0.094 g, 0.57 mmol) were added. The mixture was stirred at 90° C. for 20 h. Post processing: The mixture was filtered and concentrated in vacuo to give the crude product which was further purified by silica gel column chromatography (DCM/MeOH (V/V)=15/1) to give the title compound as brown oil (3.0 g, 4.6 mmol, 82%).

MS (ESI, pos.ion) m/z: 632.9[M+H]+.

Step 6: Methyl 4-(benzyloxy)-7-tert-butoxycarbonyl-11-oxo-2,6,7,11-tetrahydro-1H-furo[2,3-h]pyrido[2,1-a]phthalazine-10-carboxylate

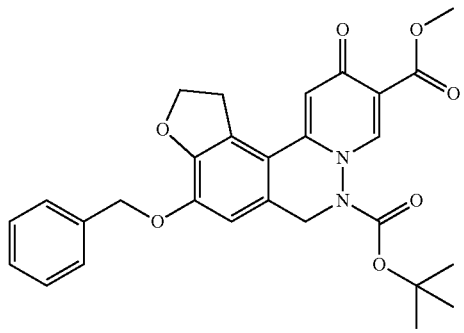 [SMILES: COC(=O)c1cn2c(cc1=O)-c1c(cc(OCc3ccccc3)c3c1CCO3)CN2C(=O)OC(C)(C)C]

Methyl 1-(((7-(benzyloxy)-4-iodo-2,3-dihydrobenzofuran-5-yl)methyl)(tert-butoxycarbonyl)amino)-4-oxo-1,4-dihydropyridine-3-carboxylate (3.0 g, 4.6 mmol), potassium acetate (0.91 g, 9.3 mmol), DMF (15 mL), palladium bromide (0.26 g, 0.93 mmol) were added into a single-necked flask. The air in the flask was replaced with nitrogen three times. The mixture was stirred at 60° C. for 12 h. Post processing: The reaction mixture was directly purified by silica gel column chromatography (DCM/CH₃OH(V/V) =20/1) to give the title compound as a gray-black solid (2.1 g, 4.0 mmol, 87%).

MS (ESI, pos.ion) m/z: 505.3[M+H]⁺.

Step 7: Methyl 4-(benzyloxy)-11-oxo-2,6,7,11-tetrahydro-1H-furo[2,3-h]pyrido[2,1-a]phthalazine-10-carboxylate

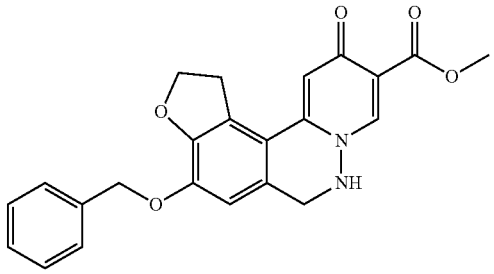 [SMILES: COC(=O)c1cn2c(cc1=O)-c1c(cc(OCc3ccccc3)c3c1CCO3)CN2]

Ethyl 4-(benzyloxy)-7-tert-butoxycarbonyl-11-oxo-2,6,7,11-tetrahydro-1H-furo[2,3-h]pyrido[2,1-a]phthalazine-10-carboxylate (2.1 g, 4.2 mmol) was dissolved in DCM (8 mL) and TFA (8 mL, 86.71 mmol). The mixture was stirred at room temperature for 2 h. Post processing: DCM (100 mL) and water (100 mL) were added successively, then the resulting mixture was extracted with DCM (100 mL×3). The organic layers were combined, washed with saturated brine (100 mL×3), and concentrated. The residue was purified by silica gel column chromatography (DCM/CH₃OH(V/V)=15/1) to give the title compound as a white solid (1.3 g, 3.2 mmol, 77%).

MS (ESI, pos.ion) m/z: 405.1[M+H]⁺.

Step 8: Methyl 4-(benzyloxy)-11-oxo-7-phenyl-2,6,7,11-tetrahydro-1H-furo[2,3-h]pyrido[2,1-a]phthalazine-10-carboxylate

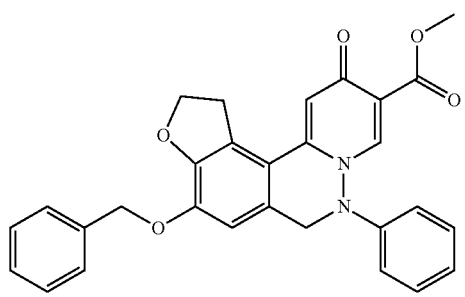 [SMILES: COC(=O)c1cn2c(cc1=O)-c1c(cc(OCc3ccccc3)c3c1CCO3)CN2c1ccccc1]

Ethyl 4-(benzyloxy)-11-oxo-2,6,7,11-tetrahydro-1H-furo[2,3-h]pyrido[2,1-a]phthalazine-10-carboxylate (400 mg, 0.99 mmol), Xantphos (0.236 g, 0.396 mmol), Pd(dba)₂ (0.116 g, 0.198 mmol), cesium carbonate (0.48 g, 1.48 mmol), DMF (10 mL) and iodobenzene (0.45 mL, 3.9 mmol) were added into a single-necked flask. The air in the flask was replaced with nitrogen. The mixture was stirred at 70° C. for 12 h. Post processing: The reaction was ended, and the heating was turned off. The mixture was diluted with water (30 mL), and then extracted with DCM (50 mL×3). The organic layers were combined, washed three times with saturated brine and concentrated in vacuo to give the residue which was purified by silica gel column chromatography (DCM/MeOH (V/V)=10/1) to give the title compound as a yellow solid (0.5 g, 1 mmol, 100%).

MS (ESI, pos.ion) m/z: 481.2[M+H]⁺.

Step 9: Methyl 4-hydroxy-11-oxo-7-phenyl-2,6,7,11-tetrahydro-1H-furo[2,3-h]pyrido[2,1-a]phthalazine-10-carboxylate

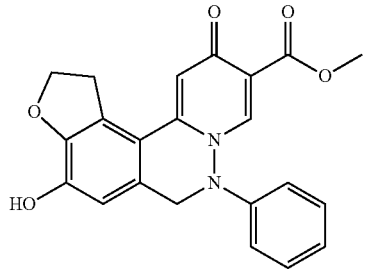 [SMILES: COC(=O)c1cn2c(cc1=O)-c1c(cc(O)c3c1CCO3)CN2c1ccccc1]

To the single-necked flask was added methyl 4-(benzyloxy)-11-oxo-7-phenyl-2,6,7,11-tetrahydro-1H-furo[2,3-h]pyrido[2,1-a]phthalazine-10-carboxylate (0.45 g, 0.94 mmol), and methanol (14 mL) and DCM (1.4 mL) were added to dissolve it. Then palladium carbon (0.25 g, 0.23 mmol, 10 mass %) was added. The air in the flask was replaced with hydrogen. The mixture was reacted for 8 h under hydrogen atmosphere. Post processing: The resulting mixture was filtered through a celite pad and washed with (DCM/MeOH(V/V)=10/1) solution. The filtrate was collected, and concentrated in vacuo to give the title compound as a brown solid (0.38 g, 0.97 mmol, 100%) which was used directly in the next step.

MS (ESI, pos.ion) m/z: 391.2[M+H]⁺.

Step 10: Methyl 4-(2-cyclopropylethoxy)-11-oxo-7-phenyl-2,6,7,11-tetrahydro-1H-furo[2,3-h]pyrido[2,1-a]phthalazine-10-carboxylate

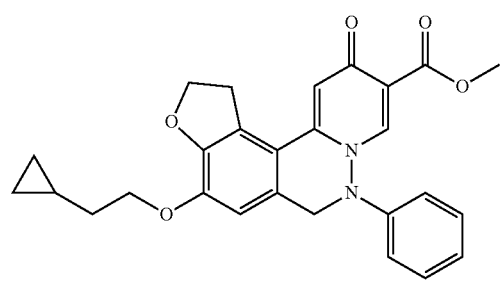 [SMILES: COC(=O)c1cn2c(cc1=O)-c1c(cc(OCCC3CC3)c3c1CCO3)CN2c1ccccc1]

Methyl 4-hydroxy-11-oxo-7-phenyl-2,6,7,11-tetrahydro-1H-furo[2,3-h]pyrido[2,1-a]phthalazine-10-carboxylate (0.35 g, 0.90 mmol), potassium carbonate (0.50 g, 3.6 mmol) and 2-cyclopropylethyl methane sulfonate (0.44 g, 2.7 mmol) were dissolved in DMF (10 mL). The mixture was heated to 80° C. and stirred overnight. Post processing: The mixture was cooled to room temperature. The mixture was diluted with water (30 mL) and extracted with DCM (10 mL×3). The organic layers were combined. The combined organic layers were washed with water (20 mL×3) and concentrated. The residue was purified by silica gel column chromatography (DCM/CH$_3$OH(V/V)=15/1) to give the title compound as a white solid (0.32 g, 0.70 mmol, 78%).

MS (ESI, pos.ion) m/z: 459.2[M+H]$^+$.

Step 11: 4-(2-Cyclopropylethoxy)-11-oxo-7-phenyl-2,6,7,11-tetrahydro-1H-furo[2,3-h]pyrido [2,1-a]phthalazine-10-carboxylic Acid

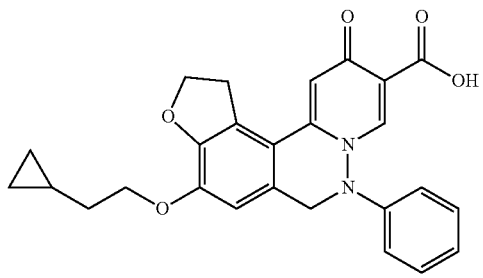 [SMILES: O=C(O)c1cn2c(cc1=O)-c1c(cc(OCCC3CC3)c3c1CCO3)CN2c1ccccc1]

To the single-necked flask were added methyl 4-(2-cyclopropylethoxy)-11-oxo-7-phenyl-2,6,7,11-tetrahydro-1H-furo[2,3-h]pyrido[2,1-a]phthalazine-10-carboxylate (0.32 g, 0.70 mmol), methanol (20 mL, 494 mmol), H$_2$O (2 mL) and LiOH·H$_2$O (0.146 g, 3.48 mmol). The mixture was stirred at room temperature for 6 h. Post processing: The mixture was concentrated in vacuo, and 1 M hydrochloric acid was added to the residue to adjust pH to 3~4. Then the mixture was extracted with DCM (10 mL×3). The organic layers were combined and concentrated in vacuo. The residue was purified by silica gel column chromatography (DCM/CH$_3$OH(V/V)=15/1) to give the title compound as a white solid (0.078 g, 0.18 mmol, 25%).

MS (ESI, pos.ion) m/z: 445.2[M+H]$^+$;

$^1$H NMR (400 MHz, CDCl$_3$) δ 15.64 (s, 1H), 8.64 (s, 1H), 7.22 (t, J=8.0 Hz, 2H), 7.05-6.99 (m, 2H), 6.61 (s, 1H), 6.58 (s, 2H), 4.83 (s, 2H), 4.71 (t, J=8.5 Hz, 2H), 4.09 (t, J=6.8 Hz, 2H), 3.53 (t, J=8.0 Hz, 2H), 1.69 (dd, J=13.8, 6.9 Hz, 3H), 0.47 (q, J=5.5 Hz, 2H), 0.12-0.06 (m, 2H).

Example 46: 4-(2-Cyclopropylethoxy)-7-(cyclopropylsulfonyl)-11-oxo-2,6,7,11-tetrahydro-1H-furo[2,3-h]pyrido[2,1-a]phthalazine-10-carboxylic Acid

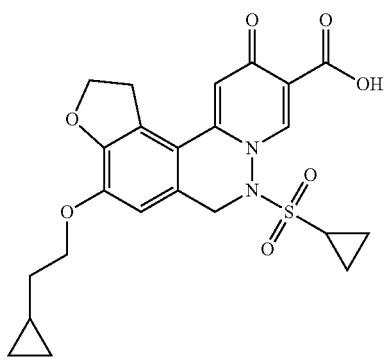 [SMILES: O=C(O)c1cn2c(cc1=O)-c1c(cc(OCCC3CC3)c3c1CCO3)CN2S(=O)(=O)C1CC1]

First, starting from ethyl 4-oxo-4H-pyran-3-carboxylate and cyclopropanesulfonyl hydrazide, referring to the synthesis steps 1-6 in Example 45, ethyl 4-(benzyloxy)-7-(cyclopropylsulfonyl)-11-oxo-2,6,7,11-tetrahydro-1H-furo[2,3-h]pyrido[2,1-a]phthalazine-10-carboxylate can be obtained. Then, starting from ethyl 4-(benzyloxy)-7-(cyclopropylsulfonyl)-11-oxo-2,6,7,11-tetrahydro-1H-furo[2,3-h]pyrido[2,1-a]phthalazine-10-carboxylate, referring to the synthesis steps 9-11 in Example 45, the title compound was obtained as awhile solid.

MS (ESI, pos.ion) m/z: 473.1[M+H]$^+$;

$^1$H NMR (400 MHz, CDCl$_3$) δ 15.04 (s, 1H), 8.76 (s, 1H), 6.92 (s, 1H), 6.78 (s, 1H), 5.13 (d, J=17.0 Hz, 1H), 4.90 (td, J=10.0, 4.7 Hz, 1H), 4.79 (d, J=16.9 Hz, 1H), 4.61 (q, J=9.7 Hz, 1H), 4.27-4.13 (m, 2H), 3.70 (dt, J=15.8, 10.3 Hz, 1H), 3.48 (s, 1H), 3.45-3.30 (m, 1H), 1.76 (q, J=6.8 Hz, 2H), 1.15-1.05 (m, 1H), 0.94 (dd, J=14.6, 6.6 Hz, 1H), 0.89-0.81 (m, 2H), 0.72-0.62 (m, 1H), 0.52 (dt, J=7.9, 5.1 Hz, 2H), 0.14 (q, J=4.8 Hz, 2H).

Example 47: 4-(2-Cyclopropylethoxy)-11-oxo-7-(thiazol-2-yl)-2,6,7,11-tetrahydro-1H-furo [2,3-h]pyrido[2,1-a]phthalazine-10-carboxylic Acid

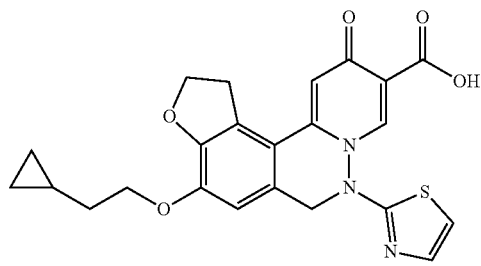 [SMILES: O=C(O)c1cn2c(cc1=O)-c1c(cc(OCCC3CC3)c3c1CCO3)CN2c1nccs1]

Starting from 2-bromothiazole and ethyl 4-(benzyloxy)-11-oxo-2,6,7,11-tetrahydro-1H-furo[2,3-h]pyrido[2,1-a]phthalazine-10-carboxylate, referring to the synthesis steps 8-11 in Example 45, the title compound was obtained as a white solid.

MS (ESI, pos.ion) m/z: 452.1[M+H]$^+$;

$^1$H NMR (600 MHz, CDCl$_3$) δ 15.39 (s, 1H), 8.73 (s, 1H), 7.25 (d, J=3.5 Hz, 1H), 6.97 (s, 1H), 6.84 (d, J=3.5 Hz, 1H), 6.75 (s, 1H), 5.00-4.53 (m, 4H), 4.16 (t, J=6.7 Hz, 2H), 1.73 (q, J=6.9 Hz, 3H), 0.84 (ddt, J=10.1, 7.3, 4.6 Hz, 2H), 0.52-0.47 (m, 2H), 0.12 (q, J=4.7 Hz, 2H).

Example 48: 4-(2-Cyclopropylethoxy)-7-isobutyryl-11-oxo-2,6,7,11-tetrahydro-1H-furo [2,3-h]pyrido[2,1-a]phthalazine-10-carboxylic Acid

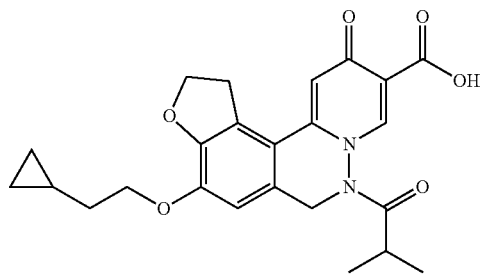 [SMILES: CC(C)C(=O)N1Cc2cc(OCCC3CC3)c3c(c2-c2cc(=O)c(C(=O)O)cn21)CCO3]

First, starting from ethyl 4-oxo-4H-pyran-3-carboxylate and isobutyl hydrazide, referring to the synthesis steps 1-6 in Example 45, ethyl 4-(benzyloxy)-7-(isobutyl acyl)-11-oxo-2,6,7,11-tetrahydro-1H-furo[2,3-h]pyrido[2,1-a]phthalazine-10-carboxylate can be obtained. Then, starting from ethyl 4-(benzyloxy)-7-(isobutyl acyl)-11-oxo-2,6,7,11-tetrahydro-1H-furo[2,3-h]pyrido[2,1-a]phthalazine-10-carboxylate, referring to the synthesis steps 9-11 in Example 45, the title compound was obtained as a white solid.

MS (ESI, pos.ion) m/z: 439.0[M+H]$^+$;

$^1$H NMR (400 MHz, DMSO-d$_6$) δ 16.12 (s, 1H), 8.59 (s, 1H), 7.19 (s, 1H), 6.96 (s, 1H), 5.45 (d, J=16.7 Hz, 1H), 4.89 (d, J=15.0 Hz, 1H), 4.75 (s, 1H), 4.47 (dd, J=18.4, 9.3 Hz, 1H), 4.14 (t, J=6.6 Hz, 2H), 3.80 (dd, J=25.3, 10.2 Hz, 1H), 3.43 (s, 1H), 3.06 (s, 1H), 1.64 (dd, J=13.2, 6.5 Hz, 2H), 1.22 (s, 3H), 0.81 (s, 4H), 0.43 (d, J=7.3 Hz, 2H), 0.13 (d, J=3.9 Hz, 2H).

Example 49: 7-Cyclopentyl-4-(2-cyclopropylethoxy)-11-oxo-2,6,7,11-tetrahydro-1H-furo [2,3-h]pyrido[2,1-a]isoquinoline-10-carboxylic Acid

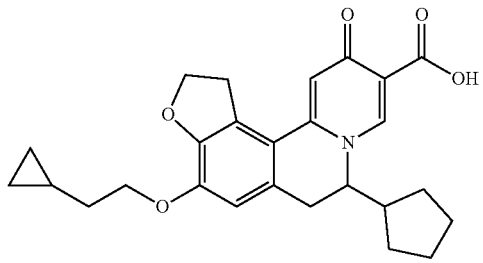 [SMILES: O=C(O)c1cn2c(cc1=O)-c1c(cc(OCCC3CC3)c3c1CCO3)CC2C1CCCC1]

First, starting from 7-(benzyloxy)-5-bromo-2,3-dihydrobenzofuran and 1-cyclopentylethanone, referring to the synthesis steps 5 to 11 in Example 2, ethyl 7-cyclopentyl-4-hydroxyl-11-oxo-2,6,7,11-tetrahydro-1H-furo[2,3-h]pyrido[2,1-a]isoquinoline-10-carboxylate can be obtained. Then, starting from ethyl 7-cyclopentyl-4-hydroxyl-11-oxo-2,6,7,11-tetrahydro-1H-furo[2,3-h]pyrido[2,1-a]isoquinoline-10-carboxylate and (2-bromoethyl) propane, referring to the synthesis steps 12 to 13 in Example 2, the title compound was obtained as a white solid.

MS (ESI, pos.ion) m/z: 436.25[M+H]$^+$;

$^1$H NMR (400 MHz, CDCl$_3$) δ 16.04 (s, 1H), 8.53 (s, 1H), 6.92 (s, 1H), 6.70 (s, 1H), 4.88 (td, J=10.1, 4.1 Hz, 1H), 4.58 (dd, J=19.5, 9.4 Hz, 1H), 4.26-4.12 (m, 2H), 4.03 (dd, J=10.2, 4.0 Hz, 1H), 3.69 (dt, J=15.4, 10.5 Hz, 1H), 3.46-3.32 (m, 2H), 2.98 (d, J=15.8 Hz, 1H), 2.03-1.86 (m, 1H), 1.85-1.60 (m, 6H), 1.51-1.40 (m, 2H), 1.39-1.20 (m, 2H), 0.96-0.78 (m, 1H), 0.56-0.49 (m, 2H), 0.17-0.12 (m, 2H).

Example 50: 7-Cyclopropyl-4-(2-cyclopropylethoxy)-11-oxo-2,6,7,11-tetrahydro-1H-furo [2,3-h]pyrido[2,1-a]isoquinoline-10-carboxylic Acid

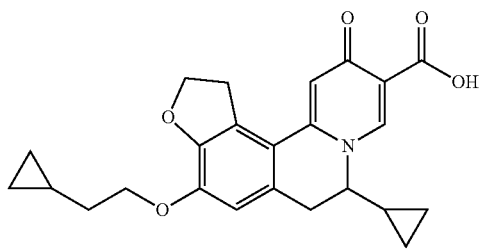

First, starting from 7-(benzyloxy)-5-bromo-2,3-dihydrobenzofuran and 1-cyclopropylethanone, referring to the synthesis steps 5 to 11 in Example 2, ethyl 7-cyclopropyl-4-hydroxyl-11-oxo-2,6,7,11-tetrahydro-1H-furo[2,3-h]pyrido[2,1-a]isoquinoline-10-carboxylate can be obtained. Then, starting from ethyl 7-cyclopropyl-4-hydroxyl-11-oxo-2,6,7,11-tetrahydro-1H-furo[2,3-h]pyrido[2,1-a]isoquinoline-10-carboxylate and (2-bromoethyl)propane, referring to the synthesis steps 12 to 13 in Example 2, the title compound was obtained as a white solid.

MS (ESI, pos.ion) m/z: 408.2[M+H]$^+$;

$^1$H NMR (400 MHz, CDCl$_3$) δ 16.10 (s, 1H), 8.64 (s, 1H), 6.95 (s, 1H), 6.76 (s, 1H), 4.82 (td, 7=9.5, 5.4 Hz, 1H), 4.62 (q, J=9.3 Hz, 1H), 4.26-4.13 (m, 2H), 3.75-3.55 (m, 1H), 3.50-3.30 (m, 3H), 3.07 (d, J=12.4 Hz, 1H), 1.85-1.70 (m, 2H), 1.15-1.03 (m, 1H), 0.94-0.80 (m, 1H), 0.78-0.65 (m, 2H), 0.64-0.56 (m, 1H), 0.55-0.49 (m, 2H), 0.48-0.40 (m, 1H), 0.15 (q, J=4.8 Hz, 2H).

Example 51: 7-Cyclopropyl-4-(1-(difluoromethyl)-1H-pyrazol-4-yl)-11-oxo-2,6,7,11-tetrahydro-1H-furo[2,3-h]pyrido[2,1-a]isoquinoline-10-carboxylic add

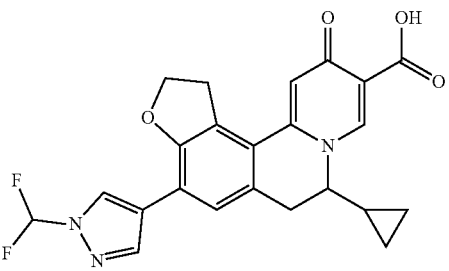 [SMILES: O=C(O)c1cn2c(cc1=O)-c1c(cc(-c3cnn(C(F)F)c3)c3c1CCO3)CC2C1CC1]

Starting from ethyl 7-cyclopropyl-4-hydroxy-11-oxo-2,6,7,11-tetrahydro-11-furo[2,3-h]pyrido[2,1-a]isoquinoline-10-carboxylate and 1-(difluoromethyl)-4-(4,4,5,5-tetramethyl-1,3,2-dioxaborolan-2-yl)-1H-pyrazole, referring to the synthesis method in Example 10, the title compound was obtained as a white solid.

MS (ESI, pos.ion) m/z: 440.2[M+H]$^+$;

1H NMR (400 MHz, DMSO-d$_6$) δ 8.91 (s, 1H), 8.71 (s, 1H), 8.42 (s, 1H), 7.92 (dd, J=81.8, 36.4 Hz, 1H), 7.74 (d, J=4.5 Hz, 1H), 7.07 (s, 1H), 4.87 (td, J=9.8, 4.7 Hz, 1H), 4.61 (q, J=9.3 Hz, 1H), 4.08-3.96 (m, 1H), 3.83 (dt, J=16.0, 10.0 Hz, 1H), 3.49-3.42 (m, 2H), 3.10 (dd, J=15.6, 2.3 Hz, 1H), 0.97-0.85 (m, 1H), 0.66 (dd, J=10.9, 5.8 Hz, 1H), 0.59-0.48 (m, 1H), 0.48-0.38 (m, 2H).

Biological Activity Test

HBV Cell Line

The chromosomal integration of HepG2,2,15 cells (SELLS, PNAS, 1987 and SELLS, JV, 1988) has a complete HBV genome and stably expresses viral RNA and viral proteins. HepG2,2,15 cells are capable of secreting mature hepatitis B virus particles and HBsAg into the culture medium. Virus particles DNA and HBsAg secreted by HepG 2,2,15 cells can be quantified by qPCR and ELISA, and the effects of compounds on viral replication and HBsAg secretion can be detected.

Test 1: Inhibition Experiment of the Compound of the Invention on HBV Virus Replication Test Method:

HepG 2,2,15 cells were inoculated with 8,000 per cell to 96-well cell culture plates in duplicate, and were cultured for 3 days until the cells grew to full-hole. Cells were treated with 4-fold serial dilutions of compounds for 10 days, and were given once every other day. The final concentration of DMSO in all pores was 0.5% and DMSO was used as a drug-free control. The supernatant was collected for quantitative detection of HBV DNA on day 11.

Viral genomic DNA was detected by qPCR method, and HBV primers were as follows:

```
HBV-For-202,
                            (SEQ ID NO: 1)
CAGGCGGGGTTTTTCTTGTTGA;

HBV-Rev-315,
                            (SEQ ID NO: 2)
GTGATTGGAGGTTGGGGACTGC.
```

The SYBR Premix Ex Taq D-Takara DRR081S kit was used, and 1 µL of cell culture supernatant was used as a template. A standard curve was made using a plasmid containing the HBV genome, and the viral copy number was calculated using the standard curve. Concentration-virus copy number was processed using Graphpad Prism 5 software, and $IC_{50}$ of compounds inhibiting virus replication was calculated by four-parameter nonlinear regression model.

Conclusion: The inhibition experiment of the compounds of the invention against HBV virus replication shows that the compounds of the invention have a good inhibitory activity against HBV DNA replication, wherein the $IC_{50}$ of inhibitory activity against HBV DNA replication of the compounds provided herein is less than 0.1 µM, and for most of the compounds, the $IC_{50}$ of inhibitory activity against HBV DNA replication is less than 0.05 µM.

The inhibitory activity of some compounds of the present invention against HBV DNA replication is shown in Table 2.

Table 2: inhibitory activity of some compounds of the present invention against HBV DNA replication Test 2

| Inhibition experiment of the compound of the invention on HBsAg secretion | |
|---|---|
| Example | DNA $IC_{50}$ (nM) |
| Example 1 | 2.36 |
| Example 2 | 1.21 |
| Example 3 | 1.60 |
| Example 4 | 3.84 |
| Example 5 | 3.40 |
| Example 6 | 0.86 |
| Example 7 | 1.87 |
| Example 8 | 0.52 |
| Example 9 | 1.10 |
| Example 10 | 0.98 |
| Example 11 | 0.78 |
| Example 12 | <0.24 |
| Example 13 | <0.24 |
| Example 14 | <0.24 |
| Example 15 | 1.81 |
| Example 16 | 2.49 |
| Example 17 | 1.51 |
| Example 22 | 2.26 |
| Example 23 | 3.36 |
| Example 25 | 0.72 |
| Example 26 | 1.09 |
| Example 27 | 2.54 |
| Example 29 | 0.97 |
| Example 30 | 1.95 |
| Example 31 | 0.72 |
| Example 33 | 1.23 |
| Example 34 | 3.72 |
| Example 35 | 2.35 |
| Example 39 | 1.65 |
| Example 40 | 1.45 |
| Example 41 | 2.09 |
| Example 43 | 1.85 |
| Example 47 | 3.31 |

Test Method:

HepG 2,2,15 cells were inoculated with 8,000 per cell to 96-well cell culture plates in duplicate, and were cultured for 3 days until the cells grew to full-hole. Cells were treated with 4-fold serial dilutions of compounds for 10 days, and were given once every other day. The final concentration of DMSO in all pores was 0.5% and DMSO was used as a drug-free control. The supernatant was collected for quantitative detection of HBsAg on day 11.

The level of HBsAg secreted by the cells after treatment of the compound was detected by ELISA method, and the method used a hepatitis B surface antigen diagnostic kit (Shanghai Kehua Biotech Co., Ltd. S10910113). 25 µL of the supernatant to be assayed (PBS was diluted to 75 µL) was added to per well in the ELISA plate, and the kit positive control and negative control were set. The ELISA plate was blocked with a cover paper and incubated at 37° C. for 60 minutes. The ELISA plate was taken out, and the cover paper was teared off, and 50 µL of enzyme conjugate was added to each well. The ELISA plate was oscillated on the shaker for 10 seconds, blocked with a cover paper and incubated at 37° C. for 30 minutes. The ELISA plate was taken out, the cover paper was teared off, and the ELISA plate was washed 5 times: each time the liquid in the hole was discarded, and the washing liquid was filled into the holes, left to stand for 60 seconds, dried, and the liquid residue was patted to dry on the absorbent paper. A freshly prepared mixture of Developer A and Developer B was added to all wells immediately after washing: 100 µL per well. The ELISA plate was oscillated on the shaker for 10 seconds, blocked with a cover paper and incubated at 37° C. for 30 minutes. 50 µL of stop solution was added to all wells. Absorbance was read on the Envision plate reader at a wavelength of 450 nm.

Concentration-HBsAg OD450 was processed using Graphpad Prism 5 software, and $IC_{50}$ of compounds inhibiting against HBsAg secretion was calculated by four-parameter nonlinear regression model.

Conclusion: The inhibition experiment of the compounds of the invention against HBsAg secretion shows that the compounds of the invention have a good inhibitory activity against HBsAg secretion, wherein the $IC_{50}$ of inhibitory activity against HBsAg secretion of the compounds provided herein is less than 0.1 µM, and for most of the compounds, the $IC_{50}$ of inhibitory activity against HBsAg secretion is less than 0.05 µM.

The inhibitory activity of some compounds of the present invention against HBsAg secretion is shown in Table 3.

Table 3: inhibitory activity of some compounds against HBsAg secretion

Test 3

Pharmacokinetic experiments of the compounds of the invention in beagle dogs, mice, and rats

| Example | HBsAg IC$_{50}$ (nM) |
|---|---|
| Example 1 | 4.21 |
| Example 2 | 1.45 |
| Example 3 | 1.4 | extraction and quantitatively analyzed by multiple reaction ion monitoring (MRM) on a triple quadrupole tandem mass spectrometer. Pharmacokinetic parameters were calculated using a noncompartmental method by WinNonLin 6.3 software.

The results of pharmacokinetic experiments of some compounds of the present invention in beagle dogs are shown in Table 4.

TABLE 4

Results of pharmacokinetic experiments of some compounds of the present invention in beagle dogs

| Test compound | Administration route | dose (mg/kg) | Cmax (ng/mL) | AUC$_{(0-t)}$ (h·ng/mL) | AUC$_{(INF)}$ (h·ng/mL) | CL (mL/min/kg) | V$_{SS}$ (1/kg) | F(%) |
|---|---|---|---|---|---|---|---|---|
| Example 15 | IV | 0.5 | 2010 | 11900 | 12200 | 0.69 | 0.23 | N/A |
| | PO | 2.5 | 7090 | 60500 | 62400 | N/A | N/A | 102.2 |
| Example 43 | IV | 0.5 | 1080 | 9030 | 9990 | 0.83 | 0.48 | N/A |
| | PO | 2.5 | 5770 | 45500 | 49300 | N/A | N/A | 100.7 |

N/A: represents untested
Conclusion: The pharmacokinetic data show that the compounds of the present invention exhibit good pharmacokinetic properties in beagle dogs when administered intravenously or orally, including good absorption (AUC$_{(0-t)}$ and AUC$_{(INF)}$) and good oral bioavailability (F).

Test 3-continued

Pharmacokinetic experiments of the compounds of the invention in beagle dogs, mice, and rats

| Example | HBsAg IC$_{50}$ (nM) |
|---|---|
| Example 3A | 0.76 |
| Example 5 | 2.35 |
| Example 6 | 1.92 |
| Example 8 | 1.63 |
| Example 9 | 2.83 |
| Example 10 | 2.34 |
| Example 10A | 0.54 |
| Example 11 | 0.92 |
| Example 12 | 0.81 |
| Example 13 | 0.34 |
| Example 14 | 0.38 |
| Example 15 | 3.13 |
| Example 17 | 3.27 |
| Example 21 | 1.55 |
| Example 23 | 1.14 |
| Example 25 | 1.40 |
| Example 26 | 1.33 |
| Example 27 | 4.65 |
| Example 29 | 2.64 |
| Example 30 | 5.30 |
| Example 31 | 1.39 |
| Example 33 | 1.36 |
| Example 34 | 2.37 |
| Example 35 | 3.29 |
| Example 39 | 0.91 |
| Example 40 | 0.54 |
| Example 41 | 0.54 |
| Example 43 | 0.98 |

(1) PK Test Experiments in Beagle Dogs

The PK test in vivo of the compound of the present invention in beagle dogs (body weight 10-12 kg, male, age 10-12 months, 3 per group with oral administration, 3 per group with intravenous injection)
Test Method:

The beagle dog was administered orally with 2.5 mg/kg or 5 mg/kg of the compound tested or intravenously injected with 1 mg/kg or 2 mg/kg of the compound tested.

After administration, venous blood was collected at time points (0.083, 0.25, 0.5, 1, 2, 4, 6, 8 and 24 hours) and collected in an anticoagulation tube to which EDTA-K$_2$ was added. Plasma samples were extracted by liquid-liquid (2) PK Test Experiments in ICR Mice The PK test in vivo of the compound of the present invention in ICR mice (body weight 20-25 g, male, age 45-60 days, 3 per group with oral administration, 3 per group with intravenous injection) Test method:

The ICR mouse was administered orally with 10 mg/kg of the compound tested or intravenously injected with 2 mg/kg or 10 mg/kg of the compound tested. After administration, eyelid vein blood was collected at time points (0.083, 0.25, 0.5, 1, 2, 4, 6, 8 and 24 hours) and collected in an anticoagulation tube to which EDTA-K$_2$ was added. Plasma samples were extracted by liquid-liquid extraction and quantitatively analyzed by multiple reaction ion monitoring (MRM) on a triple quadrupole tandem mass spectrometer. Pharmacokinetic parameters were calculated using a noncompartmental method by WinNonLin 6.3 software.

Conclusion: The pharmacokinetic data show that the compounds of the present invention have good pharmacokinetic properties in ICR mice, and have a good application prospect in anti-HBV virus.

(3) PK Test Experiments in SD Rats

The PK test in vivo of the compound of the present invention in SD rats (body weight 200-250 g, male, age 2-3 months, 3 per group with oral administration, 3 per group with intravenous injection)
Test Method:

The SD rat was administered orally with 2.5 mg/kg or 5 mg/kg of the compound tested or intravenously injected with 0.5 mg/kg or 1 mg/kg of the compound tested. After administration, venous blood was collected at time points (0.083, 0.25, 0.5, 1, 2, 5, 7 and 24 hours) and collected in an anticoagulation tube to which EDTA-K$_2$ was added. Plasma samples were extracted by liquid-liquid extraction and quantitatively analyzed by multiple reaction ion monitoring (MRM) on a triple quadrupole tandem mass spectrometer. Pharmacokinetic parameters were calculated using a noncompartmental method by WinNonLin 6.3 software.

The results of pharmacokinetic experiments of some compounds of the present invention in SD rats are shown in Table 5.

TABLE 5

Results of pharmacokinetic experiments of some compounds of the present invention in SD rats

| Test compound | Administration route | dose (mg/kg) | Cmax (ng/mL) | AUC$_{(0-t)}$ (h·ng/mL) | AUC$_{(INF)}$ (h·ng/mL) | CL (mL/min/kg) | V$_{SS}$ (1/kg) | F(%) |
|---|---|---|---|---|---|---|---|---|
| Example 2 | IV | 1 | 738 | 1210 | 1330 | 12.6 | 1.8 | N/A |
| | PO | 5 | 1860 | 10600 | 10600 | N/A | N/A | 174.5 |
| Example 3 | IV | 1 | 744 | 1630 | 1760 | 9.45 | 1.5 | N/A |
| | PO | 5 | 1810 | 14700 | 14800 | N/A | N/A | 167.4 |
| Example 9 | IV | 1 | 641 | 1180 | 1190 | 14 | 2.2 | N/A |
| | PO | 5 | 1630 | 5560 | 5590 | N/A | N/A | 94 |
| Example 13 | IV | 1 | 1000 | 2830 | 2860 | 5.84 | 1.4 | N/A |
| | PO | 5 | 1700 | 18300 | 18400 | N/A | N/A | 129 |
| Example 15 | IV | 1 | 1500 | 2140 | 2280 | 7.32 | 0.9 | N/A |
| | PO | 5 | 2170 | 17700 | 17800 | N/A | N/A | 157.9 |
| Example 17 | IV | 1 | 932 | 1610 | 1640 | 10.1 | 1.01 | N/A |
| | PO | 5 | 1620 | 10700 | 10700 | N/A | N/A | 130.6 |

N/A: represents untested
Conclusion: The pharmacokinetic data show that the compounds of the present invention exhibit good pharmacokinetic properties in SD rats when administered intravenously or orally, including good absorption (AUC$_{(0-t)}$ and AUC$_{(INF)}$) and good oral bioavailability (F).

Test 4: Stability Test of Compounds of the Invention in Liver Microsomes of Different Species
Test Method:

30 μL of a Mixed Solution of a Blank Solution and a Liver Microsomes were Added to a 96-well plate, and 15 μL of buffer containing the test compound was added to each well, and two samples in parallel were made. After pre-incubation at 37° C. for 10 min, 15 μL of NADPH solution (8 mM) was added at time points of 0 min, 15 min, 20 min and 60 min, the final concentration of the test compounds was 1 μM, the concentration of liver microsomes was 0.1 mg/mL, and the final concentration of NADPH was 2 mM. After incubation for 0 min, 15 min, 30 min and 60 min, 150 L acetonitrile (including internal standard) was added into the mixed system μ The sample diluted with acetonitrile was centrifuged at 4000 rpm for 5 min. 150 μL of the supernatant was taken to LC-MS/MS for analysis.

Conclusion: The experimental data of liver microsome stability show that the compounds of the invention have good stability in liver microsomes of different species.

What is claimed is:

1. A compound having Formula (I) or a stereoisomer, a tautomer, an N-oxide, a solvate, a metabolite, a pharmaceutically acceptable salt or a prodrug thereof,

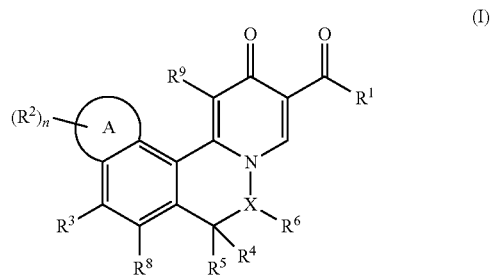

(I)

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer (HBV-For-202)

<400> SEQUENCE: 1
caggcggggt ttttcttgtt ga                                              22

<210> SEQ ID NO 2
<211> LENGTH: 22
<212> TYPE: DNA
<213> ORGANISM: Artificial Sequence
<220> FEATURE:
<223> OTHER INFORMATION: Primer (HBV-Rev-315)

<400> SEQUENCE: 2
gtgattggag gttggggact gc                                              22 wherein R¹ is R¹ᵃO— or RᵃRᵇN—;
X is CR⁷ or N;
ring A is a heterocyclyl consisting of 5 ring atoms, a heterocyclyl consisting of 6 ring atoms or a carbocyclyl consisting of 5 to 6 carbon atoms;
R³ is hydrogen, deuterium, F, Cl, Br, hydroxy, cyano, C₁₋₆ alkyl, C₂₋₆ alkynyl, C₃₋₇ cycloalkyl, heterocyclyl consisting of 3 to 10 ring atoms, C₆₋₁₀ aryl, heteroaryl of 5 to 10 ring atoms or R¹⁰—C₀₋₄ alkylene-O—, wherein each of C₁₋₆ alkyl, C₂₋₆ alkynyl, C₃₋₇ cycloalkyl, heterocyclyl consisting of 3 to 10 ring atoms, C₆₋₁₀ aryl, heteroaryl of 5 to 10 ring atoms and —C₀₋₄ alkylene- of R¹⁰—C₀₋₄ alkylene-O— is independently unsubstituted or substituted by 1, 2, 3 or 4 Rᵍ;
R¹⁰ is deuterium, R¹¹O—, C₁₋₆ alkyl, C₃₋₇ cycloalkyl, heterocyclyl consisting of 3 to 6 ring atoms, C₆₋₁₀ aryl or heteroaryl consisting of 5 to 10 ring atoms, wherein each of C₁₋₆ alkyl, C₃₋₇ cycloalkyl, heterocyclyl consisting of 3 to 6 ring atoms, C₆₋₁₀ aryl and heteroaryl consisting of 5 to 10 ring atoms is independently unsubstituted or substituted by 1, 2, 3, or 4 Rʲ;
each Rʲ and Rᵍ is independently deuterium, F, Cl, Br, CN, =O, HO—, HOOC—, R¹¹O—, R¹²—S(=O)₂—, R¹³-(C=O)—, R¹⁴¹³S(=O)₂—O—, R¹⁵¹³S(=O)₂—N(Rᶜ)-, R¹⁶—N(Rᶜ)—S(=O)₂—, R¹⁷-(C=O)—N(Rᶜ)—S(=O)₂—, amino, C₁₋₆ alkyl, C₁₋₆ alkoxy, C₁₋₆ alkylthio, C₁₋₆ alkylamino, C₂₋₆ alkenyl, C₂₋₆ alkynyl, C₃₋₇ cycloalkyl, heterocyclyl consisting of 3 to 10 ring atoms, C₆₋₁₀ aryl or heteroaryl consisting of 5 to 10 ring atoms, wherein each of amino, C₁₋₆ alkyl, C₁₋₆ alkoxy, C₁₋₆ alkylthio, C₁₋₆ alkylamino, C₂₋₆ alkenyl, C₂₋₆ alkynyl, C₃₋₇ cycloalkyl, heterocyclyl consisting of 3 to 10 ring atoms, C₆₋₁₀ aryl and heteroaryl consisting of 5 to 10 ring atoms is independently unsubstituted or substituted by 1, 2, 3 or 4 Rʷ;
each R¹¹, R¹², R¹²ᵃ, R¹³, R¹³ᵃ, R¹⁴, R¹⁵, R¹⁶ and R¹⁷ is independently hydrogen, deuterium, RᵃRᵇN—, C₁₋₆ alkyl, C₂₋₆ alkynyl, C₃₋₆ cycloalkyl, heterocyclyl consisting of 3 to 6 ring atoms, C₆₋₁₀ aryl, C₆₋₁₀ aryl C₁₋₃ alkylene or heteroaryl consisting of 5 to 10 ring atoms, wherein each of C₁₋₆ alkyl, C₂₋₆ alkynyl, C₃₋₆ cycloalkyl, heterocyclyl consisting of 3 to 6 ring atoms, C₆₋₁₀ aryl, C₆₋₁₀ aryl C₁₋₃ alkylene and heteroaryl consisting of 5 to 10 ring atoms is independently unsubstituted or substituted by 1, 2, 3 or 4 substituents selected from F, Cl, Br, CN, HO—, =O, HOOC—, RᵃRᵇN—S(=O)₂—, amino, C₁₋₆ alkyl, C₁₋₆ haloalkyl, C₁₋₆ alkoxy, C₁₋₆ alkylthio, C₁₋₆ haloalkoxy, C₁₋₆ alkylamino, C₂₋₆ alkenyl, C₂₋₆ alkynyl, C₆₋₁₀ aryl, C₃₋₇ cycloalkyl, heteroaryl consisting of 5 to 6 ring atoms, heterocyclyl of 3 to 6 ring atoms, C₁₋₆ alkoxy C₁₋₄ alkylene or C₁₋₄ alkylamino C₁₋₄ alkylene;
each Rʷ is independently deuterium, F, Cl, Br, HO—, HOOC—, =O, amino, C₁₋₆ alkyl, C₁₋₆ alkoxy, C₁₋₆ alkylthio, C₁₋₆ alkylamino, C₂₋₆ alkenyl, C₂₋₆ alkynyl, tert-butoxycarbonyl, C₁₋₆ alkyl-S(=O)₂—, C₃₋₆ cycloalkyl-S(=O)₂— or C₃₋₇ cycloalkyl, wherein each of amino, C₁₋₆ alkyl, C₁₋₆ alkoxy, C₁₋₆ alkylthio, C₁₋₆ alkylamino, C₂₋₆ alkenyl, C₂₋₆ alkynyl, tert-butoxycarbonyl, C₁₋₆ alkyl-S(=O)₂—, C₃₋₆ cycloalkyl-S(=O)₂— and C₃₋₇ cycloalkyl is independently unsubstituted or substituted by 1, 2, 3 or 4 substituents selected from F, Cl, Br, CN, OH, =O, amino, C₁₋₆ alkyl, C₁₋₆ haloalkyl, C₁₋₆ alkoxy, C₁₋₆ alkylthio, C₁₋₆ haloalkoxy or C₁₋₆ alkylamino;
each of R⁴, R⁵, R⁶, R⁷, R⁸ and R⁹ is independently hydrogen, deuterium, F, Cl, Br, R¹²ᵃ¹³S(=O)₂—, R¹³ᵃ-(C=O)—, C₁₋₆ alkyl, C₁₋₆ alkylamino, C₁₋₆ alkoxy, C₂₋₆ alkynyl, C₂₋₆ alkenyl, C₃₋₇ cycloalkyl, phenyl, heteroaryl consisting of 5 to 6 ring atoms or heterocyclyl consisting of 3 to 10 ring atoms, wherein each of C₁₋₆ alkyl, C₁₋₆ alkylamino, C₁₋₆ alkoxy, C₂₋₆ alkynyl, C₂₋₆ alkenyl, C₃₋₇ cycloalkyl, phenyl, heteroaryl consisting of 5 to 6 ring atoms and heterocyclyl consisting of 3 to 10 ring atoms is independently unsubstituted or substituted by 1, 2, 3, or 4 Rʷ;
or R⁶ and R⁴, together with the atom to which they are attached, form a carbocyclyl consisting of 5 to 6 ring atoms or a heterocyclyl consisting of 5 to 6 ring atoms, wherein each of carbocyclyl consisting of 5 to 6 ring atoms and heterocyclyl consisting of 5 to 6 ring atoms is independently unsubstituted or substituted by 1, 2, 3, or 4 Rʷ;
each R² is independently hydrogen, deuterium, F, Cl, Br, =O, C₁₋₆ alkyl, C₁₋₆ alkylamino, C₁₋₆ alkoxy, C₂₋₆ alkynyl, C₂₋₆ alkenyl, C₃₋₇ cycloalkyl, phenyl or heterocyclyl consisting of 3 to 6 ring atoms, wherein each of C₁₋₆ alkyl, C₁₋₆ alkylamino, C₁₋₆ alkoxy, C₂₋₆ alkynyl, C₂₋₆ alkenyl, C₃₋₇ cycloalkyl, phenyl and heterocyclyl consisting of 3 to 6 ring atoms is independently unsubstituted or substituted by 1, 2, 3, or 4 Rʷ;
or two R² linked to the same carbon atom, together with the carbon atom to which they are attached, form a C₃₋₆ cycloalkyl or —(C=O)—, wherein C₃₋₆ cycloalkyl is unsubstituted or substituted by 1, 2, 3, or 4 Rʷ;
each R¹ᵃ, Rᵃ, Rᵇ and Rᶜ is independently hydrogen, deuterium, C₁₋₆ alkyl, C₁₋₆ alkoxy, C₂₋₆ alkenyl, C₂₋₆ alkynyl, C₃₋₆ cycloalkyl, C₆₋₁₀ aryl, heterocyclyl consisting of 3 to 6 ring atoms or heteroaryl consisting of 5 to 10 ring atoms, wherein each of C₁₋₆ alkyl, C₁₋₆ alkoxy, C₂₋₆ alkenyl, C₂₋₆ alkynyl, C₃₋₆ cycloalkyl, C₆₋₁₀ aryl, heterocyclyl consisting of 3 to 6 ring atoms and heteroaryl consisting of 5 to 10 ring atoms is independently unsubstituted or substituted by 1, 2, 3, or 4 substituents selected from F, Cl, Br, CN, HO—, amino, C₁₋₆ alkyl, C₁₋₆ haloalkyl, C₁₋₆ alkoxy or C₁₋₆ alkylamino;
n is 0, 1, 2, 3, 4, or 5.

2. The compound of claim 1 having Formula (II):

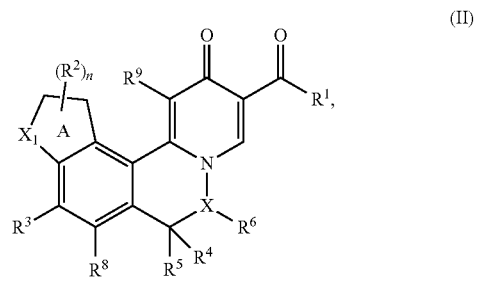

wherein X₁ is —O—, —NH—, —S—, —CH₂—O—, —O—CH₂—, —CH₂— or —CH₂—CH₂—.

3. The compound of claim 1, wherein R³ is hydrogen, deuterium, F, Cl, Br, hydroxy, cyano, C₁₋₄ alkyl, C₂₋₄ alkynyl, C₃₋₆ cycloalkyl, heterocyclyl consisting of 3 to 6 ring atoms, phenyl, heteroaryl consisting of 5 ring atoms, heteroaryl consisting of 6 ring atoms or R¹⁰—C₀₋₃alkylene-O—, wherein each of C₁₋₄ alkyl, C₂₋₄ alkynyl, C₃₋₆ cycloalkyl, heterocyclyl consisting of 3 to 6 ring atoms, phenyl, heteroaryl consisting of 5 ring atoms, heteroaryl consisting of 6 ring atoms and —$C_{0-3}$ alkylene- of $R^{10}$—$C_{0-3}$ alkylene-O— is independently unsubstituted or substituted by 1, 2, 3 or 4 $R^g$;

$R^{10}$ is deuterium, $R^{11}$O—, $C_{1-4}$ alkyl, $C_{3-6}$ cycloalkyl, heterocyclyl consisting of 3 to 6 ring atoms, phenyl, heteroaryl consisting of 5 ring atoms or heteroaryl consisting of 6 ring atoms, wherein each of $C_{1-4}$ alkyl, $C_{3-6}$ cycloalkyl, heterocyclyl consisting of 3 to 6 ring atoms, phenyl, heteroaryl consisting of 5 ring atoms and heteroaryl consisting of 6 ring atoms is independently unsubstituted or substituted by 1, 2, 3, or 4 $R^j$.

4. The compound of claim 1, wherein $R^3$ is hydrogen, deuterium, F, Cl, Br, hydroxy, cyano, methyl, ethyl, n-propyl, isopropyl, n-butyl, isobutyl, sec-butyl, tert-butyl, ethynyl, propargyl, propynyl, but-1-yne-4-yl, but-2-yne-1-yl, but-1-yne-1-yl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $R^{10}$—O—, $R^{10}$—CH$_2$—O—, $R^{10}$-(CH$_2$)$_2$—O— or $R^{10}$-(CH$_2$)$_3$—O—, wherein each of methyl, ethyl, n-propyl, isopropyl, n-butyl, isobutyl, sec-butyl, tert-butyl, ethynyl, propargyl, propynyl, but-1-yne-4-yl, but-2-yne-1-yl, but-1-yne-1-yl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, —CH$_2$— of $R^{10}$—CH$_2$—O—, —(CH$_2$)$_2$—O— of $R^{10}$-(CH$_2$)$_2$— and —(CH$_2$)$_3$— of $R^{10}$-(CH$_2$)$_3$—O— is independently unsubstituted or substituted by 1, 2, 3, or 4 $R^g$;

$R^{10}$ is deuterium, $R^{11}$O—, methyl, ethyl, n-propyl, isopropyl, n-butyl, isobutyl, sec-butyl, tert-butyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, sec-butyl, tert-butyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 $R^j$.

5. The compound of claim 1, wherein each $R^j$ and $R^g$ is independently deuterium, F, Cl, Br, CN, =O, HO—, HOOC—, $R^{11}$O—, $R^{12}$13 S(=O)$_2$—, $R^{13}$-(c=O)—, $R^{14}$13 S(=O)$_2$—O—, $R^{15}$13 S(=O)$_2$—N(R$^c$)—, $R^{16}$—N(R$^c$)—S (=O)$_2$—, $R^{17}$-(C=O)—N(R$^c$)—S(=O)$_2$—, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, heteroaryl consisting of 5 ring atoms or heteroaryl consisting of 6 ring atoms, wherein each of amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, $C_{3-6}$ cycloalkyl, heterocyclyl consisting of 3 to 6 ring atoms, phenyl, heteroaryl consisting of 5 ring atoms and heteroaryl consisting of 6 ring atoms is independently unsubstituted or substituted by 1, 2, 3 or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, $C_{1-4}$ alkyl, $C_{2-4}$ alkynyl, $C_{3-6}$ cycloalkyl, heterocyclyl consisting of 3 to 6 ring atoms, phenyl, phenyl $C_{1-2}$ alkylene, heteroaryl consisting of 5 ring atoms or heteroaryl consisting of 6 ring atoms, wherein each of $C_{1-4}$ alkyl, $C_{2-4}$ alkynyl, $C_{3-6}$ cycloalkyl, heterocyclyl consisting of 3 to 6 ring atoms, phenyl, phenyl $C_{1-2}$ alkylene, heteroaryl consisting of 5 ring atoms and heteroaryl consisting of 6 ring atoms is independently unsubstituted or substituted by 1, 2, 3 or 4 substituents selected from F, Cl, Br, CN, HO—, =O, HOOC—, $R^aR^bN$—S(=O)$_2$—, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, phenyl, $C_{3-6}$ cycloalkyl, heterocyclyl consisting of 5 ring atoms, heteroaryl consisting of 6 ring atoms, heterocyclyl of 3 to 6 ring atoms, $C_{1-4}$ alkoxy $C_{1-3}$ alkylene or $C_{1-4}$ alkylamino $C_{1-3}$ alkylene.

6. The compound of claim 1, wherein each $R^j$ and $R^g$ is independently deuterium, F, Cl, Br, CN, =O, HO—, HOOC—, $R^{11}$O—, $R^{12}$—S(=O)$_2$—, $R^{13}$-(C=O)—, $R^{14}$13 S(=O)$_2$—O—, $R^{15}$13 S(=O)$_2$—N(R$^c$)-, $R^{16}$—N(R$^c$)—S (=O)$_2$—, $R^{17}$-(C=O)—N(R$^c$)—S(=O)$_2$—, amino, methyl, ethyl, n-propyl, isopropyl, n-butyl, isobutyl, sec-butyl, tert-butyl, methoxy, ethoxy, 1-propoxy, 2-propoxy, 1-butoxy, 2-methyl-1-propoxy, 2-butoxy, alkylthio, $C_{1-3}$ alkylamino, $C_{2-4}$ alkenyl, $C_{2-4}$ alkynyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of amino, methyl, ethyl, n-propyl, isopropyl, n-butyl, isobutyl, sec-butyl, tert-butyl, methoxy, ethoxy, 1-propoxy, 2-propoxy, 1-butoxy, 2-methyl-1-propoxy, 2-butoxy, $C_{1-3}$ alkylthio, $C_{1-3}$ alkylamino, $C_{2-4}$ alkenyl, $C_{2-4}$ alkynyl, cyclopropyl, cyclobutyl, cyclopentyl, cyclohexyl, phenyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 $R^w$;

each $R^{11}$, $R^{12}$, $R^{12a}$, $R^{13}$, $R^{13a}$, $R^{14}$, $R^{15}$, $R^{16}$ and $R^{17}$ is independently hydrogen, deuterium, $R^aR^bN$—, methyl, ethyl, n-propyl, isopropyl, n-butyl, isobutyl, sec-butyl, tert-butyl, $C_{2-4}$ alkynyl, cyclopropyl, cyclobutyl, cyclopentyl, cyclohexyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, phenyl $C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, sec-butyl, tert-butyl, $C_{2-4}$ alkynyl, cyclopropyl, cyclobutyl, cyclopentyl, cyclohexyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl, piperazinyl, phenyl, phenyl $C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted by 1, 2, 3, or 4 substituents selected from F, Cl, Br, CN, HO—, =O, HOOC—, $R^aR^bN$—S(=O)$_2$—, amino, $C_{1-3}$ alkyl, $C_{1-3}$ haloalkyl, $C_{1-3}$ alkoxy, $C_{1-3}$ alkylthio, $C_{1-3}$ haloalkoxy, $C_{1-3}$ alkylamino, $C_{2-4}$ alkenyl, $C_{2-4}$ alkynyl, phenyl, $C_{3-6}$ cycloalkyl, heteroaryl consisting of 5 ring atoms, heteroaryl consisting of 6 ring atoms, heterocyclyl consisting of 3 to 6 ring atoms, $C_{1-3}$ alkoxy $C_{1-2}$ alkylene or $C_{1-3}$ alkylamino $C_{1-2}$ alkylene.

7. The compound of claim 1, wherein each $R^w$ is independently deuterium, F, Cl, Br, HO—, HOOC—, =O, amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, tert-butoxycarbonyl, $C_{1-4}$ alkyl-S(=O)$_2$—, cyclopropyl-S(=O)$_2$—, cyclopentyl-S(=O)$_2$—, cyclohexyl-S(=O)$_2$— or $C_{3-6}$ cycloalkyl, wherein each of amino, $C_{1-4}$ alkyl, $C_{1-4}$ alkoxy, $C_{1-4}$ alkylthio, $C_{1-4}$ alkylamino, $C_{2-4}$ alkenyl, $C_{2-4}$ alkynyl, tert-butoxycarbonyl, $C_{1-4}$ alkyl-S(=O)$_2$—, cyclopropyl-S(=O)$_2$—, cyclopentyl-S(=O)$_2$—, cyclohexyl-S(=O)$_2$— and $C_{3-6}$ cycloalkyl is independently unsubstituted or substituted by 1, 2, 3 or 4 substituents selected from F, Cl, Br, CN, OH, =O, amino, $C_{1-4}$ alkyl, $C_{1-4}$ haloalkyl, $C_{1-4}$ alkoxy, $C_{1-4}$ alkylthio, $C_{1-4}$ haloalkoxy or $C_{1-4}$ alkylamino;

each of $R^4$, $R^5$, $R^6$, $R^7$, $R^8$ and $R^9$ is independently hydrogen, deuterium, F, Cl, Br, $R^{12a}$13 S(=O)$_2$—, $R^{13a}$-(C=O)—, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl and heterocyclyl consisting of 3 to 6 ring atoms is independently unsubstituted or substituted by 1, 2, 3, or 4 $R^w$;

or $R^6$ and $R^4$, together with the atom to which they are attached, form cyclopentyl, cyclohexyl, pyrrolidinyl, pyrazolidinyl, imidazolidinyl, piperidinyl, morpholinyl, thiomorpholinyl or piperazinyl, wherein each of cyclopentyl, cyclohexyl, pyrrolidinyl, pyrazolidinyl, imidazolidinyl, piperidinyl, morpholinyl, thiomorpholinyl and piperazinyl is independently unsubstituted or substituted by 1, 2, 3, or 4 $R^w$.

8. The compound of claim 1, wherein each $R^w$ described herein is independently deuterium, F, Cl, Br, HO—, HOOC—, =O, amino, methyl, ethyl, n-propyl, isopropyl, n-butyl, isobutyl, sec-butyl, tert-butyl, $C_{1-4}$ alkoxy, $C_{1-4}$ alkylthio, $C_{1-4}$ alkylamino, $C_{2-4}$ alkenyl, ethynyl, propargyl, propynyl, but-1-yne-4-yl, but-2-yne-1-yl, but-1-yne-1-yl, tert-butoxycarbonyl, $C_{1-4}$ alkyl-S(=O)$_2$—, cyclopropyl-S(=O)$_2$—, cyclopentyl-S(=O)$_2$—, cyclohexyl-S(=O)$_2$—, cyclopropyl, cyclobutyl, cyclopentyl or cyclohexyl, wherein each of amino, methyl, ethyl, n-propyl, isopropyl, n-butyl, isobutyl, sec-butyl, tert-butyl, $C_{1-4}$ alkoxy, $C_{1-4}$ alkylthio, $C_{1-4}$ alkylamino, $C_{2-4}$ alkenyl, ethynyl, propargyl, propynyl, but-1-yne-4-yl, but-2-yne-1-yl, but-1-yne-1-yl, tert-butoxycarbonyl, $C_{1-4}$ alkyl-S(=O)$_2$—, cyclopropyl-S(=O)$_2$—, cyclopentyl-S(=O)$_2$—, cyclohexyl-S(=O)$_2$—, cyclopropyl, cyclobutyl, cyclopentyl and cyclohexyl is independently unsubstituted or substituted by 1, 2, 3 or 4 substituents selected from F, Cl, Br, CN, OH, =O, amino, $C_{1-4}$ alkyl, $C_{1-4}$ haloalkyl, $C_{1-4}$ alkoxy, $C_{1-4}$ alkylthio, $C_{1-4}$ haloalkoxy or $C_{1-4}$ alkylamino;

each of $R^4$, $R^5$, $R^6$, $R^7$, $R^8$ and $R^9$ is independently hydrogen, deuterium, F, Cl, Br, $R^{12a}$-S(=O)$_2$—, $R^{13a}$-(C=O)—, methyl, ethyl, n-propyl, isopropyl, n-butyl, isobutyl, sec-butyl, tert-butyl, $C_{1-4}$ alkylamino, $C_{1-4}$ alkoxy, ethynyl, propargyl, propynyl, but-1-yne-4-yl, but-2-yne-1-yl, but-1-yne-1-yl, $C_{2-4}$ alkenyl, cyclopropyl, cyclobutyl, cyclopentyl, cyclohexyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl or piperazinyl, wherein each of methyl, ethyl, n-propyl, isopropyl, n-butyl, isobutyl, sec-butyl, tert-butyl, $C_{1-4}$ alkylamino, $C_{1-4}$ alkoxy, ethynyl, propargyl, propynyl, but-1-yne-4-yl, but-2-yne-1-yl, but-1-yne-1-yl, $C_{2-4}$ alkenyl, cyclopropyl, cyclobutyl, cyclopentyl, cyclohexyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, azetidinyl, oxetanyl, thietanyl, oxiranyl, pyrrolidinyl, pyrazolidinyl, imidazolidinyl, tetrahydrofuranyl, tetrahydrothiophenyl, tetrahydropyranyl, tetrahydrothiopyranyl, piperidinyl, morpholinyl, thiomorpholinyl and piperazinyl is independently unsubstituted or substituted by 1, 2, 3, or 4 $R^w$;

or $R^6$ and $R^4$, together with the atom to which they are attached, form cyclopentyl, cyclohexyl, pyrrolidinyl, pyrazolidinyl, imidazolidinyl, piperidinyl, morpholinyl, thiomorpholinyl or piperazinyl, wherein each of cyclopentyl, cyclohexyl, pyrrolidinyl, pyrazolidinyl, imidazolidinyl, piperidinyl, morpholinyl, thiomorpholinyl and piperazinyl is independently unsubstituted or substituted by 1, 2, 3, or 4 $R^w$.

9. The compound of claim 1, wherein each $R^2$ is independently hydrogen, deuterium, F, Cl, Br, =O, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl and heterocyclyl consisting of 3 to 6 ring atoms is independently unsubstituted or substituted by 1, 2, 3, or 4 $R^w$;

or two $R^2$ linked to the same carbon atom, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted by 1, 2, 3, or 4 $R^w$;

each $R^{1a}$, $R^a$, $R^b$ and $R^c$ is independently hydrogen, deuterium, methyl, ethyl, n-propyl, isopropyl, n-butyl, isobutyl, sec-butyl, tert-butyl, $C_{1-4}$ alkoxy, $C_{2-4}$ alkenyl, $C_{2-4}$ alkynyl, $C_{3-6}$ cycloalkyl, phenyl, heterocyclyl consisting of 3 to 6 ring atoms, heteroaryl consisting of 5 ring atoms or heteroaryl consisting of 6 ring atoms, wherein each of methyl, ethyl, n-propyl, isopropyl, n-butyl, isobutyl, sec-butyl, tert-butyl, $C_{1-4}$ alkoxy, $C_{2-4}$ alkenyl, $C_{2-4}$ alkynyl, $C_{3-6}$ cycloalkyl, phenyl, heterocyclyl consisting of 3 to 6 ring atoms, heteroaryl consisting of 5 ring atoms and heteroaryl consisting of 6 ring atoms is independently unsubstituted or substituted by 1, 2, 3, or 4 substituents selected from F, Cl, Br, CN, HO—, amino, $C_{1-4}$ alkyl, $C_{1-4}$ haloalkyl, $C_{1-4}$ alkoxy or $C_{1-4}$ alkylamino.

10. The compound according to claim 1 having Formula

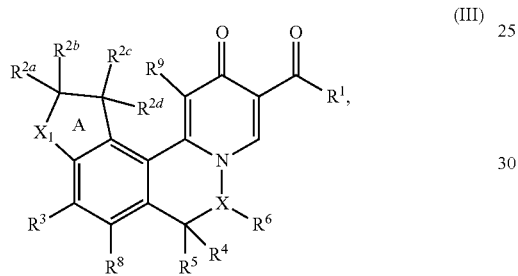

(III)

wherein $X_1$ is —O—, —NH—, —S—, —CH$_2$—O—, —O—CH$_2$—, —CH$_2$— or —CH$_2$—CH$_2$—;

each of $R^{2a}$, $R^{2b}$, $R^{2c}$ and $R^{2d}$ is independently hydrogen, deuterium, F, Cl, Br, methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl or heterocyclyl consisting of 3 to 6 ring atoms, wherein each of methyl, ethyl, n-propyl, isopropyl, n-butyl, isobutyl, sec-butyl, tert-butyl, $C_{1-4}$ alkylamino, $C_{1-4}$ alkoxy, $C_{2-4}$ alkynyl, $C_{2-4}$ alkenyl, $C_{3-6}$ cycloalkyl, phenyl and heterocyclyl consisting of 3 to 6 ring atoms is independently unsubstituted or substituted by 1, 2, 3 or 4 $R^w$;

or $R^{2a}$ and $R^{2b}$, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted with 1, 2, 3 or 4 $R^w$;

or $R^{2c}$ and $R^{2d}$, together with the carbon atom to which they are attached, form cyclopropyl, cyclobutyl, cyclopentyl, cyclohexyl or —C(=O)—, wherein each of cyclopropyl, cyclobutyl, cyclopentyl and cyclohexyl is independently unsubstituted or substituted with 1, 2, 3 or 4 $R^w$.

11. The compound of claim 1, comprising a compound of one of the following:

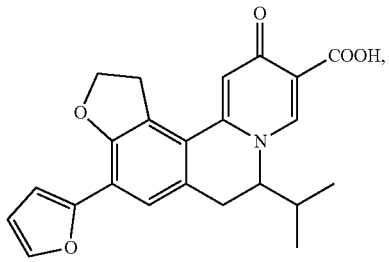

(1)

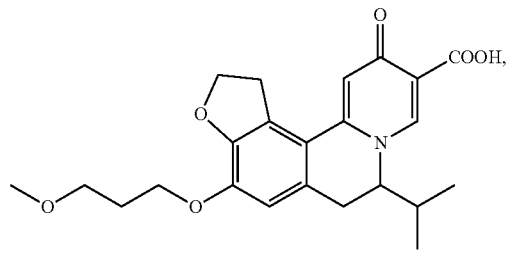

(2)

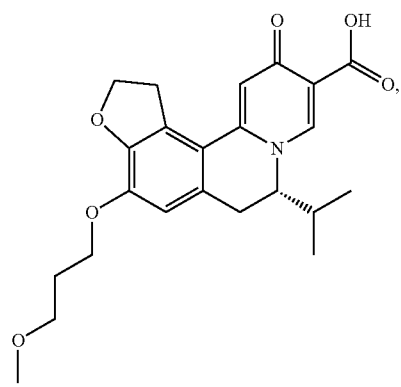

(2A)

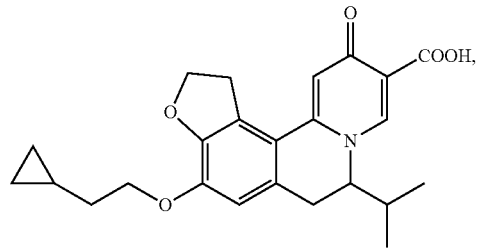

(3)

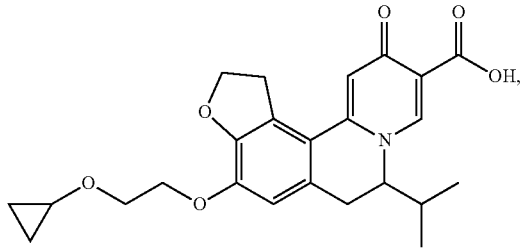

(4)

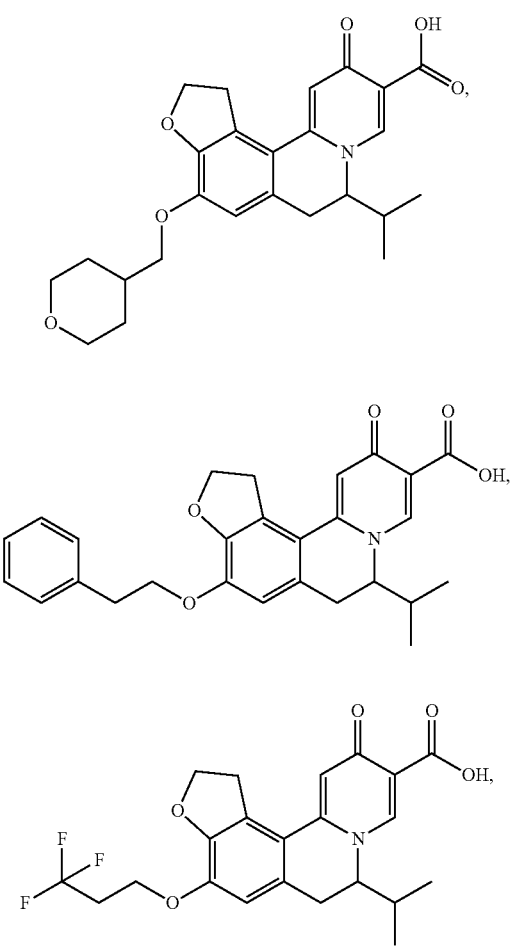
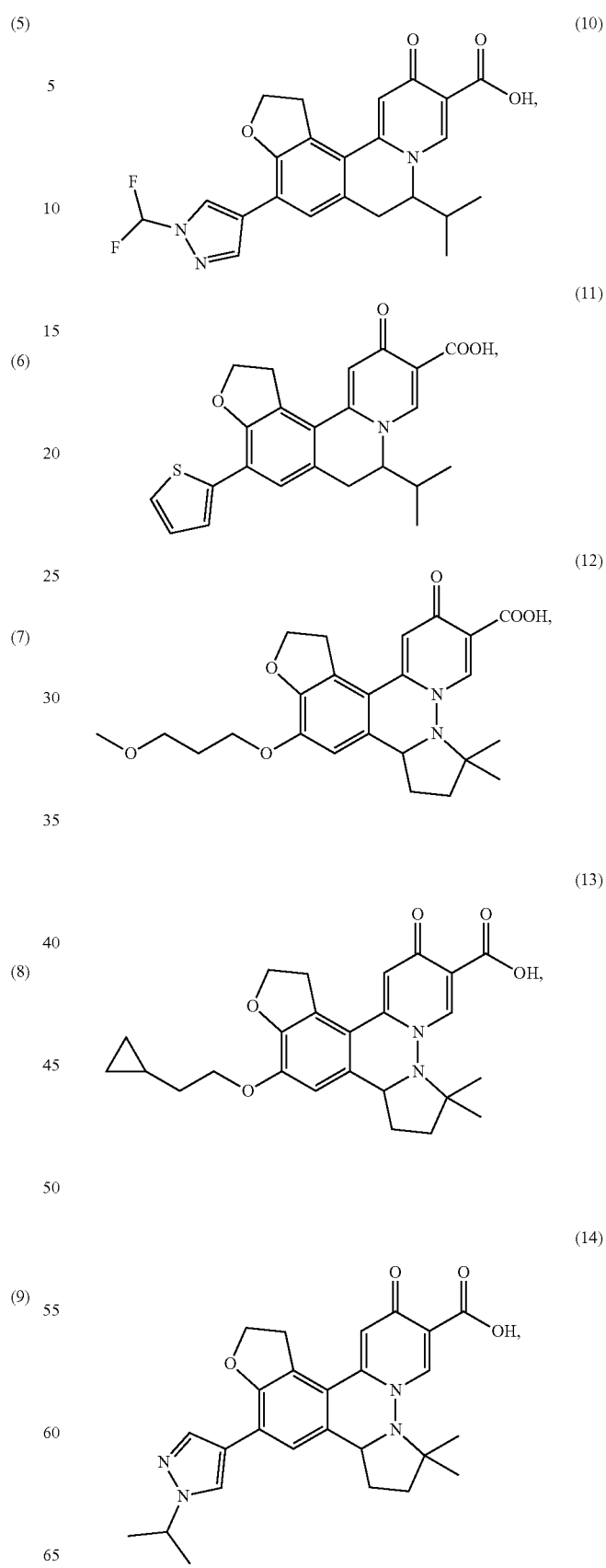

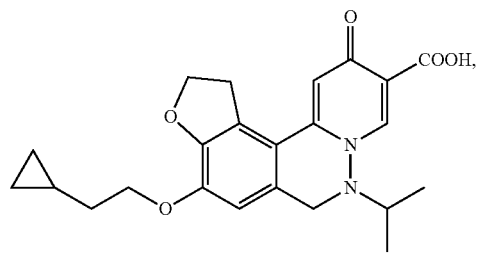
(15)
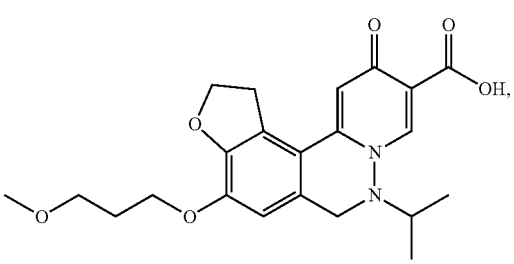
(16)
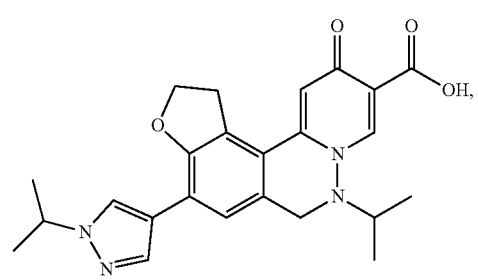
(17)
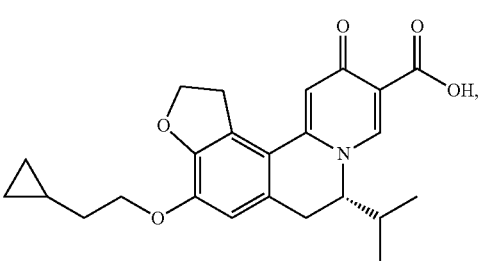
(3A)
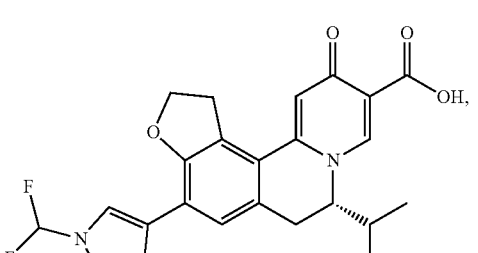
(10A)
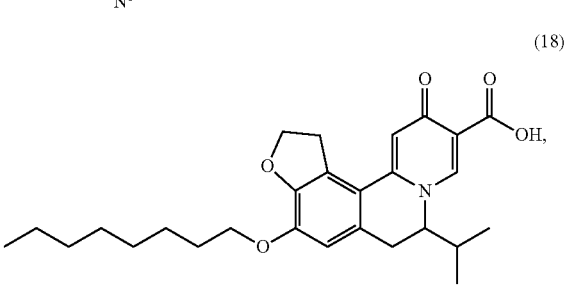
(18)
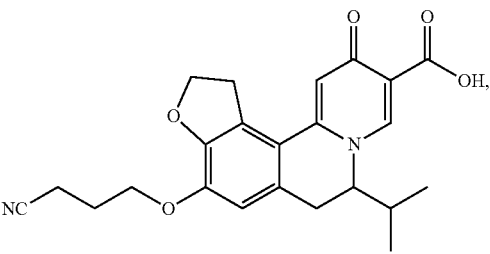
(19)
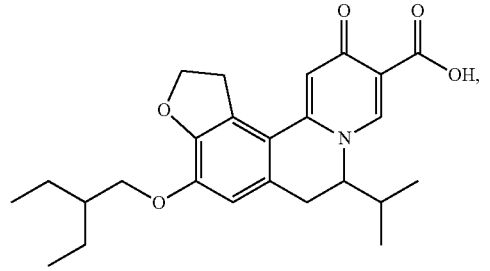
(20)
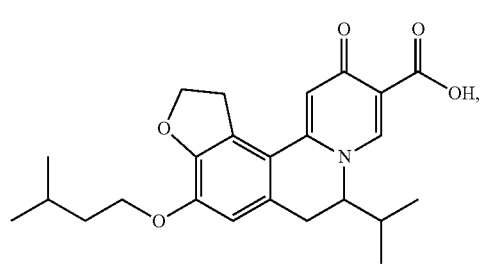
(21)
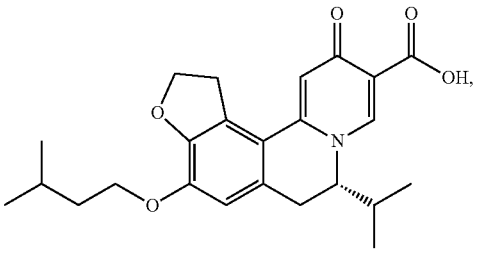
(21A)
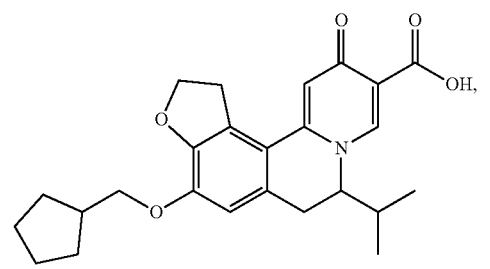
(22)

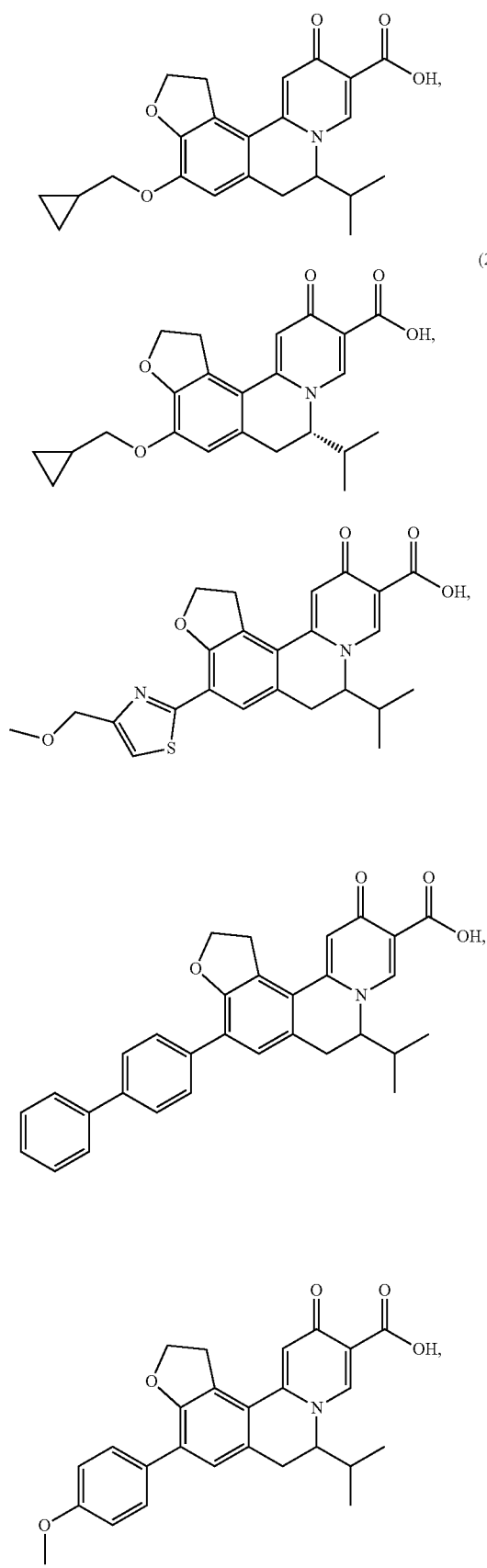
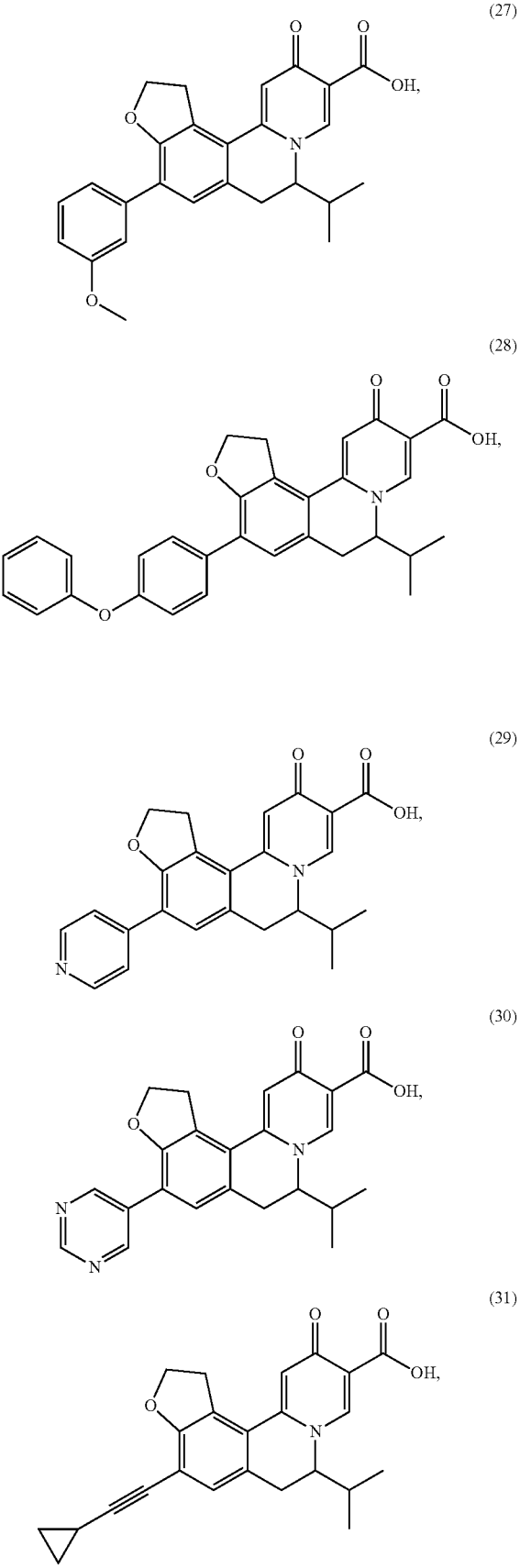

(32)
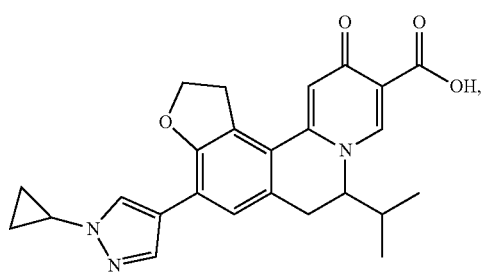
(33)
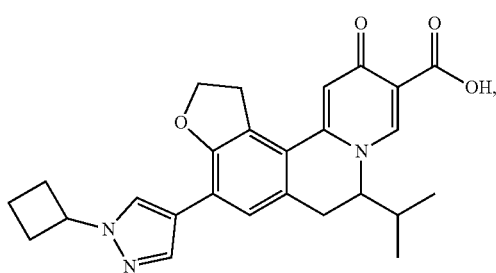
(34)
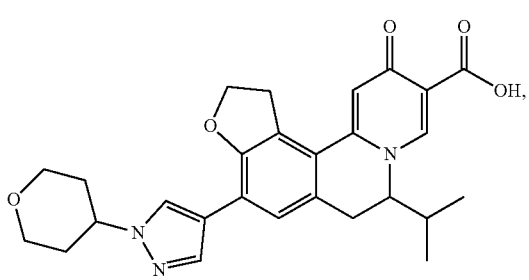
(35)
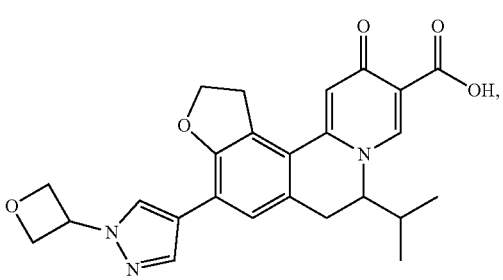
(36)
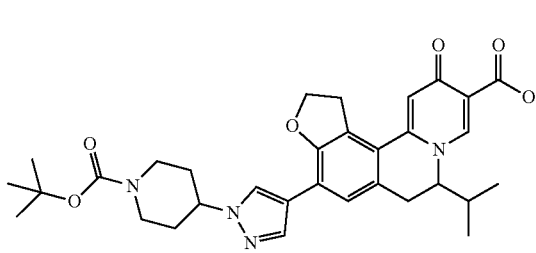
(37)
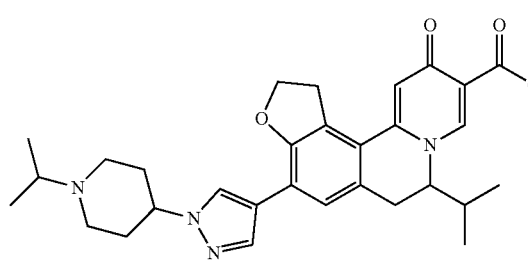
(38)
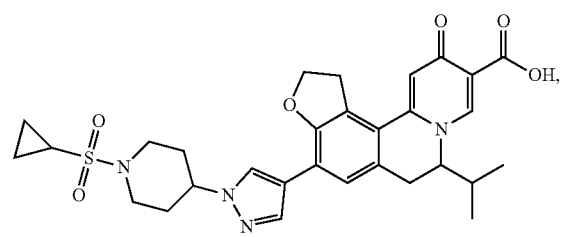
(39)
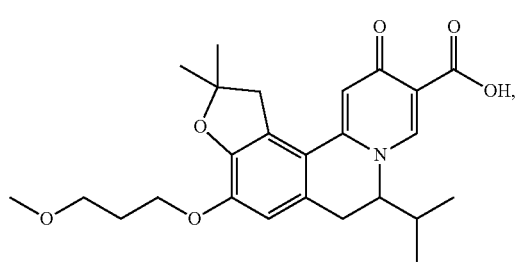
(40)
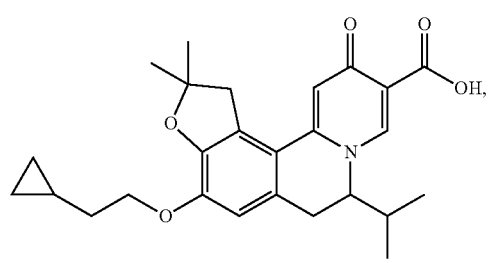
(41)
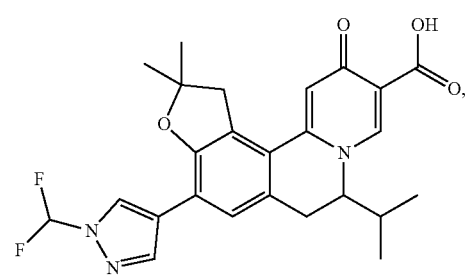
(42)
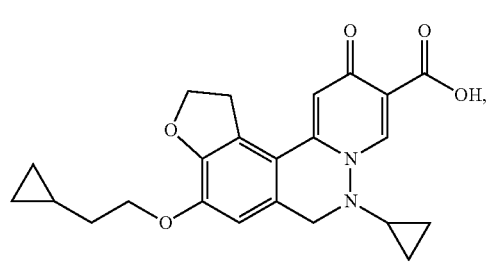
(43)
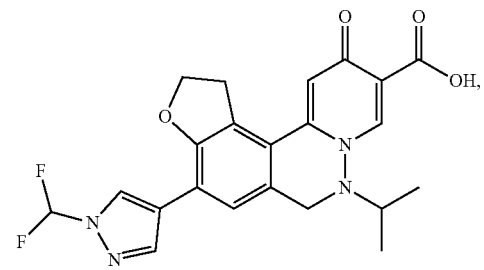

-continued
(44)
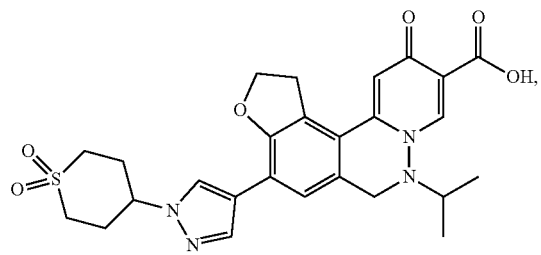
(45)
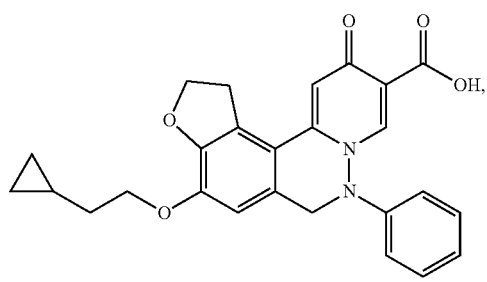
(46)
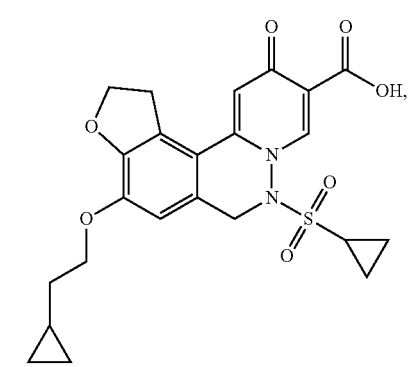
(47)
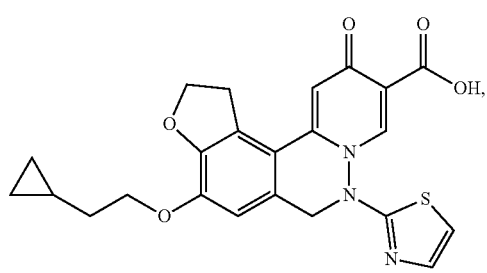
(48)
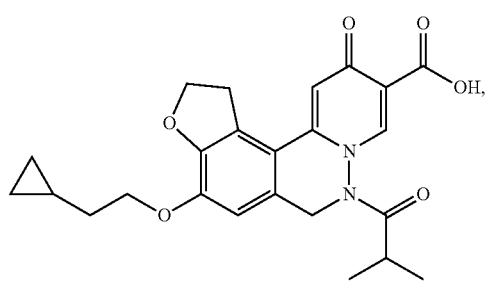
-continued
(49)
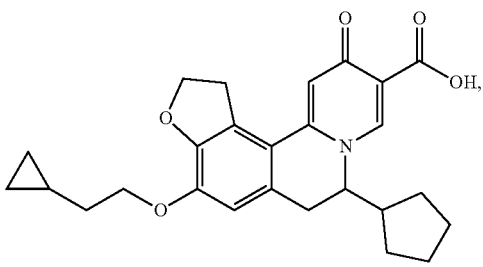
(50)
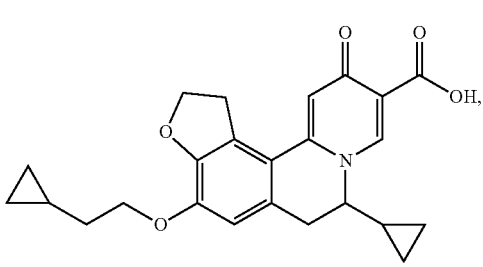
(51)
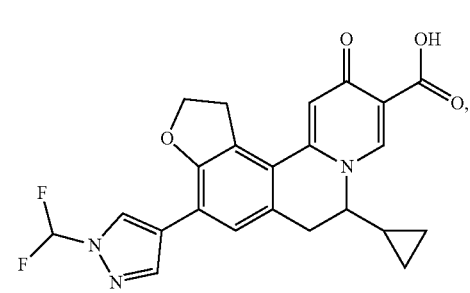
(52)
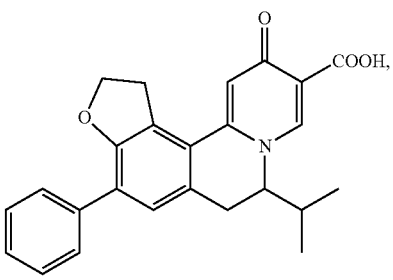
(53)
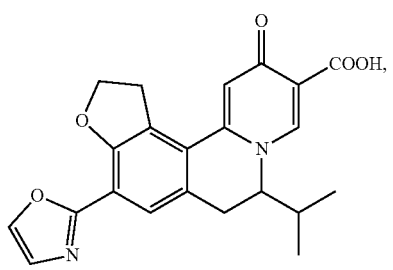

(54)
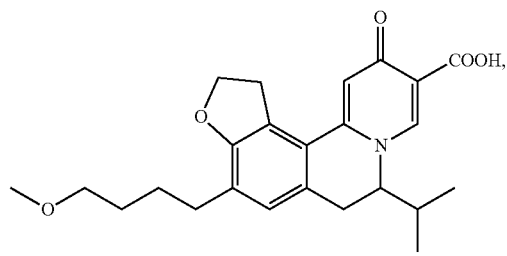
(55)
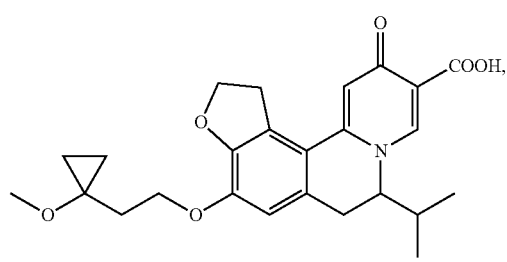
(56)
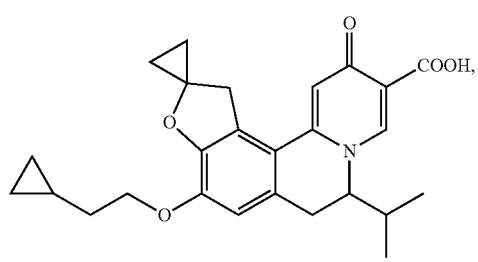
(57)
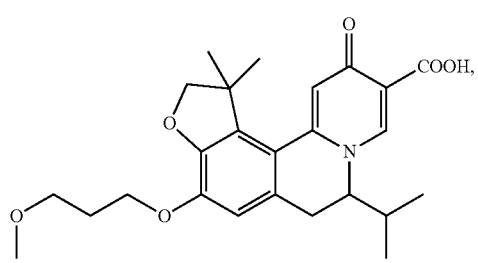
(58)
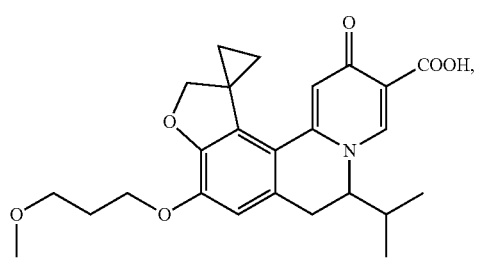
(59)
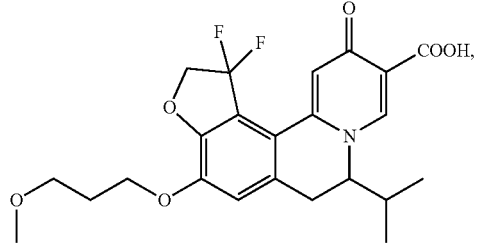
(60)
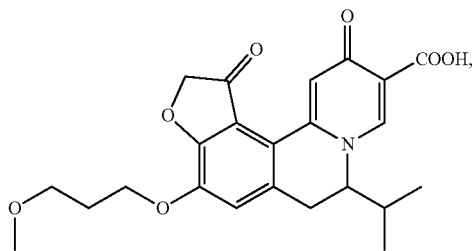
(61)
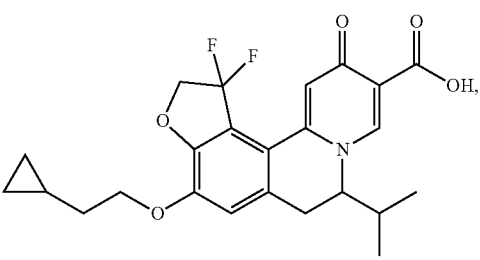
(62)
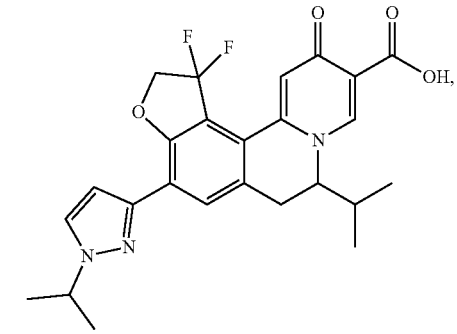
(63)
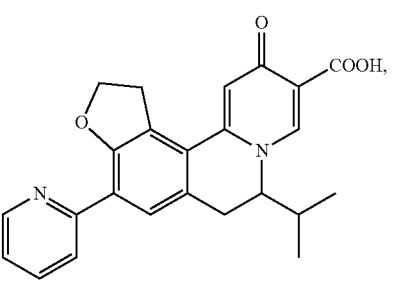
(64)
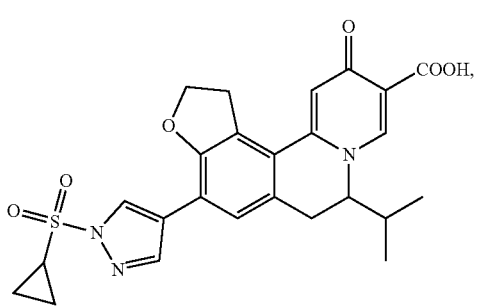

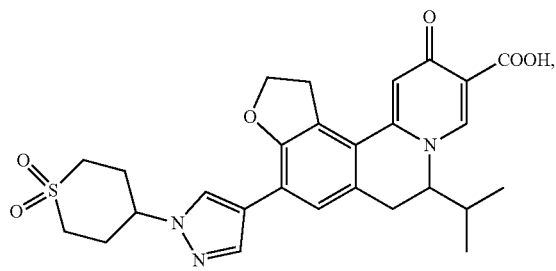
(65)
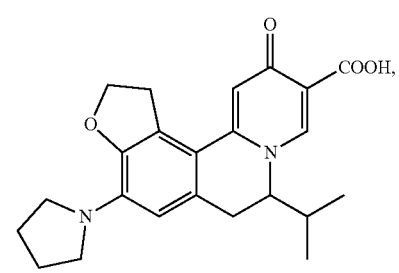
(66)
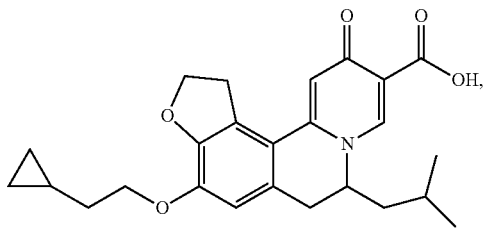
(67)
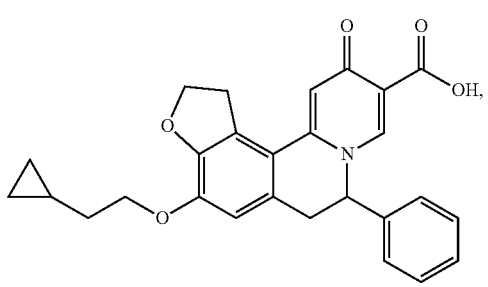
(68)
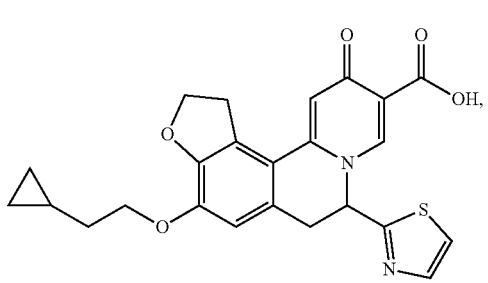
(69)
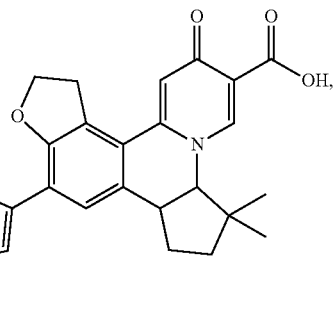
(70)
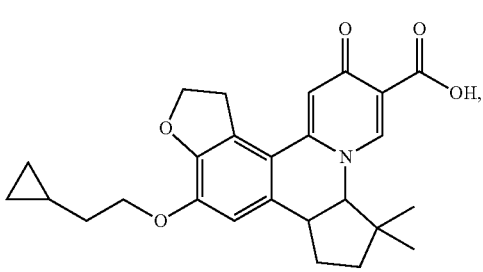
(71)
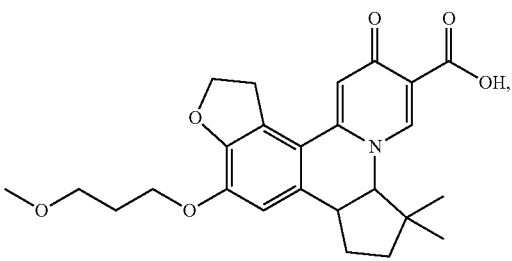
(72)
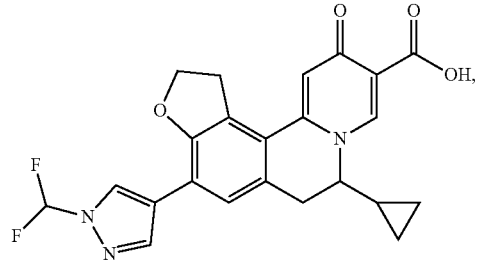
(73)
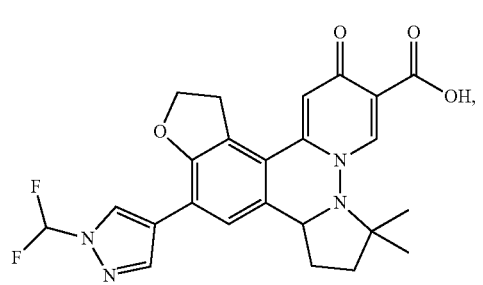
(74)

-continued
(75) 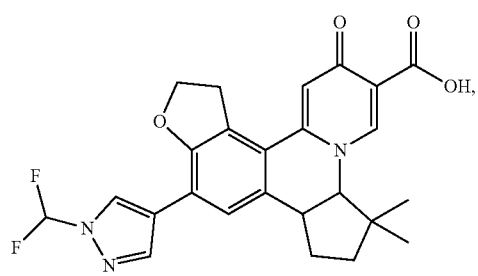
(76) 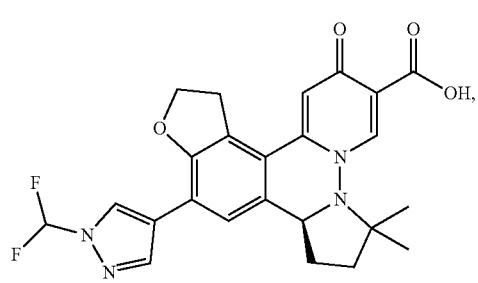
(77) 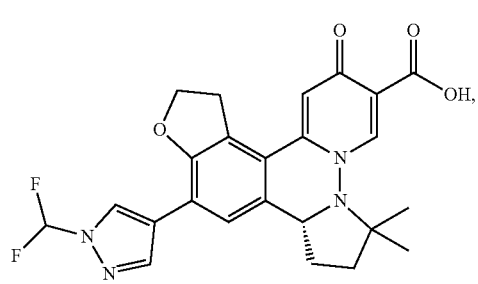
(78) 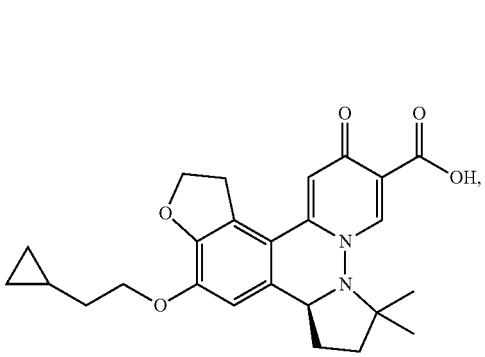
(79) 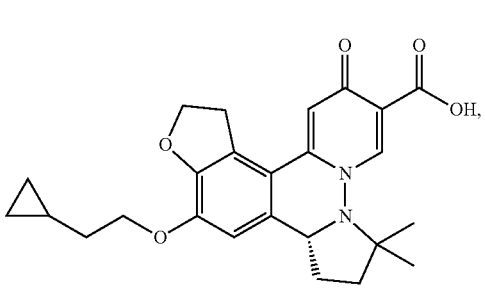
(80) 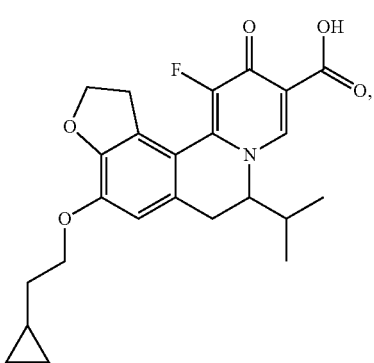
(81) 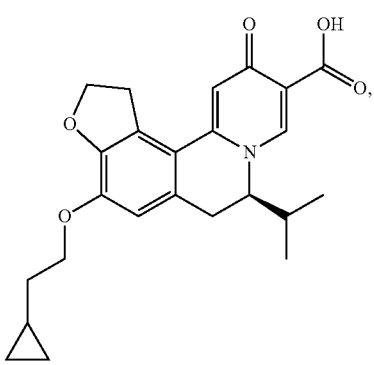
(82) 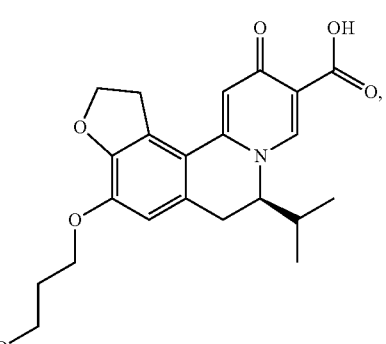
(83)

-continued

(84) 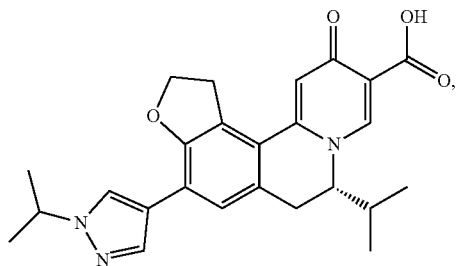

(85) 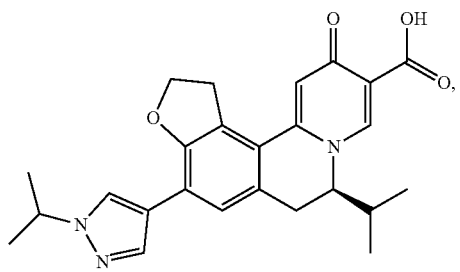

(86) 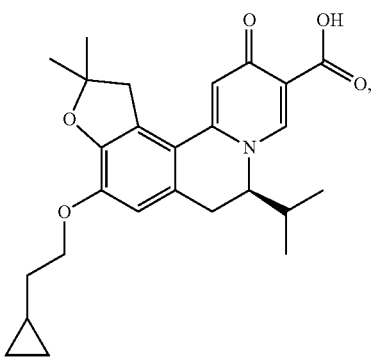

(87) 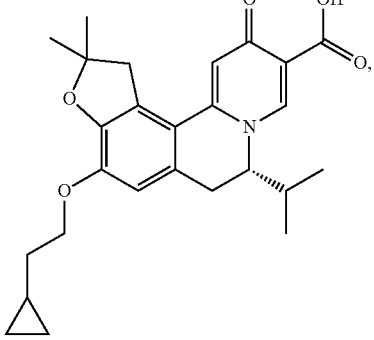

or their stereoisomers, tautomers, N-oxides, solvates, metabolites, pharmaceutically acceptable salts or prodrugs thereof.

12. A pharmaceutical composition comprising the compound of claim 1, optionally further comprising pharmaceutically acceptable excipients or combinations thereof.

13. The pharmaceutical composition of claim 12 further comprising other anti-HBV drugs, wherein other anti-HBV drugs are HBV polymerase inhibitors, immunomodulators or interferons.

14. The pharmaceutical composition of claim 13, wherein other anti-HBV drugs are lamivudine, telbivudine, tenofovir, entecavir, adefovir dipivoxil, Alfaferone, Alloferon, celmoleukin, clafidine, emtricitabine, faciclovir, interferon, Baoganling CP, intepropen, interferon α-1b, interferon α, interferon α-2a, interferon β-1a, interferon α-2, interleukin-2, mivotate, nalozolidine, peginterferon α-2a, ribavirin, interferon-A, cilostaz, Euforavac, aplori, Phosphazid, Heplisav, interferon α-2b, levamisole or propafen.

15. A method of treating or lessening viral diseases in a subject, comprising administering a therapeutically effective amount of the compound of claim 1 to the subject, wherein the viral disease is hepatitis B viral infection or a disease caused by hepatitis B viral infection.

16. The method of claim 15, wherein the disease caused by hepatitis B viral infection is cirrhosis or hepatocellular carcinoma.

17. A method of treating or lessening viral diseases in a subject, comprising administering a therapeutically effective amount of the pharmaceutical composition of claim 12 to the subject, wherein the viral disease is hepatitis B viral infection or a disease caused by hepatitis B viral infection, wherein the disease caused by hepatitis B viral infection is cirrhosis or hepatocellular carcinoma.

18. A method of inhibiting the formation or secretion of HBsAg, and/or inhibiting the formation of HBV DNA, comprising administering a therapeutically effective amount of the compound of claim 1 to the subject.

19. A method of inhibiting the formation or secretion of HBsAg, and/or inhibiting the formation of HBV DNA, comprising administering a therapeutically effective amount of the pharmaceutical composition of claim 12 to the subject.

* * * * *